(12) United States Patent
Gretzke et al.

(10) Patent No.: US 12,275,733 B2
(45) Date of Patent: Apr. 15, 2025

(54) SUBSTITUTED PYRIDO[3,4-B]INDOLES FOR THE TREATMENT OF CARTILAGE DISORDERS

(71) Applicant: Sanofi, Paris (FR)

(72) Inventors: Dirk Gretzke, Frankfurt am Main (DE); Olaf Ritzeler, Frankfurt am Main (DE); Uwe Heinelt, Frankfurt am Main (DE); Volkmar Wehner, Frankfurt am Main (DE); Friedemann Schmidt, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 18/488,871

(22) Filed: Oct. 17, 2023

(65) Prior Publication Data

US 2024/0182469 A1   Jun. 6, 2024

Related U.S. Application Data

(60) Continuation of application No. 17/409,513, filed on Aug. 23, 2021, now Pat. No. 11,827,633, which is a division of application No. 16/347,386, filed as application No. PCT/EP2017/078026 on Nov. 2, 2017, now Pat. No. 11,130,755.

(30) Foreign Application Priority Data

Nov. 7, 2016 (EP) .................................... 16306452

(51) Int. Cl.
   *C07D 471/04*   (2006.01)
   *A61K 31/437*   (2006.01)
   *A61P 19/02*    (2006.01)

(52) U.S. Cl.
   CPC .......... *C07D 471/04* (2013.01); *A61K 31/437* (2013.01); *A61P 19/02* (2018.01)

(58) Field of Classification Search
   CPC ...... C07D 471/04; A61K 31/437; A61P 19/02
   USPC ....................................................... 514/300
   See application file for complete search history.

(56) References Cited

U.S. PATENT DOCUMENTS

| | | | |
|---|---|---|---|
| 4,631,149 A | 12/1986 | Rinehart, Jr. et al. | |
| 5,010,077 A * | 4/1991 | Braestrup .............. | C07H 13/10 546/85 |
| 5,604,236 A | 2/1997 | Jakubowski | |
| 11,130,755 B2 | 9/2021 | Gretzke | |
| 11,827,633 B2 | 11/2023 | Gretzke | |
| 2013/0040977 A1 * | 2/2013 | McKnight ............ | C07D 487/04 546/276.7 |
| 2016/0303089 A1 | 10/2016 | Hagiwara | |
| 2020/0095242 A1 | 3/2020 | Gretzke | |
| 2022/0041596 A1 | 2/2022 | Gretzke | |

FOREIGN PATENT DOCUMENTS

| | | |
|---|---|---|
| EC | SP951529 A | 9/1995 |
| EP | 1134221 A1 | 9/2001 |
| GB | 2155462 A2 * | 9/1985 |
| JP | 2012171947 A | 9/2012 |
| WO | 200168648 A1 | 9/2001 |
| WO | 2003039545 A2 | 5/2003 |
| WO | 2003039545 A3 | 10/2003 |
| WO | 2008023063 A2 | 2/2008 |
| WO | 2008023063 A3 | 5/2008 |
| WO | 2008132454 A1 | 11/2008 |
| WO | 2010038153 A1 | 4/2010 |
| WO | 2015067549 A1 | 5/2015 |
| WO | 2015083750 A1 | 6/2015 |
| WO | 2018083157 A1 | 5/2018 |

OTHER PUBLICATIONS

Tarzi et al, Effect of chlorine as substituent on the photochemistry and acid-base properties of b-carboline alkaloids, Journal of Photochemistry and Photobiology, B: Biology (2006), 82(2), 79-93 (Year: 2006).*

Bonaz , Total Syntheses of Anguinomycins C & D, Synthetic Studies on Sporolides and Preparation of Eudistomin Derivatives: Biological Evaluation Against Cancer and Malaria, Dissertation, 2009, a copy of abstract) (Year: 2009).*

Aiello et al , Brominated beta-carbolines from the marine hydroid .Aglaophenia pluma Linnaeus, Tetrahedron (1987), 43(24), 5929-32 (Year: 1987).*

(Continued)

*Primary Examiner* — Taylor V Oh
(74) *Attorney, Agent, or Firm* — MORRISON & FOERSTER LLP

(57) ABSTRACT

The present invention relates to 8-aryl-substituted and 8-heteroaryl-substituted 9H-pyrido[3,4-b]indoles of the formula (I), in which A, E, G, $R^1$ to $R^6$ and $R^{10}$ are as defined in the claims, which stimulate chondrogenesis and cartilage matrix synthesis and can be used in the treatment of cartilage disorders and conditions in which a regeneration of damaged cartilage is desired, for example joint diseases such as osteoarthritis. The invention furthermore relates to processes for the synthesis of the compounds of the formula (I), their use as pharmaceuticals, and pharmaceutical compositions comprising them.

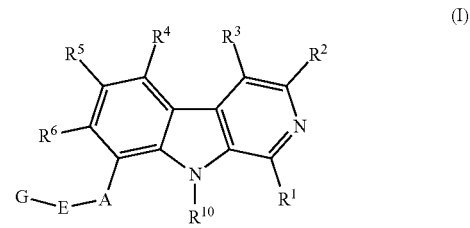

(I)

9 Claims, No Drawings

(56) References Cited

OTHER PUBLICATIONS

Nebergall et al (College Chemistry with qualitative analysis, p. 89, 1980 (Year: 1980).*
Wu, N. et al. (Mar. 17, 2014). "Transition-Metal-Catalyzed C—H Bond Functionalizations: Feasible Access to a Diversity-Oriented β-Carboline Library," Chem. Eur. J. 20(12):3408-3414.
Aigner, T. et al. (May 20, 2006; e-pub. Mar. 6, 2006). "Osteoarthritis: Pathobiology—Targets and Ways for Therapeutic Intervention," Advanced Drug Delivery Reviews 58(2):128-149.
Akiyami, H. et al. (Jan. 1996). "1α,25-dihydroxyvitamin D3 Inhibits Cell Growth and Chondrogenesis of a Clonal Mouse EC Cell Line, ATDC5," Journal of Bone Mineral Research 11(1):22-28.
Akiyami, H. et al. (Jun. 9, 1997). "Cloning of a Mouse Smoothened cDNA and Expression Patterns of Hedgehog Signalling Molecules during Chondrogenesis and Cartilage Differentiation in Clonal Mouse EC Cells, ATDC5," Biochemical and Biophysical Research Communications 235(1):142-147.
Alonso, F. et al. (Mar. 31, 2008). "Non-Conventional Methodologies for Transition-Metal Catalysed Carbon-Carbon Coupling: A Critical Overview. Part 2: The Suzuki Reaction," Tetrahedron 64(14):3047-3101.
Atsumi, T. et al. (May 1990). "A Chondrogenic Cell Line Derived From a Differentiating Culture of AT805 Teratocarcinoma Cells," Cell Differentiation and Development 30(2): 109-116.
Bendele, A.M. et al. (Apr. 1988). "Spontaneous Cartilage Degeneration in Guinea Pigs," Arthritis Rheum. 31(4):561-565.
Cox, E.D. et al. (1995). "The Pictet-Spengler Condensation: A New Direction for an Old Reaction," Chemical Reviews 95(6):1797-1842.
Darses, S. et al. (2008). "Potassium Organotrifluoroborates: New Perspectives in Organic Synthesis," Chemical Reviews 108(1):288-325.
De Crombrugghe, B. et al. (Dec. 1, 2001). "Regulatory Mechanisms in the Pathways of Cartilage and Bone Formation," Current Opinion in Cell Biology 13(6):721-728.
Domonkos, C. et al. (2015). "Synthesis and Serum Protein Binding of Novel Ring-Substituted Harmine Derivatives," RSC Advances 5(66):53809-53818, 35 pages.
European Search Report mailed on Jan. 1, 2017 for EP Application No. 16306452.0 filed Nov. 7, 2016, 5 pages.
Eyre, D.R. (Oct. 2004). "Collagens and Cartilage Matrix Homeostasis," Clinical Orthopaedics and Related Research 427:S118-S122.
Goldring, M.B. (Sep. 2000). "The Role of the Chondrocyte in Osteoarthritis," Arthritis & Rheumatism 43(9):1916-1926.
Han, F.-S. (2013). "Transition-Metal-Catalyzed Suzuki-Miyaura Cross-Coupling Reactions: A Remarkable Advance From Palladium to Nickel Catalysts," Chem. Soc. Rev. 42:5270-5298.
Hara, E.S. et al. (Feb. 2013; e-pub. Oct. 29, 2012). "Novel Chondrogenic and Chondroprotective Effects of the Natural Compound Harmine," Biochimie 95(2):374-381.
Heinegård, D. et al. (Jan. 2011; e-pub. Nov. 30, 2010). "The Role of the Cartilage Matrix in Osteoarthritis," Nature Rev. Rheumatol. 7:50-56.
Houard, X. et al. (Nov. 2013). "Homeostatic Mechanisms in Articular Cartilage and Role of Inflammation in Osteoarthritis," Current Rheumatology Reports 15(11):375, 19 pages.
International Preliminary Report on Patentability mailed on May 16, 2019 for PCT Application No. PCT/EP2017/078026 filed on Nov. 2, 2017, 6 pages.
International Search Report mailed on Dec. 1, 2017 for PCT Application No. PCT/EP2017/078026 filed on Nov. 2, 2017, 4 pages.
Ishiyama, T. et al. (Dec. 3, 2001). "Synthesis of Pinacol Arylboronates via Cross-Coupling Reaction of Bis (Pinacolato)Diboron with Chloroarenes Catalyzed by Palladium(0)-Tricyclohexylphosphine Complexes," Tetrahedron 57(49):9813-9816, 17 pages.
Jimenez, P.A. et al. (Dec. 1997). "Spontaneous Osteoarthritis in Dunkin Hartley Guinea Pigs: Histologic, Radiologic, and Biochemical Changes," Laboratory Animal Science 47(6):598-601.

Koelling, S. et al. (Apr. 3, 2009). "Migratory Chondrogenic Progenitor Cells from Repair Tissue during the Later Stages of Human Osteoarthritis," Cell Stem Cell 4(4):324-335.
Li, W. et al. (2005). "Synthesis of 3-Pyridylboronic Acid and Its Pinacol Ester. Application of 3-Pyridylboronic Acid in Suzuki Coupling to Prepare 3 Pyridin-3-Ylquinoline [Quinoline, 3-(3-Pyridinyl)-]," Organic Syntheses 81:89-97.
Lohmander, L.S. et al. (Jul. 2014). "Intraarticular Sprifermin (Recombinant Human Fibroblast Growth Factor 18) in Knee Osteoarthritis: A Randomized, Double-Blind, Placebo-Controlled Trial," Arthritis Rheumatology 66(7): 1820-1831.
Maddox, S.M. et al. (2015). "A Practical Lewis Base Catalyzed Electrophilic Chlorination of Arenes and Heterocycles," Org. Lett. 17(4):1042-1045.
Martinez, A.P. (Sep. 5, 1995). Request for Delay of Publication for Pharmaceutical Compounds SP-95-1529 and SP-95-1540, with English Translation, 6 pages.
Mehta, V.P. et al. (2011). "Microwave-Assisted C—C Bond Forming Cross-Coupling Reactions: An Overview," Chemical Society Reviews 40:4925-4936.
Mitchell, R.H. et al. (Dec. 1, 1979). "N-Bromosuccinimide-Dimethylformamide: A Mild, Selective Nuclear Monobromination Reagent for Reactive Aromatic Compounds," J. Org. Chem. 44(25):4733-4735.
Molander, G.A. et al. (Dec. 22, 2010). "Palladium-Catalyzed, Direct Boronic Acid Synthesis from Aryl Chlorides: A Simplified Route to Diverse Boronate Ester Derivatives," J. Am. Chem. Soc. 132(50):17701-17703, 13 pages.
Onuora, S. (Jun. 2014; e-pub. May 6, 2014). "Osteoarthritis: Sprifermin Shows Cartilage-Protective Effects in Knee OA," Nature Rev. Rheumatol. 10(6):322.
Prakash, G.K.S. et al. (Nov. 12, 2004). "N-Halosuccinimide/BF3-H2O, Efficient Electrophilic Halogenating Systems for Aromatics," J. Am. Chem. Soc. 126(48):15770-15776.
Rajesh, K. et al. (Jun. 23, 2007). "Bromination of Deactivated Aromatics: A Simple and Efficient Method," J. Org. Chem. 72(15):5867-5869.
Rocca, P. et al. (Apr. 16, 1993). "A New Convergent Synthesis of Alpha—Substituted—Beta—Carbolines," Tetrahedron 49(16):3325-3342.
Rocca, P. et al. (Jan. 1, 1993). "Connection Between Metalation and Cross-Coupling Strategies. A New Convergent Route to Azacarbazoles," Tetrahedron 49(1):49-64.
Shukunami, C. et al. (1996; e-pub. Apr. 15, 1996). "Chondrogenic Differentiation of Clonal Mouse Embryonic Cell Line ATDC5 In Vitro: Differentiation-dependent Gene Expression of Parathyroid Hormone (PTH)/PTH-related Peptide Receptor," J. Cell Biol. 133:457-468.
Shukunami, C. et al. (Aug. 1997). "Cellular Hypertrophy and Calcification of Embryonal Carcinoma-Derived Chondrogenic Cell Line ATDC5 In Vitro," Journal of Bone Mineral Research 12(8):1174-1188.
Shukunami, C. et al. (May 25, 1998). "Sequential Progression of the Differentiation Program by Bone Morphogenetic Protein-2 in Chondrogenic Cell Line ATDC5," Experimental Cell Research 241(1):1-11.
Smith, A.E. et al. (Mar. 2008; e-pub. Feb. 25, 2008). "Dimethoxy- and Dihalopyridyl)boronic Acids and Highly Functionalized Heteroarylpyridines by Suzuki Cross-Coupling Reactions," Eur. J. Org. Chem. 2008(8):1458-1463.
Wang, K. et al. (2015; e-pub. Oct. 1, 2015). "Investigational Drugs for the Treatment of Osteoarthritis," Expert Opin. Investig. Drugs 24(12): 1539-1556, 19 pages.
Wen, D. et al. (Jun. 2006). "A Selective Small Molecule IκB Kinase β Inhibitor Blocks Nuclear Factor κB-Mediated Inflammatory Responses in Human Fibroblast-Like Synoviocytes, Chondrocytes, and Mast Cells," Journal of Pharmacology and Experimental Therapeutics 317(3):989-1001.
Written Opinion of the International Searching Authority mailed on Dec. 1, 2017 for PCT Application No. PCT/EP2017/078026 filed on Nov. 2, 2017, 4 pages.

(56) References Cited

OTHER PUBLICATIONS

Yano, F. et al. (2013; e-pub. Oct. 5, 2012). "A Novel Disease-Modifying Osteoarthritis Drug Candidate Targeting Runx1," Ann. Rheum. Dis. 72:748-753.

* cited by examiner

SUBSTITUTED PYRIDO[3,4-B]INDOLES FOR THE TREATMENT OF CARTILAGE DISORDERS

CROSS REFERENCE TO RELATED APPLICATIONS

This application is a continuation of U.S. patent application Ser. No. 17/409,513, filed Aug. 23, 2021, which is a divisional of U.S. patent application Ser. No. 16/347,386, now U.S. Pat. No. 11,130,755, which adopts the international filing date of Nov. 2, 2017, which is a National Phase application under 35 U.S.C. § 371 of International Application No. PCT/EP2017/078026, filed Nov. 2, 2017, which claims priority to European Application No. 16306452.0, filed Nov. 7, 2016, the disclosures of each of which are incorporated herein by reference in their entireties.

The present invention relates to 8-aryl-substituted and 8-heteroaryl-substituted 9H-pyrido[3,4-b]indoles of the formula I,

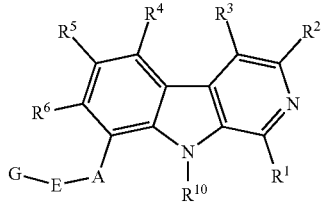

in which A, E, G, $R^1$ to $R^6$ and $R^{10}$ are as defined below, which stimulate chondrogenesis and cartilage matrix synthesis and can be used in the treatment of cartilage disorders and conditions in which a regeneration of damaged cartilage is desired, for example joint diseases such as osteoarthritis. The invention furthermore relates to processes for the synthesis of the compounds of the formula I, their use as pharmaceuticals, and pharmaceutical compositions comprising them.

Osteoarthritis, which in the following is also abbreviated as "OA" and sometimes is also referred to as osteoarthrosis, is the most common degenerative disease which primarily involves cartilage damage in joints. With increasing age, up to 80% of the population is affected. Although clinical signs of the disease are rather heterogeneous, patients suffering from OA generally demonstrate a common pathological phenotype. At early disease stages, which are characterized by moderate degradation of the cartilage lining of the joints, pain is the most prominent symptom. With progressing degradation of the cartilage and cartilage loss, an increase in pain results that is commonly accompanied by an increasing deficit in mobility of the affected joints and ultimately total immobility and loss of function. As a result of degradation of cartilage and cartilage loss, also subchondral structures start to change their morphology, leading to remodeling processes of the bone, such as a compaction of bone matter, and to the formation of cysts. In part patients also show signs of inflammation that additionally affects the synovial lining of the joint. At late stages of the disease, a total destruction of the joint is observed.

There is still an incomplete understanding of the pathophysiology of cartilage disorders such as OA, and until today no structure-modifying, or disease-modifying, therapies are available (cf. K. Wang et al., Expert Opin. Investig. Drugs, 2015, 24, 1539-1556; T. Aigner et al., Adv. Drug Deliv. Rev. 2006, 58, 128-149). Currently OA is generally treated with drugs which target pain and inflammation systemically or locally. Different non-steroidal anti-inflammatory drugs (NSAIDs) are used, as well as glucocorticoids which are administered locally by intra-articular injection. Both therapeutic strategies result in pain relief, but do not halt or reverse the progression of cartilage destruction. On top of such drug interventions, physical therapy and/or local intra-articular injections of hyaluronic acid are applied. Ultimately, a partial or total replacement of an affected joint, such as a knee or hip joint, is the only remaining choice for relieving patients from severe joint pain and restoring joint mobility and function.

Recently evidence has been generated that in particular in early stages of OA cartilage has still some potential for regeneration and self-healing, and it has been proposed to induce chondrogenesis, i.e. the process by which cartilage is generated, or stimulate cartilage growth, in order to reverse, or compensate for, cartilage destruction in OA. This concept was confirmed by recent data from clinical trials with recombinant human FGF18 (fibroblast growth factor 18, Sprifermin, AS902330), which showed cartilage protective effects in knee OA in humans (L. S. Lohmander et al., Arthritis Rheumatol. 2014, 66, 1820-1831; S. Onuora, Nature Rev. Rheumatol. 2014, 10, 322; WO 2008/023063). FGF18 is assumed to stimulate osteoblasts and, via the activation of chondrocytes, the formation of cartilage, and thus support healing, and not merely alleviate symptoms.

Articular cartilage functions as a low-friction, wear-resistant surface that covers the ends of bones and supports load transfer and motion of diarthrodial joints. These properties and functions of cartilage are owed to the composition of articular cartilage. Cartilage tissue, which is a kind of connective tissue and besides in joints is also present in intervertebral disks, for example, is built up by and contains a specialized cell type, the chondrocytes, that produce and maintain an extensive extracellular matrix composed mainly of collagen, mostly collagen type II and minor amounts of other types of collagen, of proteoglycans, mostly aggrecan, and of hyaluronic acid. The fibrillar collagen network and the highly negatively charged aggrecan confer tensile strength and compressive stiffness to the tissue (D. Heinegard et al., Nature Rev. Rheumatol. 2011, 7, 50-56). Chondrocytes, which may account to only 2% of the volume of the tissue in normal articular cartilage, maintain homeostasis of the tissue by regulation of extracellular matrix anabolism and catabolism. This continuous rebuilding of cartilage in an equilibrium of formation and degradation of the matrix, which is present under normal conditions, is disturbed in disease states such as OA, in which catabolic processes predominate.

Besides biomechanically induced modulation of the chondrocyte biosynthetic activity, several soluble factors, such as growth/differentiation factors and cytokines, have been identified to modulate anabolic and catabolic activity of chondrocytes. Anabolic cytokines that are considered to participate in cartilage repair processes, are IGF-1 (insulin-like growth factor 1), members of the TGF-β (transforming growth factor β) superfamily (for example TGF-β1, GDF5 (growth/differentiation factor 5), BMP2 (bone morphogenetic protein 2), BMP4, BMP7) and FGFs (fibroblast growth factors). bFGF (basic fibroblast growth factor) is the most potent chondrocyte mitogen, and other FGF family members, for example FGF18, may interact with IGF-1 and TGF-β to promote and maintain specific chondrocyte activities depending on the stage of the chondrocyte cell or differentiation status (M. B. Goldring, Arthritis Rheum.

2000, 43, 1916-1926). In addition to an anabolic, or synthesis promoting function, growth factors and cytokines can exert an anti-catabolic function. BMP7, which is also known as OP-1 (osteogenic protein 1), for example, has been shown to counteract low doses of IL-1 β (interleukin 1β) by inhibition of the expression of metalloproteinases MMP3 (matrix metalloproteinase 3; also known as strometysin 1) and MMP13 (also known as collagenase 3).

Among the catabolic cytokines, proinflammatory IL-1α and IL-1β as well as TNF-α (tumor necrosis factor α) are considered key factors which lead to extracellular matrix degradation by induction of the expression of proteinases, such as MMP3, MMP13, ADAMTS-4 ("A Disintegrin And Metalloproteinase with Thrombospondin Motifs"-4) and ADAMTS-5, which function as aggrecanase cleaving aggrecan, and by repression of the synthesis of the extracellular matrix synthesis components collagen II and aggrecan. Other catabolic cytokines known are IL-18, LIF (leukemia inhibitory factor) and OSM (Oncostatin M). In early osteoarthritis, chondrocytes attempt to repair a disturbed equilibrium of formation and degradation of the matrix by an endogenous repair process, but during progression of OA chondrocytes fail to maintain tissue homoeostasis, and the balance between anabolic and catabolic activity is lost and catabolic activity prevails (X. Houard et al., Curr. Rheumatol. Rep. 2013, 15, Article 375). Influencing anabolic and/or catabolic activities in favor of an increase in cartilage formation by means of appropriate active agents, similarly as observed with FGF18 in the study referred to above, offers an opportunity for treating OA.

Furthermore, recent evidence suggests the existence of progenitor cells within cartilage which might contribute to a repair response (S. Koelling et al., Cell Stem Cell 2009, 4, 324-335). Therefore, enhancement of chondrogenesis by influencing chondrocyte progenitor cells or mesenchymal stem cells arises as another therapeutic concept for treating osteoarthritis. In addition, chondrogenesis in the context of cell therapy is of relevance for cartilage repair. In particular in such approaches processes of cell differentiation and gene expression and influencing them by appropriate agents play a role. The SOX (SRY (sex determining region Y) box, or SRY-related HMG (high mobility group) box) family of transcription factors are the main inducers of chondrogenic differentiation, in particular SOX-9 which induces mesenchymal condensation and differentiation of cartilage precursor cells, followed by SOX-5 and SOX-6, which regulate the synthesis of cartilage matrix genes (B. de Crombrugghe et al., Curr. Opin. Cell Biol. 2001, 13, 721-727). However, as indicated above, until today no structure-modifying therapies for the treatment of disease states like OA have become available, and there continues to be need for concepts or active agents, which can stimulate chondrogenesis and lead to cartilage regeneration.

In WO 2010/038153 it has been described that a number of compounds of varying structures, mainly natural products such as flavonoid derivatives, are SOX transcription factor activators and stimulate chondrogenesis. In E. S. Hera et al., Biochimie 2013, 95, 374-381, and in JP 2012-171947 it has recently been described that the naturally occurring 7-alkoxy-substituted-pyrido[3,4-b]indole harmine (1-methyl-7-methoxy-9H-pyrido[3,4-b]indole or 1-methyl-7-methoxy-9H-β-carboline) has a chondrogenic effect. But as the authors point out, in view of its property profile harmine itself does not seem to be a suitable drug substance for the treatment of degenerative joint diseases, and some structurally related compounds did not exhibit an analogous activity.

Surprisingly it has been found that the 8-aryl-substituted and 8-heteroaryl-substituted 9H-pyrido[3,4-b]indoles of the formula I are potent stimulators of chondrogenesis and of cartilage formation, and exhibit other suitable properties and can be designed to exhibit a property profile suitable for the intended use, for example with regard to their solubility, which can be desired to be either high or low, in the latter case allowing for a long residence time in a joint after intra-articular administration. The compounds of the formula I induce the synthesis of major articular cartilage matrix components such as collagen type II and aggrecan in chondrocytes. Furthermore, they lead to strong induction of SOX-5, SOX-6 and SOX-9. The compounds of the formula I thus are useful as active agents for regenerating cartilage and treating joint diseases such as OA, for example.

Various other 9H-pyrido[3,4-b]indoles, which are also designated as 9H-β-carbolines, 9H-beta-carbolines or 9H-betacarbolines, have been described. For example, in U.S. Pat. No. 4,631,149 certain 9H-pyrido[3,4-b]indoles are disclosed which have antiviral, antibacterial and antitumor activity. In U.S. Pat. No. 5,604,236 9H-pyrido[3,4-b]indoles are disclosed which contain an acidic group and inhibit thromboxane synthetase, and are useful for the treatment of thromboembolic diseases. In WO 01/68648 and WO 03/039545 9H-pyrido[3,4-b]indoles are disclosed which inhibit the activity of IκB kinase and are useful for the treatment of cancer and other diseases. In WO 2008/132454 9H-pyrido[3,4-b]indoles are disclosed which are ligands for the $GABA_A$ receptor and are radiolabeled, and are useful as diagnostics in CNS disorders. In C. Domonkos et al., RSC Advances 2015, 5, 53809-53818, certain 9H-pyrido[3,4-b] indoles carrying an alkoxy substituent or substituted alkoxy substituent in position 7 of the ring system are disclosed which have anticancer activity. In WO 2015/083750 certain benzothiazole derivatives and certain 9H-pyrido[3,4-b]indole derivatives carrying an alkoxy-substituent or another substituent linked via an oxygen atom in position 7 of the ring system are disclosed which activate neuropoiesis via inhibition of dual-specificity tyrosine phosphorylation-regulated kinases (DYRK). 9H-pyrido[3,4-b]indoles which carry in the 8-position of the ring system a directly bonded carbocyclic or heterocyclic aromatic group attached via a ring carbon atom, and which do not carry a directly bonded aromatic group in another position of the ring system and do not carry an alkoxy substituent or another substituent linked via an oxygen atom in position 7 of the ring system, have not yet been described, except for the compound 8-phenyl-9H-pyrido[3,4-b]indole, which has been prepared in studies about transition metal-catalyzed C—H bond functionalizations and is disclosed in N. Wu et al., Chem. Eur. J. 2014.20, 3408-3418.

Thus, a subject of the present invention are compounds of the formula I and the pharmaceutically acceptable salts thereof,

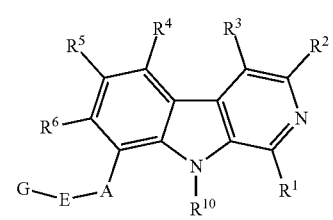

wherein

A is selected from the series consisting of phenyl and a monocyclic or bicyclic, 5-membered to 10-membered, aromatic heterocyclic group, which comprises 1 or 2 identical or different hetero ring members selected from the series consisting of N, N($R^{20}$), O and S and is bonded via a ring carbon atom, wherein phenyl and the heterocyclic group are unsubstituted or substituted on ring carbon atoms by one or more identical of different substituents $R^{21}$;

E is a direct bond or a chain consisting of 1 to 5 chain members of which 0, 1 or 2 chain members are identical or different hetero chain members selected from the series consisting of N($R^{25}$), O and S(O)$_m$, and the other chain members are identical or different groups C($R^{26}$)($R^{27}$);

G is selected from the series consisting of hydrogen, halogen, ($C_1$-$C_4$)-alkyl, cyano and $R^{30}$;

$R^1$, $R^3$, $R^4$ and $R^6$ are independently of each other selected from the series consisting of hydrogen, halogen and ($C_1$-$C_4$)-alkyl;

$R^2$ is selected from the series consisting of hydrogen, halogen, ($C_1$-$C_4$)-alkyl and ($C_1$-$C_4$)-alkyl-O—C(O)—;

$R^5$ is selected from the series consisting of hydrogen, halogen, ($C_1$-$C_4$)-alkyl, ($C_1$-$C_4$)-alkyl-O—, cyano, $R^7$—O—C(O)— and $R^8$—N(R)—C(O)—;

$R^7$, $R^8$, $R^9$, $R^{10}$, $R^{22}$, $R^{25}$, $R^{31}$, $R^{33}$, $R^{34}$ and $R^{40}$ are independently of each other selected from the series consisting of hydrogen and ($C_1$-$C_4$)-alkyl;

$R^{10}$ is selected from the series consisting of hydrogen, ($C_1$-$C_6$)-alkyl, ($C_2$-$C_6$)-alkenyl, ($C_2$-$C_6$)-alkynyl and ($C_3$-$C_7$)-cycloalkyl, wherein alkyl is unsubstituted or substituted by 1 or 2 identical or different substituents selected from the series consisting of ($C_3$-$C_7$)-cycloalkyl, Het, cyano and ($C_1$-$C_4$)-alkyl-O—, wherein all cycloalkyl groups are unsubstituted or substituted by one or more identical or different substituents selected from the series consisting of fluorine and ($C_1$-$C_4$)-alkyl;

$R^{21}$ is selected from the series consisting of halogen, ($C_1$-$C_4$)-alkyl, ($C_1$-$C_4$)-alkyl-O— and cyano, and two groups $R^{21}$ bonded to adjacent ring carbon atoms in the group A, together with the carbon atoms carrying them, can form a 5-membered to 7-membered mono-unsaturated ring, which comprises 0, 1 or 2 identical or different hetero ring members selected from the series consisting of N($R^{22}$), O and S(O), and which is unsubstituted or substituted on ring carbon atoms by one or more identical or different substituents selected from the series consisting of fluorine and ($C_1$-$C_4$)-alkyl;

$R^{26}$ and $R^{27}$ are independently of each other selected from the series consisting of hydrogen, fluorine, ($C_1$-$C_4$)-alkyl and hydroxy, and in one or two groups C($R^{26}$)($R^{27}$) the groups $R^2$ and $R^{27}$ bonded to the same carbon atom together can be oxo;

$R^{30}$ is a monocyclic or bicyclic, 3-membered to 10-membered ring, which is saturated or unsaturated and comprises 0, 1, 2 or 3 identical or different hetero ring members selected from the series consisting of N, N($R^{31}$), O and S(O)$_m$, and which is unsubstituted or substituted on ring carbon atoms by one or more identical or different substituents $R^{32}$;

$R^{32}$ is selected from the series consisting of halogen, ($C_1$-$C_4$)-alkyl, hydroxy, oxo, ($C_1$-$C_4$)-alkyl-O—, cyano, $R^{33}$—N($R^{34}$)— and Het;

Het is a monocyclic, 4-membered to 7-membered, saturated heterocyclic group, which comprises 1 or 2 identical or different hetero ring members selected from the series consisting of N, N($R^{40}$), O and S(O)$_m$, and which is unsubstituted or substituted on ring carbon atoms by one or more identical or different substituents selected from the series consisting of fluorine and ($C_1$-$C_4$)-alkyl;

m is selected from the series consisting of 0, 1 and 2, wherein all numbers m are independent of each other and can be identical or different;

wherein all alkyl groups, independently of any other substituents which can be present on an alkyl group, can be substituted by one or more fluorine substituents;

provided that the compound of the formula I is not 8-phenyl-9H-pyrido[3,4-b]indole.

If structural elements such as groups, substituents or numbers, like alkyl groups, substituents $R^{21}$ or the numbers m, for example, can occur several times in the compounds of the formula I, they are all independent of each other and can in each case have any of the indicated meanings, and they can in each case be identical to or different from any other such element. In a dialkylamino group, for example, the alkyl groups can be identical or different.

Alkyl groups, i.e. saturated hydrocarbon residues, can be linear, i.e. straight-chain, or branched. This also applies if these groups are substituted or are part of another group, for example an alkyl-O— group (alkyloxy group, alkoxy group) or an alkyloxy-substituted alkyl group. Depending on the respective definition, the number of carbon atoms in an alkyl group can be 1, 2, 3, 4, 5 or 6, or 1, 2, 3 or 4, or any subgroup of these numbers, such as 2, 3 or 4, or 1, 2 or 3, or 1 or 2, or 1. Examples of alkyl are methyl ($C_1$-alkyl), ethyl ($C_2$-alkyl), propyl ($C_3$-alkyl) including n-propyl and isopropyl, butyl ($C_4$-alkyl) including n-butyl, sec-butyl, isobutyl and tert-butyl, pentyl ($C_4$-alkyl) including n-pentyl, 1-methylbutyl, isopentyl, neopentyl and tert-pentyl, and hexyl ($C_6$-alkyl) including n-hexyl, 3,3-dimethylbutyl and isohexyl. Examples of alkyl-O— groups are methoxy, ethoxy, n-propoxy, isopropoxy, n-butoxy, isobutoxy, tert-butoxy, n-pentoxy. A substituted alkyl group can be substituted in any positions, provided that the respective compound is sufficiently stable and is suitable as a pharmaceutical active compound. The prerequisite that a specific group and a compound of the formula I are suitable as a pharmaceutical active compound, applies in general with respect to the definitions of all groups in the compounds of the formula I.

Independently of any other substituents which can be present on an alkyl group, and unless specified otherwise, alkyl groups can be substituted by one or more fluorine substituents, for example by 1, 2, 3, 4, 5, 6, 7, 8, 9, 10, 11, 12 or 13 fluorine substituents, or by 1, 2, 3, 4 or 5 fluorine substituents, or by 1, 2 or 3 fluorine substituents, or by any other number of fluorine substituents, which can be located in any positions of the alkyl group. I.e., independently of any other substituents which can be present on an alkyl group, an alkyl group can be unsubstituted by fluorine substituents, i.e. not carry fluorine substituents, or substituted by fluorine substituents, wherein all alkyl groups in the compounds of the formula I are independent of one another with regard to the optional substitution by fluorine substituents. For example, in a fluoro-substituted alkyl group one or more methyl groups can carry three fluorine substituents each and be present as trifluoromethyl groups, and/or one or more methylene groups (—$CH_2$—) can carry two fluorine substituents each and be present as difluoromethylene groups. The explanations with respect to the substitution of a group by fluorine also apply if the group additionally carries other substituents and/or is part of another group, for example of an alkyl-O— group. Examples of fluoro-substituted alkyl groups are trifluoromethyl ($CF_3$), fluoromethyl, difluoromethyl, 2-fluoroethyl, 1-fluoroethyl, 1,1-difluoroethyl, 2,2,2- trifluoroethyo, pentafluoroethyl, 3,3,3-trifluoropropyl, 2,2,3,3,3-pentafluoropropyl, 4,4,4-trifluorobutyl and heptafluoroisopropyl. Examples of fluoro-substituted alkyl-O— groups are trifluoromethoxy ($CF_3$—O—), 2,2,2-trifluoroethoxy, pentafluoroethoxy and 3,3,3-trifluoropropoxy. With respect to all groups or substituents in the compounds of the formula I which can be an alkyl group that can generally contain one or more fluorine substituents, the group $CF_3$, or a respective group such as $CF_3$—O—, and other specific fluorine-substituted groups, may be included in the definition of the group or substituent as example of groups or substituents containing fluorine-substituted alkyl.

The above explanations with respect to alkyl groups apply correspondingly to alkyl groups which in the definition of a group in the compounds of the formula I are bonded to two adjacent groups, or linked to two groups, and may be regarded as divalent alkyl groups (alkanediyl groups, alkylene groups), like in the case of the alkyl part of a substituted alkyl group or in the case of the chain E, if E does not contain a heteroatom chain member. Thus, such groups can also be linear or branched, the bonds to the adjacent groups can be located in any positions and can start from the same carbon atom or from different carbon atoms, and they can be unsubstituted or substituted by fluorine substituents independently of any other substituents. Examples of such divalent alkyl groups are —$CH_2$—, —$CH_2CH$—, —$CH_2$—$CH_2$—$CH_2$—, —$CH_2$—$CH_2$—$CH_2CH_2$—, —$CH(CH_3)$—, —$C(CH_3)_2$—, —$CH(CH)$—$CH_2$, —$CH_2$—$CH(CH_3)$—, —$C(CH_3)_2$—$CH_2$—, —$CH_2$—$C(CH_3)_2$—. Examples of fluoro-substituted divalent alkyl groups, which can contain 1, 2, 3, 4, 5 or 6 fluorine substituents, for example, are —CHF—, —$CF_2$—, —$CF_2$—$CH_2$—, —$CH_2$—$CF_2$—, —$CF_2$—$CF_2$—, —$CF(CH_3)$—, —$C(CF_3)_2$—, —$C(CH_3)_2$—$CF_2$—, —$CF_2$—$C(CH_3)$—.

The above explanations with respect to alkyl groups apply correspondingly to unsaturated hydrocarbon residues, i.e. alkenyl groups, which in one embodiment of the invention contain one double bond, and alkynyl groups, which in one embodiment of the invention contain one triple bond. Thus, for example, alkenyl groups and alkynyl groups can likewise be linear or branched. Double bonds and triple bonds can be present in any positions. The number of carbon atoms in an alkenyl group and an alkynyl group can be 2, 3, 4, 5 or 6, or any subgroup of these numbers, such as 2, 3, 4 or 5, or 3, 4 or 5, or 2, 3 or 4, for example. Examples of alkenyl groups are ethenyl (vinyl), prop-1-enyl, prop-2-enyl (allyl), but-1-enyl, but-2-enyl, but-3-enyl, 2-methylprop-2-enyl, 3-methylbut-2-enyl, hex-3-enyl, hex-4-enyl, 4-methylpent-3-enyl. Examples of alkynyl groups are ethynyl, prop-1-ynyl, prop-2-ynyl (propargyl), but-2-ynyl, but-3-ynyl, pent-2-ynyl, 4-methylpent-2-ynyl, hex-2-ynyl, hex-3-ynyl. In one embodiment of the invention, alkenyl groups and alkynyl groups contain at least three carbon atoms and are bonded to the remainder of the molecule via a carbon atom which is not part of a double bond or triple bond.

The number of ring carbon atoms in a ($C_3$-$C_7$)cycloalkyl group can be 3, 4, 5, 6 or 7, or any subgroup of these numbers, such as 3, 4, 5 or 6, or 5, 6 or 7, or 3, 4 or 5, or 3 or 4, for example. Examples of cycloalkyl are cyclopropyl, cyclobutyl, cyclopentyl, cyclohexyl and cycloheptyl.

Cycloalkyl groups can be substituted by one or more ($C_1$-$C_4$)-alkyl substituents, for example by 1, 2, 3 or 4, or 1, 3 or 3, or 1 or 2, identical or different ($C_1$-$C_4$)-alkyl substituents, for example by methyl groups, which can be located in any positions. I.e., cycloalkyl groups can be unsubstituted by ($C_1$-$C_4$)-alkyl substituents, i.e. not carry ($C_1$-$C_4$)-alkyl substituents, or substituted by ($C_1$-$C_4$)-alkyl substituents. Examples of such alkyl-substituted cycloalkyl groups are 1-methylcyclopropyl, 2,2-dimethylcyclopropyl, 1-methylcyclopentyl, 2,3-dimethylcyclopentyl, 1-methylcyclohexyl, 4-methylcyclohexyl, 4-isopropylcyclohexyl, 4-tert-butylcyclohexyl, 3,3,5,5-tetramethylcyclohexyl.

Independently of ($C_1$-$C_4$)-alkyl substituents, cycloalkyl groups can be substituted by one or more fluorine substituents, for example by 1, 2, 3, 4, 5, 6, 7, 8, 9, 10, 11, 12 or 13 fluorine substituents, or 1, 2, 3, 4 or 5 fluorine substituents, or 1, 2 or 3 fluorine substituents, or 1 or 2 fluorine substituents, which can be located in any positions and can also be present in a ($C_1$-$C_4$)-alkyl substituent. I.e., cycloalkyl groups can be unsubstituted by fluorine substituents, i.e, not carry fluorine substituents, or substituted by fluorine substituents. Examples of fluoro-substituted cycloalkyl groups are 1-fluorocyclopropyl, 2,2-difluorocyclopropyl, 3,3-difluorocyclobutyl, 1-fluorocyclohexyl, 4,4-difluorocyclohexyl, 3,3,4,4,5,5-hexafluorocyclohexyl. Cycloalkyl groups can also be substituted simultaneously by fluorine and alkyl substituents.

Examples of ($C_1$-$C_7$)cycloalkyl-substituted alkyl groups, from any one or more of which a ($C_3$-$C_7$)-cycloalkyl-substituted alkyl group representing $R^{10}$ is selected in one embodiment of the invention, are cyclopropylmethyl-, cyclobutylmethyl-, cyclopentylmethyl-, cyclohexylmethyl-, cycloheptylmethyl-, 1-cyclopropylethyl-, 2-cyclopropylethyl-, 1-cyclobutylethyl-, 2-cyclobutylethyl-, 1-cyclopentylethyl-, 2-cyclopentylethyl-, 1-cyclohexylethyl-, 2-cyclohexylethyl-, 1-cycloheptylethyl-, 2-cycloheptylethyl-, 3-cyclopropylpropyl-, 3-cyclobutylpropyl-, 3-cyclopentylpropyl-, 3-cyclohexylpropyl-, 3-cycloheptylpropyl-. In one embodiment of the invention, a ($C_3$-$C_7$)-cycloalkyl-substituted ($C_1$-$C_6$)-alkyl group is a ($C_3$-$C_7$)-cycloalkyl-($C_1$-$C_4$)-alkyl-group, in another embodiment a ($C_3$-$C_7$)-cycloalkyl-($C_1$-$C_2$)-alkyl- group, in another embodiment a ($C_3$-$C_7$)-cycloalkyl-$CH_2$— group. In the group cyclopropylmethyl-, and likewise in all other groups containing one or two terminal hyphens like the group alkyl-O—, for example, the terminal hyphens denote the free bonds via which the group is bonded to the adjacent moieties in the molecule, and thus indicates via which atoms or subgroups a group composed of several atoms or subgroups is bonded.

In substituted phenyl groups, which can represent the group A and the group $R^{30}$ the substituents can be located in any positions. In monosubstituted phenyl groups, the substituent can be located in position 2, in position 3 or in position 4. In disubstituted phenyl groups, the substituents can be located in positions 2 and 3, in positions 2 and 4, in positions 2 and 5, in positions 2 and 6, in positions 3 and 4, or in positions 3 and 5. In trisubstituted phenyl groups, the substituents can be located in positions 2, 3 and 4, in positions 2, 3 and 5, in positions 2, 3 and 6, in positions 2, 4 and 5, in positions 2, 4 and 6, or in positions 3, 4 and 5. If a phenyl group carries four substituents, some of which can be fluorine atoms, for example, the substituents can be located in positions 2, 3, 4 and 5, in positions 2, 3, 4 and 6, or in positions 2, 3, 5 and 6. If a polysubstituted phenyl group, and in general any other polysubstituted group, carries different substituents, each substituent can be located in any suitable position, and the present invention comprises all positional isomers. The number of substituents in a substituted phenyl group can be 1, 2, 3,4 or 5. In one embodiment of the invention, the number of substituents in a substituted phenyl group, and likewise the number of substituents in any other substituted group which can carry one or more substituents, such as a heterocyclic group representing the group A, the group $R^{30}$ or the group Het, is 1, 2, 3 or 4, in another embodiment 1, 2 or 3, in another embodiment 1 or 2, in another embodiment 1, wherein the number of substituents in any occurrence of such a substituted group is independent of the number of substituents in other occurrences.

In heterocyclic groups which can be present in the compounds of the formula I, including the group Het, aromatic heterocyclic groups representing the group A, heterocyclic groups representing the group $R^{30}$ and heterocyclic rings formed by two groups $R^{21}$ together with the carbon atoms carrying them, the hetero ring members can be present in any combination and located in any suitable ring positions, provided that the resulting group and the compound of the formula I are suitable and sufficiently stable as a pharmaceutical active compound. In one embodiment of the invention, two oxygen atoms in any heterocyclic ring in the compounds of the formula I cannot be present in adjacent ring positions. In another embodiment of the invention, two hetero ring members selected from the series consisting of oxygen atoms and sulfur atoms or $S(O)_m$ groups cannot be present in adjacent ring positions in any heterocyclic ring in the compounds of the formula I. In another embodiment of the invention, two hetero ring members selected from the series consisting of oxygen atoms, sulfur atoms or S(O), groups, and nitrogen atoms carrying an exocyclic group like a hydrogen atom or a substituent such as an alkyl group, cannot be present in adjacent ring positions in any heterocyclic ring in the compounds of the formula I. The choice of hetero ring members in an aromatic heterocyclic ring is limited by the prerequisite that the ring is aromatic, i.e. it comprises a cyclic system of six delocalized pi electrons in case of an aromatic monocycle or 10 delocalized pi electrons in case of an aromatic bicycle. Monocyclic aromatic heterocycles are 5-membered or 6-membered rings and, in the case of a 5-membered ring, comprise one ring heteroatom selected from the series consisting of oxygen, sulfur and nitrogen, wherein this ring nitrogen carries an exocyclic group like a hydrogen atom or a substituent like an alkyl group, and optionally one or more further ring nitrogen atoms which do not carry an exocyclic group, and, in the case of a 6-membered ring, comprise one or more nitrogen atoms as ring heteroatoms, but no oxygen atoms and sulfur atoms as ring heteroatoms. Heterocyclic groups in the compounds of the formula I can be bonded via any suitable ring carbon atom and ring nitrogen atom, unless specified otherwise. In substituted heterocyclic groups, the substituents can be located in any positions.

The number of ring heteroatoms which can be present in a heterocyclic group in the compounds of the formula I, the number of ring members which can be present, and the degree of saturation, or hydrogenation, i.e. whether the heterocyclic group is saturated and does not contain a double bond within the ring, or whether it is partially unsaturated but is not aromatic, or whether it is aromatic and thus contains two double bonds within the ring in the case of a 5-membered monocyclic aromatic heterocycle, three double bonds within the ring in the case of a 6-membered monocyclic aromatic heterocycle, and four or five double bonds for in the case of bicyclic aromatic heterocycle comprising a 6-membered ring and a 5-membered ring or two 6-membered rings, for example, is specified in the definitions of the individual groups in the compounds of the formula I. Examples of heterocyclic ring systems, from which heterocyclic groups in the compounds of the formula I including, for example, the group Het, aromatic heterocyclic groups representing the group A, heterocyclic groups representing the group $R^{30}$ and heterocyclic rings formed by two groups $R^{21}$ together with the carbon atoms carrying them, can be derived, and from any one or more of which any of the heterocyclic groups in the compounds of the formula I is selected in one embodiment of the invention, provided that the ring system is comprised by the definition of the respective group, are oxetane, thietane, azetidine, furan, tetrahydrofuran, thiophene, tetrahydrothiophene, pyrrole, pyrroline, pyrrolidine, [1,3]dioxole, [1,3]dioxolane, isoxazole ([1,2]oxazole), isoxazoline, isoxazolidine, oxazole ([1,3]oxazole), oxazoline, oxazolidine, isothiazole ([1,2]thiazole), isothiazoline, isothiazolidine, thiazole ([1,3]thiazole), thiazoline, thiazolidine, pyrazole, pyrazoline, pyrazolidine, imidazole, imidazoline, imidazolidine, [1,2,3]triazole, [1,2,4]triazole, [1,2,4]oxadiazole, [1,3,4]oxadiazole, [1,2,5]oxadiazole, [1,2,4]thiadiazole, pyran, tetrahydropyran, thiopyran, tetrahydrothiopyran, 2,3-dihydro[1,4]dioxine, [1,4]dioxane, pyridine, 1,2,5,6-tetrahydropyridine, piperidine, morpholine, thiomorpholine, piperazine, pyridazine, pyrimidine, pyrazine, [1,2,4]triazine, oxepane, thiepane, azepane, [1,3]diazepane, [1,4]diazepane, [1,4]oxazepane, [1,4]thiazepane, benzofuran, isobenzofuran, benzothiophene (benzo[b]thiophene), 1H-indole, 2,3-dihydro-1H-indole, 2H-isoindole, benzo[1,3]dioxole, benzoxazole, benzthiazole, 1H-benzimidazole, chromane, isochromane, thiochromane, benzo[1,4]dioxane, 3,4-dihydro-2H-benzo(b)[1,4]dioxepine (3,4-dihydro-2H-[1,5]benzodioxepine), 3,4-dihydro-2H-benzo[1,4]oxazine, 3,4-dihydro-2H-benzo[1,4]thiazine, quinoline, 5,6,7,8-tetrahydroquinoline, isoquinoline, 5,6,7,8-tetrahydroisoquinoline, cinnoline, quinazoline, quinoxaline, phthalazine and [1,8]naphthyridine, which can all be unsubstituted or substituted in any suitable positions as specified in the definition of the respective group in the compounds of the formula I, wherein the given degree of unsaturation is by way of example only and in the individual groups also ring systems with a higher or lower degree of saturation or unsaturation can be present in line with the definition of the group. Ring sulfur atoms, in particular in saturated and partially unsaturated heterocycles, can generally carry one or two oxo groups, i.e, doubly bonded oxygen atoms ((O), =O), and in such heterocycles a group $S(O)_m$ be present as hetero ring member, in which the number m can be 0 (zero) and thus a sulfur atom (—S—) be present in the ring, or m can be 1 and thus the group —S(O)— (—S(=O)—) be present in the ring, or m can be 2 and thus the group —S(O)$_2$— (—S(=O)$_2$—) be present in the ring.

As mentioned, unless specified otherwise, heterocyclic groups can be bonded via any suitable ring carbon atom and ring nitrogen atom, for example in the case of heterocyclic groups representing $R^{30}$. In one embodiment of the invention, any of the heterocyclic groups occurring in the compounds of the formula I in any of its occurrences is, independently of its other occurrences and independently of any other heterocyclic group, bonded via a ring carbon atom, and in another embodiment via a ring nitrogen atom, if applicable. Thus, for example, among others can an oxetane and a thietane ring be bonded via positions 2 and 3, an azetidine ring via positions 1, 2 and 3, a furan ring, a tetrahydrofuran ring, a thiophene ring and a tetrahydrothiophene ring via positions 2 and 3, a pyrrole ring and a pyrrolidine ring via positions 1, 2 and 3, an isoxazole ring and an isothiazole ring via positions 3,4 and 5, a pyrazole ring via positions 1, 3,4 and 5, an oxazole ring and a thiazole ring via positions 2, 4 and 5, an imidazole ring and an imidazolidine ring via positions 1, 2, 4 and 5, a [1,2,3]triazole ring via positions 1, 4 and 5, a [1,2,4]triazole ring via positions 1, 3 and 5, a tetrahydropyran ring and a tetrahydrothiopyran ring via positions 2, 3 and 4, a [1,4]

dioxane ring via position 2, a pyridine ring via positions 2, 3 and 4, a piperidine ring via positions 1, 2, 3 and 4, a morpholine ring and a thiomorpholine ring via positions 2, 3 and 4, a piperazine ring via positions 1 and 2, a pyrimidine ring via positions 2, 4 and 5, a pyrazine ring via position 2, an azepane ring via positions 1, 2, 3 and 4, a benzofuran ring and a benzothiophene ring via positions 2, 3, 4, 5, 6 and 7, a 1H-indole ring and a 2,3-dihydro-1H-indole ring via positions 1, 2, 3, 4, 5, 6 and 7, a benzo[1,3]dioxole ring via positions 4, 5, 6 and 7, a benzoxazole ring and a benzthiazole ring via positions 2, 4, 5, 6 and 7, a 1H-benzimidazole ring via positions 1, 2, 4, 5, 6 and 7, a benzo[1,4]dioxane ring via positions 5, 6, 7 and 8, a quinoline ring via positions 2, 3, 4, 5, 6, 7 and 8, a 5,6,7,8-tetrahydroquinoline ring via positions 2, 3 and 4, an isoquinoline ring via positions 1, 3, 4, 5, 6, 7 and 8, a 5,6,7,8-tetrahydroisoquinoline ring via positions 1, 3 and 4, for example, wherein the resulting residues of the heterocyclic groups can all be unsubstituted or substituted in any suitable positions as specified in the definition of the respective group in the compounds of the formula I.

Halogen is fluorine, chlorine, bromine or iodine. In one embodiment of the invention, halogen is in any of its occurrences, independently of any other occurrence, fluorine, chlorine or bromine, in another embodiment fluorine or chlorine, in another embodiment fluorine, in another embodiment chlorine or bromine, in another embodiment chlorine, wherein all occurrences of halogen are independent of each other.

The present invention comprises all stereoisomeric forms of the compounds of the formula I, for example all enantiomers and diastereomers including cis/trans isomers. The invention likewise comprises mixtures of two or more stereoisomeric forms, for example mixtures of enantiomers and/or diastereomers including cis/trans isomers, in all ratios. A subject of the present invention thus is a compound of the formula I, in any of its stereoisomeric forms or a mixture of stereoisomeric forms in any ratio, or a pharmaceutically acceptable salt thereof. Asymmetric centers contained in the compounds of the formula I can all independently of each other have S configuration or R configuration. The invention relates to enantiomers, both the levorotatory and the dextrorotatory antipode, in enantiomerically pure form and essentially enantiomerically pure form, and in the form of their racemate, i.e. a mixture of the two enantiomers in molar ratio of 1:1, and in the form of mixtures of the two enantiomers in all ratios. The invention likewise relates to diastereomers in the form of pure and essentially pure diastereomers and in the form of mixtures of two or more diastereomers in all ratios. The invention also comprises all cis/trans isomers of the compounds of the formula I in pure form and essentially pure form, and in the form of mixtures of the cis isomer and the trans isomer in all ratios. Cis/trans isomerism can occur in alkenyl groups and substituted rings. The preparation of individual stereoisomers, if desired, can be carried out by resolution of a mixture according to customary methods, for example, by chromatography or crystallization, or by use of stereochemically uniform starting compounds in the synthesis, or by stereoselective reactions. Optionally, before a separation of stereoisomers a derivatization can be carried out. The separation of a mixture of stereoisomers can be carried out at the stage of the compound of the formula I or at the stage of an intermediate in the course of the synthesis. For example, in the case of a compound of the formula I containing an asymmetric center the individual enantiomers can be prepared by preparing the racemate of the compound of the formula I and resolving it into the enantiomers by high pressure liquid chromatography on a chiral phase according to standard procedures, or resolving the racemate of any intermediate in the course of its synthesis by such chromatography or by crystallization of a salt thereof with an optically active amine or acid and converting the enantiomers of the intermediate into the enantiomeric forms of the final compound of the formula I, or by performing an enantioselective reaction in the course of the synthesis. The invention also comprises all tautomeric forms of the compounds of the formula I, as well as all forms containing a specific isotopic pattern, for example deuterated compounds in which one or more hydrogen atoms are present in form of the deuterium isotop.

Besides the free compounds of the formula I, i.e. the compounds of the formula I themselves in which any acidic and basic groups are not present in the form of a salt and which may also be termed "salt-free" compounds, the present invention comprises also salts of the compounds of the formula I, in particular their physiologically acceptable salts, or toxicologically acceptable salts, or pharmaceutically acceptable salts, which can be formed on one or more acidic groups, for example on carboxylic acid groups, or basic groups, for example amino group or basic heterocyclic moieties, in the compounds of the formula I. The compounds of the formula I may thus be deprotonated on an acidic group by an inorganic or organic base and used, for example, in the form of the alkali metal salts. Compounds of the formula I comprising at least one basic group may be prepared and used in the form of their acid addition salts, for example in the form of pharmaceutically acceptable salts with inorganic acids and organic acids, such as salts with hydrochloric acid and thus be present in the form of the hydrochlorides, for example. Salts can in general be prepared from acidic and basic compounds of the formula I by reaction with an acid or base in a solvent or diluent according to customary procedures. If the compounds of the formula I simultaneously contain an acidic and a basic group in the molecule, the invention also includes internal salts (betaines, zwitterions) in addition to the salt forms mentioned. The present invention also comprises all salts of the compounds of the formula I which, because of low physiological tolerability, are not directly suitable for use as a pharmaceutical, but are suitable as intermediates for chemical reactions or for the preparation of physiologically acceptable salts, for example by means of anion exchange or cation exchange.

In one embodiment of the invention an aromatic heterocyclic group representing the divalent group A is a monocyclic 5-membered or 6-membered group or a bicyclic 8-membered to 10-membered group, in another embodiment a monocyclic 5-membered or 6-membered group or a bicyclic 9-membered or 10-membered group. In one embodiment an aromatic heterocyclic group representing the group A is a monocyclic 5-membered or 6-membered group, in another embodiment it is a monocyclic 5-membered group, in another embodiment it is a monocyclic 6-membered group, in another embodiment it is a bicyclic 9-membered or 10-membered group, in another embodiment it is a bicyclic 9-membered group, and in another embodiment it is a bicyclic 10-membered group. In one embodiment the number of hetero ring members in a heterocycle representing A is 1, in another embodiment it is 2. In one embodiment the hetero ring members in a heterocycle representing A are selected from the series consisting of N, N($R^{20}$) and S, in another embodiment from the series consisting of N, N($R^{20}$) and O, in another embodiment from the series consisting of N and N($R^{20}$), in another embodiment from the series consisting of N and S, in another embodiment from the series consisting of N and O, in another embodiment they are N, and in another embodiment they are S. In the case of the group A, the hetero ring member N denotes a ring nitrogen atom which is bonded to the adjacent ring atoms in A via a single bond and a double bond and via which the ring A cannot be bonded to an another moiety in the molecule, as well as a ring nitrogen atom which is bonded to the adjacent ring atoms in A via two single bonds and which has a free valence via which the ring A can be bonded to the moiety G-E-. Examples of heterocycles, from which an aromatic heterocyclic group representing A can be derived and from any one or more of which an aromatic heterocyclic group representing A is selected in one embodiment of the invention, are furan, thiophene, pyrrole, isoxazole, oxazole, isothiazole, thiazole, pyrazole, imidazole, pyridine, pyridazine, pyrimidine, pyrazine, benzofuran, benzothiophene, 1H-indole, benzoxazole, benzthiazole, 1H-benzimidazole, 1H-indazole, 1H-pyrrolo[2,3-b]pyridine, pyrazolo[1,5-a]pyridine, quinoline, isoquinoline, cinnoline, quinazoline, quinoxaline, which can all be unsubstituted or substituted on ring carbon atoms by one or more identical or different substituents $R^{21}$. In another embodiment, an aromatic heterocyclic group representing A is derived from an aromatic heterocyclic group selected from the series consisting of thiophene, thiazole, pyrazole, imidazole, pyridine and pyrimidine, in another embodiment from the series consisting of thiophene, thiazole, pyrazole and pyridine, in another embodiment from the series consisting of thiophene, thiazole and pyridine, in another embodiment from the series consisting of thiophene, thiazole and pyrazole, in another embodiment from the series consisting of thiophene and pyridine, in another embodiment from the series consisting of thiazole and pyridine, in another embodiment from the series consisting of pyrazole and pyridine, in another from the series consisting of thiazole and pyrazole, in another embodiment an aromatic heterocyclic group representing A is derived from thiophene, in another embodiment from thiazole, in another embodiment from pyrazole, in another embodiment from pyridine, in another embodiment from pyrimidine, which can all be unsubstituted or substituted on ring carbon atoms by one or more identical or different substituents $R^{21}$. In one embodiment A is an aromatic heterocyclic group, which is unsubstituted or substituted on ring carbon atoms by one or more identical of different substituents $R^{21}$, in another embodiment A is phenyl, which is unsubstituted or substituted by one or more identical of different substituents $R^{21}$. Also a group A that is unsubstituted, i.e. that does not carry any substituents $R^{21}$, of course carries the group G-E- depicted in formula i, in which G and E can have all their meanings. As specified in the general definition of the group A, the divalent group A is bonded to the 9H-pyrido[3,4-b] indole ring depicted in formula I via a ring carbon atom. The group E, and the group G in case the group E is a direct bond, can be bonded to a ring carbon atom in the group A or to a ring nitrogen atom, i.e. to a hetero ring member N, in the group A.

If the divalent group E is a direct bond, the group G is linked to the group A via a single bond. If the group E is a chain, it consists of 1, 2, 3, 4 or 5 chain members which are defined as specified in the definition of E, to the terminal chain members of which, or to the sole chain member of which in case the chain consists of 1 chain member only, the groups G and A are bonded. In one embodiment of the invention the divalent group E is a direct bond. In another embodiment, the divalent group E is a chain consisting of 1, 2, 3, 4 or 5 chain members which are defined as specified in the definition of E. In one embodiment, the number of chain members in a chain E is 1, 2, 3 or 4, in another embodiment 2, 3, 4 or 5, in another embodiment 1, 2 or 3, in another embodiment 2, 3 or 4, in another embodiment 2 or 3, in another embodiment 1, in another embodiment 2, in another embodiment 3, in another embodiment 4. In one embodiment, 0 (zero) or 1 chain members in a chain E are identical or different hetero chain members selected from the series consisting of $N(R^{25})$, O and $S(O)_m$, in another embodiment 1 or 2 chain members are such hetero chain members, in another embodiment 0 chain member is such a hetero chain member, in another embodiment 1 chain member is such a hetero chain member, and in another embodiment 2 chain members are such heterochain members. If 2 hetero chain members are present in a chain E, in one embodiment they are not present in adjacent positions of the chain, i.e., in this embodiment they are separated by at least 1 chain member $C(R^{26})(R^{27})$, in another embodiment they are not present in adjacent positions of the chain unless one of them is the group $S(O)_m$ in which m is 1 or 2, and in another embodiment they are separated by 2 or 3, in another embodiment by 2, in another embodiment by 3, chain members $C(R^{26})(R^{27})$. In one embodiment, hetero chain members in a chain E are selected from the series consisting of $N(R^{25})$ and O, in another embodiment from the series consisting of O and $S(O)_m$, in another embodiment they are identical or different groups $N(R^{25})$, in another embodiment they are O, i.e. oxygen atoms, and in another embodiment they are identical or different groups $S(O)_m$. In one embodiment the number m in the hetero chain member $S(O)_m$ in a chain E is selected from the series consisting of 0 and 1, in another embodiment from the series consisting of 1 and 2, in another embodiment from the series consisting of 0 and 2, in another embodiment it is 0, in another embodiment it is 1, and in another embodiment it is 2. If the terminal chain member in a chain E that is bonded to the group A, or the sole chain member in case the chain consists of 1 chain member only, is bonded to a ring nitrogen atom in A, in one embodiment such terminal chain member or sole chain member is not a hetero chain member, and in another embodiment such terminal chain member or sole chain member is not a hetero chain number selected from the series consisting of $N(R^{25})$, O and $S(O)_m$ in which the number m is 0. If the terminal chain member in a chain E that is bonded to the group G, or the sole chain member in case the chain consists of 1 chain member only, is bonded to a ring nitrogen atom in a ring $R^{30}$ representing G ot to halogen atom or a cyano group representing G, in one embodiment such terminal chain member is not a hetero chain member, and in another embodiment such terminal chain member is not a hetero chain number selected from the series consisting of $N(R^{25})$, O and $S(O)_m$ in which the number m is 0.

In one embodiment of the invention the divalent group E is chosen from a direct bond and from any one or more of the chains which are present in the following examples of groups G-E-, which groups are bonded to the group A depicted in formula I by the free bond represented by the terminal hyphen, and from which groups the divalent chains E themselves are obtained by removing the group G, wherein in these groups the groups $R^{25}$, $R^{26}$ and $R^{27}$ and the number m are defined as specified above or below:

G-C($R^{26}$)($R^{27}$)—,
G-C($R^{26}$)($R^{27}$)—C($R^{26}$)($R^{27}$)—,
G-C($R^{26}$)($R^{27}$)—C($R^{26}$)($R^{27}$)—C($R^{26}$)($R^{27}$)—,
G-C($R^{26}$)($R^{27}$)—C($R^{26}$)($R^{27}$)—C($R^{26}$)($R^{27}$)—C($R^{26}$)($R^{27}$)—,
G-O—,
G-C($R^{26}$)($R^{27}$)—O—,
G-C($R^{26}$)($R^{27}$)—C($R^{26}$)($R^{27}$)—O—,

G-C(R$^{26}$)(R$^{27}$)—C(R$^{26}$)(R$^{27}$)—C(R$^{26}$)(R$^{27}$)—O—,
G-O—C(R$^{26}$)(R$^{27}$)—,
G-O—C(R$^{26}$)(R$^{27}$)—C(R$^{26}$)(R$^{27}$)—,
G-O—C(R$^{26}$)(R$^{27}$)—C(R$^{26}$)(R$^{27}$)—C(R$^{26}$)(R$^{27}$)—,
G-C(R$^{26}$)(R$^{27}$)—O—C(R$^{26}$)(R$^{27}$)—,
G-C(R$^{26}$)(R$^{27}$)—O—C(R$^{26}$)(R$^{27}$)—C(R$^{26}$)(R$^{27}$)—,
G-C(R$^{26}$)(R$^{27}$)—O—C(R$^{26}$)(R$^{27}$)—,
G-C(R$^{26}$)(R$^{27}$)—C(R$^{26}$)(R$^{27}$)—O—C(R$^{26}$)(R$^{27}$)—,
G-O—C(R$^{26}$)(R$^{27}$)—C(R$^{26}$)(R$^{27}$)—O—,
G-O—C(R$^{26}$)(R$^{27}$)—C(R$^{26}$)(R$^{27}$)—C(R$^{26}$)(R$^{27}$)—O—,
G-S(O)$_m$—,
G-C(R$^{26}$)(R$^{27}$)—S(O)$_m$—,
G-C(R$^{26}$)(R$^{27}$)—C(R$^{26}$)(R$^{27}$)—S(O)$_m$—,
G-S(O)$_m$—C(R$^{26}$)(R$^{27}$)—,
G-S(O)$_m$—C(R$^{26}$)(R$^{27}$)—C(R$^{26}$)(R$^{27}$)—,
G-N(R$^{25}$)—,
G-C(R$^{26}$)(R$^{27}$)—N(R$^{25}$)—,
G-C(R$^{28}$)(R$^{27}$)—C(R$^{26}$)(R$^{27}$)—N(R$^{25}$)—,
G-N(R$^{25}$)—C(R$^{26}$)(R$^{27}$)—,
G-N(R$^{25}$)—C(R$^{26}$)(R$^{27}$)—C(R$^{26}$)(R$^{27}$)—,
G-N(R$^{25}$)—C(R$^{26}$)(R$^{27}$)—C(R$^{26}$)(R$^{27}$)—C(R$^{26}$)(R$^{27}$)—,
G-N(R$^{25}$)—C(R$^{26}$)(R$^{27}$)—N(R$^{25}$)—,
G-N(R$^{25}$)—C(R$^{26}$)(R$^{27}$)—C(R$^{26}$)(R$^{27}$)—N(R$^{25}$)—,
G-N(R$^{25}$)—C(R$^{26}$)(R$^{27}$)—C(R$^{26}$)(R$^{27}$)—N(R$^{25}$)—C(R$^{26}$)(R$^{27}$)—,
G-N(R$^{25}$)—C(R$^{26}$)(R$^{27}$)—C(R$^{26}$)(R$^{27}$)—O—,
G-N(R$^{25}$)—C(R$^{26}$)(R$^{27}$)—C(R$^{26}$)(R$^{27}$)—C(R$^{26}$)(R$^{27}$)O—,
G-O—C(R$^{26}$)(R$^{27}$)—C(R$^{26}$)(R$^{27}$)—N(R$^{25}$)—,
G-O—C(R$^{26}$)(R$^{27}$)—C(R$^{26}$)(R$^{27}$)—N(R$^{25}$)—C(R$^{26}$)(R$^{27}$)—,
G-S(O)$_2$—N(R$^{25}$)—.

In one embodiment of the invention the group G is selected from the series consisting of hydrogen, halogen, (C$_1$-C$_4$)-alkyl and R$^{30}$, in another embodiment from the series consisting of hydrogen, (C$_1$-C$_4$)-alkyl and R$^{30}$, in another embodiment from the series consisting of hydrogen, halogen and R$^{30}$, in another embodiment from the series consisting of hydrogen and R$^{30}$, in another embodiment from the series consisting of hydrogen, halogen and (C$_1$-C$_4$)-alkyl, in another embodiment from the series consisting of of hydrogen, halogen, (C$_1$-C$_4$)-alkyl and cyano, in another embodiment G is hydrogen, and in another embodiment G is R$^{30}$.

In one embodiment of the invention any one or more of the groups R$^1$, R$^3$, R$^4$ and R$^6$ are independently of each other selected from the series consisting of hydrogen, halogen and (C$_1$-C$_2$)-alkyl, in another embodiment from the series consisting of hydrogen, halogen and C$_1$-alkyl, in another embodiment from the series consisting of hydrogen and halogen, in another embodiment from the series consisting of hydrogen and (C$_1$-C$_4$)-alkyl, in another embodiment from the series consisting of hydrogen and (C$_1$-C$_2$)-alkyl, in another embodiment from the series consisting of hydrogen and C-alkyl, and in another embodiment they are independently of each other hydrogen, in another embodiment halogen, in another embodiment (C$_1$-C$_4$)-alkyl, in another embodiment (C$_1$-C$_2$)-alkyl and in another embodiment C-alkyl.

In one embodiment of the invention the group R$^2$ is selected from the series consisting of hydrogen, halogen, (C$_1$-C$_2$)-alkyl and (C$_1$-C$_2$)-alkyl-O—C(O)—, in another embodiment from the series consisting of hydrogen, halogen, C$_1$-alkyl and (C$_1$-C$_2$)-alkyl-O—C(O)—, in another embodiment from the series consisting of hydrogen, halogen and (C$_1$-C$_4$)-alkyl, in another embodiment from the series consisting of hydrogen, halogen and (C$_1$-C$_2$)-alkyl, in another embodiment from the series consisting of hydrogen, halogen and C$_1$-alkyl, in another embodiment from the series consisting of hydrogen and halogen, in another embodiment from the series consisting of hydrogen and (C$_1$-C$_4$)-alkyl, in another embodiment from the series consisting of hydrogen and (C$_1$-C$_2$)-alkyl, in another embodiment from the series consisting of hydrogen and C$_1$-alkyl, and in another embodiment R$^2$ is hydrogen.

In one embodiment of the invention the group R$^5$ is selected from the series consisting of hydrogen, halogen, (C$_1$-C$_4$)-alkyl, (C$_1$-C$_4$)-alkyl-O— and cyano, in another embodiment from the series consisting of hydrogen, halogen, (C$_1$-C$_4$)-alkyl, cyano, R$^7$—O—C(O)— and R$^1$—N(R$^9$)—C(O)—, in another embodiment from the series consisting of hydrogen, halogen, (C$_1$-C$_4$)-alkyl and cyano, in another embodiment from the series consisting of hydrogen, halogen and (C$_1$-C$_4$)-alkyl, in another embodiment from the series consisting hydrogen and halogen, in another embodiment from the series consisting of halogen and (C$_1$-C$_4$)-alkyl, and in another embodiment R$^5$ is halogen. In one embodiment halogen representing R$^5$ is selected from the series consisting of chlorine and bromine, in another embodiment it is chlorine, and in another embodiment it is bromine. In one embodiment a (C$_1$-C$_4$)-alkyl group representing R$^5$ or present in R$^5$ is independently of any other such alkyl group a (C$_1$-C$_2$)-alkyl group, in another embodiment a C$_1$-alkyl group.

In one embodiment of the invention any one or more of the groups R$^7$, R$^8$, R$^9$, R$^{20}$, R$^{22}$, R$^{25}$, R$^{31}$, R$^{33}$, R$^{34}$ und R$^{40}$ are independently of each other selected from the series consisting of hydrogen and (C$_1$-C$_2$)-alkyl, in another embodiment from the series consisting of hydrogen and C$_1$-alkyl, and in another embodiment they are independently of each other hydrogen, in another embodiment (C$_1$-C$_4$)-alkyl, in another embodiment (C$_1$-C$_2$)-alkyl, in another embodiment C$_1$-alkyl.

In one embodiment of the invention R$^{10}$ is selected from the series consisting of hydrogen, (C$_1$-C$_6$)-alkyl, (C$_2$-C$_6$)-alkenyl and (C$_1$-C$_6$)-alkynyl, in another embodiment from the series consisting of hydrogen, (C$_1$-C$_6$)-alkyl, (C$_2$-C$_6$)-alkynyl and (C$_3$-C$_7$)-cycloalkyl, in another embodiment from the series consisting of hydrogen, (C$_1$-C$_6$)-alkyl and (C$_2$-C$_6$)-alkynyl, in another embodiment from the series consisting of hydrogen, (C$_1$-C$_6$)-alkyl and (C$_3$-C$_7$)-cycloalkyl, in another embodiment from the series consisting of hydrogen and (C$_1$-C$_6$)-alkyl, in another embodiment from the series consisting of (C$_1$-C$_6$)-alkyl, (C$_2$-C$_6$)-alkenyl, (C$_2$-C$_6$)-alkynyl and (C$_3$-C$_7$)-cycloalkyl, in another embodiment from the series consisting of (C$_1$-C$_6$)-alkyl, (C$_2$-C$_6$)-alkenyl and (C$_2$-C$_6$)-alkynyl, in another embodiment from the series consisting of (C$_1$-C$_6$)-alkyl, (C$_2$-C$_6$)-alkynyl and (C$_3$-C$_7$)-cycloalkyl, in another embodiment from the series consisting of (C$_1$-C$_6$)-alkyl and (C$_2$-C$_6$)-alkynyl, in another embodiment from the series consisting of (C$_1$-C$_6$)-alkyl and (C$_3$-C$_7$)-cycloalkyl, in another embodiment R$^{10}$ is (C$_1$-C$_6$)-alkyl, wherein in all these embodiments (C$_1$-C$_6$)-alkyl is unsubstituted or substituted by 1 or 2 identical or different substituents selected from the series consisting of (C$_3$-C$_7$)-cycloalkyl, Het, cyano and (C$_1$-C$_4$)-alkyl-O—. In one embodiment R$^{10}$ is hydrogen. In one embodiment a (C$_1$-C$_6$)-alkyl group representing R$^{10}$ is (C$_1$-C$_4$)-alkyl, in another embodiment (C$_1$-C$_3$)-alkyl, in another embodiment (C$_1$-C$_2$)-alkyl, in another embodiment C$_1$-alkyl. In one embodiment a (C$_3$-C$_7$)-alkyl group representing R$^{10}$ is unsubstituted or substituted by 1 substituent selected from the series consisting of (C$_3$-C$_7$)-cycloalkyl, Het, cyano and (C$_1$-C$_4$)-alkyl-O—. In one embodiment the substituents in a substituted alkyl group representing $R^{10}$ are selected from the series consisting of $(C_3-C_7)$-cycloalkyl, Het and cyano, in another embodiment from the series consisting of $(C_3-C_7)$-cycloalkyl, Het and $(C_1-C_4)$-alkyl-O—, in another embodiment from the series consisting of $(C_3-C_7)$-cycloalkyl and Het, and in another embodiment substituents in a substituted alkyl group representing $R^{10}$ are $(C_3-C_7)$-cycloalkyl groups, and in another embodiment substituents in a substituted alkyl group representing $R^{10}$ are groups Het. As stated above and applies to alkyl groups in general, besides the substituents specified in the definition of the group $R^{10}$ the alkyl group representing $R^{10}$ can also carry one or more fluorine substituents. Cycloalkyl groups representing $R^{10}$ or present in $R^{10}$ can be unsubstituted or substituted by one or more identical or different substituents selected from the series consisting of fluorine and $(C_1-C_4)$-alkyl.

If two groups $R^{21}$ bonded to adjacent ring carbon atoms in the group A together with the ring carbon atoms carrying them form a 5-membered to 7-membered ring, this ring is mono-unsaturated. I.e., the resulting ring contains one double bond within the ring, which double bond is present between the said two adjacent ring carbon in the aromatic ring A that are common to the ring A and the ring formed by the two groups $R^{21}$, and because of the rules of nomenclature for fused rings this double bond is regarded as a double bond present in either of the two fused rings. If two substituents $R^{21}$ together with the ring carbon atoms in A carrying them form a ring, further substituents $R^{21}$ selected from the series consisting of halogen, $(C_1-C_4)$-alkyl, $(C_1-C_4)$-alkyl-O— and cyano can additionally be present in the group A. The case that two groups $R^{21}$ bonded to adjacent ring carbon atoms in A together with the carbon atoms carrying them form a 5-membered to 7-membered ring, can in other terms be regarded as two groups $R^{21}$ together forming a divalent residue comprising a chain of 3 to 5 members, of which 0, 1 or 2 are identical or different heteroatom moieties selected from the series consisting of $N(R^2)$, O and $S(O)_m$, the terminal atoms of which are bonded to the two adjacent ring carbon atoms in the group A. Examples of such divalent residues, from any one or more of which two groups $R^{21}$ bonded to adjacent ring carbon atoms in A are selected in one embodiment of the invention, are the residues —CH$_2$—CH$_2$CH$_2$—, —CH$_2$—CH$_2$CH$_2$—CH$_2$—, —CH$_2$—CH$_2$—CH$_2$—CH$_2$CH$_2$—, —O—CH$_2$CH$_2$—, —CH$_2$CH$_2$—O—, —O—CH$_2$—CH$_2$—CH$_2$, —CH$_2$—CH$_2$—CH$_2$O—, —O—CH$_2$O—, —O—CH$_2$—CH$_2$O—, —O—CH$_2$CH$_2$CH$_2$—O—, —N(R$^{22}$)—CH$_2$—CH$_2$O—, —O—CH$_2$CH—N(R$^{22}$)—, —S(O)$_m$—CH$_2$CH$_2$—N(R$^{22}$)— and —N(R$^{22}$)—CH$_2$CH$_2$—S(O)$_m$—, which can all be substituted on carbon atoms by one or more identical or different substituents selected from the series consisting of fluorine and $(C_1-C_4)$-alkyl, and can thus also be present, for example, as the residues —O—CF$_2$—O—, —O—C(CH$_3$)$_2$—O—, —O—CH(CHs)—CH$_2$—, —CH(CHs)—CH$_2$O—, —O—C(CH$_3$)$_2$—CH$_2$, —C(CH$_3$)$_2$—CH$_2$—O—. In one embodiment, the hetero ring members which are optionally present in a ring formed by two groups $R^{21}$ bonded to adjacent ring carbon atoms in Ar together with the carbon atoms carrying them, are selected from the series consisting of $N(R^{22})$ and O, in another embodiment from the series consisting of O and $S(O)_m$, and in another embodiment they are O (oxygen atoms). In one embodiment, the ring which can be formed by two groups $R^{21}$ bonded to adjacent ring carbon atoms in A together with the ring carbon atoms carrying them, is a 5-membered or 6-membered ring, in another embodiment a 5-membered ring, in another embodiment a 6-membered ring. In one embodiment, the ring which can be formed by two groups $R^{21}$ bonded to adjacent carbon atoms in A together with the carbon atoms carrying them, comprises 0 ring heteroatoms, i.e. it is a carbocyclic ring, and in another embodiment it comprises 1 or 2 identical or different hetero ring members. In one embodiment, the number of substituents selected from the series consisting of fluorine and $(C_1-C_4)$-alkyl on a ring formed by two groups $R^{21}$ together with the carbon atoms carrying them, is 1, 2, 3 or 4, in another embodiment 1, 2 or 3, in another embodiment 1 or 2, in another embodiment 1, and in another embodiment it is 0.

In one embodiment of the invention $R^{21}$ is selected from the series consisting of halogen, $(C_1-C_4)$-alkyl and $(C_1-C_4)$-alkyl-O—, in another embodiment from the series consisting of halogen, $(C_1-C_4)$-alkyl and cyano, in another embodiment from the series consisting of halogen and $(C_1-C_4)$-alkyl, and in another embodiment they are halogen, and in all these embodiments two groups $R^{21}$ bonded to adjacent ring carbon atoms in A, together with the carbon atoms carrying them, can form a 5-membered to 7-membered mono-unsaturated ring, which comprises 0, 1 or 2 identical or different hetero ring members selected from the series consisting of $N(R^{22})$, O and S(O), and which is unsubstituted or substituted on ring carbon atoms by one or more identical or different substituents selected from the series consisting of fluorine and $(C_1-C_4)$-alkyl.

In one embodiment of the invention $R^{21}$ is selected from the series consisting of halogen, $(C_1-C_4)$-alkyl, $(C_1-C_4)$-alkyl-O— and cyano, in another embodiment from the series consisting of halogen, $(C_1-C_4)$-alkyl and $(C_1-C_4)$-alkyl-O—, in another embodiment from the series consisting of halogen, $(C_1-C_4)$-alkyl and cyano, in another embodiment from the series consisting of halogen and $(C_1-C_4)$-alkyl, and in another embodiment they are halogen, and in all these embodiments two groups $R^{21}$ bonded to adjacent ring carbon atoms in A, together with the carbon atoms carrying them, do not form a 5-membered to 7-membered mono-unsaturated ring.

In one embodiment a $(C_1-C_4)$-alkyl group representing $R^{21}$ or present in a $(C_1-C_4)$-alkyl-O— group representing $R^{21}$ is independently of any other such alkyl group a $(C_1-C_3)$-alkyl group, in another embodiment a $(C_1-C_2)$-alkyl group, in another embodiment a $C_1$-alkyl group. In one embodiment halogen representing $R^{21}$ is selected from the series consisting of fluorine, chlorine and bromine, in another embodiment from the series consisting fluorine and chlorine, in another embodiment it is fluorine, and in another embodiment it is chlorine.

If in a group $C(R^{26})(R^{27})$ in a chain E the groups $R^{26}$ and $R^{27}$ bonded to the same carbon atom together are oxo, i.e. an oxygen atom bonded via a double bond ((O), =O), they together with the carbon atom carrying them form a divalent carbonyl group (—C(O)—, —(C=O)—). If adjacent to such a carbonyl group a hetero chain member such as $N(R^{25})$ or O, for example, is present in a chain E, or if such a carbonyl group is bonded to a ring nitrogen in the group A or in the group $R^{30}$ representing the group G, a carboxylic acid amide moiety, a carboxylic acid ester moiety or a carboxylic acid moiety results. In one embodiment of the invention in one group $C(R^{26})(R^{27})$ in a chain E the groups $R^{26}$ and $R^{27}$ bonded to the same carbon atom together can be oxo, in another embodiment in none group $C(R^{26})(R^{27})$ in a chain E the groups $R^{26}$ and $R^{27}$ bonded to the same carbon atom together are oxo.

In one embodiment of the invention $R^{26}$ and $R^{27}$ are independently of each other selected from the series consisting of hydrogen, fluorine and $(C_1-C_4)$-alkyl, in another embodiment from the series consisting of hydrogen, $(C_1-C_4)$-alkyl and hydroxy, in another embodiment from the series consisting of hydrogen and $(C_1-C_4)$-alkyl, in another embodiment from the series consisting of hydrogen and fluorine, and in another embodiment they are hydrogen, and in all these embodiments in one or two groups $C(R^{26})(R^{27})$ in a chain E the groups $R^{26}$ and $R^{27}$ bonded to the same carbon atom together can be oxo.

In one embodiment $R^6$ and $R^{27}$ are independently of each other selected from the series consisting of hydrogen, fluorine, $(C_1-C_4)$-alkyl and hydroxy, in another embodiment from the series consisting of hydrogen, fluorine and $(C_1-C_4)$-alkyl, in another embodiment from the series consisting of hydrogen, $(C_1-C_4)$-alkyl and hydroxy, in another embodiment from the series consisting of hydrogen and $(C_1-C_4)$-alkyl, in another embodiment from the series consisting of hydrogen and fluorine, and in another embodiment they are hydrogen, and in all these embodiments in none of the groups $C(R^{26})(R^{27})$ in a chain E the groups $R^{26}$ and $R^{27}$ bonded to the same carbon atom together are oxo.

In one embodiment a $(C_1-C_4)$-alkyl group representing $R^{26}$ or $R^{27}$ is independently of any other such alkyl group a $(C_1-C_3)$-alkyl group, in another embodiment a $(C_1-C_2)$-alkyl group, in another embodiment a $C_1$-alkyl group.

The group $R^{30}$ representing the group G is a residue of a monocyclic and bicyclic ring containing 3, 4, 5, 6, 7, 8, 9 or 10 ring members. In one embodiment of the invention, the number of ring members in a monocyclic group Rao is 3, 4, 5, 6 or 7, in another embodiment 3, 4, 5 or 6, in another embodiment 3 or 4, in another embodiment 4, 5 or 6, in another embodiment 5, 6 or 7, in another embodiment 5 or 6, in another embodiment 3, in another embodiment 4, in another embodiment 5, in another embodiment 6, and the number of ring members in a bicyclic group $R^{30}$ is 6, 7, 8, 9 or 10, in another embodiment 7, 8, 9 or 10, in another embodiment 8, 9 or 10, in another embodiment 9, and in another embodiment 10. In one embodiment, the number of ring members of the cyclic group $R^3$ is from 3 to 10 in the case of a carbocyclic ring, and from 4 to 10 in the case of a heterocyclic ring. In one embodiment, the cyclic group $R^{30}$ is monocyclic, in another embodiment it is bicyclic. A bicyclic group $R^{30}$ can be a fused ring system or a bridged ring system or a spirocyclic ring system. In one embodiment, a bicyclic group $R^{30}$ is a fused or bridged ring system, in another embodiment it is a fused ring system.

An unsaturated group representing $R^{30}$ can be aromatic, i.e. it contains two double bonds within the ring in the case of a 5-membered monocyclic aromatic heterocycle which double bonds, together with an electron pair on a ring heteroatom, form a delocalized cyclic system of six pi electrons, and three double bonds within the ring in the case of a phenyl group or a 6-membered monocyclic aromatic heterocycle, or two, three, four or five double bonds within two fused rings in the case of a bicyclic group comprising one or two aromatic rings, or it can be partially unsaturated, i.e., it contains one or more, for example one or two, double bonds within the ring via which it is bonded, but is not aromatic within this ring. In one embodiment of the invention the cyclic group $R^{30}$ is a saturated group, in another embodiment it is an unsaturated group including partially unsaturated groups and aromatic groups. In another embodiment $R^{30}$ is a saturated group or a partially unsaturated group, in another embodiment it is a saturated group or an aromatic group, in another embodiment it is a saturated group, and in another embodiment it is an aromatic group.

The cyclic group $R^{30}$ can be a carbocyclic group, i.e. comprise 0 (zero) hetero ring members, or a heterocyclic group, i.e. comprise 1, 2 or 3 identical or different hetero ring members selected from the series consisting of N, $N(R^{31})$, O and $S(O)_m$. In the case of the group $R^{30}$, the hetero ring member N denotes a ring nitrogen atom which is bonded to the adjacent ring atoms via two single bonds and which has a free valence via which the ring $R^{30}$ is bonded to the group E, as occurs in a pyrrole ring, pyrazole ring, piperidine ring or morpholine ring, for example, as well as a ring nitrogen atom which is bonded to the adjacent ring atoms via a single bond and a double bond or via three single bonds and via which the ring $R^{30}$ cannot be bonded to the group E, unless quaternization is present, as occurs in a pyridine ring, thiazole ring, quinoline ring or 1-azabicyclo[2.2.2]octane ring, for example. In one embodiment, $R^{30}$ comprises 0, 1 or 2 identical or different hetero ring members, in another embodiment 0 or 1 hetero ring member, and in another embodiment $R^{30}$ comprises 0 hetero ring member and thus is a carbocyclic group. In another embodiment $R^{30}$ is a heterocyclic group which comprises 1, 2 or 3 identical or different hetero ring members, in another embodiment 1 or 2 identical or different hetero ring members, in another embodiment 1 hetero ring members. In one embodiment, the hetero ring members in $R^{30}$ are selected from the series consisting of N, $N(R^{31})$ and O, in another embodiment from the series consisting of N, $N(R^{31})$ and $S(O)_m$, in another embodiment from the series consisting of N, O and $S(O)_m$, in another embodiment from the series consisting of N and $N(R^{31})$, in another embodiment from the series consisting of N and O, in another embodiment from the series consisting of $N(R^{31})$ and O, in another embodiment they are N, in another embodiment they are $N(R^{31})$, and in another embodiment they are O. In one embodiment two hetero ring members in a group $R^{30}$ can only be present in adjacent ring positions if one them is $S(O)_m$, in which m is 1 or 2, or if one of them is N which is bonded to the two adjacent ring atoms via a single bond and a double bond and does not have a free valence via which the ring $R^{30}$ is bonded to the group E. In the latter embodiment, two oxygen atoms, for example, can thus not be present in adjacent ring positions in $R^{30}$. Heterocyclic groups $R^{30}$ can be bonded to the group E via a ring nitrogen atom, i.e. a hetero ring member N, or a ring carbon atom. In one embodiment a heterocyclic group $R^{30}$ is bonded via a ring carbon atom, in another embodiment it is bonded via a ring nitrogen atom, i.e. a hetero ring member N.

Examples of carbocyclic groups, which can represent $R^{30}$ and any one or more of which may be included in the definition of $R^{30}$ in one embodiment, and from any one or more of which $R^3$ is selected in another embodiment, are cycloalkyl groups such as $(C_3-C_7)$-cycloalkyl including cyclopropyl, cyclobutyl, cyclopentyl, cyclohexyl and cycloheptyl, cycloalkenyl groups such as $(C_5-C_7)$-cycloalkenyl including cyclopentenyl, cyclohexenyl and cycloheptenyl, bicycloalkyl groups such as $(C_6-C_{10})$-bicycloalkyl, phenyl groups, indanyl groups including indan-1-yl and indan-2-yl, and naphthalenyl (naphthyl) groups including naphthalen-1-yl and naphthalen-2-yl, for example, which can all be unsubstituted or substituted by one or more identical or different substituents $R^{32}$. The explanations given above, for example with respect to cycloalkyl groups, for example their optional substitution by fluorine substituents and $(C_1-C_4)$-alkyl substituents, and with respect to phenyl groups apply accordingly to such groups representing Re.

Examples of heterocyclic groups, which can represent $R^{30}$ and any one or more of which may be included in the definition of $R^{30}$ in one embodiment, and from any one or more of which $R^{30}$ is selected in another embodiment, are oxetanyl including oxetan-2-yl and oxetan-3-yl, tetrahydrofuranyl including tetrahydrofuran-2-yl and tetrahydrofuran-3-yl, tetrahydropyranyl including tetrahydropyran-2-yl, tetrahydropyran-3-yl and tetrahydropyran-4-yl, oxepanyl including oxepan-2-yl, oxepan-3-yl and oxepan-4-yl, tetrahydrothiophene including tetrahydrothiophen-2-yl and tetrahydrothiophen-3-yl, tetrahydrothiopyranyl including tetrahydrothiopyran-2-yl, tetrahydrothiopyran-3-yl and tetrahydrothiopyran-4-yl, azetidinyl including azetidin-1-yl, azetidin-2-yl and azetidin-3-yl, pyrrolidinyl including pyrrolidin-1-yl, pyrrolidin-2-yl and pyrrolidin-3-yl, piperidinyl including piperidin-1-yl, piperidin-2-yl, piperidin-3-yl and piperidin-4-yl, 1,2-dihydropyridinyl including 1,2-dihydropyridin-1-yl, 1,2-dihydropyridin-2-yl, 1,2-dihydropyridin-3-yl, 1,2-dihydropyridin-4-yl, 1,2-dihydropyridin-5-yl and 1,2-dihydropyridin-6-yl, 1,2,3,6-tetrahydropyridinyl including 1,2,3,6-tetrahydropyridin-1-yl, 1,2,3,6-tetrahydropyridin-2-yl, 1,2,3,6-tetrahydropyridin-3-yl, 1,2,3,6-tetrahydropyridin-4-yl, 1,2,3,6-tetrahydropyridin-5-yl and 1,2,3,6-tetrahydropyridin-6-yl, azepanyl including azepan-1-yl, azepan-2-yl, azepan-3-yl and azepan-4-yl, 1-azabicyclo[2.2.2]octanyl including 1-azabicyclo[2.2.2]octan-2-yl, 1-azabicyclo[2.2.2]octan-3-yl and 1-azabicyclo[2.2.2]octan-4-yl, [1,3]dioxolanyl including [1,3]dioxolan-2-yl and [1,3]dioxolan-4-yl, [1,4]dioxanyl including [1,4]dioxan-2-yl, [1,3]oxazolidinyl including [1,3]oxazolidin-2-yl, [1,3]oxazolidin-3-yl, [1,3]oxazolidin-4-yl and [1,3]oxazolidin-5-yl, [1,3]thiazolidinyl including [1,3]thiazolidin-2-yl, [1,3]thiazolidin-3-yl, [1,3]thiazolidin-4-yl and [1,3]thiazolidin-5-yl, imidazolidinyl including imidazolidin-1-yl, imidazolidin-2-yl, imidazolidin-4-yl, morpholinyl including morpholin-2-yl, morpholin-3-yl and morpholin-4-yl, thiomorpholinyl including thiomorpholin-2-yl, thiomorpholin-3-yl and thiomorpholin-4-yl, piperazinyl including piperazin-1-yl and piperazin-2-yl, furanyl including furan-2-yl and furan-3-yl, thiophenyl (thienyl) including thiophen-2-yl and thiophen-3-yl, pyrrolyl including pyrrol-1-yl, pyrrol-2-yl and pyrrol-3-yl, isoxazolyl including isoxazol-3-yl, isoxazol-4-yl and isoxazol-5-yl, oxazolyl including oxazol-2-yl, oxazol-4-yl and oxazol-5-yl, thiazolyl including thiazol-2-yl, thiazol-4-yl and thiazol-5-yl, pyrazolyl including pyrazol-1-yl, pyrazol-3-yl, pyrazol-4-yl and pyrazol-5-yl, imidazolyl including imidazolyl-1-yl, imidazol-2-yl, imidazol-4-yl and imidazol-5-yl, [1,2,4]triazolyl including [1,2,4]triazol-1-yl, [1,2,4]triazol-3-yl and [1,2,4]triazol-5-yl, pyridinyl (pyridyl) including pyridin-2-yl, pyridin-3-yl and pyridin-4-yl, pyridazinyl including pyridazin-3-yl and pyridazin-4-yl, pyrimidinyl including pyrimidin-2-yl, pyrimidin-4-yl and pyrimidinyl-5-yl, pyrazinyl including pyrazin-2-yl, indolyl including indol-1-yl, indol-2-yl, indol-3-yl, indol-4-yl, indol-5-yl, indol-6-yl and indol-7-yl, benzimidazolyl including benzimidazol-1-yl, benzimidazol-2-yl, benzimidazol-4-yl, benzimidazol-5-yl, benzimidazol-6-yl and benzimidazol-7-yl, quinolinyl including quinolin-2-yl, quinolin-3-yl, quinolin-4-yl, quinolin-5-yl, quinolin-6-yl, quinolin-7-yl and quinolin-8-yl, isoquinolinyl including quinolin-1-yl, quinolin-3-yl, quinolin-4-yl, quinolin-5-yl, quinolin-6-yl, quinolin-7-yl and quinolin-8-yl, 2,3-dihydrobenzo[1,4]dioxinyl including 2,3-dihydrobenzo[1,4]dioxin-2-yl, 2,3-dihydrobenzo[1,4]dioxin-5-yl and 2,3-dihydrobenzo[1,4]dioxin-6-yl, quinazolinyl including quinazolin-2-yl, quinazolin-4-yl, quinazolin-5-yl, quinazolin-6-yl, quinazolin-7-yl and quinazolin-8-yl, which can all be unsubstituted or substituted on ring carbon atoms by one or more identical or different substituents $R^{32}$ and, if applicable, which can all carry on ring nitrogen atoms capabable of carrying a substituent a $(C_1-C_4)$-alkyl substituent corresponding to the denotation $(C_1-C_4)$-alkyl of the group $R^{31}$ occurring in the hetero ring member $N(R^{31})$ in $R^{30}$, and can carry on all ring sulfur atoms capable of carrying oxygen atoms one or two oxygen atoms corresponding to the oxygen atoms in the hetero ring member $S(O)_m$ in $R^3$.

In one embodiment of the invention, the number of substituents $R^{32}$ which can be present on carbon atoms in $R^{30}$, is 1, 2, 3, 4, 5 or 6, in another embodiment it is 1, 2, 3, 4 or 5, in another embodiment it is 1, 2, 3 or 4, in another embodiment it is 1, 2 or 3, in another embodiment it is 1 or 2, in another embodiment it is 1. In one embodiment, $R^{30}$ is unsubstituted.

In one embodiment of the invention the group $R^{32}$ is selected from the series consisting of halogen, $(C_1-C_4)$-alkyl, hydroxy, oxo, $(C_1-C_4)$-alkyl-O—, $R^{33}$—$N(R^{34})$— and Het, in another embodiment from the series consisting of halogen, $(C_1-C_4)$-alkyl, $(C_1-C_4)$-alkyl-O—, $R^{33}$—$N(R^{34})$— and Het, in another embodiment from the series consisting of halogen, $(C_1-C_4)$-alkyl, hydroxy, oxo, $(C_1-C_4)$-alkyl-O— and $R^{33}$—$N(R^3)$—, in another embodiment from the series consisting of halogen, $(C_1-C_4)$-alkyl, hydroxy, oxo and $(C_1-C_4)$-alkyl-O—, in another embodiment from the series consisting of halogen, $(C_1-C_4)$-alkyl, oxo and $(C_1-C_4)$-alkyl-O—, in another embodiment from the series consisting of halogen, $(C_1-C_4)$-alkyl and $(C_1-C_4)$-alkyl-O—, in another embodiment from the series consisting of halogen and $(C_1-C_4)$-alkyl, in another embodiment they are halogen, and in another embodiment they are $(C_1-C_4)$-alkyl. In one embodiment a $(C_1-C_4)$-alkyl group representing $R^{32}$ or present in a $(C_1-C_4)$-alkyl-O— group representing $R^{32}$ is independently of any other such alkyl group a $(C_1-C_3)$-alkyl group, in another embodiment a $(C_1-C_2)$-alkyl group, in another embodiment a $C_1$-alkyl group. In one embodiment halogen representing $R^{32}$ is selected from the series consisting of fluorine, chlorine and bromine, in another embodiment from the series consisting fluorine and chlorine, in another embodiment it is fluorine, in another embodiment it is chlorine, and in another embodiment it is bromine.

The group Het contains 4, 5, 6 or 7 ring members. In one embodiment of the invention, Het is 4-membered to 6-membered, in another embodiment 4-membered or 5-membered, in another embodiment 5-membered or 6-membered, in another embodiment 4-membered, in another embodiment 5-membered, in another embodiment 6-membered. In one embodiment, Het comprises 1 hetero ring member. In one embodiment, the hetero ring members in Het are selected from the series consisting of N, $N(R^{40})$) and O, in another embodiment from the series consisting of N and $N(R^{40})$, in another embodiment from the series consisting of O and $S(O)_m$, in another embodiment they are O. In one embodiment two hetero ring members in a group Het can only be present in adjacent ring positions if one them is $S(O)_m$ in which m is 1 or 2, in another embodiment two hetero ring members in a group Het are not present in adjacent ring positions. In the latter embodiment two oxygen atoms, for example, can thus not be present in adjacent ring positions. The group Het can be bonded via a ring nitrogen atom, i.e. a hetero ring member N, or a ring carbon atom. In one embodiment Het is bonded via a ring carbon atom, in another embodiment it is bonded via a ring nitrogen atom, i.e. a hetero ring member N. In the case of the group Het the hetero ring member N denotes a ring nitrogen atom which is bonded to the adjacent ring atoms in Het via two single bonds and which has a free valence via which the ring Het is bonded to another moiety in the molecule, as occurs in the case of a pyrrolidine ring, piperidine ring or morpholine ring, for example. Examples of heterocyclic groups, from any one or more of which Het is chosen in one embodiment, are oxetanyl, tetrahydrofuranyl, tetrahydropyranyl, oxepanyl, tetrahydrothiophenyl, tetrahydrothiopyranyl, azetidinyl, pyrrolidinyl, piperidinyl, azepanyl, morpholinyl, thiomorpholinyl and piperazinyl, including the more specific groups in which the binding position is specified and which are listed above in the section relating to the group $R^{30}$. In one embodiment, the number of optional substituents on ring carbon atoms in a group Het is 1, 2, 3 or 4, in another embodiment it is 1, 2 or 3, in another embodiment it is 1 or 2, in another embodiment it is 1. In one embodiment Het is unsubstituted. In one embodiment, substituents on ring carbon atoms in Het are $(C_1-C_4)$-alkyl group, in another embodiment $(C_1-C_3)$-alkyl groups, in another embodiment $(C_1-C_2)$-alkyl groups, in another embodiment C-alkyl groups.

In one embodiment of the invention the number m, which is an integer, is in any of its occurrences, independently of any other occurrence, selected from the numbers 0 and 2, in another embodiment 1 and 2, in another embodiment it is 0, in another embodiment it is 1 and in another embodiment it is 2.

A subject of the invention are all compounds of the formula I wherein any one or more structural elements such as groups, residues, substituents and numbers are defined as in any of the specified embodiments or definitions of the elements, or have one or more of the specific meanings which are mentioned herein as examples of elements, wherein all combinations of one or more definitions of compounds or elements and/or specified embodiments and/or specific meanings of elements are a subject of the present invention. Also with respect to all such compounds of the formula I, all their stereoisomeric forms and mixtures of stereoisomeric forms in any ratio, and their pharmaceutically acceptable salts are a subject of the present invention.

As an example of compounds of the invention, which with respect to any structural elements are defined as in specified embodiments of the invention or definitions of such elements, compounds of the formula I may be mentioned, wherein
- A is phenyl, which is unsubstituted or substituted on ring carbon atoms by one or more identical of different substituents $R^{21}$;
- E is a direct bond;
- G is selected from the series consisting of hydrogen, halogen, $(C_1-C_4)$-alkyl and cyano;
- and all other groups and numbers are defined as in the general definition of the compounds of the formula I or in any specified embodiments of the invention or definitions of structural elements, and the pharmaceutically acceptable salts thereof.

As another such example compounds of the formula I may be mentioned, wherein
- A is phenyl, which is unsubstituted or substituted on ring carbon atoms by one or more identical of different substituents $R^{20}$;
- E is a direct bond;
- G is $R^3$;
- and all other groups and numbers are defined as in the general definition of the compounds of the formula I or in any specified embodiments of the invention or definitions of structural elements, and the pharmaceutically acceptable salts thereof.

As another such example compounds of the formula I may be mentioned, wherein
- A is phenyl, which is unsubstituted or substituted on ring carbon atoms by one or more identical of different substituents $R^{21}$;
- E is a chain consisting of 1 to 5 chain members of which 0, 1 or 2 chain members are identical or different hetero chain members selected from the series consisting of $N(R^{25})$, O and $S(O)_m$, and the other chain members are identical or different groups $C(R^{26})(R^{27})$;
- G is selected from the series consisting of hydrogen, halogen, $(C_1-C_4)$-alkyl and cyano;
- and all other groups and numbers are defined as in the general definition of the compounds of the formula I or in any specified embodiments of the invention or definitions of structural elements, and the pharmaceutically acceptable salts thereof.

As another such example compounds of the formula I may be mentioned, wherein;
- A is phenyl, which is unsubstituted or substituted on ring carbon atoms by one or more identical of different substituents $R^{21}$;
- E is a chain consisting of 1 to 5 chain members of which 0, 1 or 2 chain members are identical or different hetero chain members selected from the series consisting of $N(R^{25})$, O and $S(O)_m$, and the other chain members are identical or different groups $C(R^{26})(R^{27})$;
- G is $R^{30}$;
- and all other groups and numbers are defined as in the general definition of the compounds of the formula I or in any specified embodiments of the invention or definitions of structural elements, and the pharmaceutically acceptable salts thereof.

As another such example compounds of the formula I may be mentioned, wherein
- A is a monocyclic or bicyclic, 5-membered to 10-membered, aromatic heterocyclic group, which comprises 1 or 2 identical or different hetero ring members selected from the series consisting of N, $N(R^{20})$, O and S and is bonded via a ring carbon atom, and which is unsubstituted or substituted on ring carbon atoms by one or more identical of different substituents $R^{21}$;
- E is a direct bond;
- G is selected from the series consisting of hydrogen, halogen, $(C_1-C_4)$-alkyl and cyano;
- and all other groups and numbers are defined as in the general definition of the compounds of the formula I or in any specified embodiments of the invention or definitions of structural elements, and the pharmaceutically acceptable salts thereof.

As another such example compounds of the formula I may be mentioned, wherein
- A is a monocyclic or bicyclic, 5-membered to 10-membered, aromatic heterocyclic group, which comprises 1 or 2 identical or different hetero ring members selected from the series consisting of N, $N(R^{20})$, O and S and is bonded via a ring carbon atom, and which is unsubstituted or substituted on ring carbon atoms by one or more identical of different substituents $R^{21}$;
- E is a direct bond;
- G is $R^{30}$;
- and all other groups and numbers are defined as in the general definition of the compounds of the formula I or in any specified embodiments of the invention or definitions of structural elements, and the pharmaceutically acceptable salts thereof.

As another such example compounds of the formula I may be mentioned, wherein
- A is a monocyclic or bicyclic, 5-membered to 10-membered, aromatic heterocyclic group, which comprises 1 or 2 identical or different hetero ring members selected from the series consisting of N, $N(R^2)$, O and S and is bonded via a ring carbon atom, and which is unsubstituted or substituted on ring carbon atoms by one or more identical of different substituents $R^{21}$;
- E is a chain consisting of 1 to 5 chain members of which 0, 1 or 2 chain members are identical or different hetero chain members selected from the series consisting of $N(R^2)$, O and $S(O)_m$, and the other chain members are identical or different groups $C(R^2)(R^{17})$;
- G is selected from the series consisting of hydrogen, halogen, $(C_1\text{-}C_4)$-alkyl and cyano;
- and all other groups and numbers are defined as in the general definition of the compounds of the formula I or in any specified embodiments of the invention or definitions of structural elements, and the pharmaceutically acceptable salts thereof.

As another such example compounds of the formula I may be mentioned, wherein;
- A is a monocyclic or bicyclic, 5-membered to 10-membered, aromatic heterocyclic group, which comprises 1 or 2 identical or different hetero ring members selected from the series consisting of N, $N(R^{20})$, O and S and is bonded via a ring carbon atom, and which is unsubstituted or substituted on ring carbon atoms by one or more identical of different substituents $R^{21}$;
- E is a chain consisting of 1 to 5 chain members of which 0, 1 or 2 chain members are identical or different hetero chain members selected from the series consisting of $N(R^{25})$, O and $S(O)_m$, and the other chain members are identical or different groups $C(R^{26})(R^{27})$;
- G is $R^{30}$
- and all other groups and numbers are defined as in the general definition of the compounds of the formula I or in any specified embodiments of the invention or definitions of structural elements, and the pharmaceutically acceptable salts thereof.

As another such example, compounds of the formula I may be mentioned wherein
- A is selected from the series consisting of phenyl and a monocyclic, 5-membered or 6-membered, aromatic heterocyclic group, which comprises 1 or 2 identical or different hetero ring members selected from the series consisting of N, $N(R^{20})$, O and S and is bonded via a ring carbon atom, wherein phenyl and the heterocyclic group are unsubstituted or substituted on ring carbon atoms by one or more identical of different substituents $R^{21}$;
- E is a direct bond or a chain consisting of 1 to 4 chain members of which 0, 1 or 2 chain members are identical or different hetero chain members selected from the series consisting of $N(R^{25})$, O and $S(O)_m$, and the other chain members are identical or different groups $C(R^{26})(R^{27})$;
- G is selected from the series consisting of hydrogen, halogen, $(C_1\text{-}C_4)$-alkyl and $R^{30}$;
- $R^1$, $R^3$, $R^4$ and $R^5$ are independently of each other selected from the series consisting of hydrogen, halogen and $(C_1\text{-}C_3)$-alkyl;
- $R^2$ is selected from the series consisting of hydrogen, halogen and $(C_1\text{-}C_3)$-alkyl;
- $R^5$ is selected from the series consisting of hydrogen, halogen, $(C_1\text{-}C_4)$-alkyl, $(C_1\text{-}C_4)$-alkyl-O— and cyano;
- $R^{10}$ is selected from the series consisting of hydrogen, $(C_1\text{-}C_6)$-alkyl and $(C_3\text{-}C_7)$-cycloalkyl, wherein alkyl is unsubstituted or substituted by 1 substituent selected from the series consisting of $(C_3\text{-}C_7)$-cycloalkyl, Het, cyano and $(C_1\text{-}C_4)$-alkyl-O—, and wherein all cycloalkyl groups are unsubstituted or substituted by one or more identical or different substituents selected from the series consisting of fluorine and $(C_1\text{-}C_4)$-alkyl;
- $R^{20}$, $R^{22}$, $R^{25}$, $R^{31}$ and $R^{40}$ are independently of each other selected from the series consisting of hydrogen and $(C_1\text{-}C_4)$-alkyl;
- $R^{21}$ is selected from the series consisting of halogen, $(C_1\text{-}C_4)$-alkyl, $(C_1\text{-}C_4)$-alkyl-O— and cyano, and two groups $R^{21}$ bonded to adjacent ring carbon atoms in the group A, together with the carbon atoms carrying them, can form a 5-membered or 6-membered mono-unsaturated ring, which comprises 0, 1 or 2 identical or different hetero ring members selected from the series consisting of $N(R^{22})$, O and $S(O)_m$ and which is unsubstituted or substituted on ring carbon atoms by one or more identical or different substituents selected from the series consisting of fluorine and $(C_1\text{-}C_4)$-alkyl;
- $R^{26}$ and $R^{27}$ are independently of each other selected from the series consisting of hydrogen, fluorine, $(C_1\text{-}C_3)$-alkyl and hydroxy, and in one group $C(R^{26})(R^{27})$ the groups $R^{26}$ and $R^{27}$ bonded to the same carbon atom together can be oxo;
- $R^{30}$ is a monocyclic or bicyclic, 3-membered to 10-membered ring, which is saturated or unsaturated and comprises 0, 1, 2 or 3 identical or different hetero ring members selected from the series consisting of N, $N(R^{31})$, O and $S(O)_m$, and which is unsubstituted or substituted on ring carbon atoms by one or more identical or different substituents $R^{32}$;
- $R^{32}$ is selected from the series consisting of halogen, $(C_1\text{-}C_4)$-alkyl, hydroxy, oxo, $(C_1\text{-}C_4)$-alkyl-O— and cyano;
- Het is a monocyclic, 4-membered to 6-membered, saturated heterocyclic group, which comprises 1 or 2 identical or different hetero ring members selected from the series consisting of N, $N(R^{40})$ and O, and which is unsubstituted or substituted on ring carbon atoms by one or more identical or different substituents selected from the series consisting of fluorine and $(C_1\text{-}C_4)$-alkyl;
- m is selected from the series consisting of 0, 1 and 2, wherein all numbers m are independent of each other and can be identical or different;
- wherein all alkyl groups, independently of any other substituents which can be present on an alkyl group, can be substituted by one or more fluorine substituents;
- and the pharmaceutically acceptable salts thereof.

As another such example, compounds of the formula I may be mentioned, wherein
- A is selected from the series consisting of phenyl and a monocyclic, 5-membered or 6-membered, aromatic heterocyclic group, which comprises 1 or 2 identical or different hetero ring members selected from the series consisting of N, $N(R^{20})$, O and S and is bonded via a ring carbon atom, wherein phenyl and the heterocyclic group are unsubstituted or substituted on ring carbon atoms by one or more identical of different substituents $R^{21}$;
- E is a direct bond or a chain consisting of 1 to 4 chain members of which 0, 1 or 2 chain members are identical or different hetero chain members selected from the series consisting of N($R^{25}$) and O, and the other chain members are identical or different groups C($R^{26}$)($R^{27}$);

G is selected from the series consisting of hydrogen, ($C_1$-$C_4$)-alkyl and $R^{30}$;

$R^1$ and $R^4$ are independently of each other selected from the series consisting of hydrogen, halogen and ($C_1$-$C_3$)-alkyl;

$R^2$ is selected from the series consisting of hydrogen, halogen and ($C_1$-$C_3$)-alkyl;

$R^3$ and $R^6$ are independently of each other selected from the series consisting of hydrogen, halogen and $C_1$-alkyl;

$R^5$ is selected from the series consisting of hydrogen, halogen, ($C_1$-$C_4$)-alkyl and cyano;

$R^{10}$ is selected from the series consisting of hydrogen, ($C_1$-$C_6$)-alkyl and ($C_3$-$C_7$)-cycloalkyl, wherein alkyl is unsubstituted or substituted by 1 substituent selected from the series consisting of ($C_3$-$C_7$)-cycloalkyl, Het, cyano and ($C_1$-$C_4$)-alkyl-O—, and wherein all cycloalkyl groups are unsubstituted or substituted by one or more identical or different substituents selected from the series consisting of fluorine and ($C_1$-$C_4$)-alkyl;

$R^{20}$, $R^{22}$, $R^{21}$, $R^{31}$ and $R^{40}$ are independently of each other selected from the series consisting of hydrogen and ($C_1$-$C_4$)-alkyl;

$R^{21}$ is selected from the series consisting of halogen, ($C_1$-$C_4$)-alkyl, ($C_1$-$C_4$)-alkyl-O— and cyano, and two groups $R^{21}$ bonded to adjacent ring carbon atoms in the group A, together with the carbon atoms carrying them, can form a 5-membered or 6-membered mono-unsaturated ring, which comprises 0, 1 or 2 identical or different hetero ring members selected from the series consisting of N($R^{22}$) and O, and which is unsubstituted or substituted on ring carbon atoms by one or more identical or different substituents selected from the series consisting of fluorine and C-alkyl;

$R^{26}$ and $R^{27}$ are independently of each other selected from the series consisting of hydrogen, fluorine, ($C_1$-$C_6$)-alkyl and hydroxy, and in one group C($R^{26}$)($R^{27}$) the groups $R^{26}$ and $R^{27}$ bonded to the same carbon atom together can be oxo;

$R^{30}$ is a monocyclic or bicyclic, 3-membered to 10-membered ring, which is saturated or aromatic and comprises 0, 1 or 2 identical or different hetero ring members selected from the series consisting of N, N($R^{31}$), O and S(O)$_m$, and which is unsubstituted or substituted on ring carbon atoms by one or more identical or different substituents $R^{32}$;

$R^{32}$ is selected from the series consisting of halogen, ($C_1$-$C_4$)-alkyl, hydroxy, oxo and ($C_1$-$C_4$)-alkyl-O—;

Het is a monocyclic, 4-membered to 6-membered, saturated heterocyclic group, which comprises 1 hetero ring member selected from the series consisting of N($R^{40}$) and O, and which is unsubstituted or substituted on ring carbon atoms by one or more identical or different substituents selected from the series consisting of fluorine and ($C_1$-$C_3$)-alkyl;

m is selected from the series consisting of 0, 1 and 2, wherein all numbers m are independent of each other and can be identical or different;

wherein all alkyl groups, independently of any other substituents which can be present on an alkyl group, can be substituted by one or more fluorine substituents; and the pharmaceutically acceptable salts thereof.

As another such example, compounds of the formula I may be mentioned, wherein

A is selected from the series consisting of phenyl and a monocyclic, 5-membered or 6-membered, aromatic heterocyclic group, which comprises 1 or 2 identical or different hetero ring members selected from the series consisting of N, N($R^{20}$) and S and is bonded via a ring carbon atom, wherein phenyl and the heterocyclic group are unsubstituted or substituted on ring carbon atoms by one or more identical of different substituents $R^{21}$;

E is a direct bond or a chain consisting of 1 to 4 chain members of which 0 or 1 chain members are identical or different hetero chain members selected from the series consisting of N($R^{25}$) and O, and the other chain members are identical or different groups C($R^{26}$)($R^{27}$);

G is selected from the series consisting of hydrogen and $R^{30}$;

$R^1$ and $R^4$ are independently of each other selected from the series consisting of hydrogen, halogen and ($C_1$-$C_2$)-alkyl;

$R^2$ is selected from the series consisting of hydrogen, halogen and ($C_1$-$C_2$)-alkyl;

$R^3$ and $R^6$ are independently of each other selected from the series consisting of hydrogen, halogen and $C_1$-alkyl;

$R^5$ is selected from the series consisting of hydrogen, halogen and ($C_1$-$C_2$)-alkyl;

$R^{10}$ is selected from the series consisting of hydrogen, ($C_1$-$C_4$)-alkyl and ($C_3$-$C_5$)-cycloalkyl, wherein alkyl is unsubstituted or substituted by 1 substituent selected from the series consisting of ($C_3$-$C_5$)-cycloalkyl and Het, and wherein all cycloalkyl groups are unsubstituted or substituted by one or more identical or different substituents ($C_1$-$C_2$)-alkyl;

$R^{20}$, $R^{25}$ and $R^{31}$ are independently of each other selected from the series consisting of hydrogen and ($C_1$-$C_3$)-alkyl;

$R^{21}$ is selected from the series consisting of halogen, ($C_1$-$C_4$)-alkyl, ($C_1$-$C_4$)-alkyl-O— and cyano;

$R^{26}$ and $R^{27}$ are independently of each other selected from the series consisting of hydrogen, fluorine, C-alkyl and hydroxy, and in one group C($R^{26}$)($R^{27}$) the groups $R^{26}$ and $R^{27}$ bonded to the same carbon atom together can be oxo;

$R^{30}$ is a monocyclic 3-membered to 6-membered or bicyclic 9-membered to 10-membered ring, which is saturated or aromatic and comprises 0, 1 or 2 identical or different hetero ring members selected from the series consisting of N, N($R^{31}$) and O, and which is unsubstituted or substituted on ring carbon atoms by one or more identical or different substituents $R^{32}$;

$R^{32}$ is selected from the series consisting of halogen, ($C_1$-$C_3$)-alkyl, hydroxy and oxo;

Het is a monocyclic, 4-membered or 5-membered, saturated heterocyclic group, which comprises 1 hetero ring member which is O, and which is unsubstituted or substituted on ring carbon atoms by one or more identical or different substituents ($C_1$-$C_3$)-alkyl;

wherein all alkyl groups, independently of any other substituents which can be present on an alkyl group, can be substituted by one or more fluorine substituents;

and the pharmaceutically acceptable salts thereof.

As another such example, compounds of the formula I may be mentioned, wherein

A is selected from the series consisting of phenyl and the aromatic heterocyclic groups pyrazolyl and pyridinyl, wherein phenyl and the heterocyclic groups are unsubstituted or substituted on ring carbon atoms by one or more identical of different substituents $R^{21}$;

E is a direct bond or a chain consisting of 1 to 3 chain members of which 0 or 1 chain member is a hetero chain member which is O, and the other chain members are identical or different groups $C(R^{26})(R^{27})$;

G is selected from the series consisting of hydrogen and $R^{30}$;

$R^1$ and $R^4$ are independently of each other selected from the series consisting of hydrogen, halogen and $C_1$-alkyl;

$R^2$ is selected from the series consisting of hydrogen, halogen and $C_1$-alkyl;

$R^3$ and $R^6$ are hydrogen;

$R^5$ is selected from the series consisting of halogen and $(C_1$-$C_2)$-alkyl;

$R^{10}$ is selected from the series consisting of hydrogen, $(C_1$-$C_4)$-alkyl and $(C_3$-$C_5)$-cycloalkyl, wherein alkyl is unsubstituted or substituted by 1 substituent selected from the series consisting of $(C_3$-$C_5)$-cycloalkyl and Het;

$R^{21}$ is selected from the series consisting of halogen, $(C_1$-$C_4)$-alkyl, $(C_1$-$C_4)$-alkyl-O— and cyano;

$R^{26}$ and $R^{27}$ are independently of each other selected from the series consisting of hydrogen, fluorine and $C_1$-alkyl;

$R^{30}$ is a monocyclic, 3-membered to 6-membered ring, which is saturated or aromatic and comprises 0, 1 or 2 identical or different hetero ring members selected from the series consisting of N, $N(R^{31})$ and O, and which is unsubstituted or substituted on ring carbon atoms by one or more identical or different substituents $R^{32}$;

$R^{31}$ is selected from the series consisting of hydrogen and $(C_1$-$C_3)$-alkyl;

$R^{32}$ is selected from the series consisting of halogen and $(C_1$-$C_3)$-alkyl;

Het is a monocyclic, 4-membered or 5-membered, saturated heterocyclic group, which comprises 1 hetero ring member which is O, and which is unsubstituted or substituted on ring carbon atoms by one or more identical or different substituents $(C_1$-$C_3)$-alkyl;

wherein all alkyl groups, independently of any other substituents which can be present on an alkyl group, can be substituted by one or more fluorine substituents; and the pharmaceutically acceptable salts thereof.

A subject of the invention also is a compound of the formula I which is selected from any of the specific compounds of the formula I which are disclosed herein, or is any one of the specific compounds of the formula I which are disclosed herein, irrespective thereof whether they are disclosed as a free compound and/or as a specific salt, or a pharmaceutically acceptable salt thereof, wherein the compound of the formula I is a subject of the invention in any of its stereoisomeric forms or a mixture of stereoisomeric forms in any ratio, if applicable. For example, a subject of the invention is a compound of the formula I which is selected from the series consisting of:

6-Bromo-9-ethyl-1-methyl-8-(1-pyridin-3-ylmethyl-1H-pyrazol-4-yl)-9H-pyrido[3,4-b]indole, 6-Chloro-1,5-dimethyl-8-[4-(3-methyl-oxetan-3-yl-methoxy)-phenyl]-9H-pyrido[3,4-b]indole, 2-(4-[6-Chloro-9-(2,2,2-trifluoroethyl)-9H-pyrido[3,4-b]indol-8-yl]pyrazol-1-yl)ethanol, 6-Chloro-1-methyl-8-[4-(2-pyrazol-1-ylethoxy)-phenyl]-9H-pyrido[3,4-b]indole, 6-Bromo-9-ethyl-1,3-dimethyl-8-(1-methyl-1H-pyrazol-4-yl)-9H-pyrido[3,4-b]indole, 6-Chloro-8-(4-methoxy-phenyl)-1,9-dimethyl-9H-pyrido[3,4-b]indole, 6-Chloro-8-(4-methoxy-phenyl)-1,5-dimethyl-9H-pyrido[3,4-b]indole, 8-(4-Methoxy-phenyl)-1-methyl-9H-pyrido[3,4-b]indole-6-carbonitrile, 6-Chloro-1-methyl-8-[4-(1-methyl-1H-imidazol-2-yl-methoxy)-phenyl]-9H-pyrido[3,4-b]indole, 6-Chloro-1,5-dimethyl-8-[4-(2-pyrazol-1-yl-ethoxy)-phenyl]-9H-pyrido[3,4-b]pyridine, 6-Chloro-9-cyclopropylmethyl-8-(2,6-dichloro-pyridin-3-yl)-9H-pyrido[3,4-b]indole, 6-Chloro-8-(2,6-dichloro-pyridin-3-yl)-9-ethyl-9H-pyrido[3,4-b]indole, 8-(2,6-Dichloro-pyridin-3-yl)-1,6-dimethyl-9H-pyrido[3,4-b]indole, 6-Chloro-9-ethyl-1-methyl-8-(1-pyridin-3-ylmethyl-1H-pyrazol-4-yl)-9H-pyrido[3,4-b]indole, 6-Chloro-8-(4-chloro-phenyl)-9-ethyl-1-methyl-9H-pyrido[3,4-b]indole, 6-Chloro-8-(4-methoxy-phenyl)-1-methyl-9H-pyrido[3,4-b]indole, 6-Chloro-8-chroman-6-yl-1-methyl-9H-pyrido[3,4-b]indole, 6-Chloro-8-[4-(2-imidazol-1-yl-ethoxy)-phenyl]-1-methyl-9H-pyrido[3,4-b]indole, 6-Bromo-9-ethyl-1-methyl-8-(1-methyl-1H-pyrazol-4-yl)-9H-pyrido[3,4-b]indole, 4-(6-Chloro-1-methyl-9H-pyrido[3,4-b]indol-8-yl)-pyridin-2-ylamine, 6-Chloro-1-methyl-8-[4-(1-methyl-pyrrolidin-3-yl-methoxy)-phenyl]-9H-pyrido[3,4-b]indole, 6-Chloro-9-ethyl-1-methyl-8-[4-(3-methyl-oxetan-3-yl-methoxy)-phenyl]-9H-pyrido[3,4-b]indole, 6-Bromo-9-ethyl-1-methyl-8-[4-(3-methyl-oxetan-3-yl-methoxy)-phenyl]-9H-pyrido[3,4-b]indole, and 6-Chloro-9-cyclopropylmethyl-8-(1-pyridin-3-ylmethyl-1H-pyrazol-4-yl)-9H-pyrido[3,4-b]indole, or which is any one of these compounds, and its pharmaceutically acceptable salts.

Another subject of the present invention are processes for the preparation of the compounds of the formula I which are outlined below and by which the compounds of the formula I and intermediates occurring in the course of their synthesis, and salts thereof, are obtainable. The compounds of the formula I can in general be prepared by using procedures and techniques which per se are known to a person skilled in the art. In one of the processes a compound of the formula I is prepared, for example, by cross-coupling of a compound of the formula I with an organoboron compound of the formula III under the conditions of the well-known Suzuki reaction, also known as Suzuki-Miyaura cross-coupling reaction, or another Suzuki-type reaction or modifications thereof, in the presence of a transition metal catalyst. The reaction is reviewed in F. Alonso et al., Tetrahedron 2008, 64, 3047-3101, for example.

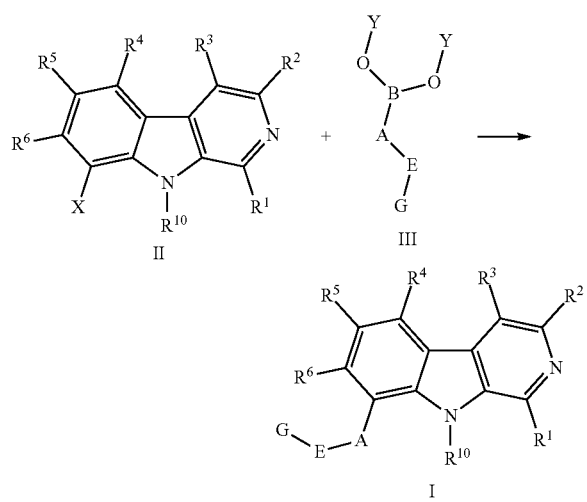

The groups $R^1$ to $R^6$ and $R^{10}$ in the compound of the formula II and the groups A, E and G in the compound of the formula III are defined as in the compound of the formula I, and in addition functional groups can be present in protected form or in the form of a precursor group, which is subsequently converted into the final group. The group X in the compound of the formula II is suitable leaving group, such as halogen selected from the series consisting of chlorine, bromine and iodine, in one embodiment of the invention from the series consisting of bromine and iodine, or a sulfonyloxy group like trifluoromethanesulfonyloxy ($CF_3$—$SO_2$—O—), for example.

The groups Y in the compound of the formula III are hydrogen, and in this case the compound of the formula III thus is a boronic acid, or ($C_1$-$C_4$)-alkyl, in one embodiment of the invention ($C_1$-$C_3$)-alkyl like methyl, ethyl or isopropyl, and in this case the compound of the formula III is a boronic acid alkyl ester, or the two groups Y, together with the —O—B—O— moiety to which they are bonded, form a saturated 5-membered or 6-membered ring, which comprises 2 or 3 carbon atoms as ring atoms in addition to the —O—B—O— moiety and is unsubstituted or substituted by one or more ($C_1$-$C_4$)-alkyl substituents, for example methyl substituents, and in this case the compound of the formula III is a cyclic boronic acid alkyl ester. In the latter case the ring formed by the two groups Y, together with the —O—B—O— moiety to which they are bonded, is a 1,3,2-dioxaborolane ring or 1,3,2-dioxaborinane ring, which are unsubstituted or substituted by one or more ($C_1$-$C_4$)-alkyl substituents, for example a 4,4,5,5-tetramethyl-1,3,2-dioxaborolane ring as present in the pinacol ester (2,3-dimethyl-2,3-butanediol ester) of the respective boronic acid, or a 5,5-dimethyl-1,3,2-dioxaborinane ring as present in the neopentyl glycol ester (2,2-dimethyl-1,3-propanediol ester) of the respective boronic acid. In one embodiment of the invention the compound of the formula III is a boronic acid or a cyclic boronic acid alkyl ester as specified afore. In another embodiment the compound of the formula III is a boronic acid or a boronic acid pinacol ester, i.e., the groups Y are hydrogen or, together with the —O—B—O— moiety to which they are bonded, form a 4,4,5,5-tetramethyl-1,3,2-dioxaborolane ring. Alternatively, instead of with a compound of the formula III, a compound of the formula II can be reacted with an organotrifluoroborate salt, such as a potassium organotrifluoroborate, i.e. a compound of the formula G-E-A-$BF_3^-K^+$ in which the groups A, E and G are defined as in the compound of the formula I and in addition functional groups can be present in protected form or in the form of a precursor group, which salts can be obtained from boronic acids and fluorides such as potassium hydrogen difluoride and are reviewed in S. Darses et al., Chem. Rev. 2008, 108, 288-325, for example.

The reaction of the compounds of the formula II with the compounds of the formula III is generally performed in an inert solvent, such as a hydrocarbon like benzene or toluene, an ether like 1,2-dimethoxyethane (DME), tetrahydrofuran (THF) or dioxane, an amide like dimethylformamide (DMF), an alcohol like ethanol or isobutanol, a nitrile like acetonitrile, or water, or a mixture of such solvents, for example in toluene or in a mixture of 1,2-dimethoxyethane and water in a ratio of from about 5:1 to about 2:1 by volume, for example in a ratio of about 3:1 by volume. The reaction is generally performed at elevated temperatures, such as at temperatures from about 50° C. to about 150° C., for example at temperatures from about 90° C. to about 130° C., in a heated flask or vessel or in a microwave vessel heated in a microwave irradiation device (cf. V. P. Metha et al., Chem. Soc. Rev. 2011, 40, 4925-4936). The reaction time generally is from about 5 minutes to about 24 hours, for example from about 10 minutes to about 10 hours, depending on the particulars of the specific case such as the reactivity of the reactants and the chosen temperature.

As transition metal catalyst in Suzuki reactions and similar cross-coupling reactions commonly palladium compounds are employed, but other metal catalysts such as nickel catalysts can also be used (cf. F.-S. Han, Chem. Soc. Rev. 2013, 42, 5270-5298, for example). Examples of palladium compounds which can be employed as catalysts in the reaction of the compounds of the formula II with the compounds of the formula III, are palladium(II) salts like palladium(II) diacetate or palladium(II) dichloride, which can also be employed in the presence of a phosphine such as 1,1'-bis(diphenylphosphino)ferrocene, tricyclohexylphosphine or triphenylphosphine, and palladium complexes like tetrakis(triphenylphosphine)palladium(0), bis(tri-tert-butylphosphine)palladium(0), bis(triphenylphosphine)palladium(II) dichloride, bis(tri-tert-butylphosphine)palladium(II) dichloride, 1,1'-bis(diphenylphosphino)ferrocene-palladium(II) dichloride which is abbreviated herein as "BDFP" and which is commonly employed in the form of a complex with dichloromethane, or bis(dibenzylideneacetone)palladium(0) in the presence of tri-tert-butylphosphine.

Palladium catalysts on solid supports like iron oxide, magnesium oxide, magnesium lanthanum oxide, apatite or anionic clay materials as well as polymer-supported palladium catalysts can also be used. The amount of the catalyst is generally from about 0.001 mol to about 0.02 mol, for example from about 0.001 to about 0.01 mol, catalyst per mol of compound of the formula II, depending on the reactivity of the compounds to be reacted, the catalyst and the reaction conditions chosen. In one embodiment of the invention tetrakis(triphenylphosphine)palladium(0) or BDFP are employed as catalysts in the reaction of the compounds of the formula II with the compounds of the formula III.

Suzuki reactions and similar cross-coupling reactions are generally performed in the presence of a base. Examples of bases which can be employed in the reaction of the compounds of the formula II with the compounds of the formula III, are alkali metal carbonates like sodium carbonate, potassium carbonate or cesium carbonate, alkali metal phosphates like tripotassium phosphate, alkali metal hydroxides like sodium hydroxide or potassium hydroxide, alkali metal fluorides like potassium fluoride or cesium fluoride, and suitable amines like triethylamine, diisopropylethylamine or 1,8-diazabicyclo[5.4.0]undec-7-ene (DBU). In one embodiment of the invention an alkali metal carbonate, for example sodium carbonate, is employed as base in the reaction of the compounds of the formula II with the compounds of the formula III.

Boronic acids and boronic acid esters of the formula III can be obtained via various procedures for the synthesis of such compounds described in the literature, for example from organometallic compounds, such as organolithium compounds or Grignard compounds which can in turn be obtained from the respective halides, i.e. compounds of the formula G-E-A-halogen in which the groups A, E and G are defined as in the compound of the formula I and in addition functional groups can be present in protected form or in the form of a precursor group, such as the respective bromides and iodides, by reaction with borate esters, such as trimethyl borate or triisopropyl borate (cf. A. E. Smith et al., Eur. J. Org. Chem. 2008, 1458-1463; W. Li et al., Org. Synth. 2009, 81, 89-97; for example), or from the respective halides and diboronic acid (tetrahydroxydiboron) or diboronic acid esters such as the pinacol ester (bis(pinacolato)diboron, 4,4,4',4',5,5,5',5'-octamethyl-2,2'-bi-1,3,2-dioxaborolane) in the presence of a palladium catalyst (cf. T. Ishiyama et al., Tetrahedron 2001, 57, 9813-9816; G. A. Molander et al., J. Am. Chem. Soc. 2010, 132, 17701-17703, for example). In view of the wide synthetic utility of boronic acids and boronic acid esters, a large number of compounds of the formula III and related boronic acids and boronic acid esters, which can be used to prepare the compounds of the formula I according to the present invention, are commercially available.

Compounds of the formula I in which the group X is chlorine, bromine or iodine, can be obtained according to standard procedures for aromatic chlorination, bromination and iodination, for example by means of N-chlorosuccinimide (NCS), N-bromosuccinimide (NBS) and N-iodosuccinimide (NIS) (cf. S. M. Maddox et al., Org. Lett. 2015, 17, 1042-1045; R. H. Mitchell et al., J. Org. Chem. 1979, 44, 4733-4735; K. Rajesh et al., J. Org. Chem. 2007, 72, 5867-5869; G. K. S. Prakash et al., J. Am. Chem. Soc. 2004, 126, 15770-15776, for example). These agents can also be used for the introduction of halogen substituents in other positions of the pyrido[3,4-b]indole ring system, such as in position 6, depending on the substitution pattern in the respective starting compound and the reaction conditions. For example, suitably substituted compounds of the formula IV can be converted into compounds of the formula IIa in which the group $X^a$ is chlorine, bromine or iodine, by treatment with NCS, NBS or NIS, which together are abbreviated herein as $NX^aS$, for example in a solvent such as water in the presence of an acid such as hydrochloric acid, sulfuric acid or phosphoric acid at temperatures from about 20° C. to about 100° C.

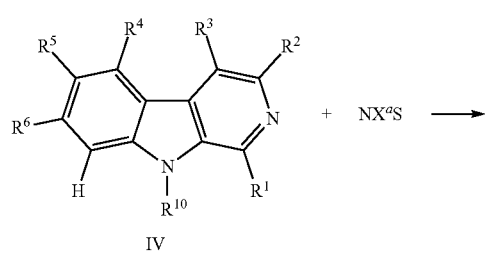

IV

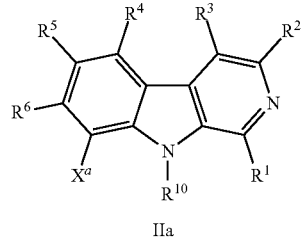

IIa

Similarly can compounds of the formula IVa, in which the group $R^{5a}$ is chlorine, bromine or iodine, be obtained by treatment of suitably substituted compounds of the formula V with $NX^aS$, for example compounds of the formula IVa in which $R^{5a}$ is chlorine by treatment with NCS in water and hydrochloric acid.

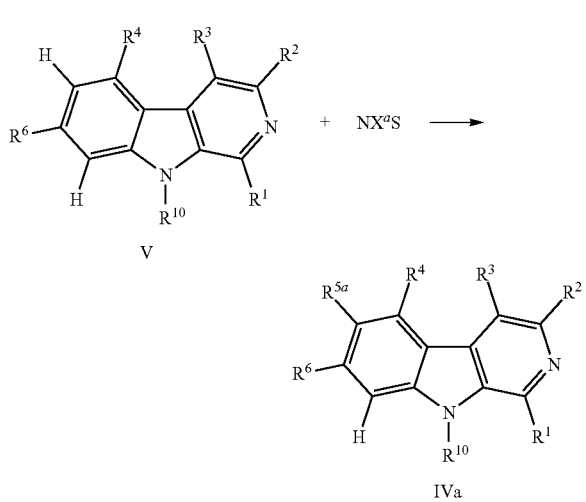

IVa

The groups $R^1$ to $R^6$ and $R^{10}$ in the compound of the formula IIa, IV, IVa and V are defined as in the compound of the formula I, and in addition can functional groups be present in protected form or in the form of a precursor group. Compounds of the formula IVa in which $R^5$ is chlorine can then be converted, for example by treatment with NBS or NIS, into compounds of the formula IIa in which $R^5$ is chlorine and $X^a$ is bromine or iodine, which can then be reacted with compounds of the formula III to give compounds of the formula I in which $R^5$ is chlorine, for example.

Compounds of the formula II and related compounds useful for the preparation of compounds of the formula II such as compounds of the formula IV and V can be prepared according to various processes described in the literature, or analogously to processes described in the literature, and many of them are commercially available, such as the compounds harmane (1-methyl-9H-pyrido[3,4-b]indole), norharmane (9H-pyrido[3,4-b]indole), 6-chloro-9H-pyrido[3,4-b]indole, 6-bromo-9H-pyrido[3,4-b]indole, 6-chloro-1-methyl-9H-pyrido[3,4-b]indole or 6-bromo-1-methyl-9H-pyrido[3,4-b]indole, for example. Examples of well-known processes of which use can be made in the preparation of compounds of the formula II and related compounds, which start from indole precursors which in turn are available via various processes described in literature, are processes involving Bischler-Napieralski type cyclizations or Pictet-Spengler type cyclizations and the cyclization of indole derivatives comprising two oxo-substituted groups in positions 2 and 3 of the indole ring system.

From suitably substituted indole derivatives of the formula VI carrying an optionally substituted 2-acylamino-ethyl moiety in position 3 of the indole ring system, compounds of the formula VII can be obtained in a Bischler-Napieralski type cyclization by treatment with phosphorus oxychloride (phosphoryl trichloride) or a mixture of phosphorus oxychloride and phosphorus pentoxide at elevated temperatures, such as at temperatures from about 60° C. to about 120° C., for example at about 80° C., in an inert solvent such as a hydrocarbon like benzene or a nitrile like acetonitrile or without a solvent. The compounds of the formula VII are then oxidized, or dehydrogenated, to compounds of the formula VIII, for example by treatment with nitrobenzene at elevated temperatures, such as at about reflux temperature, or by treatment with potassium dichromate in a solvent such as water and acetic acid at elevated temperatures, such as at about reflux temperature of the solvent.

From suitably substituted indole derivatives of the formula IX carrying an optionally substituted 2-amino-ethyl moiety in position 3 of the indole ring system, and aldehydes of the formula X compounds of the formula XI can be obtained in a Pictet-Spengler type cyclization, for example under acidic conditions such as in water in the presence of sulfuric acid at elevated temperatures, such as at about 65° C., or in an alcohol such as ethanol in the presence of hydrochloric acid at elevated temperatures, such as at about reflux temperature of the solvent (cf. E. D. Cox et al., Chem. Rev. 1995, 95, 1797-1842, for example). The compounds of the formula XI are then oxidized, or dehydrogenated, to compounds of the formula VIII, for example by treatment with potassium dichromate in a solvent such as water and acetic acid at elevated temperatures, such as at about reflux temperature of the solvent, or by treatment with palladium in a solvent such as xylene at elevated temperatures, such as at about reflux temperature of the solvent.

In another synthetic approach to compounds of the formula I and related compounds suitably substituted indole

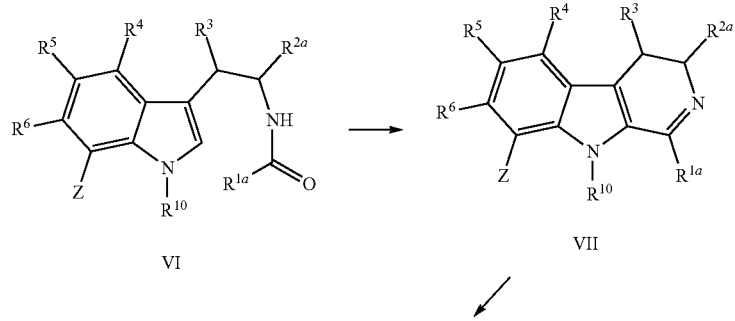

VI  VII

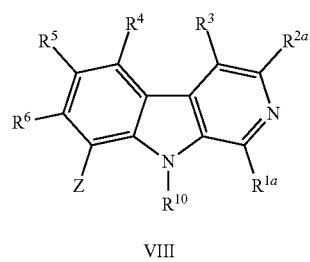

VIII

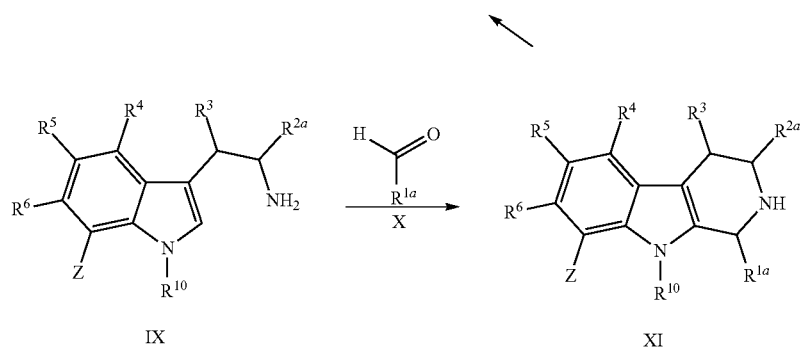

IX  XI derivatives of the formula XII, which can be obtained by acylating indole derivatives carrying an optionally substituted 2-oxo-ethyl group in position 3 of the indole ring system with an acylating agent in the presence of a catalyst such as zinc chloride, are cyclized to compounds of the formula VIII by treatment with a source of ammonia, such as an ammonium salt like ammonium acetate, in a solvent such as acetic acid at elevated temperatures, such as at about

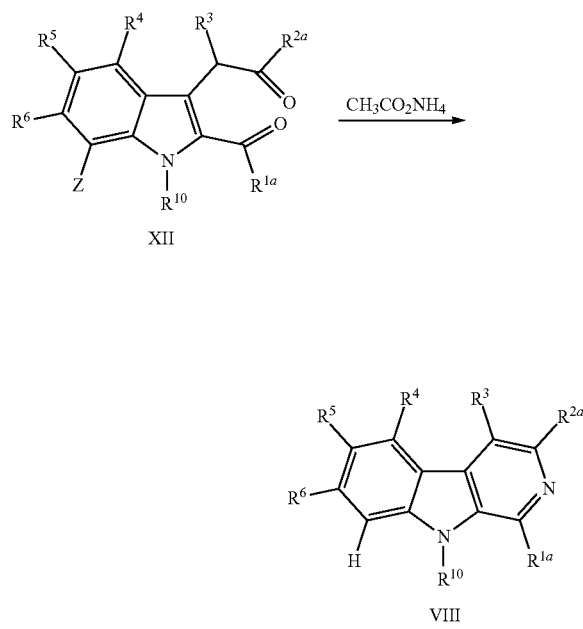

XII

CH₃CO₂NH₄

VIII

In a further synthetic approach aniline derivatives of the formula XIII carrying a 3-fluoro-pyridin-4-yl group in position 2, which can be obtained, for example, under the conditions of the Suzuki reaction or another Suzuki-type reaction reaction in the presence of transition metal catalyst such as BDFP from the respective 2-bromo-aniline and a 3-fluoro-pyridine carrying in position 4 a boronic acid group or acyclic or cyclic boronic acid ester group defined as the group of the formula $(Y-O)_2-B-$ in the compounds of the formula II, are cyclized to compounds of the formula VIII by treatment with a base, for example an alkali metal compound such as an amide like lithium bis(trimethylsilyl) amide, in a solvent such as an ether like tetrahydrofuran or dioxane at temperatures of from about 20° C. to about 30° C., or with another cyclization agent (cf. P. Rocca et al., Tetrahedron 1993, 49, 49-64; P. Rocca et al., Tetrahedron 1993, 49, 3325-3342).

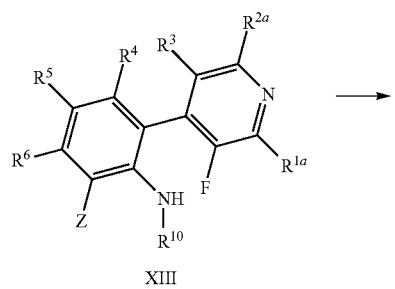

XIII

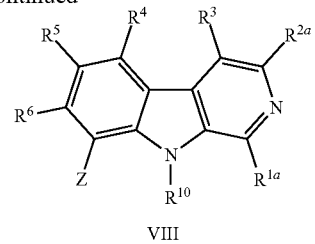

VIII

The groups $R^3$ to $R^6$ and $R^{10}$ in the compounds of the formulae VI, VII, VIII, IX, XI, XII and XIII are defined as in the compounds of the formula I, and in addition can functional groups be present in protected form or in the form of a precursor group. The group $R^{1a}$ in the compounds of the formulae VI, VII, VIII, X, XI, XII and XIII is selected from the series consisting of hydrogen and $(C_1-C_4)$-alkyl, in one embodiment from the series consisting of hydrogen and $(C_1-C_2)$-alkyl, in another embodiment from the series consisting of hydrogen and $C_1$-alkyl, and in another embodiment is hydrogen and in another embodiment is $(C_1-C_4)$-alkyl, for example $C_1$-alkyl. The group $R^{2a}$ in the compounds of the formulae VI, VII, VIII, IX, XI, XII and XIII is selected from the series consisting of hydrogen, $(C_1-C_4)$-alkyl and $(C_1-C_4)$-alkyl-O—C(O)—, in one embodiment from the series consisting of hydrogen and $(C_1-C_4)$-alkyl, in another embodiment from the series consisting of hydrogen and $(C_1-C_2)$-alkyl, in another embodiment from the series consisting of hydrogen and $C_1$-alkyl, and in another embodiment is hydrogen and in another embodiment is $(C_1-C_4)$-alkyl, for example $C_1$-alkyl. The group Z in the compounds of the formulae VI, VII, VIII, IX, XI, XII and XIII is selected from the series consisting of hydrogen, chlorine, bromine, iodine, hydroxy and $(C_1-C_4)$-alkyl-O—, in one embodiment from the series consisting of hydrogen, chlorine, bromine and iodine, in another embodiment from the series consisting of hydrogen, bromine and iodine, in another embodiment from the series consisting of chlorine, bromine and iodine, in another embodiment from the series consisting of bromine and iodine, in another embodiment from the series consisting of hydroxy and $(C_1-C_4)$-alkyl-O—, in another embodiment it is hydrogen, and in another embodiment it is bromine. Compounds of the formula VIII in which Z is chlorine, bromine or iodine, are compounds of the formulae II and IIa which can be used in the reaction with compounds of the formula III to give compounds of the formula I. Compounds of the formula VIII in which Z is hydrogen, can be converted into compounds of the formulae II and IIa, which can be used in the reaction with compounds of the formula III to give compounds of the formula I, by halogenation as outlined above. Compounds of the formula VIII in which Z is $(C_1-C_4)$-alkyl-O—, can be converted into compounds of the formula VIII in which Z is hydroxy under standard condition for the cleavage of alkyl ethers, for example by treatment with boron tribromide. Compounds of the formula VIII in which Z is hydroxy can be converted under standard conditions into compounds of the formula II in which the group X is a sulfonyloxy group, for example a trifluoromethanesulfonyloxy group which can be introduced by treatment of the compound of the formula VIII with trifluoromethanesulfonic acid anhydride, and the obtained compound of the formula II be used in the reaction with compounds of the formula III to give compounds of the formula I.

As mentioned above, the group $R^{10}$ in the compounds of the formulae II, IIa, IV, IVa, V, VI, VII, VIII, IX, XI, XII and XIII is defined as in the compounds of the formula I, and in addition can functional groups be present in protected form or in the form of a precursor group, and can thus be hydrogen, or be different from hydrogen and be an optionally substituted $(C_1-C_6)$-alkyl group, $(C_1-C_6)$-alkenyl group, $(C_2-C_6)$-alkynyl group and optionally substituted $(C_3-C_7)$-cycloalkyl group. Groups $R^{10}$ which are different from hydrogen, can be present in the starting compound for the synthesis of a compound of the formula I or introduced at any stage in course of the synthesis, for example in a compound of the formula II, IIa, IV, IVa, V or VIII, as well as in a final compound of the formula I according to the invention, by reaction of the respective compound in which $R^{10}$ is hydrogen with an electrophilic compound of the formula XIV, for example an alkylating agent if an optionally substituted alkyl group representing $R^{10}$ is to be introduced, as illustrated by the example of a compound of the formula IIb, which is a compound of the formula IIa in which $R^{10}$ is hydrogen and can be converted by reaction with a compound of the formula XIV into a compound of the formula IIc.

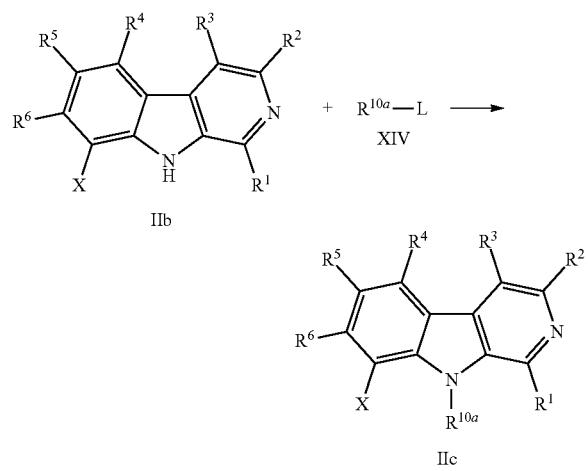

The groups $R^1$ to $R^6$ and X in the compounds of the formulae IIb and IIc are defined as in the compounds of the formula IIe. The group $R^{10a}$ in the compounds of the formulae IIc and XIV is selected from the series consisting of $(C_1-C_6)$-alkyl, $(C_2-C_6)$-alkenyl, $(C_1-C_6)$-alkynyl and $(C_3-C_7)$-cycloalkyl, wherein alkyl is unsubstituted or substituted by 1 or 2 identical or different substituents selected from the series consisting of $(C_3-C_7)$-cycloalkyl, Het, cyano and $(C_1-C_4)$-alkyl-O—, wherein all cycloalkyl groups are unsubstituted or substituted by one or more identical or different substituents selected from the series consisting of fluorine and $(C_1-C_4)$-alkyl. The group L in the compounds of the formula XIV is a nucleophilically substitutable leaving group, such as halogen selected from the series consisting of chlorine, bromine and iodine, or a sulfonyloxy group like methanesulfonyloxy, trifluoromethanesulfonyloxy or 4-toluenesulfonyloxy, for example. The reaction of compounds of the formula IIb and compounds of the formulae I, II, IV, IVa, V or VIII in which $R^{10}$ is hydrogen, with compounds of the formula XIV can be performed under standard conditions for the reaction of electrophilic compounds such as alkylating agents, for example, with nitrogen heterocycles and other nitrogen compounds in which a hydrogen atom on the nitrogen atom can be replaced by a group such as an alkyl group, for example. In a favorable manner such reactions are performed in the presence of a base, such an alkali metal hydride like sodium hydride or an alkali metal alkoxide like sodium ethoxide or sodium tert-butoxide or an alkali metal carbonate like potassium carbonate or cesium carbonate, in an inert solvent, such as an amide like dimethylformamide or N-methyl-2-pyrrolidone or a ketone like acetone or butan-2-one or an ether like tetrahydrofuran or dioxane, at temperatures of from about 20° C. to about 100° C., for example temperatures of from about 20° C. to about 60° C. In one embodiment, the reaction of a compound of the formula IIb or a compound of the formulae I, II, IV, IVa, V or VIII in which $R^{10}$ is hydrogen, with a compound of the formula XIV is performed in the presence of an alkali metal carbonate like potassium carbonate or cesium carbonate in a solvent like dimethylformamide at temperatures of from about 20° C. to about 30° C.

In another process a compound of the formula I is prepared by chemical modification, or introduction or transformation of functional groups, of a compound which has been prepared from a compound of the formula II and a compound of the formula III as described above. The compound that is modified chemically can be a compound of the formula I according to the present invention, as well as a compound which is not covered by the definition of the compounds of the formula I according to the present invention. Such chemical modifications can be performed in the moiety G-E-A- or in the groups $R^1$ to $R^6$ and $R^{10}$, for example. Such chemical modifications can also be performed in another stage of the synthesis of the compounds of the formula I, for example in compounds of the formula II.

For example, a hydroxy group can be reacted with a carboxylic acid in the presence of an activating agent, such as carbodiimide or an N,N'-carbonyldiazole or another customary coupling reagent, or with a reactive carboxylic acid derivative such as a carboxylic acid chloride to give an acyloxy group, i.e, a carboxylic acid ester group. A hydroxy group can be etherified by alkylation with a halogen compound, for example a bromide or iodide, in the presence of a base such an alkali metal hydride like sodium hydride or an alkali metal carbonate like potassium carbonate or cesium carbonate in an inert solvent such as an amide like dimethylformamide or N-methyl-2-pyrrolidone or a ketone like acetone or butan-2-one at temperatures of from about 20° C. to about 120° C., or with the respective alcohol under the conditions of the Mitsunobu reaction in the presence of a phosphine like triphenylphosphine or tributylphosphine and an azodicarboxylic acid derivative like diethyl azodicarboxylate or diisopropyl azodicarboxylate in an inert solvent such as an ether like tetrahydrofuran. An ether group initially present can be cleaved, for example by means of boron tribromide or an acid, and the resulting hydroxy group then converted into various other groups. By reaction with an isocyanate, a hydroxy group can be converted into an N-substituted carbamic acid ester. By treatment with a halogenating agent such as thionyl chloride or a phosphorus halide a hydroxy group can be replaced by a halogen atom.

Halogen atoms can also be introduced according to various other procedures described in the literature. Fluorine atoms can be introduced by means of reagents such as diethylaminosulfur trifluoride or N-fluoro-2,4,6-trimethylpyridinium triflate, for example, and similar reagents. A halogen atom, as well as a hydroxy group after activation by conversion into a reactive leaving group such as a methanesulfonyloxy group, trifluoromethanesulfonyloxy group or 4-toluenesulfonyloxy group, can be replaced with a variety of groups, including groups such as cyano, trifluoromethyl, pentafluoroethyl, carboxylic acid, carboxamide, amino, alkyl, aryl or heterocyclic groups, in a substitution reaction, which may also be catalyzed by transition metals such as by a palladium catalyst, a nickel catalyst or a copper catalyst. By halogen/metal exchange, as well as by hydrogen/metal exchange, for example by treatment with an organolithium compound, and subsequent reaction with a wide range of electrophiles various substituents can be introduced.

A carboxylic acid ester group or a cyano group can be hydrolyzed under acidic or basic conditions to give a carboxylic acid. A cyano group can be hydrolyzed partially to give a primary amide. A carboxylic acid group can be activated or converted into a reactive derivative as indicated above, and reacted with an alcohol or an amine or ammonia to give an ester or amide. A carboxylic acid group, which may have been obtained by saponification of an ester group, can be converted into a hydrogen atom by decarboxylation, for example by heating a metal salt of the carboxylic acid. A primary amide can be dehydrated to give a nitrile. A carboxylic acid group, carboxylic acid ester group, aldehyde group or ketone group can be reduced to an alcohol, for example with a complex hydride such as lithium aluminium hydride, lithium borohydride or sodium borohydride, or reacted with an organometal compound such as a Grignard compound, for example, to give an alcohol. A hydroxy group can be oxidized to an oxo group, for example by means of pyridinium chlorochromate or the Dess-Martin periodinane reagent.

An amino group and a suitable ring nitrogen atom in a heterocycle can be modified under standard conditions for acylation or sulfonylation, for example by reaction with an activated carboxylic acid or a reactive carboxylic acid derivative like a carboxylic acid chloride or anhydride, or a sulfonyl chloride. An amino group and a suitable ring nitrogen atom in a heterocycle can be alkylated by reaction with optionally substituted alkyl halogenides like chlorides, bromides or iodides or sulfonyloxy compounds like toluenesulfonyloxy, methanesulfonyloxy or trifluoromethanesulfonyloxy compounds, generally in the presence of a base such as potassium carbonate, cesium carbonate, sodium hydride or potassium tert-butoxide, for example, or by reductive amination of carbonyl compounds in the presence of a complex hydride reducing agent. A nitro group can be reduced to an amino group with various reducing agents, such as sulfides, dithionites, iron, complex hydrides or by catalytic hydrogenation. A cyano group and a carboxamide group can be reduced to an amino-substituted methyl group. A sulfur atom in an alkyl-S— group or in a heterocyclic ring can be oxidized with a peroxide like hydrogen peroxide or a peracid to give a sulfoxide moiety (S(O)) or a sulfone moiety $(S(O)_2)$.

All such reactions useful for the preparation of compounds of the formula I are known per se and can be carried out in a manner familiar to a person skilled in the art according to, or analogously, to procedures which are described in the standard literature, for example in Houben-Weyl, Methods of Organic Chemistry, Thieme; or Organic Reactions, John Wiley & Sons; or R. C. Larock, Comprehensive Organic Transformations: A Guide to Functional Group Preparations, 2. ed. (1999), John Wiley & Sons, and the references quoted therein. As applies in general and is known to the person skilled in the art, it may in certain cases become necessary to specifically adapt reaction conditions or choose specific reagents from a variety of reagents that can in principle be employed in a reaction, or otherwise take specific measures for achieving a desired conversion, for example to use protection group techniques.

In the course of the preparation of the compounds of the formula I it can generally be advantageous or necessary in order to reduce or prevent undesired reactions or side reactions in a synthesis step, to block functional groups temporarily by protecting groups suited to the specific synthesis problem, or to have them present, or introduce them, in the form of precursor groups, and later convert them into the desired functional groups. This applies to all reactions in the course of the synthesis of the compounds of the formula I including the synthesis of intermediates and the synthesis of starting compounds and building blocks. Such strategies are well known to a person skilled in the art and are described, for example, in P. G. M. Wuts and T. W. Greene, Greene's Protective Groups in Organic Synthesis, 4. ed. (2007), John Wiley & Sons. Examples of precursor groups are cyano groups and nitro groups. As already mentioned, a cyano group can in a later step be transformed by hydrolysis into a carboxylic acid derivative or by reduction into a aminomethyl group, and a nitro group can be transformed by reduction like catalytic hydrogenation into an amino group. Examples of protective groups which may be mentioned, are benzyl protective groups, for example benzyl ethers of hydroxy compounds and benzyl esters of carboxylic acids, from which the benzyl group can be removed by catalytic hydrogenation in the presence of a palladium catalyst, tert-butyl protective groups, for example tert-butyl esters of carboxylic acids or tert-butyl ethers of hydroxy groups, from which the tert-butyl group can be removed by treatment with trifluoroacetic acid, acyl protective groups, for example ester and amides of hydroxy compounds and amino compounds, which can be cleaved again by acidic or basic hydrolysis, or alkoxycarbonyl protective groups, for example tert-butoxycarbonyl derivatives of amino compounds, which can be cleaved again by treatment with trifluoroacetic acid.

In all processes for the preparation of the compounds of the formula I, workup of the reaction mixture and the purification of the product is performed according to customary methods known to the skilled person which include, for example, quenching of a reaction mixture with water, adjustment of a certain pH, precipitation, extraction, drying, concentration, crystallization, distillation and chromatography. As further examples of methods applicable in the synthesis of the compounds of the formula I, microwave assistance for speeding-up, facilitating or enabling reactions may be mentioned, and separation techniques like preparative high pressure liquid chromatography (HPLC), which can be used for separating mixtures of isomers which may occur in a reaction. Also for the characterization of the products, customary methods are used, such as NMR, UV, IR and mass spectroscopy.

Another subject of the present invention are the novel starting compounds and intermediates occurring in the synthesis of the compounds of the formula I, including the compounds of the formulae II, IIa, IIb, IIc, III, IV, IVa. V, VI, VII, VIII, IX, XI, XII, XIII and XIV, wherein the groups $R^1$ to $R^6$, $R^{1a}$, $R^{2a}$, $R^{5a}$, $R^{10a}$, L, X, $X^a$, Y and Z are defined as above, in any of their stereoisomeric forms or a mixture of stereoisomeric forms in any ratio, and their salts, and their use as synthetic intermediates or starting compounds. All general explanations, specifications of embodiments and definitions of numbers and groups given above with respect to the compounds of the formula I apply correspondingly to the said intermediates and starting compounds. A subject of the invention are in particular the novel specific starting compounds and intermediates described herein. Independently thereof whether they are described as a free compound and/or as a specific salt, they are a subject of the invention both in the form of the free compounds and in the form of their salts, and if a specific salt is described, additionally in the form of this specific salt.

The compounds of the formula I and their pharmaceutically acceptable salts according to the present invention stimulate chondrogenesis and cartilage formation and induce the formation of articular cartilage matrix components and of SOX transcription factors, in particular SOX-5, SOX-6 and SOX-9, and are useful as active drug substances in pathological conditions in which chondrogenesis or cartilage formation is decreased or inappropriate or a stimulation of chondrogenesis or cartilage formation or induction of the formation of articular cartilage matrix components or SOX transcription factors is desired, such as in the therapy or prophylaxis of osteoarthritis and other diseases mentioned above or below. The activity of the compounds of the formula I can be determined in the assays described below or in other in vitro, ex vivo or in vivo assays and models known to the person skilled in the art. To allow the comparison of compound activities determined in different experiments, given the natural biological variation of the chondrogenic response between different experiments, in the determination of the activity of the compounds in assays such as those described below an internal reference compound at a constant concentration is included in all experiments, and the activity of the compounds, such as collagen type II induction or proteoglycan induction, is calculated in percent in relation to the internal reference compound at its concentration. As internal reference compound any active compound can be used, for example the compound 1-methyl-8-[4-(quinolin-2-ylmethoxy)phenoxy]-4,5-dihydro-1H-thieno[3,4-g]indazole-6-carboxamide known as TD-198946 (F. Yano et al., Ann. Rheum. Dis. 2013, 72, 748-753), or a compound of the present invention such as the compound of example 28, for example.

Because of their pharmacological properties, the compounds of the present invention are suitable for the treatment of all disorders in the progression of which a reduced or insufficient chondrogenesis or cartilage formation or level of SOX transcription factors is involved including, for example, the indications described in the introduction of the present application. The invention relates in particular to the use of a compound of the formula I or a pharmaceutically acceptable salt thereof for the treatment of degenerative joint disorders and degenerative cartilage changes including osteoarthritis, primary osteoarthritis, secondary osteoarthritis, age-related erosive hand osteoarthritis, osteoarthrosis, rheumatoid arthritis, misalignment syndromes of joints, spondylosis, chondrolysis following joint trauma or prolonged joint immobilization after meniscus or patella injuries or ligament tears and degenerative disk diseases; any type of fibrosis and inflammatory processes; pain including acute pain like pain following injuries and post-operative pain and chronic pain like pain associated with chronic musculoskeletal diseases, back pain, pain associated with osteoarthritis or rheumatoid arthritis and pain associated with inflammation; chronic disorders of the locomotor system such as inflammatory, immunologically or metabolically related acute and chronic arthritides, arthropathies, myalgias and disturbances of bone metabolism; connective tissue disorders such as collagenoses, and wound-healing disturbances; for example. The treatment of diseases such as degenerative joint disorders, degenerative cartilage changes, osteoarthritis, misalignment syndromes of joints or degenerative disk diseases, for example, can be carried out in various joints including knee, hip, shoulder, elbow and hand joints and intervertebral joints, and includes also the aspect of regeneration of the cartilage or of a meniscus in a joint and intervertebral disc regeneration, respectively.

The treatment of diseases is to be understood herein as generally meaning both the therapy of existing pathological changes or malfunctions of the organism or of existing symptoms with the aim of relief, alleviation or cure in a subject in need thereof, and the prophylaxis or prevention of pathological changes or malfunctions of the organism or of symptoms in a subject susceptible thereto and in need of such a prophylaxis or prevention, with the aim of a prevention or suppression of their occurrence or of an attenuation in the case of their occurrence. In one embodiment of the invention the treatment of diseases is the therapy of existing pathological changes or malfunctions, in another embodiment it is the prophylaxis or prevention of pathological changes or malfunctions. The treatment of diseases can occur both in acute cases and in chronic cases.

The compounds of the formula I and their pharmaceutically acceptable salts can therefore be used in animals, in particular in mammals and specifically in humans, as a pharmaceutical or medicament on their own, in mixtures with one another, or in the form of pharmaceutical compositions. A subject of the present invention also are the compounds of the formula I and their pharmaceutically acceptable salts for use as a pharmaceutical. A subject of the present invention further are pharmaceutical compositions and medicaments which comprise at least one compound of the formula I and/or a pharmaceutically acceptable salt thereof as an active ingredient, in an effective dose for the desired use, and a pharmaceutically acceptable carrier, i.e. one or more pharmaceutically innocuous, or nonhazardous, vehicles and/or excipients, and optionally one or more other pharmaceutically active compounds.

A subject of the present invention are also the compounds of the formula I and their pharmaceutically acceptable salts for use in the treatment of the diseases mentioned above or below, including the treatment of any one of the mentioned diseases, for example the treatment of degenerative joint disorders, degenerative cartilage changes, fibrosis, inflammatory processes or pain, wherein treatment of diseases comprises their therapy and prophylaxis as mentioned above, or for use as a stimulator of chondrogenesis or cartilage formation or as an inducer of SOX transcription factors. A subject of the present invention also are the use of the compounds of the formula I and their pharmaceutically acceptable salts for the manufacture of a medicament for the treatment of the diseases mentioned above or below, including the treatment of any one of the mentioned diseases, for example the treatment of degenerative joint disorders, degenerative cartilage changes, fibrosis, inflammatory processes or pain, wherein treatment of diseases comprises their therapy and prophylaxis as mentioned above, or a medicament for stimulating chondrogenesis or cartilage formation or inducing SOX transcription factors. A subject of the present invention are also methods for the treatment of the diseases mentioned above or below, including the treatment of any one of the mentioned diseases, for example the treatment of degenerative joint disorders, degenerative cartilage changes, fibrosis, inflammatory processes or pain, wherein treatment of diseases comprises their therapy and prophylaxis as mentioned above, and methods for stimulating chondrogenesis or cartilage formation or inducing SOX transcription factors, which comprise administering an efficacious amount of at least one compound of the formula I and/or a pharmaceutically acceptable salt thereof to a subject in need thereof. A subject of the present invention further are the compound 8-phenyl-9H-pyrido[3,4-b]indole and its pharmaceutically acceptable salts for use as a pharmaceutical, pharmaceutical compositions and medicaments which comprise the compound 8-phenyl-9H-pyrido[3,4-b]indole and/or a pharmaceutically acceptable salt thereof and a pharmaceutically acceptable carrier, and the compound 8-phenyl-9H-pyrido[3,4-b]indole and its pharmaceutically acceptable salts for use in the treatment of the diseases mentioned above or below, including the treatment of any one of the mentioned diseases, for example the treatment of degenerative joint disorders, degenerative cartilage changes, fibrosis, inflammatory processes or pain, wherein treatment of diseases comprises their therapy and prophylaxis as mentioned above, or for use as a stimulator of chondrogenesis or cartilage formation or as an inducer of SOX transcription factors.

The compounds of the formula I and their pharmaceutically acceptable salts, and pharmaceutical compositions and medicaments comprising them, can be administered enterally, for example by oral or rectal administration in the form of pills, tablets, lacquered tablets, coated tablets, granules, hard and soft gelatin capsules, solutions, syrups, emulsions, suspensions, aerosol mixtures or suppositories, or parenterally. Parenteral administration can be carried out, for example, intravenously, intra-articularly, intraperitoneally, intramuscularly or subcutaneously, for example by injection or Infusion, in the form solutions, suspensions, microcapsules, implants or rods or other suitable galenical forms. Administration can also be carried out topically, percutaneously or transdermally, for example, and in other ways, the preferred form of administration being depending on the particulars of the specific case. For topical administration to external tissue, such as to the skin or in the mouth, formulations such as ointments, creams, lotions, tinctures, powders, solutions, suspensions, pastes, gels, sprays, aerosols or oils can be used. Pharmaceutical formulations adapted for transdermal administration can be administered as plasters for extended, close contact with the epidermis of the recipient. In the case of ointments, the active ingredient can be employed either with a paraffinic or a water-miscible cream base, and the active ingredient can be formulated to give a cream with an oil-in-water cream base or a water-in-oil cream base.

The pharmaceutical compositions according to the invention are prepared in a manner known per se and familiar to the person skilled in the art by admixing one or more pharmaceutically acceptable inert inorganic and/or organic vehicles and excipients with one or more compounds of the formula I and/or pharmaceutically acceptable salts thereof, and bringing them into a suitable form for dosage and administration, which can then be used in human medicine or veterinary medicine. For the production of pills, tablets, coated tablets and hard gelatin capsules it is possible to use, for example, lactose, cornstarch or derivatives thereof, talc, stearic acid or its salts. For the production of gelatin capsules and suppositories fats, waxes, semisolid and liquid polyols, natural or hardened oils, for example, can be used. For the production of solutions, for example injection solutions, or of emulsions or syrups water, saline, alcohols, glycerol, polyols, sucrose, invert sugar, glucose, vegetable oils, for example, can be used, and for the production of microcapsules, implants or rods copolymers of glycolic acid and lactic acid, for example, can be used. The pharmaceutical compositions normally contain from about 0.5% to about 90% by weight of the compounds of the formula I and/or their pharmaceutically acceptable salts. The amount of the active ingredient of the formula I and/or its pharmaceutically acceptable salts in the pharmaceutical compositions normally is from about 0.1 mg to about 1000 mg, for example from about 1 mg to about 500 mg, per unit dose. Depending on the kind of the pharmaceutical composition and other particulars of the specific case, the amount may deviate from the indicated ones.

In addition to the active ingredients of the formula I and/or their pharmaceutically acceptable salts and to vehicles, or carrier substances, the pharmaceutical compositions can contain excipients, or auxiliaries or additives, such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I, and/or their pharmaceutically acceptable salts. In case a pharmaceutical composition contains two or more compounds of the formula I, the selection of the individual compounds can aim at a specific overall pharmacological profile of the pharmaceutical composition. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds.

When using the compounds of the formula I in the treatment of diseases, the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches known to the person skilled in the art. In general, in the case of a daily administration the daily dose for achieving the desired results in an adult weighing about 75 kg is from about 0.01 mg/kg to about 100 mg/kg, for example from about 0.1 mg/kg to about 50 mg/kg, such as from about 0.1 mg/kg to about 10 mg/kg, in each case in mg per kg of body weight. The daily dose can be divided, in particular in the case of the administration of relatively large amounts, into several, for example 2, 3 or 4, part administrations. In the case of intra-articular administration, which usually is carried at longer time intervals, such as weekly or bi-weekly or monthly, for example, the dose per administration in general is from about 0.1 mg per joint to about 100 mg per joint, for example from about 0.5 mg per joint to about 50 mg per joint, such as from about 1 mg per joint to about 75 mg per joint. As usual, depending on individual behavior it may be necessary to deviate upwards or downwards from the doses indicated.

The compounds of the present invention are also useful as standard or reference compounds in tests or assays involving chondrogenesis or induction of SOX transcription factors. For such use, for example in pharmaceutical research, the compounds may be provided in a commercial kit. For example, a compound of the present invention can be used as a reference in an assay to compare its known activity to a compound with an unknown activity. Furthermore, the compounds of the formula I can be used as synthesis intermediates for the preparation of other compounds, in particular of other pharmaceutically active compounds, which may be obtained from the compounds of the formula I by introduction of substituents or modification of functional groups, for example.

The following examples illustrate the present invention.

EXAMPLES

Abbreviations used are explained below or correspond to the usual conventions.

ACN acetonitrile
BDFP 1,1'-bis(diphenylphosphino)ferrocene-palladium (II) dichloride dichloromethane complex
DCM dichloromethane
DMF N,N-dimethytformamide
DMSO dimethyl sulfoxide
EA ethyl acetate
FA formic acid
HEP n-heptane
MeOH methanol
RT retention time
TFA trifluoroacetic acid
THF tetrahydrofuran When example compounds containing a basic group were purified by preparative high pressure liquid chromatography (HPLC) on reversed phase (RP) column material and, as customary, the eluent was a gradient mixture of water and acetonitrile containing an acid such as trifluoroacetic acid, they were usually obtained in part or completely in the form of their acid addition salts such as the salt with trifluoroacetic acid, depending on the details of the workup such as evaporation or lyophilization conditions. In the names in the heading of the examples and the structural formulae such a trifluoroacetic acid component of an example compound, as well as the acid component of other acid addition salts such as hydrochlorides, for example, in the form of which part of the example compounds have been isolated, is generally not specified.

Reactions were generally performed under argon as protective gas. Solvents such as dichloromethane, ethanol, dimethylformamide, methanol, tetrahydrofuran and the like were generally employed as commercially available dry solvents. "Room temperature" means a temperature of 20° C. to 25° C. Reactions under microwave irradiation were carried out in a Personal Chemistry Emrys Optimizer microwave synthesizer in vessels of capacities from 0.5 mi to 20 ml. Solvents were generally evaporated under reduced pressure at temperatures ranging from 35° C. to 45° C. on a rotary evaporator. Chromatography over silica gel was carried out manually (flash chromatography) or supported by semiautomatic cartridge systems such as Companion (CombiFlash) or Flashmaster II (Jones Chromatography). Purifications by preparative RP HPLC were generally performed with columns of a diameter of 25 mm or 30 mm and a length of 250 mm filled with RP18 silica gel of 10 μm particle size, eluting with a gradient of water and acetonitrile containing trifluoroacetic acid or hydrochloric acid.

The example compounds were generally characterized by analytical HPLC with ultraviolet detection at 220 nm and 254 nm and mass spectrometry (MS) detection with electrospray ionization (ESI) (LCUV/ESI-MS coupling; LC/MS), and by $^1$H nuclear magnetic resonance spectroscopy ($^1$H NMR). The LC/MS analyses were based on the UV chromatograms at 220 nm and 254 nm and the ion current from the mass spectrometer at different ionisation modes (e.g. ESI+, ESI−) with the help of ion extracts of the expected ion masses. $^1$H NMR spectra were recorded at 400 MHz or 500 MHz or 600 MHz in DMSO-$d_6$ as solvent at 298 K, unless specified otherwise. In the NMR characterization, the chemical shift a (in ppm) and the multiplicities (s=singlet, d=doublet, t=triplet, q=quartet, dd=doublet of doublets, br=broad) and the number of hydrogen atoms (H) of the peaks are given. In the LC/MS characterization, the HPLC method specified below, the retention time (RT) in minutes, and generally the mass-to-charge-ratio m/z of the peak of the molecular ion representing the monoisotopic mass, or of a related ion which was formed depending on the ionization mode, is given. In most cases, the ionization mode was positive electrospray ionization (ESI+), and the mass-to-charge-ratio of the ion $[M+H]^+$ is given. When no significant $[M+H]^+$ peak was obtained, the mass-to-charge-ratio of another characteristic mass signal such as $[M+2H]^{++}$ or an ion of an addition compound with a solvent molecule or $[M-H]^-$, which was formed depending on the ionization mode, such as negative electrospray ionization (ESI−) in the case of the latter ion, is given.

The particulars of the HPLC methods in the LC/MS characterization were as follows.

Method LC1
Column: Merck Chromolith FastGrad RP-18e, 2×50 mm, monolithic; flow: 2.0 ml/min; eluent A: water+0.05% TFA, eluent B: ACN+0.05% TFA; gradient: 98% A: 2% B (0.0 min) to 98% A: 2% B (0.2 min) to 2% A: 98% B (2.4 min) to 2% A: 98% B (3.2 min) to 98% A: 2% B (3.3 min) to 98% A: 2% B (4.0 min)

Method LC2
Column: Merck Chromolith FastGrad RP-18e, 2×50 mm, monolithic; flow: 2.4 ml/min; eluent A: water+0.05% TFA, eluent B: ACN+0.05% TFA; gradient: 98% A: 2% B (0.0 min) to 98% A: 2% B (0.2 min) to 2% A: 98% B (2.4 min) to 2% A: 98% B (3.2 min) to 98% A: 2% B (3.3 min) to 98% A: 2% B (4.0 min)

Method LC3
Column: Waters UPLC BEH C18, 2.1×50 mm, 1.7 μm; flow: 0.9 ml/min; temperature 55° C.; eluent A: water+0.05% FA, eluent B: ACN+0.035% FA; gradient: 95% A: 5% B (0.0 min) to 5% A: 95% B (1.1 min) to 5% A: 95% B (1.7 min) to 95% A: 5% B (1.8 min) to 95% A: 5% B (2.0 min)

Method LC4
Column: Waters UPLC BEH C18, 2.1×50 mm, 1.7 μm; flow: 0.9 ml/min; temperature 55° C.; eluent A: water+0.05% FA, eluent B: ACN+0.035% FA; gradient: 95% A: 5% B (0.0 min) to 5% A: 95% B (2.0 min) to 5% A: 95% B (2.6 min) to 95% A: 5% B (2.7 min) to 95% A: 5% B (3.0 min)

Method LC5
Column: Waters UPLC BEH C18, 2.1×50 mm, 1.7 μm; flow: 0.9 ml/min; temperature 55° C.; eluent A: water+0.05% FA, eluent B: ACN+0.035% FA; gradient: 98% A: 2% B (0.0 min) to 5% A: 95% B (2.0 min) to 5% A: 95% B (2.6 min) to 98% A: 2% B (2.7 min) to 98% A: 2% B (3.0 min)

Method LC6
Column: Waters UPLC BEH C18, 2.1×50 mm, 1.7 μm; flow: 0.9 ml/min; temperature 55° C.; eluent A: water+0.1% FA, eluent B: ACN+0.08% FA; gradient: 95% A: 5% B (0.0 min) to 5% A: 95% B (1.1 min) to 5% A: 95% B (1.7 min) to 95% A: 5% B (1.8 min) to 95% A: 5% B (2.0 min)

Method LC7
Column: Waters XBridge C18, 4.6×50 mm, 2.5 μm; flow: 1.6 ml/min; temperature 30° C.; eluent A: water+0.1% FA, eluent B: ACN+0.08% FA; gradient: 97% A: 3% B (0.0 min)

to 2% A: 98% B (18.0 min) to 2% A: 98% B (19.0 min) to 97% A: 3% B (19.5 min) to 97% A: 3% B (20.0 min)

Method LC8

Column: Waters XBridge C18, 4.6×50 mm, 2.5 µm; flow: 1.3 ml/min; temperature 30° C.; eluent A: water+0.1% FA, eluent B: ACN+0.1% FA; gradient: 97% A: 3% B (0.0 min) to 40% A: 60% B (3.5 min) to 2% A: 98% B (4.0 min) to 2% A: 98% B (5.0 min) to 97% A: 3% B (5.2 min) to 97% A: 3% B (6.5 min)

Method LC9

Column: Waters XBridge C18, 4.6×50 mm, 2.5 µm; flow: 1.7 mi/min; temperature 50° C.; eluent A: water+0.05% TFA, eluent B: ACN+0.05% TFA; gradient: 95% A: 5% B (0.0 min) to 95% A: 5% B (0.2 min) to 5% A: 95% B (2.4 min) to 5% A: 95% B (3.5 min) to 95% A: 5% B (3.6 min) to 95% A: 5% B (4.5 min)

Method LC10

Column: Waters XBridge C18, 4.6×50 mm, 2.5 µm; flow: 1.3 ml/min; eluent A: water+0.05% TFA, eluent B: ACN+0.05% TFA: gradient: 95% A: 5% B (0.0 min) to 95% A: 5% B (0.3 min) to 5% A: 95% B (3.5 min) to 5% A: 95% B (4.0 min) to 95% A: 5% B (4.5 min)

Method LC11

Column: YMC-Pack Jsphere H80, 2.1×33 mm, 4.0 µm; flow: 1.0 ml/min; eluent A: water+0.05% TFA, eluent B: ACN+0.05% TFA; gradient: 98% A: 2% B (0.0 min) to 98% A: 2% B (1.0 min) to 5% A: 95% B (5.0 min) to 5% A: 95% B (6.25 min)

Method LC12

Column: YMC-Pack Jsphere H80, 2.1×33 mm, 4.0 µm; flow: 0.9 ml/min; eluent A: water+0.05% TFA, eluent B: MeOH+0.05% TFA; gradient: 98% A: 2% B (0.0 min) to 98% A: 2% B (1.0 min) to 5% A: 95% B (5.0 min) to 5% A: 95% B (6.25 min)

Method LC13

Column: Phenomenex Luna C18, 2.0×10 mm, 3.0 µm; flow: 1.1 ml/min; room temperature; eluent A: water+0.05% TFA, eluent B: ACN; gradient: 93% A: 7% B (0.0 min) to 5% A: 95% B (1.2 min) to 5% A: 95% B (1.4 min) to 93% A: 7% B (1.45 min)

Method LC14

Column: Phenomenex Luna C18, 2.0×10 mm, 3.0 µm; flow: 1.1 ml/min; room temperature; eluent A: water+0.05% TFA, eluent B: ACN; gradient: 93% A: 7% B (0.0 min) to 5% A: 95% B (1.0 min) to 5% A: 95% B (1.45 min) to 93% A: 7% B (1.5 min)

Exemplary Procedures for the Synthesis of Intermediates

Intermediate 1.
8-Bromo-6-chloro-9H-pyrido[3,4-b]indole

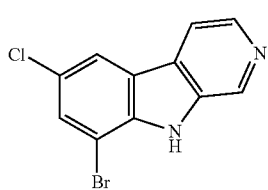 [SMILES: Clc1cc(Br)c2[nH]c3cnccc3c2c1]

a) 6-Chloro-9H-pyrido[3,4-b]indole

N-Chlorosuccinimide (9.78 g, 73.29 mmol) was added in portions with exclusion of light to a solution of norharmane hydrochloride (10.0 g, 48.86 mmol) in water (100 ml) and 1 M hydrochloric acid (100 ml). The mixture was stirred at room temperature overnight and subsequently for 2 h with cooling in ice (0° C. to 5° C.). After dilution with water (50 ml), the precipitate was filtered off with suction, washed with water and dried in a drying cabinet. 7.1 g (76%) of the title compound was obtained.

LC/MS (Method LC10): RT=2.26 min; m/z=203.1 [M+H]⁺ b) 8-Bromo-6-chloro-9H-pyrido[3,4-b]indole

6-Chloro-9H-pyrido[3,4-b]indole (0.5 g, 2.09 mmol) was placed in water (10 ml) and 1 M hydrochloric acid (10 ml). N-Bromosuccinimide (0.37 g, 2.09 mmol) was added in portions with exclusion of light. The mixture was stirred at room temperature. After 1.5 days conversion to the product was complete, as shown by reaction monitoring by LC/MS. The precipitate was filtered off with suction, washed with water and dried in a drying cabinet to yield 642 mg of the title compound in the form its hydrochloride salt.

LC/MS (Method LC10): RT=2.16 min; m/z=281.0 [M+H]⁺

Intermediate 2. 8-Bromo-6-chloro-9-cyclopropylmethyl-9H-pyrido[3,4-b]indole

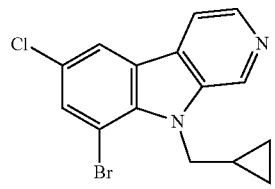 [SMILES: Clc1cc(Br)c2c(c1)c1ccncc1n2CC1CC1]

a) 6-Chloro-9-cyclopropylmethyl-9H-pyrido[3,4-b]indole

6-Chloro-9H-pyrido[3,4-b]indole (2.0 g, 9.87 mmol) was placed in DMF (40 ml) and treated with cesium carbonate (8.04 g, 24.68 mmol) and cyclopropylmethyl bromide (1.33 g, 0.965 ml, 9.87 mmol). The mixture was stirred at room temperature overnight. The mixture was admixed with water (20 ml) and extracted with EA (3×50 ml). The combined organic phases were washed with a saturated sodium chloride solution, dried over magnesium sulfate and filtered, and the solvent was removed under reduced pressure. 2.5 g (99%) of the title compound was obtained.

LC/MS (Method LC6): RT=0.93 min; m/z=257.2 [M+H]⁺ b) 8-Bromo-6-chloro-9-cyclopropylmethyl-9H-pyrido[3,4-b]indole

6-Chloro-9-(cyclopropylmethyl)-9H-pyrido[3,4-b]indole (0.5 g, 1.94 mmol) was placed in water (4.78 ml) and 1 M hydrochloric acid (4.78 ml). N-Bromosuccinimide (0.52 g, 2.92 mmol) was added in portions with exclusion of light. The mixture was stirred at room temperature overnight. Further N-bromosuccinimide (0.52 g, 2.92 mmol) was added and the mixture stirred at room temperature for 1 day, when reaction monitoring showed complete conversion to the product. The mixture was extracted with EA (3×20 ml), the combined organic phases were shaken with saturated sodium chloride solution, the organic phase was dried over magnesium sulfate and filtered, and the solvent was removed under reduced pressure. 516 mg of crude product was obtained, which was purified by preparative RP HPLC. The fractions containing the product were combined and concentrated, and the residue freeze-dried to yield 169 mg (19%) of the title compound in the form of its salt with trifluoroacetic acid.

LC/MS (Method LC6): RT=1.21 min; m/z=334.9 [M+H]$^+$

Intermediate 3. 8-Bromo-6-chloro-1-methyl-9H-pyrido[3,4-b]indole

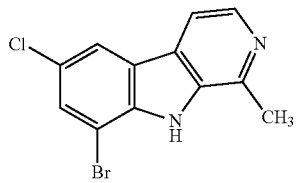

a) 6-Chloro-1-methyl-9H-pyrido[3,4-b]indole

N-Chlorosuccinimide (1.92 g, 54.32 mmol) was added in portions with exclusion of light to a solution of harmane (2.50 g, 13.72 mmol) in water (60 ml) and 1 M hydrochloric acid (60 ml). The mixture was stirred at room temperature overnight and subsequently for 2 h with cooling in ice (0 to 5° C.). Reaction monitoring by LC/MS showed complete conversion to the product. The precipitate was filtered off with suction, washed with water and dried at 50° C. in a drying cabinet to give 2.2 g (64%) of the title compound in the form of its hydrochloride.

LC/MS (Method LC10): RT=2.35 min; m/z=217.0 [M+H]$^+$ b) 8-Bromo-6-chloro-1-methyl-9H-pyrido[3,4-b]indole 6-Chloro-1-methyl-9H-pyrido[3,4-b]indole hydrochloride (10.00 g, 39.51 mmol) was placed in water (250 ml) and 1 M hydrochloric acid (250 ml). N-Bromosuccinimide (7.03 g, 39.51 mmol) was added in portions with exclusion of light. The mixture was stirred at room temperature overnight. Further N-bromosuccinimide (0.52 g, 2.92 mmol) was added and the mixture stirred at room temperature for 1 day. Reaction monitoring showed complete conversion to the product, and a fine pale yellow precipitate had formed. After cooling for 2 h in ice-water, the precipitate was filtered off with suction and dried to constant weight at 45° C. under reduced pressure to give 13.00 g (99%) of the title compound in the form of its hydrochloride.

LC/MS (Method LC11): RT=2.52 min; m/z=295.1 [M+H]$^+$

Intermediate 4. 8-Bromo-6-chloro-9-cyclopropylmethyl-1-methyl-9H-pyrido[3,4-b]indole

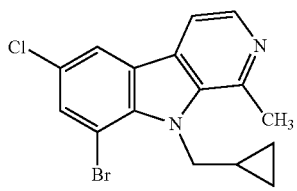 [SMILES: Cc1nccc2c3cc(Cl)cc(Br)c3n(CC3CC3)c12]

8-Bromo-6-chloro-1-methyl-9H-pyrido[3,4-b]indole (4.22 g, 12.71 mmol) was placed in DMF (40 ml) and treated with cesium carbonate (10.35 g, 31.78 mmol) and cyclopropylmethyl bromide (1.72 g, 12.71 mmol). The mixture was stirred at room temperature overnight. Reaction monitoring by LC/MS showed complete conversion to the product. The mixture was admixed with water (20 ml) and extracted with EA (3×50 ml). The combined organic phases were washed with saturated sodium chloride solution, dried over magnesium sulfate and filtered, and the solvent was removed under reduced pressure. 4.2 g of crude product was obtained, which was purified by preparative RP HPLC. The fractions containing the product were pooled and concentrated, and the residue freeze-dried to yield 2.22 g (50%) of the title compound in the form of its salt with trifluoroacetic acid.

LC/MS (Method LC6): RT=1.13 min; m/z=349.0 [M+H]$^+$

Intermediate 5. 6-Chloro-8-iodo-1-methyl-9H-pyrido[3,4-b]indole

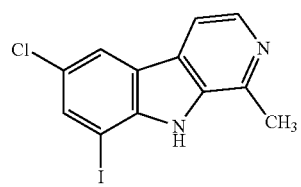 [SMILES: Cc1nccc2c1[nH]c1c(I)cc(Cl)cc12]

a) 6-Chloro-8-iodo-1-methyl-9H-pyrido[3,4-b]indole

85% phosphoric acid (155 ml) was added to 6-chloro-1-methyl-9H-pyrido[3,4-b]indole hydrochloride (13.1 g). After stirring for 30 min additional phosphoric acid (60 ml) was added. After cooling to 0° C. N-iodosuccinimide (12.8 g) was added in 3 portions within 6 h. After stirring for 16 h in the dark at room temperature further N-iodosuccinimide (3.0 g) was added. After stirring for 24 h the reaction mixture was added to a stirred mixture of ice and water (600 ml). After 30 min the precipitate was filtered off and washed with ice-water. Then 10 N sodium hydroxide solution was added to the filtrate and the pH adjusted to 10. The newly formed precipitate was filtered off with suction and combined with the first precipitate. Water was added to the combined precipitates, and the pH adjusted to 9 with 10 N sodium hydroxide solution. After stirring for 1 h, the solid was filtered off with suction, treated with acetone (250 ml) and filtered off with suction again. This procedure was repeated twice with diethyl ether, and the obtained solid was dried in vacuo at 38° C. Then the solid was dissolved in MeOH with addition of some DMF, and adsorbed to silica gel. After removal of the solvent the silica gel was given on top of a Buchner funnel filled with silica gel. The silica gel was first washed with DCM to remove impurities, and then with a mixture of DCM and MeOH (20:1). The DCM/MeOH filtrate was concentrated in vacuo and the residue was treated with diethyl ether containing some acetone. The solid was filtered off with suction and dried in vacuo to yield 10 g of the title compound.

LC/MS (Method LC13): RT=0.74 min; m/z=343.0 [M+H]$^+$

Intermediate 6. 6-Chloro-9-ethyl-8-iodo-1-methyl-9H-pyrido[3,4-b]indole

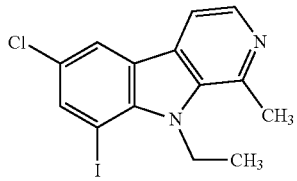

b) 6-Chloro-9-ethyl-8-iodo-1-methyl-9H-pyrido[3,4-b]indole 6-chloro-8-iodo-1-methyl-9H-pyrido[3,4-b]indole (3.00 g, 8.76 mmol) was dissolved in DMF (25 ml), and cesium carbonate (7.13 g, 21.89 mmol) and iodoethane (858 μl, 10.51 mmol) were added with stirring. After stirring for 16 h under an argon atmosphere, water and DCM were added. After phase separation the aqueous phase was extracted 3 times with DCM. The combined organic layers were washed with brine, dried over sodium sulfate and concentrated in vacuo. The residue was purified by chromatography over silica gel with DCM/MeOH (95:5) to yield 2.1 g of the title compound.

LC/MS (Method LC14): RT=0.87 min; m/z=371.1 [M+H]$^+$

Intermediate 7. 6-Bromo-8-iodo-1-methyl-9H-pyrido[3,4-b]indole

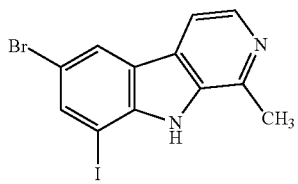

a) 6-Bromo-1-methyl-9H-pyrido[3,4-b]indole

Harmane (2 g) was suspended in 2 M hydrochloric acid (60 ml) and N-bromosuccinimide (2.15 g) was added with stirring. After stirring for 16 h the reaction mixture was set to pH 9 with 2 N sodium hydroxide solution under cooling. Then EA was added, the phases were separated, and the aqueous phase was extracted 3 times with EA. The combined organic phases were dried over sodium sulfate, filtered and concentrated in vacuo. The residue was purified by chromatography over silica gel with DCM/MeOH (gradient) to yield 1.69 g of the title compound.

LC/MS (Method LC4): RT=1.35 min; m/z=261.1 [M+H]$^+$ b) 6-Bromo-8-iodo-1-methyl-9H-pyrido[3,4-b]indole Phosphoric acid (25 ml) was added to 6-chloro-1-methyl-9H-pyrido[3,4-b]indole (1.56 g), followed by N-iodosuccinimide (1.61 g). The mixture was stirred for 16 h at room temperature in the dark. Then the mixture was adjusted to pH 9 with 10 M sodium hydroxide solution under cooling. EA was added and the phases were separated, and the aqueous phase was extracted 3 times with EA. The combined organic phases were dried over sodium sulfate, filtered and concentrated in vacuo. The residue was purified by chromatography over silica gel with HEP/EA (1:0 to 0:1, gradient) to yield 1.39 g of the title compound.

LC/MS (Method LC8): RT=3.05 min; m/z=387.0 [M+H]$^+$

Intermediate 8. 6-Bromo-9-ethyl-8-iodo-1-methyl-9H-pyrido[3,4-b]indole

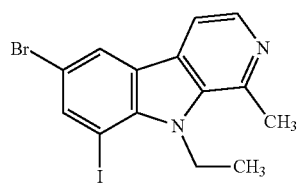 [SMILES: CCn1c2c(I)cc(Cl)cc2c2ccnc(C)c21]

6-Bromo-9-ethyl-8-iodo-1-methyl-9H-pyrido[3,4-b]indole

6-Bromo-8-iodo-1-methyl-9H-pyrido[3,4-b]indole (700 mg) was dissolved in DMF (10 ml), and cesium carbonate (1.47 g) and iodoethane (180 μl) were added with stirring. After stirring for 2 h under an argon atmosphere additional iodoethane (180 μl) was added and stirring was continued for an additional 2 h. Then water and EA were added. The phases were separated, and the aqueous phase was extracted 3 times with EA. The combined organic phases were washed with brine, dried over sodium sulfate, filtered and concentrated in vacuo. The residue was purified by chromatography over silica gel with HEP/EA (gradient)) to yield 650 mg of the title compound.

LC/MS (Method LC4): RT=1.65 min; m/z=415.0 [M+H]$^+$

Intermediate 9. 6-Chloro-8-iodo-1,9-dimethyl-9H-pyrido[3,4-b]indole

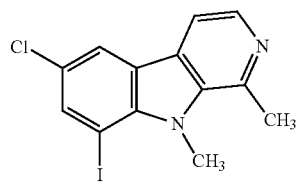 [SMILES: Cc1nccc2c3cc(Cl)cc(I)c3n(C)c12]

6-Chloro-8-iodo-1-methyl-9H-pyrido[3,4-b]indole (1 g) was dissolved in DMF (10 ml), and cesium carbonate (2.38 g) and iodomethane (220 μl) were added with stirring. After stirring for 16 h under argon atmosphere water and DCM were added. After phase separation, the aqueous phase was extracted 3 times with DCM. The combined organic phases were washed with brine, dried over sodium sulfate, filtered and concentrated in vacuo. The residue was purified by chromatography over silica gel with DCM/MeOH (gradient) to yield 440 mg of the title compound.

LC/MS (Method LC5): RT=1.38 min; m/z=357.0 [M+H]$^+$

Intermediate 10. 8-Bromo-6-chloro-9-ethyl-1-methyl-9H-pyrido[3,4-b]indole

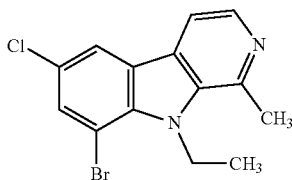 [SMILES: CCn1c2c(Br)cc(Cl)cc2c2ccnc(C)c21]

The title compound was synthesized from harmane analogously to the synthesis of intermediates 3 and 4 using bromoethane.

LC/MS (Method LC12): RT=3.32 min; m/z=323.0 [M+H]$^+$

Intermediate 11. 8-Bromo-6-chloro-9-ethyl-9H-pyrido[3,4-b]indole

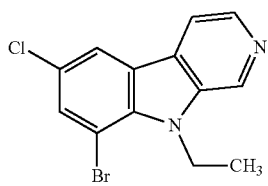 [SMILES: CCn1c2cnccc2c2cc(Cl)cc(Br)c21]

The title compound was synthesized from norharmane analogously to the synthesis of intermediates 3 and 4 using bromoethane.

LC/MS (Method LC10): RT=2.73 min; m/z=309.0 [M+H]$^+$

Intermediate 12. 8-Bromo-6-chloro-1-isopropyl-9H-pyrido[3,4-b]indole

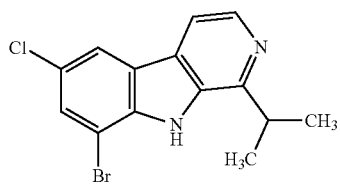 [SMILES: CC(C)c1nccc2c1[nH]c1c(Br)cc(Cl)cc12]

a) 1-isopropyl-9H-pyrido[3,4-b]indole

A catalytic amount of palladium on charcoal (ca. 100 mg) was added to a solution of 1-isopropyl-2,3,4,9-tetrahydro-1H-pyrido[3,4-b]indole (3.00 g, 14 mmol) in xylene (20 ml) and the mixture was stirred at 150° C. for 7 days. The catalyst was separated from the reaction mixture while hot by filtration through a silica gel layer, and the silica gel layer was washed with a small amount of MeOH. The combined organic phases were concentrated and afforded 2.280 g (77%) of the title compound, which was used in the next step without further purification.

LC/MS (Method LC6): RT=0.89 min; m/z=209.1 [M−H]$^−$ b) 6-Chloro-1-isopropyl-9H-pyrido[3,4-b]indole

N-Chlorosuccinimide (1.74 g, 12.00 mmol) was added in portions with exclusion of light to a solution of 1-isopropyl-9H-pyrido[3,4-b]indole (2.28 g, 13.72 mmol) in 2 M hydrochloric acid (100 ml). The mixture was stirred at room temperature overnight. Further N-chlorosuccinimide (0.5 g, 3.82 mmol) was added in portions, and the mixture stirred for 1 day. Reaction monitoring by LC/MS showed complete conversion to the product. The mixture was diluted with water (200 ml), neutralized with conc. aqueous sodium hydroxide solution and shaken with EA. The organic phase was separated, dried over magnesium sulfate and concentrated to give 2.60 g (quantitative yield) of the title compound.

LC/MS (Method LC6): RT=0.98 min; m/z=245.1 [M+H]$^+$ c) 8-Bromo-6-chloro-1-isopropyl-9H-pyrido[3,4-b]indole

N-Bromosuccinimide (2.73 g, 15.33 mmol) was added in portions with exclusion of light to a solution of 6-chloro-1-isopropyl-9H-pyrido[3,4-b]indole (2.50 g, 10.22 mmol) in 2 M hydrochloric acid (40 ml). The mixture was stirred at room temperature overnight. Reaction monitoring by LC/MS showed complete conversion to the product. The mixture was neutralized with 2 M aqueous sodium hydroxide solution and shaken with EA. The organic phase was separated, dried over magnesium sulfate and concentrated to give 3.30 g (quantitative) of the crude title compound, which was used in the next step without further purification.

LC/MS (Method LC6): RT=1.06 min; m/z=323.0 [M+H]$^+$

Intermediate 13. 8-Bromo-6-chloro-1-ethyl-9H-pyrido[3,4-b]indole

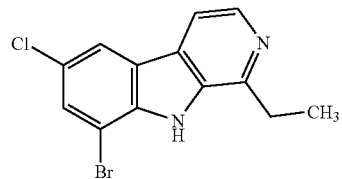 [SMILES: CCc1nccc2c1[nH]c1c(Br)cc(Cl)cc12]

The title compound was synthesized from 1-ethyl-2,3,4,9-tetrahydro-1H-pyrido[3,4-b]indole analogously to the synthesis of intermediate 12.

LC/MS (Method LC6); RT=1.04 min; m/z=309.0 [M+H]$^+$

Intermediate 14. 8-Bromo-9-but-2-ynyl-6-chloro-9H-pyrido[3,4-b]indole

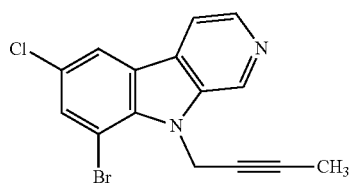 [SMILES: CC#CCn1c2cnccc2c2cc(Cl)cc(Br)c21]

8-Bromo-6-chloro-9H-pyrido[3,4-b]indole (2.0 g, 7.1 mmol) in DMF (28 ml) was treated with cesium carbonate (5.79 g, 17.76 mmol) and 1-bromo-but-2-yne (0.95 g, 7.1 mmol). The mixture was stirred at room temperature overnight. Reaction monitoring by LC/MS showed no conversion to the product. Two further additions of the 1-bromo-2-butyne compound, one equivalent each time, were made and the mixture was stirred over several days. The mixture was admixed with water (10 ml) and extracted with EA (3×50 ml). The combined organic phases were washed with saturated sodium chloride solution, dried over magnesium sulfate and filtered, and the solvent was removed under reduced pressure. The product was purified by preparative RP HPLC. The fractions containing the product were pooled and concentrated, and the residue freeze-dried. 809 mg (25%) of the title compound was obtained in the form of its salt with trifluoroacetic acid.

LC/MS (Method LC8): RT=3.74 min; m/z=333.1 [M+H]$^+$

Intermediate 15. 8-Bromo-6-chloro-9-(2,2,2-trifluoroethyl)-9H-pyrido[3,4-b]indole

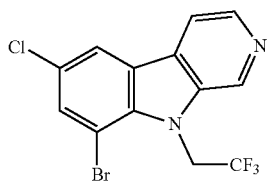 [SMILES: FC(F)(F)Cn1c2cnccc2c2cc(Cl)cc(Br)c21]

8-Bromo-6-chloro-9H-pyrido[3,4-b]indole (5.2 g, 21.75 mmol) in DMF (41 ml) was treated with cesium carbonate (17.72 g, 54.38 mmol) and 2,2,2-trifluoroethyl trifluoromethanesulfonate (5.30 g, 22.84 mmol). The mixture was stirred at room temperature overnight. Reaction monitoring by LC/MS showed complete conversion to the product. The mixture was admixed with water (20 ml) and extracted with EA (3×50 ml). The combined organic phases were washed with saturated sodium chloride solution, dried over magnesium sulfate and filtered, and the solvent was removed under reduced pressure. The crude product was purified by preparative RP HPLC. The fractions containing the product were combined and concentrated, and the residue freeze-dried. 1 g (13%) of the title compound were obtained in the form of its salt with trifluoroacetic acid.

LC/MS (Method LC2): RT=1.33 min; m/z=363.0 [M+H]$^+$

Intermediate 16. 8-Bromo-6-chloro-9-(2-methoxyethyl)-9H-pyrido[3,4-b]indole

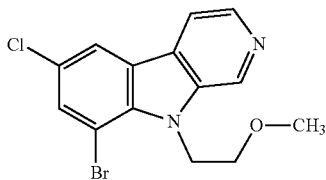 [SMILES: COCCn1c2cnccc2c2cc(Cl)cc(Br)c21]

8-Bromo-6-chloro-9H-pyrido[3,4-b]indole (1.0 g, 3.55 mmol) in DMF (10 ml) was treated with cesium carbonate (3.4 g, 17.76 mmol) and 2-bromoethyl methyl ether (0.59 g, 4.26 mmol). The mixture was treated in an ultrasonic bath for 1 h and then stirred at room temperature for 3 days. The solid was filtered off with suction, and the filtrate was concentrated. The crude product was purified by preparative RP HPLC. The fractions containing the product were combined and concentrated, and the residue freeze-dried. 0.56 g (35%) of the title compound was obtained in the form of its salt with trifluoroacetic acid.

LC/MS (Method LC8): RT=3.14 min; m/z=339.0 [M+H]$^+$

Intermediate 17. 6-Chloro-8-iodo-1,5-dimethyl-9H-pyrido[3,4-b]indole

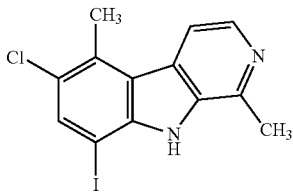 [SMILES: Cc1nccc2c1[nH]c1c(I)cc(Cl)c(C)c12]

a) 1,5-Dimethyl-9H-pyrido[3,4-b]indole

Water (150 ml) was added to 4-methyl-DL-tryptophan (1.5 g) at room temperature. Under ice cooling concentrated sulfuric acid (400 µl) and acetaldehyde (585 µl) were added. The mixture was heated to 65° C. for 1.5 h. Then acetic acid (12 ml) was added and the first portion of potassium dichromate (30 mg). After heating to reflux additional 6 portions of potassium dichromate (30 mg) were added until LC/MS control showed complete disappearance of the starting material. After cooling, a saturated sodium carbonate solution was added, followed by solid sodium carbonate to neutralise the solution. Then EA was added, the phases were separated and the aqueous phase was extracted twice with EA. The combined organic phases were dried over sodium sulfate, filtered and concentrated in vacuo to yield 677 mg of the title compound.

LC/MS (Method LC5): RT=1.03 min; m/z=197.1 [M+H]$^+$ b) 6-Chloro-1,5-dimethyl-9H-pyrido[3,4-b]indole 2 N HCl (30 ml) was added to 1,5-dimethyl-9H-pyrido[3,4-b]indole (677 mg) under stirring at room temperature, followed by N-chlorosuccinimide (517 mg). Stirring was continued for 1 h. After standing overnight the pH of the reaction mixture was adjusted to pH 9 by 10 M sodium hydroxide solution under ice cooling. Then EA was added, the phases were separated and the aqueous phase was extracted twice with EA. The combined organic phases were dried over sodium sulfate, filtered and concentrated in vacuo. The residue was purified by chromatography over silica gel with HEP/EA to yield 515 mg of the title compound.

LC/MS (Method LC5): RT=1.20 min; m/z=231.1 [M+H]$^+$ c) 6-Chloro-8-iodo-1,5-dimethyl-9H-pyrido[3,4-b]indole Phosphoric acid (18 ml) was added to 6-chloro-1,5-dimethyl-9H-pyrido[3,4-b]indole (500 mg), followed by N-iodosuccinimide (512 mg), and the mixture stirred for 2.5 h at room temperature in the dark. Then further N-iodosuccinimide (51 mg) was added and stirring was continued for 20 h. The reaction mixture was poured into ice water and the pH adjusted to 9 by 10 M sodium hydroxide solution. The precipitate was filtered off with suction and EA added to the filtrate. The phases were separated and the organic layer dried over sodium sulfate and concentrated in vacuo. The residue was purified by chromatography over silica gel with DCM/ethanol (gradient). The fractions containing the product were combined and concentrated, and the residue freeze-dried to yield 683 mg of the title compound.

LC/MS (Method LC5): RT=1.38 min; m/z=356.9 [M+H]$^+$

Intermediate 18. 8-Bromo-1,6-dimethyl-9H-pyrido[3,4-b]indole

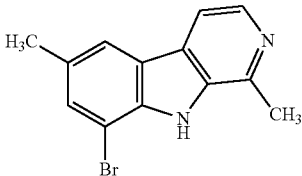

a) N-(2-(7-Bromo-5-methyl-1H-indol-3-yl)ethyl)acetamide 2-(7-Bromo-5-methyl-1H-indol-3-yl)ethylamine hydrochloride (3.6 g) was converted into the free base by treatment with 1 M sodium hydroxide solution and DCM, separation of the phases, extraction of the aqueous phase with DCM, and drying of the combined DCM phases over sodium sulfate, filtration and concentration in vacuo. The amine was suspended in dry DCM (60 ml), and triethylamine (2.42 ml) was added. After cooling of the mixture to −40° C., acetyl chloride (1.03 ml) was added with stirring. After 30 min at −30° C. the reaction mixture was poured into ice water (100 ml). The DCM was removed in vacuo, and the remaining aqueous phase was extracted three times with EA. The combined EA phases were dried over sodium sulfate, filtrated and concentrated in vacuo to yield 4.74 g of the crude title compound.

LC/MS (Method LC5): RT=1.74 min; m/z=293.2 [M−H]$^−$ b) 8-Bromo-1,6-dimethyl-4,9-dihydro-3H-pyrido[3,4-b]indole N-(2-(7-Bromo-5-methyl-1H-indol-3-yl)ethyl)acetamide (4.27 g) was dissolved in dry ACN (50 ml), and phosphorus oxychloride (6.62 ml) and phosphorus pentoxide (14.38 g) were added. After heating to 80° C. the reaction mixture was stirred at this temperature for 2 h. Then ice was added and the pH of the mixture was adjusted to 9 with 2 M sodium hydroxide solution. This aqueous mixture was extracted with EA (three times), and the combined EA phases were dried, filtered and concentrated in vacuo. The residue was dissolved in DCM, and the organic phase was extracted with a saturated sodium hydrogencarbonate solution, dried, filtered and concentrated in vacuo to yield 2.1 g of the title compound. The original aqueous phase was additionally extracted with DCM (three times), and the combined DCM phases were dried, filtered and concentrated in vacuo to yield an additional 0.91 g of the title compound.

LC/MS (Method LC8): RT=2.81 min; m/z=277.1 [M+H]$^+$ c) 8-Bromo-1,6-dimethyl-9H-pyrido[3,4-b]indole 8-Bromo-1,6-dimethyl-4,9-dihydro-3H-pyrido[3,4-b]indole (3 g) was suspended in nitrobenzene (25 ml) and heated to 220° C. After 30 min the reaction mixture was cooled to room temperature and purified by chromatography over silica gel, first with HEP, then with DCM/MeOH 9:1. The fractions containing the product were combined and concentrated in vacuo. The residue was subject to a further chromatography over silica gel with DCM/MeOH (gradient). The fractions containing the product combined and concentrated in vacuo to yield 1 g of the title compound.

LC/MS (Method LC5): RT=1.44 min; m/z=275.1 [M+H]$^+$

Intermediate 19. 8-Bromo-9-ethyl-1,6-dimethyl-9H-pyrido[3,4-b]indole

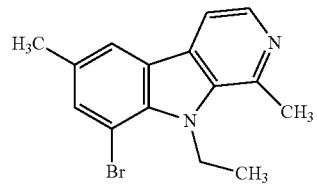

8-Bromo-1,6-dimethyl-9H-pyrido[3,4-b]indole (1 g) was dissolved in DMF (8 ml), and cesium carbonate (2.96 g) and iodoethane (350 µl) were added with stirring. After stirring for 3 h under an argon atmosphere, water and EA were added. The phases were separated and the aqueous phase was extracted 3 times with EA. The combined organic phases were washed with brine, dried over sodium sulfate and concentrated in vacuo. The residue was purified by chromatography over silica gel with DCM/MeOH to yield: 740 mg of the title compound.

LC/MS (Method LC5): RT=1.59 min; m/z=303.2 [M+H]$^+$

Intermediate 20. 6-Bromo-8-iodo-1,3-dimethyl-9H-pyrido[3,4-b]indole

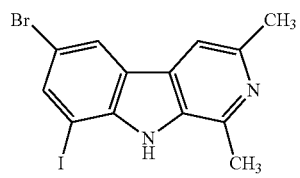 [SMILES: Cc1cc2c([nH]c3c(I)cc(Br)cc32)c(C)n1]

a) 1-(1H-indol-3-yl)propan-2-one

Under argon 2-(1H-indol-3-yl)-N-methoxy-N-methylacetamide (3.00 g, 13.75 mmol) was dissolved in THF (60 ml) and the solution cooled to 0° C. A methylmagnesium bromide solution in THF (27.49 ml, 27.49 mmol) was slowly added with stirring. After 2 h a second portion of methylmagnesium bromide solution (27.49 ml, 27.49 mmol) and after 3 h a third portion of methylmagnesium bromide solution (27.49 ml, 27.49 mmol) were added. Then an aqueous ammonium chloride solution was added, followed by EA. The phases were separated, and the organic phase was washed with water and brine, dried, filtered and concentrated in vacuo. The residue was purified by chromatography over silica gel with HEP/EA (gradient) to yield 2.35 g of the title compound.

LC/MS (Method LC5): RT=1.56 min; m/z=174.1 [M+H]$^+$ b) 1-(2-Acetyl-1H-indol-3-yl)propan-2-one

Under an argon atmosphere 1-(1H-indol-3-yl)propan-2-one (2.34 g, 13.5 mmol) was dissolved in diethyl ether (35 ml). The solution was slowly added to zinc chloride (2.76 g, 20.26 mmol) in diethyl ether (50 ml) with stirring at 0° C. Stirring was continued for 30 min and then acetyl chloride (1.92 ml, 27.02 mmol) was added. After stirring for 3 h, ice water was added, followed by an aqueous ammonium chloride solution and EA. The phases were separated, and the organic phase was washed with saturated sodium hydrogencarbonate solution and brine, dried over sodium sulfate, filtered and concentrated in vacuo. The residue was purified by chromatography over silica gel with DCM/MeOH (gradient) to yield 1.39 g of the title compound.

LC/MS (Method LC): RT=1.58 min; m/z=216.1 [M+H]$^+$ c) 1,3-Dimethyl-9H-pyrido[3,4-b]indole 1-(2-Acetyl-1H-indol-3-yl)propan-2-one (1.38 g, 6.41 mmol) was dissolved in acetic acid (15 ml) and ammonium acetate (988 mg) was added. After stirring for 1 h at 60° C. the reaction mixture was cooled to 0° C. in an ice bath, the pH was set to 9 with 2 M sodium hydroxide solution, and the mixture was extracted three times with DCM. The combined organic phases were dried over sodium sulfate, filtered and concentrated in vacuo. The residue was purified by chromatography over silica gel with DCM/MeOH (gradient) to yield 810 mg of the title compound.

LC/MS (Method LC5): RT=1.06 min; m/z=197.1 [M+H]$^+$ d) 6-Bromo-1,3-dimethyl-9H-pyrido[3,4-b]indole

2 N Hydrochloric acid (35 ml) was added to 1,3-dimethyl-9H-pyrido[3,4-b]indole (812 mg, 4.14 mmol) under stirring at room temperature, followed by N-bromosuccinimide (810 mg, 4.55 mmol). Stirring was continued for 16 h. Then the pH of the reaction mixture was adjusted to pH 9 with 10 M sodium hydroxide solution under ice cooling, EA was added, the phases were separated, and the aqueous phase was extracted twice with EA. The combined organic phases were dried over sodium sulfate, filtered and concentrated in vacuo to yield 1.17 g of the title compound.

e) 6-Bromo-8-iodo-1,3-dimethyl-9H-pyrido[3,4-b]indole

Phosphoric acid (18 ml) was added to 6-bromo-1,3-dimethyl-9H-pyrido[3,4-b]indole (1.14 g, 4.14 mmol), followed by N-iodosuccinimide (1.05 g, 4.56 mmol), and the reaction mixture stirred overnight at room temperature in the dark. Then the mixture was poured into ice water and the pH adjusted to 9 with 10 M sodium hydroxide solution. The precipitate was filtered off with suction, and EA was added to the filtrate. The phases were separated and the aqueous layer was extracted three times with EA. The precipitate was stirred with EA for 15 min, filtered off with suction and washed with further EA. The combined EA phases solutions were washed with brine, dried over sodium sulfate, filtered and concentrated in vacuo. The residue was purified by chromatography over silica gel with HEP/EA (gradient) to yield 480 mg of the title compound.

LC/MS (Method LC8): RT=3.25 min; m/z=400.9 [M+H]$^+$

Intermediate 21. 6-Bromo-9-ethyl-8-iodo-1,3-dimethyl-9H-pyrido[3,4-b]indole

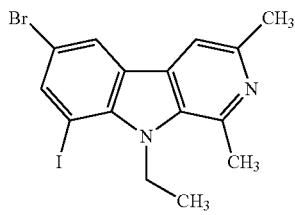

6-Bromo-8-iodo-1,3-dimethyl-9H-pyrido[3,4-b]indole (475 mg, 1.18 mmol) was dissolved in DMF (5 ml), and cesium carbonate (965 mg) and iodoethane (114 μl) were added with stirring. After stirring for 16 h under an argon atmosphere, water and DCM were added. The phases were separated, and the aqueous phase was extracted 3 times with DCM. The combined organic phases were washed with brine, dried over sodium sulfate and concentrated in vacuo. The residue was purified by chromatography over silica gel with DCM/MeOH (gradient) to yield 470 mg of the title compound.

LC/MS (Method LC5): RT=1.66 min: m/z=428.9 [M+H]$^+$

Intermediate 22. 8-Bromo-6-chloro-9-(3-methyloxetan-3-ylmethyl)-9H-pyrido[3,4-b]indole

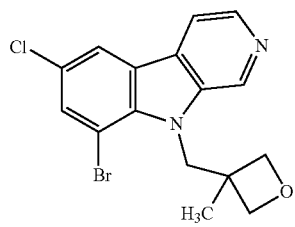 [SMILES: CC1(Cn2c3cnccc3c3cc(Cl)cc(Br)c32)COC1]

a) 2-Bromo-4-chloro-6-(3-fluoropyridin-4-yl)aniline 2,6-Dibromo-4-chloroaniline (6.5 g) was dissolved in a mixture of DME (180 mi) and water (60 mi). After addition of sodium carbonate (9.66 g) the flask was flushed with argon and the mixture was heated to reflux. 3-Fluoro-4-(4,4,5,5-tetramethyl-1,3,2-dioxaborolan-2-yl)pyridine (5.13 g) and BDFP (1.86 g) were suspended in dry DMF (40 mi) and added to the reaction mixture via a syringe pump over 5 h. After 2 h further BDFP (0.186 g) was added separately to the reaction mixture. When the addition was finished the mixture was cooled, filtered and concentrated in vacuo, and EA and a saturated sodium hydrogencarbonate solution were added to the residue. The phases were separated, the organic phase was washed with brine, dried over sodium sulfate, filtered and concentrated in vacuo. The residue was purified by chromatography over silica gel with HEP/EA (1:0 to 2:1). 2.02 g of the title compound was obtained.

LC/MS (Method LC5): RT=1.95 min; m/z=301.0 [M+H]$^+$ b) 2-Bromo-4-chloro-6-(3-fluoropyridin-4-yl)-N-(3-methyloxetan-3-ylmethyl)aniline 2-Bromo-4-chloro-6-(3-fluoropyridin-4-yl)aniline (500 mg) was dissolved in DMF (10 mi), and cesium hydroxide (750 mg) was added. After flushing with argon 3-bromomethyl-3-methyloxetane (330 mg) was added and the reaction mixture was stirred for 64 h at room temperature. Then a saturated sodium hydrogencarbonate solution and EA were added to the mixture. The phases were separated and the aqueous phase was extracted three times with EA. The combined organic phases were washed with brine, dried over sodium sulfate, filtered and concentrated in vacuo. The residue was purified by chromatography over silica gel with HEP/EA (gradient) to yield 284 mg of the title compound and 235 mg of 8-bromo-6-chloro-9-(3-methyloxetan-3-ylmethyl)-9H-pyrido[3,4-b]indole (compound of step c)).

LC/MS (Method LC5): RT=2.04 min; m/z=385.1 [M+H]$^+$ c) 8-Bromo-6-chloro-9-(3-methyloxetan-3-ylmethyl)-9H-pyrido[3,4-b]indole

2-Bromo-4-chloro-6-(3-fluoropyridin-4-yl)-N-(3-methyloxetan-3-ylmethyl)aniline (282 mg) was dissolved in THF (20 mi), flushed with argon, and a lithium bis(trimethylsilyl)amide solution (0.73 mi, 0.73 mmol in THF) was added with stirring. After 2 h further lithium bis(trimethylsilyl)amide solution (0.73 mi) was added, and stirring was continued for 16 h. Then a saturated ammonium chloride solution was added, followed by EA, and the phases were separated. The organic phase was washed with a saturated sodium hydrogencarbonate solution and brine, dried over sodium sulfate, filtered and concentrated in vacuo. The residue was purified by chromatography over silica gel with HEP/EA (gradient) to yield 176 mg of the title compound.

LC/MS (Method LC5): RT=1.63 min; m/z=365.1 [M+H]$^+$

Exemplary procedures for the synthesis of compounds of the formula I

Example 1. 6-Chloro-9-ethyl-8-pyridin-3-yl-9H-pyrido[3,4-b]indole

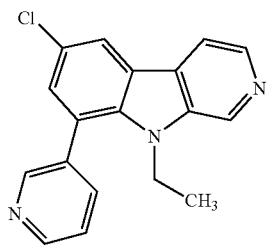 [SMILES: CCn1c2cnccc2c2cc(Cl)cc(-c3cccnc3)c21]

Tetrakis(triphenylphosphine)palladium(0) (40.45 mg) was added to a solution of 8-bromo-6-chloro-9-ethyl-pyrido[3,4-b]indole (0.31 g, 1 mmol) in degassed toluene (5 ml) under an argon atmosphere in a 25 ml two-necked flask with reflux condenser. The mixture was stirred for 10 min at room temperature, then treated with a solution of 3-pyridineboronic acid (147.5 mg, 1.2 mmol) in ethanol and an aqueous sodium carbonate solution (2 M, 0.7 ml), and stirred for 8 h at 100° C. After addition of water (10 ml) the mixture was extracted with EA (3×20 ml). The combined organic layers were washed with brine, dried over potassium sulfate, filtered and concentrated in vacuo. The remaining solid was treated with ACN/TFA (9:1) and an insoluble portion filtered off. The filtrate was concentrated and the residue purified by preparative RP HPLC. The fractions containing the product were combined and lyophilized to yield 65 mg of the title compound in the form of its salt with trifluoroacetic acid. LC/MS (Method LC10): RT=2.15 min; m/z=308.0 [M+H]$^+$

Example 2. 6-Chloro-8-(1-(pyridin-3-ylmethyl)-1H-pyrazol-4-yl)-9-(2,2,2-trifluoroethyl)-9H-pyrido[3,4-b]indole

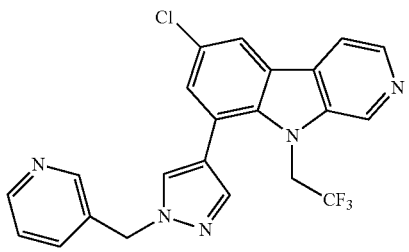 [SMILES: FC(F)(F)Cn1c2cnccc2c2cc(Cl)cc(-c3cnn(Cc4cccnc4)c3)c21]

Degassed DME (25 ml) and degassed water (8 ml) were charged in a 25 ml microwave reaction flask under argon. 8-Bromo-6-chloro-9-(2,2,2-trifluoroethyl)-9H-pyrido[3,4-b]indole (500 mg, 1.38 mmol), sodium carbonate (583 mg, 5.50 mmol), 1-pyridin-3-ylmethyl-1H-pyrazole-4-boronic acid pinacol ester (588 mg, 2.06 mmol), and BDFP (224 mg, 0.28 mmol) were added, and the mixture was treated in a microwave device at 130° C. for 11 min. The reaction mixture was concentrated and the residue purified by preparative RP HPLC. 510 mg (67%) of the title compound was obtained in the form of its salt with trifluoroacetic acid.

LC/MS (Method LC3): RT=1.08 min; m/z=442.0 [M+H]$^+$

Example 3. 9-(But-2-ynyl)-6-chloro-8-(2,6-dichloropyridin-3-yl)-9H-pyrido[3,4-b]indole

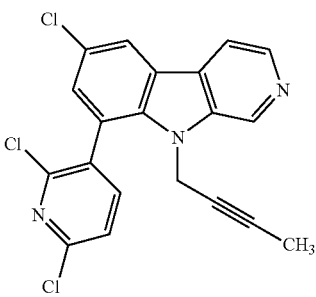 [SMILES: CC#CCn1c2cnccc2c2cc(Cl)cc(-c3ccc(Cl)nc3Cl)c21]

8-Bromo-9-but-2-ynyl-6-chloro-pyrido[3,4-b]indole (385 mg, 0.86 mmol), cesium carbonate (560 mg, 1.72 mmol), 2,6-dichloropyridin-3-boronic acid pinacol ester (471 mg, 1.72 mmol) and BDFP (201 mg. 0.25 mmol) were reacted and the reaction mixture worked-up analogously as described for the compound of example 47 to yield 84 mg (16%) of the title compound in the form of its salt with trifluoroacetic acid.

LC/MS (Method LC12): RT=3.62 min; m/z=400.1 [M+H]$^+$

Example 4. 2-(6-Chloro-8-(2,6-dichloropyridin-3-yl)-9H-pyrido[3,4-b]indol-9-yl)acetonitrile

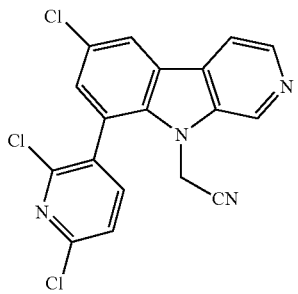 [SMILES: N#CCn1c2cnccc2c2cc(Cl)cc(-c3ccc(Cl)nc3Cl)c21]

6-Chloro-8-(2,6-dichloropyridin-3-yl)-9H-pyrido[3,4-b]indole (324 mg, 0.7 mmol) was placed in DMF (2 ml) and treated with potassium carbonate (242 mg, 1.75 mmol) and bromoacetonitrile (85 mg, 0.7 mmol). The mixture was stirred at room temperature overnight, then admixed with water (5 ml) and extracted with EA (3×10 mi). The combined organic phases were washed with a saturated sodium chloride solution, dried over magnesium sulfate and filtered, and the solvent was removed under reduced pressure. The crude product was purified by preparative RP HPLC. The fractions containing the product were pooled, concentrated and freeze-dried. 36 mg (10%) of the title compound was obtained in the form of its salt with trifluoroacetic acid.

LC/MS (Method LC6): RT=0.99 min; m/z=387.1 [M+H]⁺

Example 5. 6-Bromo-9-ethyl-1-methyl-8-(1-pyridin-3-ylmethyl-1H-pyrazol-4-yl)-9H-pyrido[3,4-b]indole

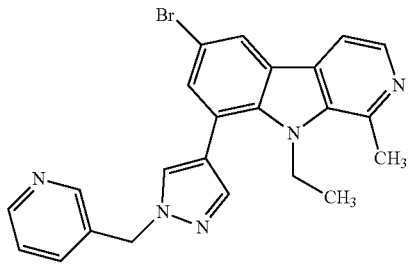 [SMILES: CCn1c2c(-c3cnn(Cc4cccnc4)c3)cc(Br)cc2c2ccnc(C)c21]

6-Bromo-9-ethyl-8-iodo-1-methyl-9H-pyrido[3,4-b]indole (200 mg) was dissolved in DME (6 ml) and water (2 ml) in a microwave vessel, and sodium carbonate (204 mg), 3-((4-(4,4,5,5-tetramethyl-1,3,2-dioxaborolan-2-yl)-1H-pyrazol-1-yl)methyl)pyridine (137 mg) and BDFP (79 mg) were added. The mixture was treated for 10 min at 100° C. in a microwave oven. Then further 3-((4-(4,4,5,5-tetramethyl-1,3,2-dioxaborolan-2-yl)-1H-pyrazol-1-yl)methyl)pyridine (69 mg) was added and the mixture again treated for 10 min at 100° C. in a microwave oven. After cooling the mixture was filtered and the filtrate concentrated in vacuo. After addition of a saturated sodium hydrogencarbonate solution the mixture was extracted three times with DCM. The combined organic phases were dried over sodium sulfate, filtered and concentrated in vacuo. After preparative RP HPLC the fractions containing the product were combined and lyophilized. 145 mg of the title compound were obtained in the form of its salt with trifluoroacetic acid. After addition of a saturated sodium hydrogencarbonate solution to 60 mg of this salt the mixture was extracted three times with DCM. The combined organic phases were dried over sodium sulfate, filtered and concentrated in vacuo. The residue was treated with water and some ACN added. After lyophilization 48 mg of the title compound were obtained.

LC/MS (Method LC5): RT=1.27 min; m/z=446.2 [M+H]⁺

Examples 6 and 7. 6-Chloro-9-ethyl-1-methyl-8-[1-(2-methyl-pyridin-3-ylmethyl)-2H-pyrazol-3-yl]-9H-pyrido[3,4-b]indole and 6-chloro-9-ethyl-1-methyl-8-[2-(2-methyl-pyridin-3-ylmethyl)-1H-pyrazol-3-yl]-9H-pyrido[3,4-b]indole 6-Chloro-9-ethyl-1-methyl-8-(1H-pyrazol-3-yl)-9H-pyrido[3,4-b]indole (150 mg) was dissolved in dry DMF (3 ml) in a microwave vessel and cesium carbonate (470 mg) and 3-(bromomethyl)-2-methylpyridine hydrochloride (161 mg) were added with stirring. After treating this mixture for 1 h at 100° C. in a microwave oven the mixture was cooled and further 3-(bromomethyl)-2-methylpyridine hydrochloride (54 mg) was added. After further 1.5 h at 100° C. in the microwave oven the mixture was cooled, filtered and concentrated in vacuo. After addition of a saturated sodium hydrogencarbonate solution the mixture was extracted four times with DCM. The combined organic phases were dried over sodium sulfate, filtered and concentrated in vacuo. After preparative RP HPLC the fractions containing each of the two isomeric products were combined and lyophilized.

Example 6. 6-Chloro-9-ethyl-1-methyl-8-[1-(2-methyl-pyridin-3-ylmethyl)-1H-pyrazol-3-yl]-9H-pyrido[3,4-b]indole

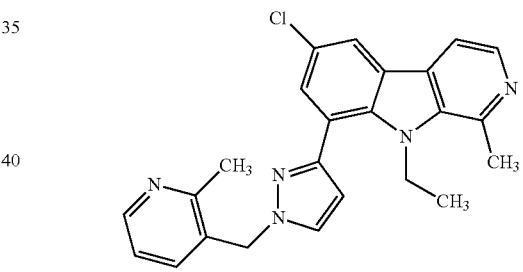

91 mg of the title compound were obtained in the form of its salt with trifluoroacetic acid, of which 60 mg were treated with sodium hydrogencarbonate as described in example 5 to yield 41 mg of the free base.

LC/MS (Method LC4): RT=1.16 min; m/z=416.2 [M+H]⁺

Example 7. 6-Chloro-9-ethyl-1-methyl-8-[2-(2-methyl-pyridin-3-ylmethyl)-2H-pyrazol-3-yl]-9H-pyrido[3,4-b]indole

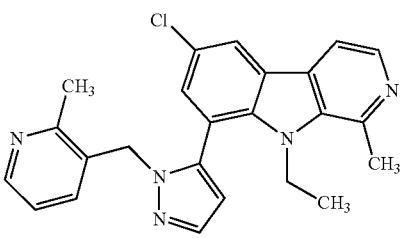 [SMILES: CCn1c2c(-c3ccnn3Cc3cccnc3C)cc(Cl)cc2c2ccnc(C)c21]

69 mg of the title compound were obtained in the form of its salt with trifluoroacetic acid, of which 51 mg were treated with sodium hydrogencarbonate as described in example 5 to yield 24 mg of the free base.

LC/MS (Method LC4): RT=1.16 min; m/z=416.2 [M+H]$^+$

Example 8. 6-Chloro-1,5-dimethyl-8-[4-(3-methyl-oxetan-3-ylmethoxy)-phenyl]-9H-pyrido[3,4-b]indole

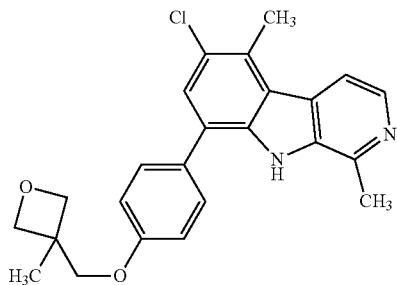 [SMILES: Cc1nccc2c1[nH]c1c(-c3ccc(OCC4(C)COC4)cc3)cc(Cl)c(C)c12]

The title compound was synthesized analogously to the synthesis of the compound of example 27 in two microwave vessels. 170 mg of 6-chloro-8-iodo-1,5-dimethyl-9H-pyrido[3,4-b]indole and 116 mg of 4-(3-methyloxetan-3-ylmethoxy)-phenylboronic acid were used in each run. The reaction mixture was treated for 10 min at 100° C. in a microwave oven. After HPLC purification the fractions containing the product were combined and concentrated to remove the ACN, and then neutralised with a saturated sodium hydrogencarbonate solution. The mixture was extracted twice with EA and the combined organic phases were dried over sodium sulfate, filtered and concentrated in vacuo. The residue was treated with ethanol and water to form a milky suspension which was stirred for 1 h. Then the slurry was concentrated in vacuo and dried in high vacuum overnight. 190 mg of the title compound was obtained.

LC/MS (Method LC5): RT=1.56 min; m/z=407.1 [M+H]$^+$

Example 9. 6-Chloro-8-(2,5-dimethyl-2H-pyrazol-3-yl)-9-ethyl-1-methyl-9H-pyrido[3,4-b]indole

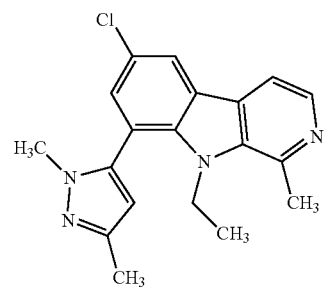 [SMILES: CCn1c2c(-c3cc(C)nn3C)cc(Cl)cc2c2ccnc(C)c21]

6-Chloro-9-ethyl-8-iodo-1-methyl-9H-pyrido[3,4-b]indole (320 mg) was dissolved in a mixture of DME (9 ml) and water (3 ml). After addition of sodium carbonate (370 mg) the reaction mixture was flushed with argon. After heating to reflux, 1,3-dimethyl-5-(4,4,5,5-tetramethyl-1,3,2-dioxaborolan-2-yl)-1H-pyrazole (192 mg) and BDFP (70 mg) in dry DMF (3 ml) were added to the reaction mixture via a syringe pump over 4 h. After 1 h an extra portion of 7 mg of BDFP was added to the reaction mixture. When the addition via the syringe pump was finished, the mixture was cooled, filtered and concentrated in vacuo. The crude product was first purified by chromatography over silica gel with DCM/MeOH (gradient) and then by preparative RP HPLC. The fractions containing the product were combined and lyophilized. 187 mg of the title compound were obtained in the form of its salt with trifluoroacetic acid. After addition of a saturated sodium hydrogencarbonate solution to 157 mg of this salt the mixture was extracted three times with DCM. The combined organic layers were dried over sodium sulfate, filtered and concentrated in vacuo to yield 80 mg of the title compound.

LC/MS (Method LC5): RT=1.40 min; m/z=339.2 [M+H]$^+$

Example 10. 2-(4-[6-Chloro-9-(2,2,2-trifluoroethyl)-9H-pyrido[3,4-b]indol-8-yl]pyrazol-1-yl)ethanol

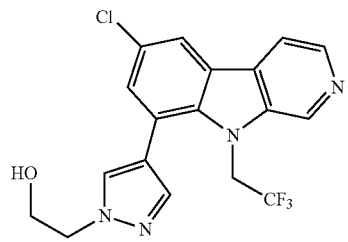 [SMILES: OCCn1cc(-c2cc(Cl)cc3c4ccncc4n(CC(F)(F)F)c23)cn1]

2-(4-(6-Chloro-9-(2,2,2-trifluoroethyl)-9H-pyrido[3,4-b]indol-8-yl)-pyrazol-1-yl]-ethyl acetate (238.1 mg, 0.55 mmol) was dissolved in MeOH (4 ml) and 2 equivalents of sodium methoxide (25% solution in MeOH) was added. The reaction mixture was stirred for 2 h at room temperature. The solvent was removed in vacuo and the residue was purified by HPLC. The obtained product was dissolved in EA, washed with a saturated sodium hydrogencarbonate solution, and the organic phase was dried and concentrated in vacuo. The residue was recrystallized from HEP/EA to yield 72.5 mg of the title compound. LC/MS (Method LC4): RT=1.32 min; m/z=395.3 [M+H]$^+$ Example 11. 6-Chloro-8-(1-phenyl-1H-pyrazol-4-yl)-9-(2,2,2-trifluoroethyl)-9H-pyrido[3,4-b]indole

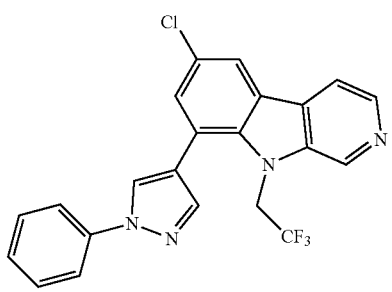 [SMILES: FC(F)(F)Cn1c2cnccc2c2cc(Cl)cc(-c3cnn(-c4ccccc4)c3)c21]

6-Chloro-8-(1H-pyrazol-4-yl)-9-(2,2,2-trifluoroethyl)-9H-pyrido[3,4-b]indole (130 mg) was dissolved in dry DMF (10 ml), phenylboronic acid (68 mg), copper(II) acetate (76 mg) and pyridine (66 mg) were added and the resulting mixture was stirred for 2 h. After standing overnight at room temperature the mixture was filtered and concentrated in vacuo. The residue was purified by RP HPLC. The fractions containing the product were combined and lyophilized. 41 mg of the title compound were obtained in the form of its salt with trifluoroacetic acid.

LC/MS (Method LC4): RT=1.77 min; m/z=427.2 [M+H]$^+$

Example 12. tert-Butyl 4-(6-chloro-9-(2,2,2-trifluoroethyl)-9H-pyrido[3,4-b]indol-8-yl)-1H-pyrazole-1-carboxylate

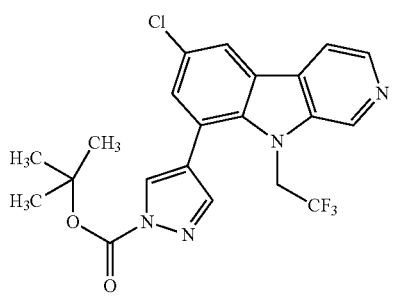 [SMILES: CC(C)(C)OC(=O)n1cc(-c2cc(Cl)cc3c4ccncc4n(CC(F)(F)F)c23)cn1]

6-Chloro-8-(1H-pyrazol-4-yl)-9-(2,2,2-trifluoroethyl)-9H-pyrido[3,4-b]indole (94.0 mg, 0.27 mmol) was dissolved in dry DCM (5 ml) and N-ethyl-diisopropylamine (34.64 mg, 0.27 mmol, 50.0 µl), di-tert-butyl dicarbonate (58.49 mg, 0.27 mmol) and 4-dimethylaminopyridine (3.27 mg, 30.0 µmol) were added. The reaction mixture was stirred 2 h at room temperature. Then additional 0.5 equivalents each of N-ethyl-diisopropylamine, di-tert-butyl dicarbonate and 4-dimethylaminopyridine were added, and the reaction mixture was stirred overnight at room temperature. To the reaction mixture water was added, the organic phase was separated, dried, and the solvent was removed in vacuo. The residue was purified by MPLC with HEP/EA. 68.0 mg of the title compound were obtained.

LC/MS (Method LC6): RT=1.24 min: m/z=451.0 [M+H]$^+$

Example 13. 6-Chloro-1-methyl-8-[4-(2-(1H-pyrazol-1-yl)ethoxy)-phenyl]-9H-pyrido[3,4-b]indole

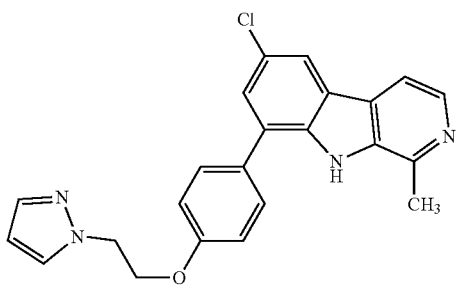 [SMILES: Cc1nccc2c1[nH]c1c(-c3ccc(OCCn4cccn4)cc3)cc(Cl)cc12]

A microwave reaction vessel was charged with 6-chloro-8-iodo-1-methyl-9H-pyrido[3,4-b]indole (250 mg), sodium carbonate (310 mg), 4-[2-(1H-pyrazol-1-yl)ethoxy]-benzeneboronic acid pinacol ester (229 mg), BDFP (119 mg), DME (7.5 ml) and water (2.5 ml). After 10 min at 100° C. in a microwave oven the reaction mixture was filtered and a saturated solution of sodium hydrogencarbonate and DCM were added to the filtrate. After phase separation the aqueous phase was extracted twice with DCM. The combined DCM phases were dried over sodium sulphate, filtered and concentrated in vacuo. The residue was purified by RP HPLC. The fractions containing the product were combined, the ACN was removed in vacuo and the remaining aqueous solution was lyophilized. The residue was treated with a saturated solution of sodium hydrogencarbonate and DCM. After phase separation the aqueous phase was extracted twice with DCM. The combined DCM phases were dried over sodium sulphate, filtered and concentrated in vacuo to yield 207 mg of the title compound.

LC/MS (Method LC5): RT=1.63 min; m/z=403.2 [M+H]$^+$

Example 14. 8-(4-Methoxy-phenyl)-1,6-dimethyl-9H-pyrido[3,4-b]indole

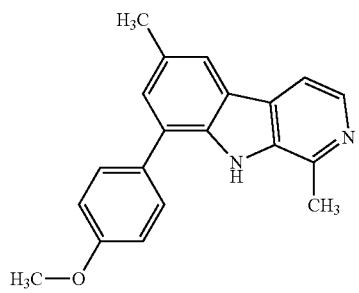 [SMILES: COc1ccc(-c2cc(C)cc3c2[nH]c2c(C)nccc23)cc1]

8-Bromo-1,6-dimethyl-9H-pyrido[3,4-b]indole (200 mg) was dissolved in a mixture of DME (9 ml) and water (3 ml). After addition of sodium carbonate (310 mg) the reaction mixture was flushed with argon. After heating to reflux a mixture of 4-methoxyphenylboronic acid pinacol ester (255 mg) and BDFP (119 mg) in dry DMF (4 ml) were given to the reaction mixture via a syringe pump over 3 h. After 1 h an extra portion of 59 mg of BDFP was added to the reaction mixture. When the addition via the syringe pump was finished, the mixture was cooled, filtered and concentrated in vacuo. The crude product was dissolved in EA, and the EA phase was washed with a saturated sodium hydrogencarbonate solution, dried, filtered and concentrated in vacuo. The residue was purified by a preparative RP HPLC. The fractions containing the product were combined and lyophilized. 30 mg of the title compound were obtained in the form of its salt with trifluoroacetic acid. LC/MS (Method LC5): RT=1.63 min; m/z=303.2 [M+H]$^+$ Example 15. 9-Ethyl-1,6-dimethyl-8-(1-methyl-1H-pyrazol-4-yl)-9H-pyrido[3,4-b]indole

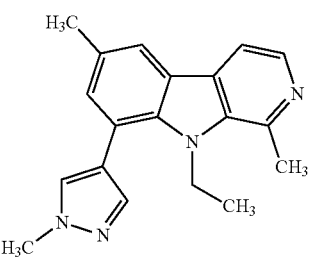 [SMILES: CCn1c2c(-c3cnn(C)c3)cc(C)cc2c2ccnc(C)c21]

A microwave reaction vessel was charged with 8-bromo-9-ethyl-1,6-dimethyl-9H-pyrido[3,4-b]indole (200 mg), sodium carbonate (280 mg), 1-methyl-4-(4,4,5,5-tetramethyl-1,3,2-dioxaborolan-2-yl)-1H-pyrazole (206 mg), BDFP (108 mg), DME (9 ml) and water (3 ml). After 12 min at 130° C. in a microwave oven the mixture was filtered and the filtrate concentrated in vacuo. The residue was dissolved in EA. The resulting solution was washed with a saturated sodium hydrogencarbonate solution, dried over sodium sulfate, filtered and concentrated in vacuo. The residue was purified by preparative RP HPLC. The fractions containing the product were combined and lyophilized. 7 mg of the title compound were obtained in the form of its salt with trifluoroacetic acid.

LC/MS (Method LC5): RT=1.43 min; m/z=305.2 [M+H]$^+$

Example 16. 6-Bromo-1,3-dimethyl-8-[4-(2-pyrazol-1-yl-ethoxy)-phenyl]-9H-pyrido[3,4-b]indole

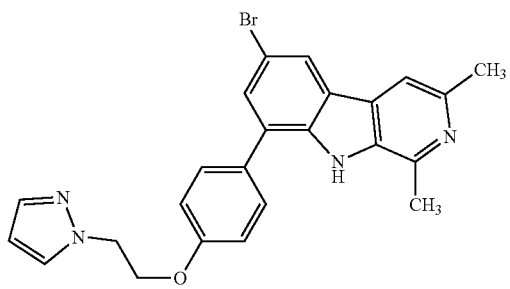 [SMILES: Cc1cc2c([nH]c3c(-c4ccc(OCCn5cccn5)cc4)cc(Br)cc32)c(C)n1]

A microwave reaction vessel was charged with 6-bromo-8-iodo-1,3-dimethyl-9H-pyrido (3,4-b)indole (200 mg), 1-(2-(4-(4,4,5,5-tetramethyl-1,3,2-dioxaborolan-2-yl)phenoxy)ethyl)-1H-pyrazole (157 mg), BDFP (81 mg), sodium carbonate (211 mg), DME (6 ml) and water (2 ml). After 10 min at 100° C. in a microwave oven the mixture was cooled and a saturated sodium hydrogencarbonate solution followed by DCM was added. The phases were separated and the organic phase was dried over sodium sulfate, filtered and concentrated in vacuo. The residue was purified by preparative RP HPLC. The fractions containing the product were combined and lyophilized. 162 mg of the title compound was obtained in the form of its salt with trifluoroacetic acid.

LC/MS (Method LC5): RT=1.67 min; m/z=461.2 [M+H]$^+$

Example 17. 6-(6-Chloro-9-ethyl-1-methyl-9H-pyrido[3,4-b]indol-8-yl)-3-methoxy-pyridin-2-ylamine

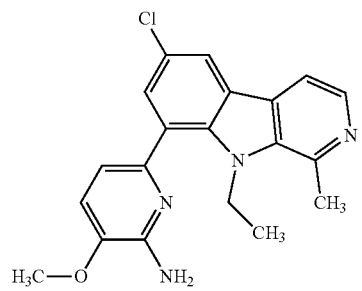 [SMILES: CCn1c2c(-c3ccc(OC)c(N)n3)cc(Cl)cc2c2ccnc(C)c21]

A microwave reaction vessel was charged with 6-chloro-9-ethyl-8-iodo-1-methyl-9H-pyrido[3,4-b]indole (250 mg), 6-amino-5-methoxypyridin-2-ylboronic acid (860 mg), BDFP (111 mg), sodium carbonate (71 mg), DME (6 ml) and water (2 ml). After 10 min at 100° C. in a microwave oven the mixture was cooled and filtered. 1 N hydrochloric acid was added to the filtrate, which was washed twice with DCM. The aqueous phase was set to pH 9 with 1 N sodium hydroxide solution and extracted three times with DCM. The combined organic phases were dried over sodium sulfate, filtered and concentrated in vacuo. The residue was purified by preparative RP HPLC. The fractions containing the product were combined, the ACN was removed in vacuo and the aqueous residue lyophilized to yield 50 mg of the title compound in the form of its salt with trifluoroacetic acid.

LC/MS (Method LC5): RT=1.42 min; m/z=367.2 [M+H]$^+$

Example 18. 6-Chloro-9-ethyl-1-methyl-8-[3-phenyl-isoxazol-5-yl)-9H-pyrido[3,4-b]indole

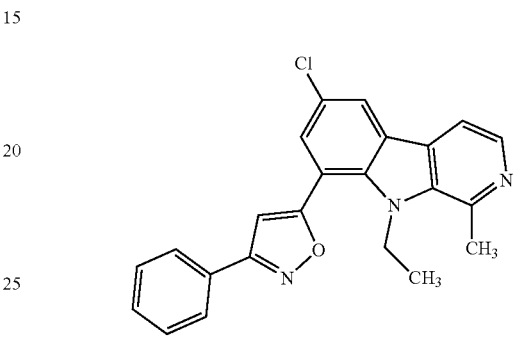

A microwave reaction vessel was charged with 6-chloro-9-ethyl-8-iodo-1-methyl-9H-pyrido[3,4-b]indole (200 mg), 3-phenyl-5-(4,4,5,5-tetramethyl-1,3,2-dioxaborolan-2-yl) isoxazole (176 mg), BDFP (89 mg), sodium carbonate (286 mg), DME (8 ml) and water (3 ml). After 15 min at 100° C. in a microwave oven the mixture was cooled, filtered, and a saturated sodium hydrogencarbonate solution followed by DCM were added to the filtrate. The phases were separated and the aqueous phase was extracted three times with DCM. The combined organic phases were dried over sodium sulfate, filtered and concentrated in vacuo. The residue was purified by preparative RP HPLC. The fractions containing the product were combined, the ACN was removed in vacuo and the remaining aqueous solution was lyophilized to yield 178 mg of the title compound in the form of its salt with trifluoroacetic acid. 135 mg of this salt was treated with a saturated sodium hydrogencarbonate solution and DCM. The phases were separated and the aqueous phase was extracted twice with DCM. The combined organic phases were dried over sodium sulfate, filtered and concentrated in vacuo. The residue was treated with water, filtered off with suction and dried in high vacuum at 40° C. to yield 106 mg of the title compound.

LC/MS (Method LC8): RT=3.79 min; m/z=388.1 [M+H]$^+$

Examples 19 and 20. 6-Chloro-9-ethyl-1-methyl-8-(2-methyl-2H-pyrazol-3-yl)-9H-pyrido[3,4-b]indole and 6-chloro-9-ethyl-1-methyl-8-(1-methyl-1H-pyrazol-3-yl)-9H-pyrido[3,4-b]indole 6-Chloro-9-ethyl-1-methyl-8-(1H-pyrazol-3-yl)-9H-pyrido[3,4-b]indole (95 mg) was dissolved in dry DMF (3 ml), and sodium hydride (15 mg) was added with stirring. After stirring for 30 min, iodomethane (48 mg) was added and stirring was continued for an additional 16 h. Then EA was added and the solution was washed with water and brine. The organic phase was dried over sodium sulfate, filtered and concentrated in vacuo. The residue was purified by preparative RP HPLC. The fractions containing each of the two isomeric products were combined, the ACN was removed in vacuo, the aqueous residues were set basic with a saturated hydrogencarbonate solution and extracted three times with DCM. The combined organic phases were dried over sodium sulfate, filtered, concentrated in vacuo, and the residue dissolved in water/ACN and lyophilized.

Example 19. 6-Chloro-9-ethyl-1-methyl-8-(2-methyl-2H-pyrazol-3-yl)-9H-pyrido[3,4-b]indole

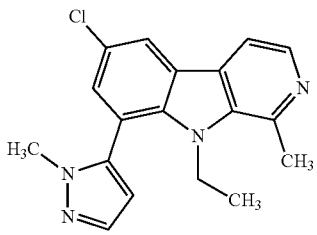 [SMILES: CCn1c2c(-c3ccnn3C)cc(Cl)cc2c2ccnc(C)c21]

20 mg of the title compound, the more polar of the two isomers, were obtained, LC/MS (Method LC4): RT=1.30 min; m/z=325.2 [M+H]$^+$ Example 20. 6-Chloro-9-ethyl-1-methyl-8-(1-methyl-1H-pyrazol-3-yl)-9H-pyrido[3,4-b]indole

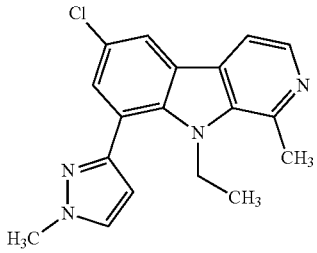 [SMILES: CCn1c2c(-c3ccn(C)n3)cc(Cl)cc2c2ccnc(C)c21]

32 mg of the title compound, the less polar of the two isomers, was obtained.
LC/MS (Method LC4): RT=1.32 min; m/z=325.2 [M+H]$^+$ Example 21. 6-Bromo-9-ethyl-1,3-dimethyl-8-(1-methyl-1H-pyrazol-4-yl)-9H-pyrido[3,4-b]indole

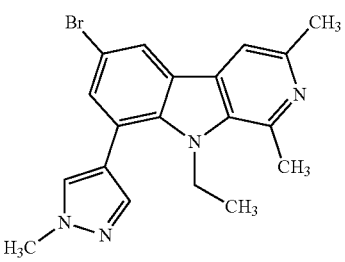

In a microwave reaction vessel (20 mi) 6-bromo-9-ethyl-8-iodo-1,3-dimethyl-9H-pyrido[3,4-b]indole (465 mg, 1.08 mmol) was dissolved in a mixture of DME (12 ml) and water (4 ml). Then 1-methyl-4-(4,4,5,5-tetramethyl-1,3,2-dioxaborolan-2-yl)-1H-pyrazole (225.48 mg, 1.08 mmol), sodium carbonate (459.43 mg, 4.33 mmol) and BDFP (177 mg) were added and the mixture was treated for 10 min at 100° C. in a microwave oven. Then further 1-methyl-4-(4,4,5,5-tetramethyl-1,3,2-dioxaborolan-2-yl)-1H-pyrazole (112 mg) and BDFP (89 mg) were added and the mixture was heated for 12 min at 120° C., followed by additional 15 min at 130° C., in a microwave oven. After cooling a saturated sodium hydrogencarbonate solution and DCM were added and the phases were separated. The organic phase was dried over sodium sulfate, filtered and concentrated in vacuo. The residue was purified by preparative RP HPLC. The fractions containing the product were combined and lyophilized to yield 280 mg of the title compound in the form of its salt with trifluoroacetic acid.
LC/MS (Method LC5): RT=1.52 min; m/z=383.1 [M+H]$^+$ Example 22. 6-Chloro-8-(4-methoxy-phenyl)-1,9-dimethyl-9H-pyrido[3,4-b]indole

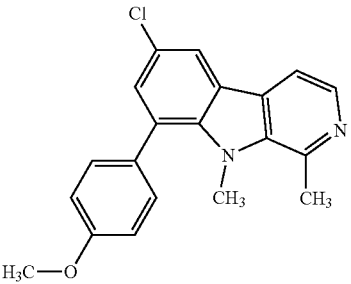 [SMILES: COc1ccc(-c2cc(Cl)cc3c4ccnc(C)c4n(C)c23)cc1]

In a microwave reaction vessel (10 ml) 6-chloro-8-iodo-1,9-dimethyl-9H-pyrido[3,4-b]indole (200 mg, 561 µmol) was dissolved in a mixture of DME (6 ml) and water (2 ml). Then 2-(4-methoxyphenyl)-4,4,5,5-tetramethyl-1,3,2-dioxaborolane (131 mg, 561 µmol), sodium carbonate (238 mg, 2.24 mmol) and BDFP (92 mg, 110 µmol) were added, and the mixture was treated for 10 min at 100° C., and then for 15 min at 120° C. in a microwave oven. After cooling, a sodium hydrogencarbonate solution and DCM were added and the phases were separated. The aqueous phase was extracted three times with DCM. The combined organic phases were dried over sodium sulfate, filtered and concentrated in vacuo. The residue was purified by preparative RP HPLC. The fractions containing the product were combined and lyophilized. 47 mg of the title compound in the form of its salt with trifluoroacetic acid was obtained.
LC/MS (Method LC4): RT=1.52 min; m/z=337.2 [M+H]$^+$ Example 23. 6-Chloro-1-methyl-8-(2-methyl-2,3-dihydro-benzofuran-5-yl)-9H-pyrido[3,4-b]indole

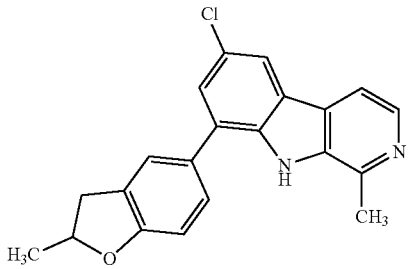 [SMILES: Cc1nccc2c1[nH]c1c(-c3ccc4c(c3)CC(C)O4)cc(Cl)cc12]

In a microwave reaction vessel (10 ml) 6-chloro-8-iodo-1-methyl-9H-pyrido[3,4-b]indole (200 mg, 580 µmol) was dissolved in a mixture of DME (6 ml) and water (2 ml). Then 2-methyl-2,3-dihydrobenzofuran-5-ylboronic acid (103.92 mg, 583.83 µmol), sodium carbonate (248 mg) and BDFP (95 mg) were added and the mixture was treated for 10 min at 100° C. in a microwave oven. After cooling, a saturated sodium hydrogencarbonate solution and DCM were added and the phases were separated. The aqueous phase was extracted three times with DCM. The combined organic phases were dried over sodium sulfate, filtered and concentrated in vacuo. The residue was purified by preparative RP HPLC. The fractions containing the product were combined and lyophilized to yield 120 mg of the title compound in the form of its salt with trifluoroacetic acid. 88 mg of this salt were treated with a saturated sodium hydrogencarbonate solution and DCM. The aqueous phase was removed by means of a Chem Elut cartridge, and the organic phase was concentrated in vacuo to yield 52 mg of the title compound.

LC/MS (Method LC4): RT=1.56 min; m/z=349.2 [M+H]$^+$

Example 24. [4-(6-Chloro-1-methyl-9H-pyrido[3,4-b]indol-8-yl)-phenyl]-phenyl-methanol

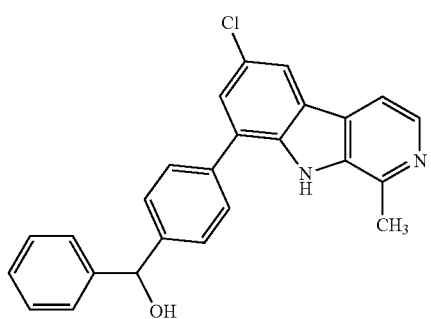 [SMILES: Cc1nccc2c1[nH]c1c(-c3ccc(C(O)c4ccccc4)cc3)cc(Cl)cc12]

Under an argon atmosphere 4-(6-chloro-1-methyl-9H-pyrido[3,4-b]indol-8-yl)-benzaldehyde (60 mg) was dissolved in in dry THF with stirring. The solution was cooled to 0° C., and a phenyl magnesium bromide solution (0.41 ml; 1 M in THF) was added with stirring. After the addition was complete the ice bath was removed. After 20 h water was added, and the aqueous phase was extracted three times with EA. The combined organic phases were dried over sodium sulfate, filtered and concentrated in vacuo. The residue was purified by chromatography over silica gel with DCM/MeOH (gradient). The fractions containing the product were combined and concentrated in vacuo to yield 38 mg of the title compound.

LC/MS (Method LC4): RT=1.54 min; m/z=399.2 [M+H]$^+$

Example 25. 6-Chloro-1,9-dimethyl-8-(1-methyl-1H-pyrazol-4-yl)-9H-pyrido[3,4-b]indole

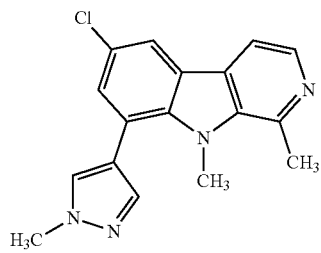 [SMILES: Cc1nccc2c3cc(Cl)cc(-c4cnn(C)c4)c3n(C)c12]

In a microwave reaction vessel (10 ml) 6-chloro-8-iodo-1,9-dimethyl-9H-pyri do[3,4-b]indole (206 mg, 577 µmol) was dissolved in a mixture of DME (6 ml) and water (2 ml). Then 1-methyl-4-(4,4,5,5-tetramethyl-1,3,2-dioxaborolan-2-yl)-1H-pyrazole (120 mg, 577.70 µmol), sodium carbonate (244.92 mg, 2.31 mmol) and BDFP 94 mg were added and the mixture was treated for 15 min at 120° C. in a microwave oven. To complete the conversion, the mixture was treated for another 15 min at 120° C. in a microwave oven. After cooling, a sodium hydrogencarbonate solution and DCM were added and the phases were separated. The aqueous phase was extracted three times with DCM. The combined organic phases were dried over sodium sulfate, filtered and concentrated in vacuo. The residue was purified by preparative RP HPLC. The fractions containing the product were combined and lyophilized. The obtained product was further purified by another preparative RP HPLC, followed by chromatography over silica gel with DCM/MeOH (gradient), to yield 12 mg of the title compound.

LC/MS (Method LC4): RT=1.24 min; m/z=311.2 [M+H]$^+$

Example 26. (2-[4-(6-Chloro-9-ethyl-1-methyl-9H-pyrido[3,4-b]indol-8-yl)-phenoxy]-ethyl)-diisopropyl-amine

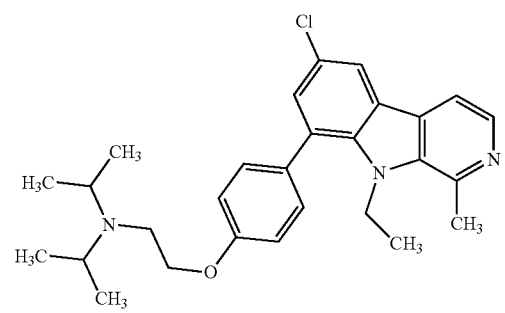 [SMILES: CCn1c2c(-c3ccc(OCCN(C(C)C)C(C)C)cc3)cc(Cl)cc2c2ccnc(C)c21]

a) 8-(4-(2-Bromoethoxy)phenyl)-6-chloro-9-ethyl-1-methyl-9H-pyrido[3,4-b]indole

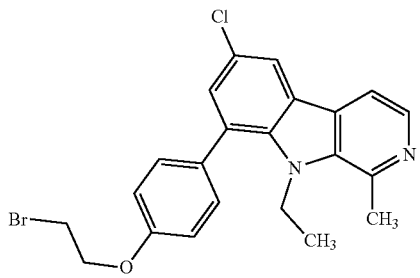 [SMILES: CCn1c2c(-c3ccc(OCCBr)cc3)cc(Cl)cc2c2ccnc(C)c21]

The title compound was synthesized analogously to the synthesis of the compound of example 31, using 4-(2-bromoethoxy)phenylboronic acid.
LC/MS (Method LC8): RT=3.89 min; m/z=443.2 [M+H]$^+$ b) (2-[4-(6-Chloro-9-ethyl-1-methyl-9H-pyrido[3,4-b]indol-8-yl)-phenoxy]-ethyl)-diisopropyl-amine In a microwave vessel 8-(4-(2-bromoethoxy)phenyl)-6-chloro-9-ethyl-1-methyl-9H-pyrido[3,4-b]indole (70 mg) was dissolved in diisopropylamine (3 ml). The mixture was treated for 10 h at 100° C. in a microwave oven. After cooling the amine was removed in vacuo and the residue was purified by chromatography over silica gel with DCM/MeOH (gradient). The fractions containing the product were combined and concentrated in vacuo. The residue was dissolved in a mixture of ACN and water containing 0.05% hydrogen chloride, and the solution lyophilized. 14 mg of the title compound was obtained in the form of (2-[4-(6-chloro-9-ethyl-1-methyl-9H-pyrido[3,4-b]indol-8-yl)-phenoxy]-ethyl)-diisopropyl-amine dihydrochloride.
LC/MS (Method LC8): RT=2.74 min; m/z=464.3 [M+H]$^+$ Example 27. 6-Chloro-8-(4-methoxy-phenyl)-1,5-dimethyl-9H-pyrido[3,4-b]indole

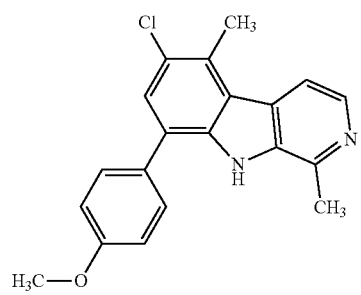 [SMILES: COc1ccc(-c2cc(Cl)c(C)c3c2[nH]c2c(C)nccc23)cc1]

In a microwave reaction vessel (10 ml) 6-chloro-8-iodo-1,5-dimethyl-9H-pyrido[3,4-b]indole (180 mg, 504.78 µmol) was dissolved in a mixture of DME (6 ml) and water (2 ml). Then 2-(4-methoxyphenyl)-4,4,5,5-tetramethyl-1,3,2-dioxaborolane (118.17 mg, 504.78 µmol), sodium carbonate (214.00 mg, 2.02 mmol) and BDFP (82.44 mg, 100.96 µmol) were added, and the mixture was treated for 15 min at 120° C. in a microwave oven. After cooling, a sodium hydrogencarbonate solution and DCM were added and the phases were separated. The aqueous phase was extracted three times with DCM. The combined organic phases were dried over sodium sulfate, filtered and concentrated in vacuo. The residue was purified by preparative RP HPLC. The fractions containing the product were combined and lyophilised. 92 mg of the title compound in the form of its salt with trifluoroacetic acid was obtained.
LC/MS (Method LC4): RT=1.56 min; m/z=337.2 [M+H]$^+$ Example 28. 6-Chloro-9-ethyl-1-methyl-8-[4-(2-morpholin-4-yl-ethoxy)-phenyl]-9H-pyrido[3,4-b]indole

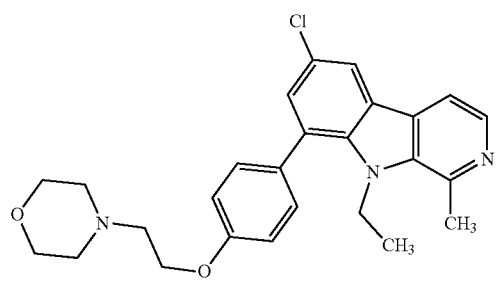 [SMILES: CCn1c2c(-c3ccc(OCCN4CCOCC4)cc3)cc(Cl)cc2c2ccnc(C)c21]

In a microwave vessel 8-(4-(2-bromoethoxy)phenyl)-6-chloro-9-ethyl-1-methyl-9H-pyrido[3,4-b]indole (31 mg) was dissolved in morpholine (2 ml). The mixture was treated for 15 min at 100° C. in a microwave oven. After cooling the amine was removed in vacuo and the residue was purified by chromatography over silica gel with DCM/MeOH (gradient). The fractions containing the product were combined and concentrated in vacuo. The residue was dissolved in a mixture of ACN and water containing 0.05% hydrochloric acid and lyophilized. 25 mg of the title compound in the form of 6-chloro-9-ethyl-1-methyl-8-[4-(2-morpholin-4-yl-ethoxy)-phenyl]-9H-pyrido[3,4-b]indole dihydrochloride was obtained.
LC/MS (Method LC8): RT=2.48 min; m/z=450.3 [M+H]$^+$ Example 29. [4-(6-Chloro-1-methyl-9H-pyrido[3,4-b]indol-8-yl)-benzyl]-cyclopentyl-amine

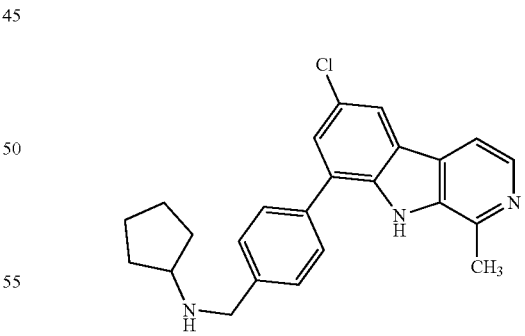

4-(6-Chloro-1-methyl-9H-pyrido[3,4-b]indol-8-yl)-benzylamine (80 mg) was dissolved in DME (2 ml) and acetic acid (0.250 ml). After the addition of cyclopentanone (127 mg) the reaction mixture war stirred for 15 min at room temperature. Then sodium triacetoxyborohydride (111 mg) was added. After stirring for 2 h, DCM was added to the reaction mixture and the solution washed with a saturated sodium hydrogencarbonate solution and brine. The organic phase was dried over sodium sulfate, filtered and concentrated in vacuo. The residue was purified by preparative RP HPLC. The fractions containing the product were combined, the ACN was removed in vacuo and the residue was lyophilized to yield 88 mg of the title compound in the form of its salt with trifluoroacetic acid. 65 mg of this salt was treated a with saturated sodium hydrogencarbonate solution and EA. The phases were separated, and the aqueous phase was extracted twice with EA. The combined organic phases were dried over sodium sulfate, filtered and concentrated in vacuo to yield 44 mg of the title compound.

LC/MS (Method LC4): RT=1.15 min; m/z=390.2 [M+H]+

Example 30. 6-Chloro-9-ethyl-1-methyl-8-(4-morpholin-4-ylmethyl-phenyl)-9H-pyrido[3,4-b]indole

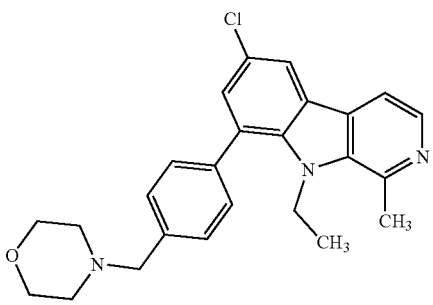 [SMILES: CCn1c2c(-c3ccc(CN4CCOCC4)cc3)cc(Cl)cc2c2ccnc(C)c21]

4-(6-Chloro-9-ethyl-1-methyl-9H-pyrido[3,4-b]indol-8-yl)benzaldehyde (94 mg) was dissolved in DME (2 ml) and acetic acid (0.16 ml). After addition of morpholine (28 mg) the reaction mixture was stirred for 15 min at room temperature. Then sodium triacetoxyborohydride (144 mg) was added. After stirring for 16 h, DCM was added to the reaction mixture, the solution washed with a saturated sodium hydrogencarbonate solution and brine. The organic phase was dried over sodium sulfate, filtered and concentrated in vacuo. The residue was purified by preparative RP HPLC. The fractions containing the product were combined, the ACN was removed in vacuo and the residue was lyophilised to yield 45 mg of the title compound in the form of its salt with trifluoroacetic acid.

LC/MS (Method LC4): RT=1.07 min; m/z=420.3 [M+H]+

Example 31. 4-(6-Chloro-1-methyl-9H-pyrido[3,4-b]indol-8-yl)-benzaldehyde

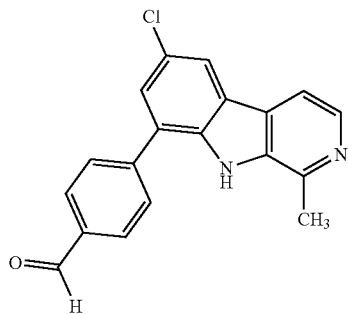 [SMILES: Cc1nccc2c1[nH]c1c(-c3ccc(C=O)cc3)cc(Cl)cc12]

In a microwave reaction vessel (10 ml) 6-chloro-8-iodo-1-methyl-9H-pyrido[3,4-b]indole (150 mg) was dissolved in a mixture of DME (5 ml) and water (1.5 ml). Then 4-formylphenylboronic acid (66 mg), sodium carbonate (185 mg) and BDFP (72 mg) were added and the mixture was treated for 10 min at 100° C. in a microwave oven. After cooling, water and DCM were added and the phases were separated. The aqueous phase was extracted three times with DCM. The combined organic phases were dried over sodium sulfate, filtered and concentrated in vacuo. The residue was purified by preparative RP HPLC. The fractions containing the product were combined, the ACN was removed in vacuo and the residue was neutralised with a saturated sodium hydrogencarbonate solution. After extraction with DCM (three times) the organic phases were combined, dried over sodium sulfate, filtered and concentrated in vacuo to yield 60 mg of the title compound. A part of this product was dissolved in a mixture of water, ACN and TFA and lyophilised to yield 10 mg of the title compound in the form of its salt with trifluoroacetic acid.

LC/MS (Method LC4): RT=1.40 min; m/z=321.1 [M+H]+

Example 32. [4-(6-Chloro-1-methyl-9H-pyrido[3,4-b]indol-8-yl)-phenyl]-pyridin-2-yl-methanol

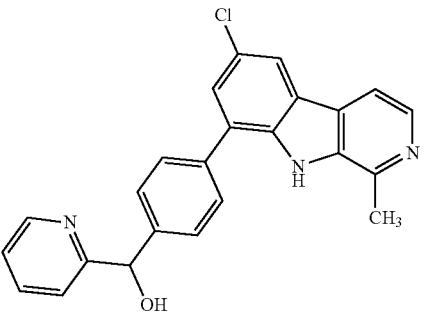 [SMILES: Cc1nccc2c1[nH]c1c(-c3ccc(C(O)c4ccccn4)cc3)cc(Cl)cc12]

Under an argon atmosphere 4-(6-chloro-9-ethyl-1-methyl-9H-pyrido[3,4-b]indol-8-yl)benzaldehyde (60 mg) was dissolved in dry THF (10 ml) with stirring. The solution was cooled to 0° C., and 2-pyridylmagnesium bromide (2.24 ml; 0.25 M in THF) was added with stirring. After the addition was complete, the ice bath was removed. After 1 h, further 2-pyridylmagnesium bromide (1.12 ml) was added. After 1.5 h a saturated ammonium chloride solution was added, and the aqueous phase was extracted three times with EA. The combined organic phases were dried over sodium sulfate, filtered and concentrated in vacuo. The residue was purified by chromatography over silica gel with HEP/EA (gradient). The fractions containing the product were combined and concentrated in vacuo. The product was purified by preparative RP HPLC. The fractions containing the product were combined, the ACN removed in vacuo, and the residue was lyophilized to yield 60 mg of the title compound in the form of its salt with trifluoroacetic acid.

LC/MS (Method LC4): RT=1.30 min; m/z=400.2 [M+H]+

Example 33. 8-(4-Methoxy-phenyl)-1-methyl-9H-pyrido[3,4-b]indole-6-carbonitrile

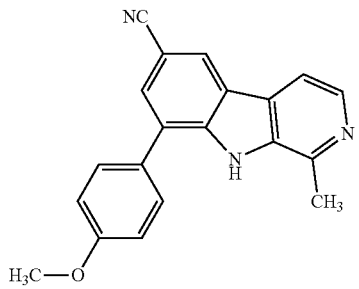 [SMILES: COc1ccc(-c2cc(C#N)cc3c2[nH]c2c(C)nccc23)cc1]

In a microwave vessel 6-bromo-8-(4-methoxyphenyl)-1-methyl-9H-pyrido[3,4-b]indole (100 mg, 272.30 µmol) was dissolved in NMP (5 ml) and copper(I) cyanide (487.77 mg, 5.45 mmol) was added. The mixture was treated for 2 h at 200° C. in a microwave oven. After cooling, a saturated ammonium chloride solution was added and the aqueous phase was extracted three times with EA. The combined organic phases were dried with sodium sulfate, filtered and concentrated in vacuo. The residue was purified by preparative RP HPLC. The fractions containing the product were combined, the ACN was removed in vacuo and the residue was lyophilised to yield 30 mg of the title compound in the form of its salt with trifluoroacetic acid.

LC/MS (Method LC4): RT=1.32 min; m/z=314.2 [M+H]$^+$

Example 34. 6-Chloro-1-methyl-8-[4-(quinolin-2-ylmethoxy)-phenyl]-9H-pyrido[3,4-b]indole

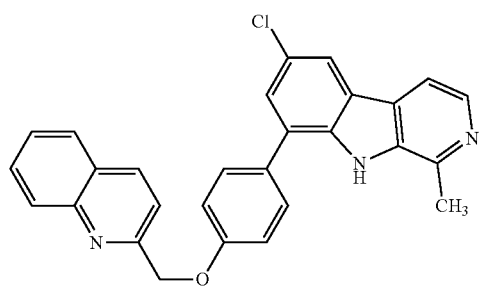 [SMILES: Cc1nccc2c1[nH]c1c(-c3ccc(OCc4ccc5ccccc5n4)cc3)cc(Cl)cc12]

a) 4-(6-Chloro-1-methyl-9H-pyrido[3,4-b]indol-8-yl)phenol

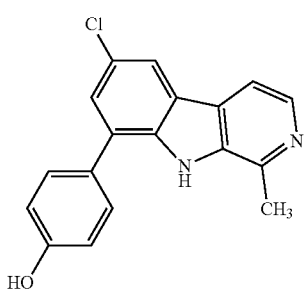 [SMILES: Cc1nccc2c1[nH]c1c(-c3ccc(O)cc3)cc(Cl)cc12]

A microwave reaction vessel was charged with 6-chloro-8-iodo-1-methyl-9H-pyrido[3,4-b]indole (200 mg), 4-hydroxyphenylboronic acid (201 mg), BDFP (96 mg), sodium carbonate (248 mg), DME (8 ml) and water (3 ml). After 15 min at 100° C. in a microwave oven the mixture was cooled, filtered and concentrated in vacuo. EA was added to the residue, and the organic phase was washed twice with water, dried over sodium sulfate, filtered and concentrated in vacuo to yield 167 mg of the title compound, which was directly used in the next step.

b) 6-Chloro-1-methyl-8-[4-(quinolin-2-ylmethoxy)-phenyl]-9H-pyrido[3,4-b]indole 4-(6-Chloro-1-methyl-9H-pyrido[3,4-b]indol-8-yl)phenol (167 mg) was dissolved in DMF (5 ml). After addition of 2-(chloromethyl)quinoline hydrochloride (125 mg) the reaction mixture war stirred for 3 h at 60° C. Then water was added and the aqueous phase was extracted three times with EA. The combined organic phases were washed with brine, dried over sodium sulfate, filtered and concentrated in vacuo. The residue was purified by preparative RP HPLC. The fractions containing the product were combined, the ACN was removed in vacuo, and the precipitate formed was filtered off with suction and dried at 40° C. to yield 50 mg of the title compound in the form of its salt with trifluoroacetic acid. 36 mg of this salt was treated with a saturated sodium hydrogencarbonate solution, the solid was filtered off with suction, washed with water and dried at 40° C. to yield 20 mg of the title compound.

LC/MS (Method LC4): RT=1.62 min; m/z=450.3 [M+H]$^+$

Examples 35 and 36. 8-(4-Methoxy-phenyl)-1-methyl-9H-pyrido[3,4-b]indole-6-carboxylic acid and 8-(4-Methoxy-phenyl)-1-methyl-9H-pyrido[3,4-b]indole-6-carboxamide 8-(4-Methoxy-phenyl)-1-methyl-9H-pyrido[3,4-b]indole-6-carbonitrile trifluoroacetic acid salt (21 mg) was suspended in concentrated sulfuric acid (3 ml) under cooling in an ice bath, and heated for 4 h at 90° C. After cooling, the mixture was concentrated in vacuo. The residue was purified by preparative RP HPLC. The fractions containing each of the two products were combined, the ACN was removed in vacuo, and the residue was lyophilised.

Example 35. 8-(4-Methoxy-phenyl)-1-methyl-9H-pyrido[3,4-b]indole-6-carboxylic acid

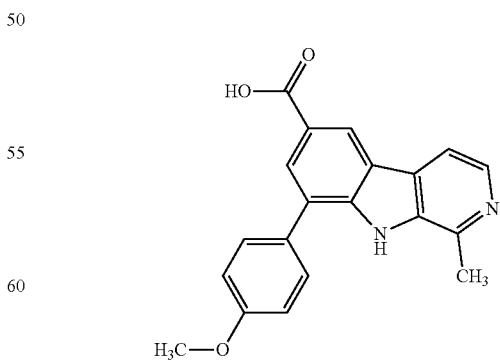

4 mg of the title compound were obtained in the form of its salt with trifluoroacetic acid.

LC/MS (Method LC4): RT=1.15 min; m/z=333.2 [M+H]$^+$

Example 36. 8-(4-Methoxy-phenyl)-1-methyl-9H-pyrido[3,4-b]indole-6-carboxamide

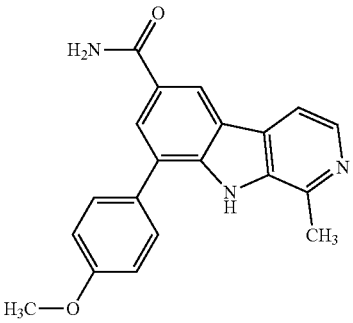 [SMILES: COc1ccc(-c2cc(C(N)=O)cc3c2[nH]c2c(C)nccc23)cc1]

7 mg of the title compound were obtained in the form of its salt with trifluoroacetic acid.

LC/MS (Method LC8): RT=2.33 min; m/z=332.2 [M+H]$^+$

Example 37. 8-[3-(5-Bromo-pyrimidin-2-yloxy)-phenyl]-6-chloro-1-methyl-9H-pyrido[3,4-b]indole

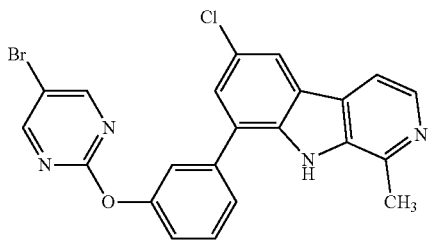 [SMILES: Cc1nccc2c1[nH]c1c(-c3cccc(Oc4ncc(Br)cn4)c3)cc(Cl)cc12]

a) 3-(6-Chloro-1-methyl-9H-pyrido[3,4-b]indol-8-yl)phenol

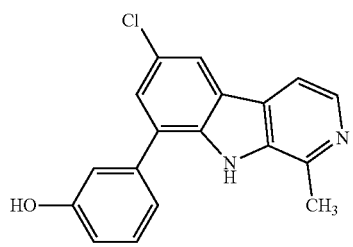 [SMILES: Cc1nccc2c1[nH]c1c(-c3cccc(O)c3)cc(Cl)cc12]

Three microwave reaction vessels were each charged with 6-chloro-8-iodo-1-methyl-9H-pyrido[3,4-b]indole (200 mg), 3-hydroxyphenylboronic acid (200 mg), sodium carbonate (247 mg), BDFP (96 mg), DME (8 ml) and water (3 ml). After 15 min at 100° C. in a microwave oven the mixtures of the three vessels were combined, filtered and concentrated in vacuo. EA was added to the residue and the organic phase was washed twice with water, dried over sodium sulfate, filtered and concentrated in vacuo. The residue was treated with diethyl ether and filtered off with suction to yield 541 mg of the title compound, which was directly used in the next step.

b) 8-[3-(5-Bromo-pyrimidin-2-yloxy)-phenyl]-6-chloro-1-methyl-9H-pyrido[3,4-b]indole 4-(6-Chloro-1-methyl-9H-pyrido[3,4-b]indol-8-yl)phenol (135 mg) was dissolved in DMF (5 ml). After addition of 5-bromo-2-chloropyrimidine (101 mg), the reaction mixture war stirred for 3 h at 60° C. Then water was added and the aqueous phase was extracted three times with DCM. The combined organic phases were washed with brine, dried over sodium sulfate, filtered and concentrated in vacuo. The residue was purified by preparative RP HPLC. The fraction containing the product were combined, the ACN was removed in vacuo and the residue was lyophilized. The product was further purified by chromatography over silica gel with EA/HEP (1:1 to 1:0). The fractions containing the product were combined and concentrated in vacuo. The residue was lyophilized in water/TFA to yield 48 mg of the title compound in the form of its salt with trifluoroacetic acid.

LC/MS (Method LC5): RT=1.54 min; m/z=465.1 [M+H]$^+$

Example 38. 6-Bromo-9-ethyl-1-methyl-8-(1-quinolin-2-ylmethyl-1H-pyrazol-4-yl)-9H-pyrido[3,4-b]indole

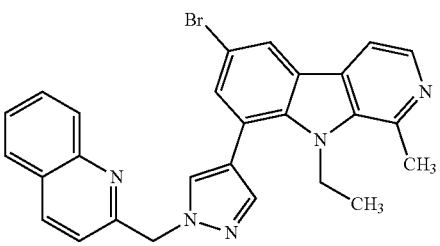 [SMILES: CCn1c2c(-c3cnn(Cc4ccc5ccccc5n4)c3)cc(Br)cc2c2ccnc(C)c21]

In a microwave reaction vessel (10 ml) dry DMF (5 ml) was added to 6-bromo-9-ethyl-1-methyl-8-(1H-pyrazol-4-yl)-9H-pyrido[3,4-b]indole (50 mg, 140.75 µmol) and 2-(chloromethyl)quinoline hydrochloride (45.20 mg, 211.13 µmol), followed by cesium carbonate (138 mg) The mixture was treated for 2 h at 120° C. in a microwave oven. Then further cesium carbonate (69 mg) was added and the mixture treated for another 2 h at 120° C. in a microwave oven. After filtration, the mixture was concentrated in vacuo, and the residue was purified by preparative RP HPLC. The fractions containing the product were combined, the ACN was removed in vacuo and the residue lyophilised to yield 42 mg of the title compound in the form of its salt with trifluoroacetic acid.

LC/MS (Method LC4): RT=1.50 min; m/z=496.3 [M+H]$^+$

Example 39. 6-Chloro-1-methyl-8-[4-(1-methyl-1H-imidazol-2-ylmethoxy)-phenyl]-9H-pyrido[3,4-b]indole

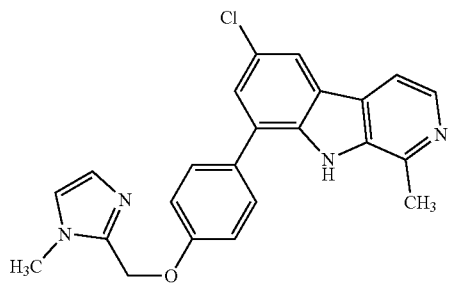 [SMILES: Cc1nccc2c1[nH]c1c(-c3ccc(OCc4nccn4C)cc3)cc(Cl)cc12]

Dry DMF (4 ml) was added to 4-(6-chloro-1-methyl-9H-pyrido[3,4-b]indol-8-yl)phenol (90 mg), 2-(chloromethyl)-1-methyl-1H-imidazole hydrochloride (49 mg) and potassium carbonate (201 mg), and the mixture was stirred for 2 h at 60° C. Then water was added, and the precipitate was filtered off with suction and purified by chromatography over silica gel with EA/HEP (2:3 to 1:0), followed by DCM. The fractions containing the product were combined and concentrated in vacuo. The residue was dissolved in 1 N hydrochloric acid and the solution washed with DCM. Then a 1 N sodium hydroxide solution was added and the precipitate was filtered off. After washing with water the precipitate was dried at 40° C. to yield 23 mg of the title compound.

LC/MS (Method LC5): RT=1.11 min; m/z=403.2 [M+H]$^+$

Example 40. 6-Chloro-8-[4-([1,4]dioxan-2-yl-methoxy)-phenyl]-1-methyl-9H-pyrido[3,4-b]indole

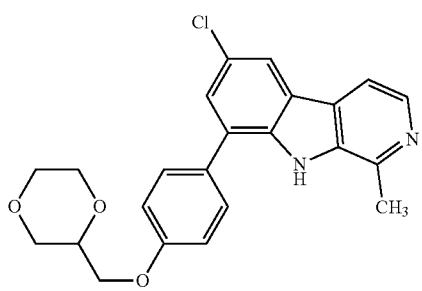 [SMILES: Cc1nccc2c1[nH]c1c(-c3ccc(OCC4COCCO4)cc3)cc(Cl)cc12]

Dry DMF (4 ml) was added to 4-(6-chloro-1-methyl-9H-pyrido[3,4-b]indol-8-yl)phenol (100 mg), 1,4-dioxan-2-yl-methyl 4-methylbenzenesulfonate (97 mg) and cesium carbonate (530 mg), and the mixture was stirred for 4 h at 80° C. Then a saturated sodium hydrogencarbonate solution was added, and the aqueous phase was extracted three times with DCM. The combined organic phases were dried over sodium sulfate, filtered and concentrated in vacuo. The residue was purified by preparative RP HPLC. The fractions containing the product were combined, the ACN was removed in vacuo and the residue was lyophilized to yield 62 mg of the title compound in the form of its salt with trifluoroacetic acid. 33 mg of this salt was treated with a saturated sodium hydrogencarbonate solution and DCM. After phase separation the aqueous phase was extracted twice with DCM. The combined organic phases were dried over sodium sulfate, filtered and concentrated in vacuo to yield 12 mg of the title compound.

LC/MS (Method LC5): RT=1.45 min; m/z=409.3 [M+H]$^+$

Example 41. 6-Chloro-1-methyl-8-[4-(quinazolin-2-ylmethoxy)-phenyl]-9H-pyrido[3,4-b]indole

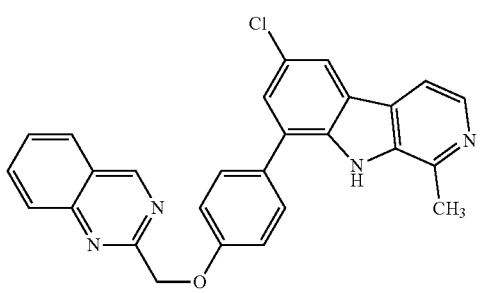

Dry DMF (4 ml) was added to 4-(6-chloro-1-methyl-9H-pyrido[3,4-b]indol-8-yl)phenol (100 mg), 2-(chloromethyl)quinazoline (61 mg) and potassium carbonate (224 mg), and the mixture was stirred for 4 h at 80° C. Then further potassium carbonate (10 mg) was added and the mixture stirred for another 3 h at 80° C. After cooling, a saturated sodium hydrogencarbonate solution was added and the aqueous phase was extracted three times with DCM. The combined organic phases were dried over sodium sulfate, filtered and concentrated in vacuo. The residue was purified by preparative RP HPLC. The fractions containing the product were combined, the ACN was removed in vacuo and the residue was lyophilized to yield 37 mg of the title compound in the form of its salt with trifluoroacetic acid. 29 mg of this salt was treated with a saturated sodium hydrogencarbonate solution and the mixture stirred for 2 h. Then the solid was filtered off, washed with water and dried at 40° C. to yield 18 mg of the title compound.

LC/MS (Method LC5): RT=1.51 min; m/z=451.2 [M+H]$^+$

Examples 42 and 43. 8-(4-[2-(4-Bromo-1H-pyrazol-1-yl)-ethoxy]-phenyl)-6-chloro-1-methyl-9H-pyrido[3,4-b]indole and 3-bromo-8-(4-[2-(4-bromo-1H-pyrazol-1-yl)-ethoxy]-phenyl)-6-chloro-1-methyl-9H-pyrido[3,4-b]indole Dry DMF (4 ml) was added to 8-(4-(2-(1H-pyrazol-1-yl)ethoxy)phenyl)-6-chloro-1-methyl-9H-pyrido[3,4-b]indole (52 mg), followed by N-bromosuccinimide (44 mg) The mixture was stirred for 3 h at 40° C. Further N-bromosuccinimide (22 mg) was added and the mixture stirred for another 3 h at 40° C. After standing overnight at room temperature, water was added and the aqueous phase was extracted three times with DCM. The combined organic phases were dried over sodium sulfate, filtered and concentrated in vacuo. The residue was purified by preparative RP HPLC. The fraction containing each of the two products were combined, the ACN was removed in vacuo and the residue was lyophilized.

Example 42. 8-(4-[2-(4-Bromo-pyrazol-1-yl)-ethoxy]-phenyl)-6-chloro-1-methyl-9H-pyrido[3,4-b]indole

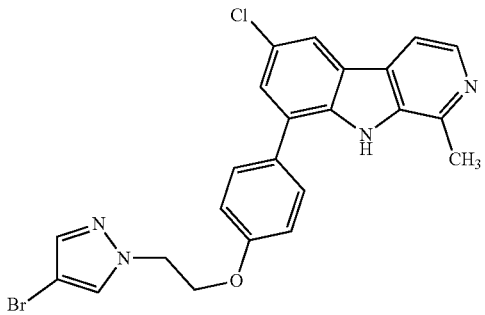 [SMILES: Cc1nccc2c1[nH]c1c(-c3ccc(OCCn4cc(Br)cn4)cc3)cc(Cl)cc12]

7 mg of the title compound were obtained in the form of its salt with trifluoroacetic acid.
LC/MS (Method LC5): RT=1.57 min; m/z=481.1 [M+H]$^+$ Example 43. 3-Bromo-8-(4-[2-(4-bromo-pyrazol-1-yl)-ethoxy]-phenyl)-6-chloro-1-methyl-9H-pyrido[3,4-b]indole

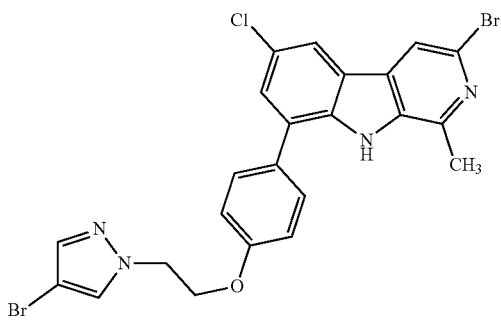 [SMILES: Cc1nc(Br)cc2c1[nH]c1c(-c3ccc(OCCn4cc(Br)cn4)cc3)cc(Cl)cc12]

5 mg of the title compound were obtained in the form of its salt with trifluoroacetic acid.
LC/MS (Method LC5): RT=2.13 min; m/z=559.0 [M+H]$^+$ Example 44. 2-[4-(6-Chloro-9-ethyl-1-methyl-9H-pyrido[3,4-b]indol-8-yl)-pyrazol-1-yl]-ethanol

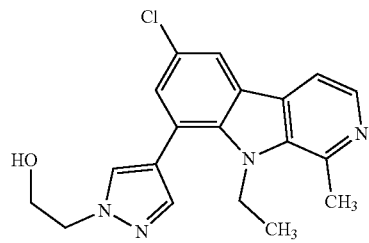 [SMILES: CCn1c2c(-c3cnn(CCO)c3)cc(Cl)cc2c2ccnc(C)c21]

8-(1-((1,3-Dioxolan-2-yl)methyl)-1H-pyrazol-4-yl)-6-chloro-9-ethyl-1-methyl-9H-pyrido[3,4-b]indole trifluoroacetic acid salt (55 mg) was stirred in a mixture of ACN (1.5 ml) and 2 N hydrochloric acid (0.5 ml) for 16 h. After removal of the solvent in vacuo the residue was purified by preparative RP HPLC. The fractions containing the product were combined, the ACN was removed in vacuo and the residue was lyophilized to yield 18 mg of the title compound in the form of its salt with trifluoroacetic acid.
LC/MS (Method LC4): RT=1.16 min: m/z=355.2 [M+H]$^+$ Example 45. 6-Chloro-1,5-dimethyl-8-[4-(2-pyrazol-1-yl-ethoxy)-phenyl]-9H-pyrido[3,4-b]pyridine

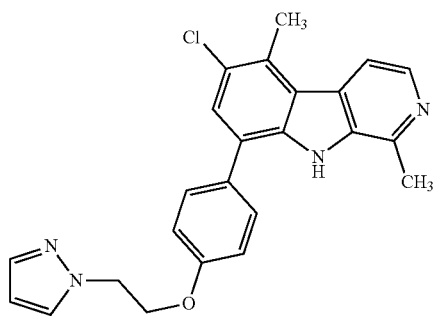 [SMILES: Cc1nccc2c1[nH]c1c(-c3ccc(OCCn4cccn4)cc3)cc(Cl)c(C)c12]

The title compound was synthesized analogously to the synthesis of the compound of example 8, using 185 mg of 6-chloro-8-iodo-1,5-dimethyl-9H-pyrido[3,4-b]indole and 170 mg of 1-(2-(4-(4,4,5,5-tetramethyl-1,3,2-dioxaborolan-2-yl)phenoxy)ethyl)-1H-pyrazole and treating the reaction mixture in a microwave oven for 15 min at 100° C. After purification by HPLC, the residue of the extraction with EA was directly lyophilized, using water/ACN as the solvent. 129 mg of the title compound was obtained.
LC/MS (Method LC5): RT=1.52 min; m/z=417.1 [M+H]$^+$ Example 46. 6-Chloro-9-cyclopropylmethyl-8-(2,6-dichloro-pyridin-3-yl)-pyrido[3,4-b]indole

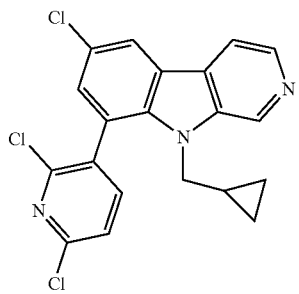 [SMILES: Clc1cc(-c2ccc(Cl)nc2Cl)c2c(c1)c1ccncc1n2CC1CC1]

8-Bromo-6-chloro-9-cyclopropylmethyl-pyrido[3,4-b]indole (3 g, 8.94 mmol) was dissolved in degassed DME (150 ml) and degassed water (48 ml). After addition of sodium carbonate (3.8 g, 35.75 mmol) the reaction mixture was flushed with argon. After heating to reflux, 2,6-dichloro-3-pyridinylboronic acid (3.4 g, 17.72 mmol) and BDFP (1.46 g. 1.79 mmol) were dissolved in dry DMF (45 ml), and the solution added to the reaction mixture via a syringe pump over 8 h. After 2.5 h an extra amount of 1.46 g (1.79 mmol) of BDFP was added to the reaction mixture. When the addition via the syringe pump was finished, the mixture was cooled, filtered, the precipitate washed with DCM and the filtrate concentrated in vacuo. The crude product was purified by preparative HPLC. The fractions containing the product were combined and lyophilized. 1.33 g of the title compound were obtained in the form of 6-chloro-9-cyclopropylmethyl-8-(2,6-dichloro-pyridin-3-yl)-pyrido[3,4-b]indole trifluoroacetic acid salt. This salt was dissolved in EA, and the solution washed with a saturated sodium hydrogencarbonate solution and water. The organic phase was dried over sodium sulfate, filtered and concentrated in vacuo. The residue was purified by chromatography over a 30 g SiO$_2$ cartridge (EA:HEP 4:1). The fractions containing the product were concentrated in vacuo and the residue was treated with a HEP/EA mixture (15 ml, 4:1) and the mixture treated in a sonication bath. The solvent was removed in vacuo and the obtained solid dried under high vacuum to yield 711 mg of the title compound.

LC/MS (Method LC3): RT=1.08 min; m/z=402.0 [M+H]$^+$

Example 47. 5-(6-Chloro-9-cyclopropylmethyl-1-methyl-9H-pyrido[3,4-b]indol-8-yl)-pyridine-2-carbonitrile

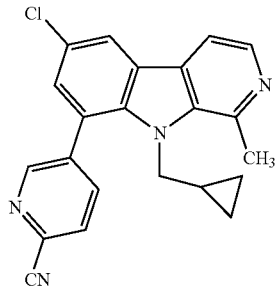 [SMILES: Cc1nccc2c3cc(Cl)cc(-c4ccc(C#N)nc4)c3n(CC3CC3)c12]

Degassed dioxane (15 ml, abs.) and degassed water (4 ml) were charged in a 25 ml two-necked flask under argon. 8-Bromo-6-chloro-9-cyclopropylmethyl-1-methyl-pyrido[3,4-b]indole (300 mg, 0.86 mmol), sodium carbonate (272.8 mg, 2.57 mmol), 2-cyanopyridine-5-boronic acid pinacol ester (217.0 mg, 0.94 mmol) and BDFP (175.2 mg, 0.21 mmol) were added, and the mixture was heated under reflux for 12 h. EA (5 ml) was added, the reaction mixture was filtered through a kieselgur cartridge and eluted with EA (4×10 ml). The combined organic phases were concentrated and the residue was purified by preparative HPLC. 149 mg (36%) of the title compound was obtained in the form of its salt with trifluoroacetic acid.

LC/MS (Method LCB): RT=1.10 min; m/z=373.2 [M+H]$^+$

Example 48. 5-(6-Chloro-9-cyclopropylmethyl-1-methyl-9H-pyrido[3,4-b]indol-8-yl)-3-methyl-pyridine-2-carbonitrile

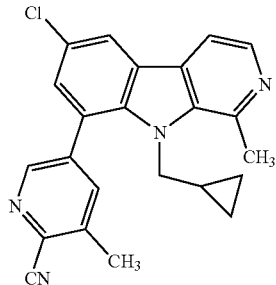 [SMILES: Cc1cc(-c2cc(Cl)cc3c4ccnc(C)c4n(CC4CC4)c23)cnc1C#N]

8-Bromo-6-chloro-9-cyclopropylmethyl-1-methyl-pyrido[3,4-b]indole (300.0 mg, 0.86 mmol), cesium carbonate (559.0 mg. 1.72 mmol), BDFP (201.0 mg, 0.25 mmol) and 2-cyano-3-methylpyridine-5-boronic acid pinacol ester (419 mg, 1.72 mmol) were reacted and worked up analogously as described for the compound of example 47. 273 mg (64%) of the title compound was obtained in the form of its salt with trifluoroacetic acid.

LC/MS (Method LC6): RT=1.13 min; m/z=387.1 [M+H]$^+$

Example 49. 6-Chloro-9-cyclopropymethyl-1-methyl-8-(4-methyl-3,4-dihydro-2H-pyrido[3,2-b][1,4]oxazin-7-yl)-9H-pyrido[3,4-b]indole

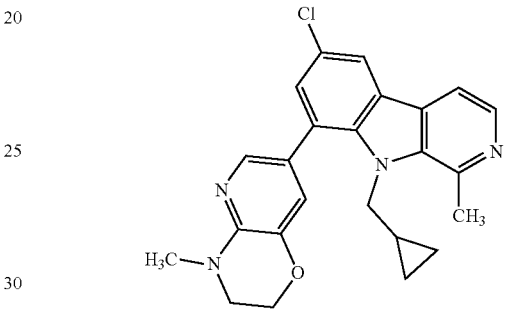

8-Bromo-6-chloro-9-cyclopropylmethyl-1-methyl-pyrido[3,4-b]indole (250.0 mg, 0.71 mmol), sodium carbonate (227.3 mg, 2.15 mmol), BDFP (146.0 mg. 0.18 mmol) and 4-methyl-7-(4,4,5,5-tetramethyl-1,3,2-dioxaborolan-2-yl)-3,4-dihydro-2H-pyrido[3,2-b][1,4]oxazine (197 mg, 0.72 mmol) were reacted and worked up analogously as described for the compound of example 47. 335 mg (88%) of the title compound was obtained in the form of its salt with trifluoroacetic acid.

LC/MS (Method LC6): RT=1.09 min; m/z=419.2 [M+H]$^+$

Example 50. 6-Chloro-9-cyclopropylmethyl-1-methyl-8-(6-pyrrolidin-1-ylpyridin-3-yl)-9H-pyrido[3,4-b]indole

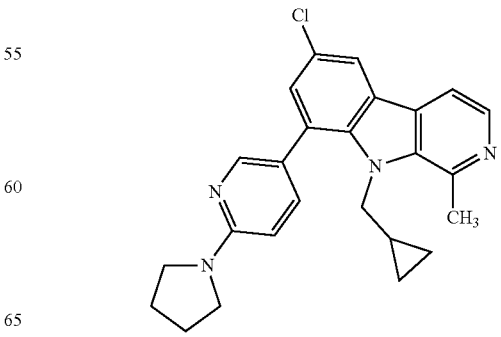

8-Bromo-6-chloro-9-cyclopropylmethyl-1-methyl-pyrido[34-b]indole (270 mg, 0.77 mmol), cesium carbonate (403 mg, 1.54 mmol), 2-(pyrrolidin-1-yl)-5-(4,4,5,5-tetramethyl-1,3,2-dioxaborolan-2-yl)pyridine (424 mg, 1.55 mmol) and BDFP (45 mg) were reacted and worked up analogously as described for the compound of example 47. 213 mg (52%) of the title compound was obtained in the form of its salt with trifluoroacetic acid.

LC/MS (Method LC6): RT=1.01 min; m/z=417.2 [M+H]$^+$

Example 51. 6-Chloro-9-cyclopropylmethyl-1-methyl-8-[6-(4-methyl-piperazin-1-yl)-pyridin-3-yl]-pyrido[3,4-b]indole

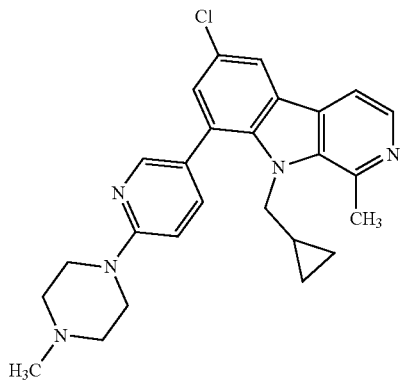 [SMILES: Cc1nccc2c3cc(Cl)cc(-c4ccc(N5CCN(C)CC5)nc4)c3n(CC3CC3)c12]

8-Bromo-6-chloro-9-cyclopropylmethyl-1-methyl-pyrido[3,4-b]indole (270 mg, 0.77 mmol), cesium carbonate (504 mg, 1.55 mmol), 2-(4-methylpiperazin-1-yl)pyridine-5-boronic acid pinacol ester (469 mg, 1.55 mmol) and BDFP (181 mg, 0.22 mmol) were reacted and worked up analogously as described for the compound of example 47. 320 mg (74%) of the title compound was obtained in the form of its salt with trifluoroacetic acid.

LC/MS (Method LC6): RT=0.93 min; m/z=446.2 [M+H]$^+$

Example 52. 6-Chloro-8-(4-methoxy-phenyl)-9-(3-methyl-oxetan-3-ylmethyl)-9H-pyrido[3,4-b]indole

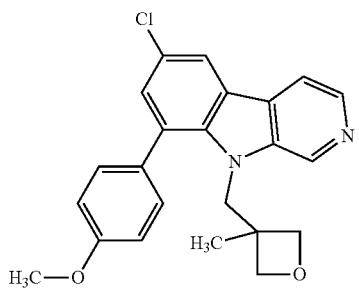 [SMILES: COc1ccc(-c2cc(Cl)cc3c4ccncc4n(CC4(C)COC4)c23)cc1]

A microwave reaction vessel was charged with 8-bromo-6-chloro-9-(3-methyl-oxetan-3-ylmethyl)-9H-pyrido[3,4-b]indole (173 mg), sodium carbonate (201 mg), 2-(4-methoxyphenyl)-4,4,5,5-tetramethyl-1,3,2-dioxaborolane (166 mg), BDFP (77 mg), DME (6 ml) and water (2 ml). After 12 min at 130° C. in a microwave oven the mixture was filtered and the filtrate concentrated in vacuo. The residue was first purified by chromatography over silica gel followed by a further purification by preparative RP HPLC. The fractions containing the product were combined, the ACN was removed in vacuo, the aqueous phase set to a basic pH with saturated sodium hydrogencarbonate solution, and extracted three times with EA. The combined organic phases were dried over sodium sulfate, filtered and concentrated in vacuo to yield 103 mg of the title compound.

LC/MS (Method LC5): RT=1.70 min; m/z=393.3 [M+H]$^+$

Example 53. 6-Chloro-5-(6-chloro-9-cyclopropylmethyl-9H-pyrido[3,4-b]indol-8-yl)-pyridin-2-ylamine In a microwave vessel 6-chloro-9-cyclopropylmethyl-8-(2,6-dichloro-pyridin-3-yl)-pyrido[3,4-b]indole (20 mg) was dissolved in N-methyl-2-pyrrolidinone (0.5 ml), and an ammonia solution (0.1 ml, 25% in water) was added. After 2 h at 160° C. in a microwave oven further ammonia solution (0.1 ml) was added and heating was continued for 1.75 h at 200° C. After cooling, the mixture was concentrated in vacuo and the residue purified by preparative RP HPLC. The fractions containing the product were combined, the ACN was removed in vacuo and the residue was lyophilized to yield 30 mg of the title compound in the form of its salt with trifluoroacetic acid.

LC/MS (Method LC5): RT=1.59 min; m/z=383.1 [M+H]$^+$

The example compounds of the formula I listed in Table 1 were synthesized analogously to the syntheses of example compounds of the formula I described above. In Table 1, in the column "Ex. No." the number of the example is given, in the column "LC/MS" the number of the HPLC method specified above which was used in the LC/MS characterization of the example compound is given, in the column "RT" the observed HPLC retention time in minutes is given, and in the column "MS" the mass-to-charge ratio m/z of the observed molecular ion or a related ion and the kind of the ion is given. Like in the case of the compounds of the formula I whose synthesis is described in detail above, the ionization method in the MS characterization was ES+ if the specified ion is [M+H]$^+$ or another positive ion, and ES− if the specified ion is [M−H]$^−$ or another negative ion.

TABLE 1

| Ex. No. | Structure | Name | LC/MS | RT [min] | MS |
|---|---|---|---|---|---|
| 54 | 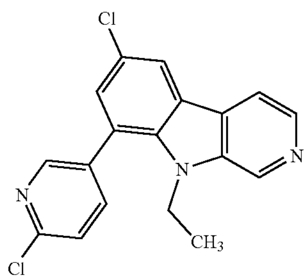 | 6-Chloro-8-(6-chloro-pyridin-3-yl)-9-ethyl-9H-pyrido[3,4-b]indole | LC10 | 2.77 | 342.0 [M + H]$^+$ |
| 55 | 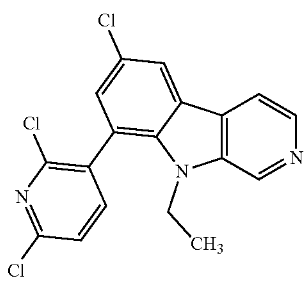 | 6-Chloro-8-(2,6-dichloro-pyridin-3-yl)-9-ethyl-9H-pyrido[3,4-b]indole | LC9 | 2.10 | 376.1 [M + H]$^+$ |
| 56 | 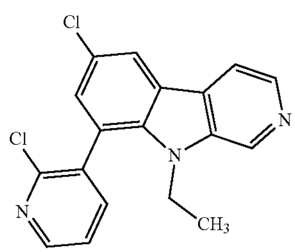 [SMILES: CCn1c2cnccc2c2cc(Cl)cc(-c3cccnc3Cl)c21] | 6-Chloro-8-(2-chloro-pyridin-3-yl)-9-ethyl-9H-pyrido[3,4-b]indole | LC11 | 2.62 | 342.1 [M + H]$^+$ |
| 57 | 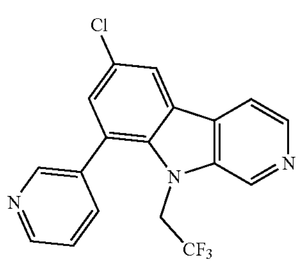 [SMILES: FC(F)(F)Cn1c2cnccc2c2cc(Cl)cc(-c3cccnc3)c21] | 6-Chloro-8-pyridin-3-yl-9-(2,2,2-trifluoro-ethyl)-9H-pyrido[3,4-b]indole | LC1 | 1.21 | 362.1 [M + H]$^+$ |
| 58 | 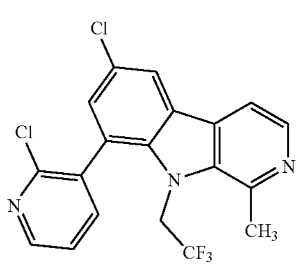 | 6-Chloro-8-(2-chloro-pyridin-3-yl)-9-ethyl-1-methyl-9H-pyrido[3,4-b]indole | LC1 | 1.36 | 356.1 [M + H]$^+$ |

TABLE 1-continued

| Ex. No. | Structure | Name | LC/MS | RT [min] | MS |
|---|---|---|---|---|---|
| 59 | 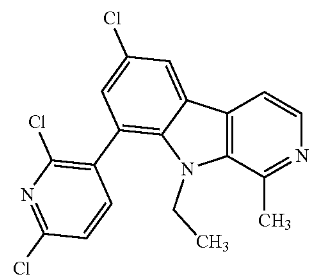 [SMILES: CCn1c2c(-c3ccc(Cl)nc3Cl)cc(Cl)cc2c2ccnc(C)c21] | 6-Chloro-8-(2,6-dichloro-pyridin-3-yl)-9-ethyl-1-methyl-9H-pyrido[3,4-b]indole | LC6 | 1.15 | 390.1 [M + H]⁺ |
| 60 | 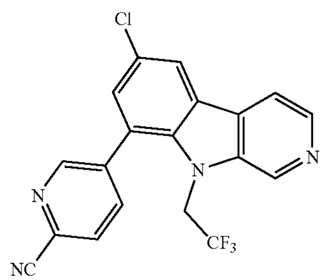 [SMILES: N#Cc1ccc(-c2cc(Cl)cc3c4ccncc4n(CC(F)(F)F)c23)cn1] | 5-[6-Chloro-9-(2,2,2-trifluoro-ethyl)-9H-pyrido[3,4-b]indol-8-yl]-pyridine-2-carbonitrile | LC8 | 3.86 | 387.2 [M + H]⁺ |
| 61 | 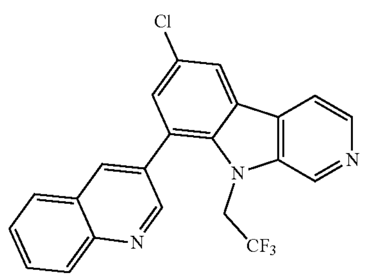 [SMILES: FC(F)(F)Cn1c2cnccc2c2cc(Cl)cc(-c3cnc4ccccc4c3)c21] | 6-Chloro-8-quinolin-3-yl-9-(2,2,2-trifluoro-ethyl)-9H-pyrido[3,4-b]indole | LC3 | 1.45 | 412.2 [M + H]⁺ |
| 62 | 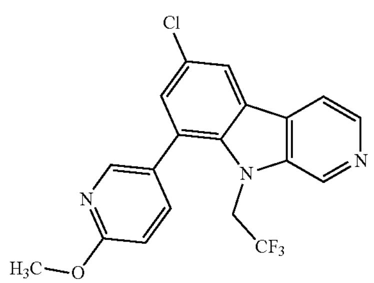 [SMILES: COc1ccc(-c2cc(Cl)cc3c4ccncc4n(CC(F)(F)F)c23)cn1] | 6-Chloro-8-(6-methoxy-pyridin-3-yl)-9-(2,2,2-trifluoro-ethyl)-9H-pyrido[3,4-b]indole | LC11 | 2.85 | 392.1 [M + H]⁺ |
| 63 | 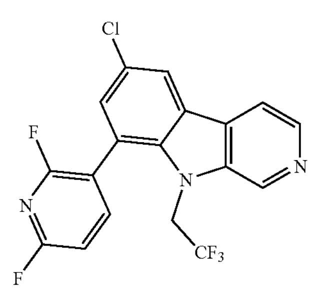 [SMILES: Fc1ccc(-c2cc(Cl)cc3c4ccncc4n(CC(F)(F)F)c23)c(F)n1] | 6-Chloro-8-(2,6-difluoro-pyridin-3-yl)-9-(2,2,2-trifluoro-ethyl)-9H-pyrido[3,4-b]indole | LC11 | 2.84 | 398.2 [M + H]⁺ |

TABLE 1-continued

| Ex. No. | Structure | Name | LC/MS | RT [min] | MS |
|---|---|---|---|---|---|
| 64 | 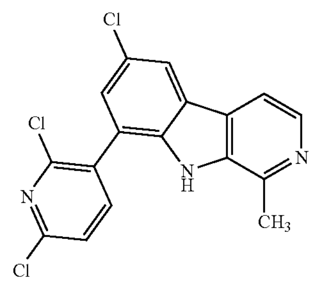 [SMILES: Cc1nccc2c1[nH]c1c(-c3ccc(Cl)nc3Cl)cc(Cl)cc12] | 6-Chloro-8-(2,6-dichloro-pyridin-3-yl)-1-methyl-9H-pyrido[3,4-b]indole | LC6 | 1.05 | 362.0 [M + H]⁺ |
| 65 | 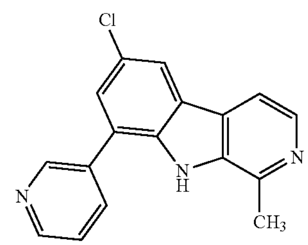 [SMILES: Cc1nccc2c1[nH]c1c(-c3cccnc3)cc(Cl)cc12] | 6-Chloro-1-methyl-8-pyridin-3-yl-9H-pyrido[3,4-b]indole | LC11 | 2.12 | 294.2 [M + H]⁺ |
| 66 | 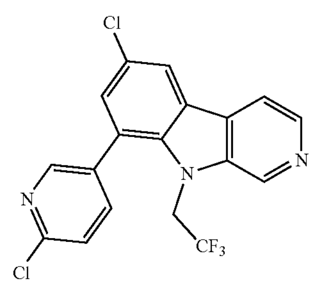 | 6-Chloro-8-(6-chloro-pyridin-3-yl)-9-(2,2,2-trifluoro-ethyl)-9H-pyrido[3,4-b]indole | LC8 | 3.89 | 396.2 [M + H]⁺ |
| 67 | 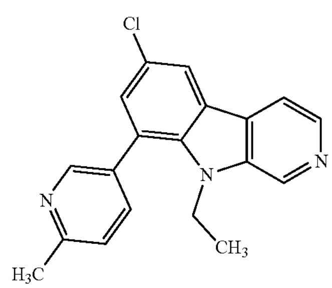 [SMILES: CCn1c2cnccc2c2cc(Cl)cc(-c3ccc(C)nc3)c21] | 6-Chloro-9-ethyl-8-(6-methyl-pyridin-3-yl)-9H-pyrido[3,4-b]indole | LC11 | 2.10 | 322.2 [M + H]⁺ |
| 68 | 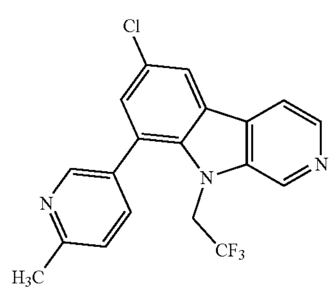 | 6-Chloro-8-(6-methyl-pyridin-3-yl)-9-(2,2,2-trifluoro-ethyl)-9H-pyrido[3,4-b]indole | LC11 | 2.22 | 376.2 [M + H]⁺ |

TABLE 1-continued

| Ex. No. | Structure | Name | LC/MS | RT [min] | MS |
|---|---|---|---|---|---|
| 69 | 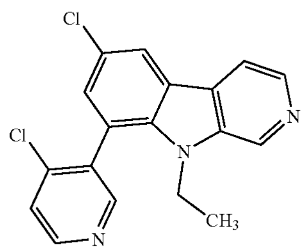 | 6-Chloro-8-(4-chloro-pyridin-3-yl)-9-(2,2,2-trifluoro-ethyl)-9H-pyrido[3,4-b]indole | LC1 | 1.46 | 396.0 [M + H]+ |
| 70 | 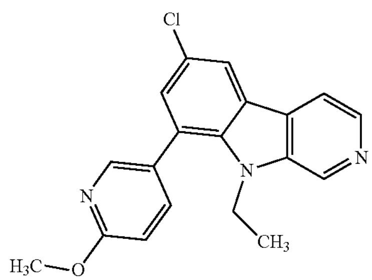 | 6-Chloro-9-ethyl-8-(6-methoxy-pyridin-3-yl)-9H-pyrido[3,4-b]indole | LC11 | 2.77 | 338.2 [M + H]+ |
| 71 | 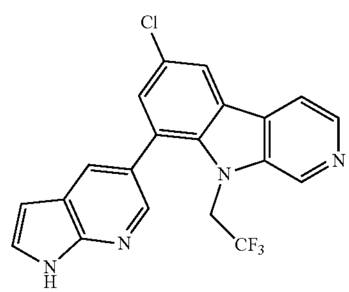 [SMILES: FC(F)(F)Cn1c2cnccc2c2cc(Cl)cc(-c3cnc4[nH]ccc4c3)c21] | 6-Chloro-8-(1H-pyrrolo[2,3-b]pyridin-5-yl)-9-(2,2,2-trifluoro-ethyl)-9H-pyrido[3,4-b]indole | LC4 | 1.52 | 401.2 [M + H]+ |
| 72 | 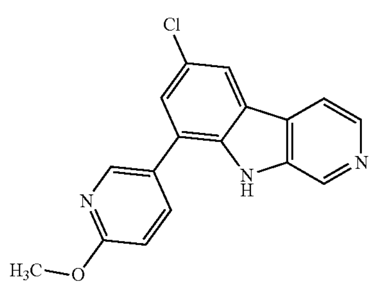 [SMILES: COc1ccc(-c2cc(Cl)cc3c2[nH]c2cnccc23)cn1] | 6-Chloro-8-(6-methoxy-pyridin-3-yl)-9H-pyrido[3,4-b]indole | LC6 | 1.35 | 310.1 [M + H]+ |
| 73 | 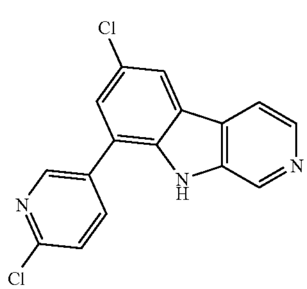 [SMILES: Clc1cc(-c2ccc(Cl)nc2)c2[nH]c3cnccc3c2c1] | 6-Chloro-8-(6-chloro-pyridin-3-yl)-9H-pyrido[3,4-b]indole | LC1 | 1.34 | 314.0 [M + H]+ |

TABLE 1-continued

| Ex. No. | Structure | Name | LC/MS | RT [min] | MS |
|---|---|---|---|---|---|
| 74 | 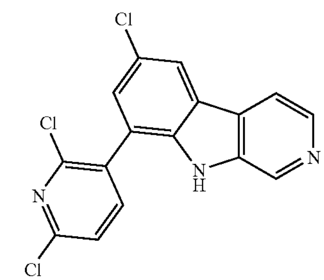 [SMILES: Clc1cc(-c2ccc(Cl)nc2Cl)c2[nH]c3cnccc3c2c1] | 6-Chloro-8-(2,6-dichloro-pyridin-3-yl)-9H-pyrido[3,4-b]indole | LC1 | 1.43 | 348.0 [M + H]+ |
| 75 | 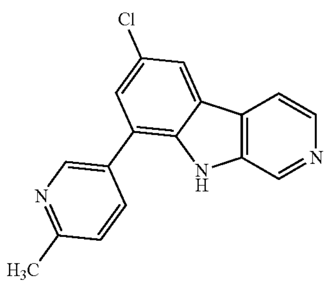 [SMILES: Cc1ccc(-c2cc(Cl)cc3c2[nH]c2cnccc23)cn1] | 6-Chloro-8-(6-methyl-pyridin-3-yl)-9H-pyrido[3,4-b]indole | LC1 | 1.06 | 294.1 [M + H]+ |
| 76 | 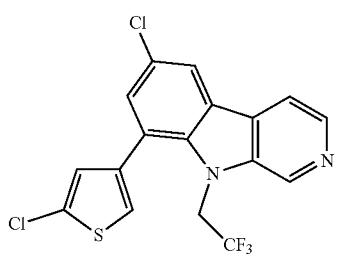 [SMILES: FC(F)(F)Cn1c2cnccc2c2cc(Cl)cc(-c3csc(Cl)c3)c21] | 6-Chloro-8-(5-chloro-thiophen-3-yl)-9-(2,2,2-trifluoro-ethyl)-9H-pyrido[3,4-b]indole | LC6 | 1.29 | 401.1 [M + H]+ |
| 77 | 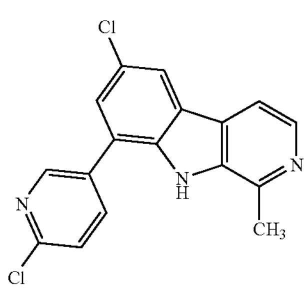 [SMILES: Cc1nccc2c1[nH]c1c(-c3ccc(Cl)nc3)cc(Cl)cc12] | 6-Chloro-8-(6-chloro-pyridin-3-yl)-1-methyl-9H-pyrido[3,4-b]indole | LC3 | 1.03 | 328.0 [M + H]+ |
| 78 | 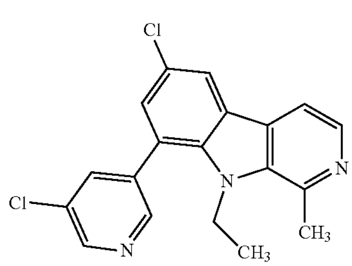 [SMILES: CCn1c2c(-c3cncc(Cl)c3)cc(Cl)cc2c2ccnc(C)c21] | 6-Chloro-8-(5-chloro-pyridin-3-yl)-9-ethyl-1-methyl-9H-pyrido[3,4-b]indole | LC1 | 1.40 | 356.1 [M + H]+ |

TABLE 1-continued

| Ex. No. | Structure | Name | LC/MS | RT [min] | MS |
|---|---|---|---|---|---|
| 79 | 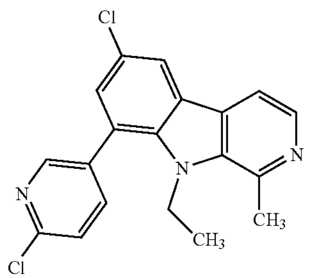 [SMILES: CCn1c2c(-c3ccc(Cl)nc3)cc(Cl)cc2c2ccnc(C)c21] | 6-Chloro-8-(6-chloro-pyridin-3-yl)-9-ethyl-1-methyl-9H-pyrido[3,4-b]indole | LC3 | 1.09 | 356.0 [M + H]⁺ |
| 80 | 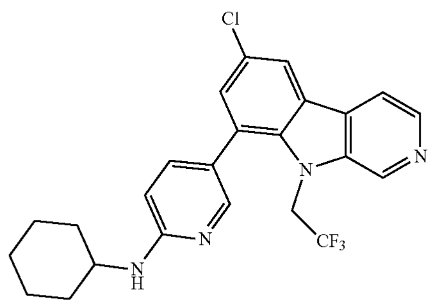 [SMILES: FC(F)(F)Cn1c2cnccc2c2cc(Cl)cc(-c3ccc(NC4CCCCC4)nc3)c21] | (5-[6-Chloro-9-(2,2,2-trifluoro-ethyl)-9H-pyrido[3,4-b]indol-8-yl]-pyridin-2-yl)-cyclohexyl-amine | LC6 | 1.11 | 459.3 [M + H]⁺ |
| 81 | 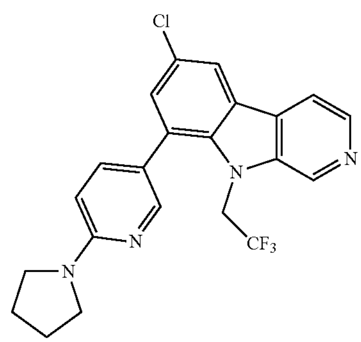 [SMILES: FC(F)(F)Cn1c2cnccc2c2cc(Cl)cc(-c3ccc(N4CCCC4)nc3)c21] | 6-Chloro-8-(6-pyrrolidin-1-yl-pyridin-3-yl)-9-(2,2,2-trifluoro-ethyl)-9H-pyrido[3,4-b]indole | LC12 | 2.68 | 431.1 [M + H]⁺ |
| 82 | 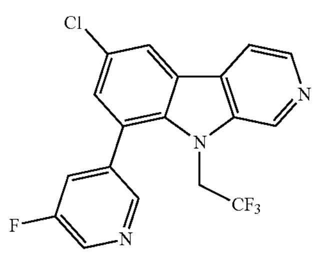 [SMILES: Fc1cncc(-c2cc(Cl)cc3c4ccncc4n(CC(F)(F)F)c23)c1] | 6-Chloro-8-(5-fluoro-pyridin-3-yl)-9-(2,2,2-trifluoro-ethyl)-9H-pyrido[3,4-b]indole | LC12 | 3.29 | 380.0 [M + H]⁺ |
| 83 | 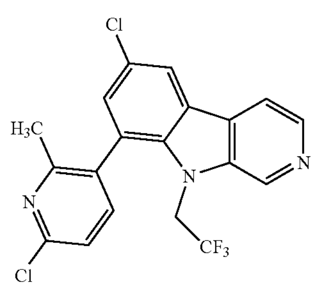 [SMILES: Cc1nc(Cl)ccc1-c1cc(Cl)cc2c3ccncc3n(CC(F)(F)F)c12] | 6-Chloro-8-(6-chloro-2-methyl-pyridin-3-yl)-9-(2,2,2-trifluoro-ethyl)-9H-pyrido[3,4-b]indole | LC12 | 3.62 | 410.0 [M + H]⁺ |

TABLE 1-continued

| Ex. No. | Structure | Name | LC/MS | RT [min] | MS |
|---|---|---|---|---|---|
| 84 | 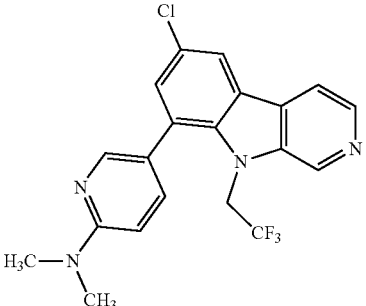 | (5-[6-Chloro-9-(2,2,2-trifluoro-ethyl)-9H-pyrido[3,4-b]indol-8-yl]-pyridin-2-yl)-dimethyl-amine | LC12 | 2.57 | 405.1 [M + H]⁺ |
| 85 | 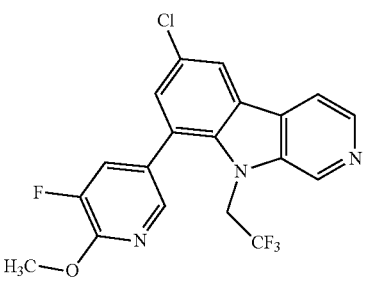 [SMILES: COc1ncc(-c2cc(Cl)cc3c4ccncc4n(CC(F)(F)F)c23)cc1F] | 6-Chloro-8-(5-fluoro-6-methoxy-pyridin-3-yl)-9-(2,2,2-trifluoro-ethyl)-9H-pyrido[3,4-b]indole | LC12 | 3.82 | 410.2 [M + H]⁺ |
| 86 | 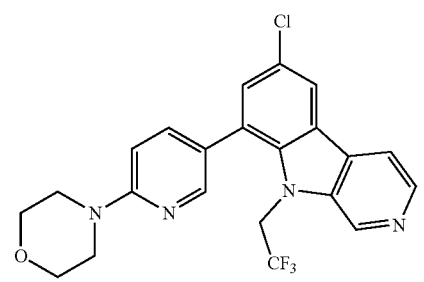 [SMILES: FC(F)(F)Cn1c2cnccc2c2cc(Cl)cc(-c3ccc(N4CCOCC4)nc3)c21] | 6-Chloro-8-(6-morpholin-4-yl-pyridin-3-yl)-9-(2,2,2-trifluoro-ethyl)-9H-pyrido[3,4-b]indole | LC12 | 3.55 | 447.1 [M + H]⁺ |
| 87 | 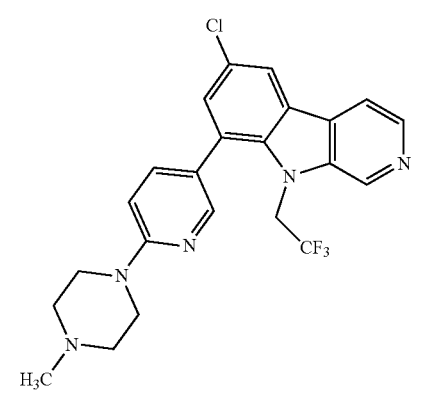 [SMILES: CN1CCN(c2ccc(-c3cc(Cl)cc4c5ccncc5n(CC(F)(F)F)c34)cn2)CC1] | 6-Chloro-8-[6-(4-methyl-piperazin-1-yl)-pyridin-3-yl]-9-(2,2,2-trifluoro-ethyl)-9H-pyrido[3,4-b]indole | LC12 | 2.82 | 460.1 [M + H]⁺ |
| 88 | 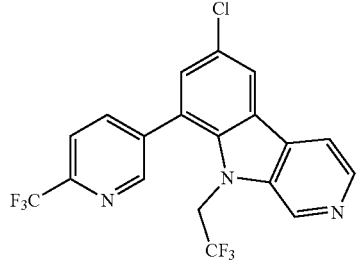 [SMILES: FC(F)(F)Cn1c2cnccc2c2cc(Cl)cc(-c3ccc(C(F)(F)F)nc3)c21] | 6-Chloro-9-(2,2,2-trifluoro-ethyl)-8-(6-trifluoromethyl-pyridin-3-yl)-9H-pyrido[3,4-b]indole | LC12 | 3.75 | 430.0 [M + H]⁺ |

TABLE 1-continued

| Ex. No. | Structure | Name | LC/MS | RT [min] | MS |
|---|---|---|---|---|---|
| 89 | 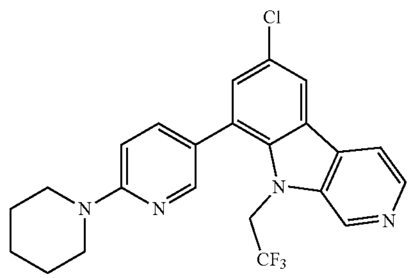 [SMILES: FC(F)(F)Cn1c2cnccc2c2cc(Cl)cc(-c3ccc(N4CCCCC4)nc3)c21] | 6-Chloro-8-(3,4,5,6-tetrahydro-2H-[1,2']bipyridinyl-5'-yl)-9-(2,2,2-trifluoro-ethyl)-9H-pyrido[3,4-b]indole | LC4 | 1.72 | 445.2 [M + H]$^+$ |
| 90 | 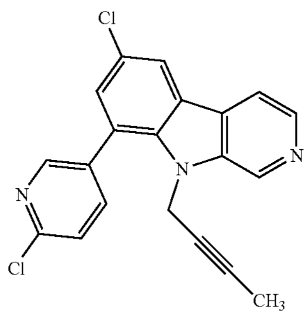 [SMILES: CC#CCn1c2cnccc2c2cc(Cl)cc(-c3ccc(Cl)nc3)c21] | 9-But-2-ynyl-6-chloro-8-(6-chloro-pyridin-3-yl)-9H-pyrido[3,4-b]indole | LC12 | 3.35 | 366.1 [M + H]$^+$ |
| 91 | 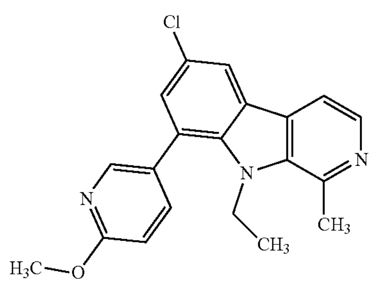 [SMILES: CCn1c2c(-c3ccc(OC)nc3)cc(Cl)cc2c2ccnc(C)c21] | 6-Chloro-9-ethyl-8-(6-methoxy-pyridin-3-yl)-1-methyl-9H-pyrido[3,4-b]indole | LC8 | 3.25 | 352.2 [M + H]$^+$ |
| 92 | 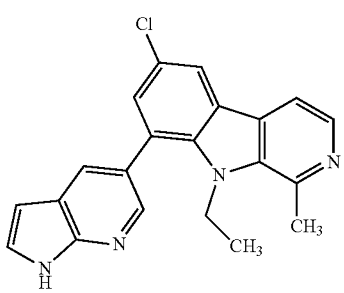 [SMILES: CCn1c2c(-c3cnc4[nH]ccc4c3)cc(Cl)cc2c2ccnc(C)c21] | 6-Chloro-9-ethyl-1-methyl-8-(1H-pyrrolo[2,3-b]pyridin-5-yl)-9H-pyrido[3,4-b]indole | LC6 | 1.06 | 361.2 [M + H]$^+$ |
| 93 | 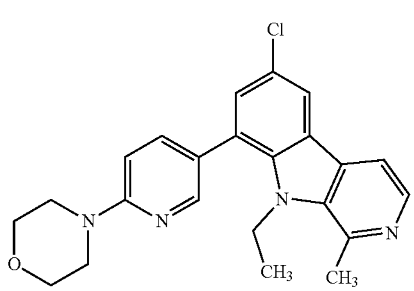 [SMILES: CCn1c2c(-c3ccc(N4CCOCC4)nc3)cc(Cl)cc2c2ccnc(C)c21] | 6-Chloro-9-ethyl-1-methyl-8-(6-morpholin-4-yl-pyridin-3-yl)-9H-pyrido[3,4-b]indole | LC6 | 0.97 | 407.2 [M + H]$^+$ |

TABLE 1-continued

| Ex. No. | Structure | Name | LC/MS | RT [min] | MS |
|---|---|---|---|---|---|
| 94 | 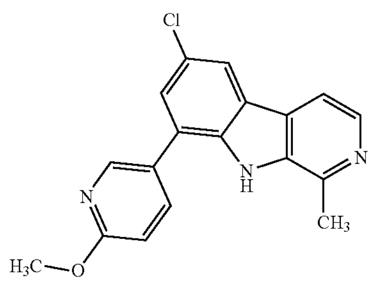 [SMILES: COc1ccc(-c2cc(Cl)cc3c2[nH]c2c(C)nccc23)cn1] | 6-Chloro-8-(6-methoxy-pyridin-3-yl)-1-methyl-9H-pyrido[3,4-b]indole | LC6 | 1.07 | 324.2 [M + H]+ |
| 95 | 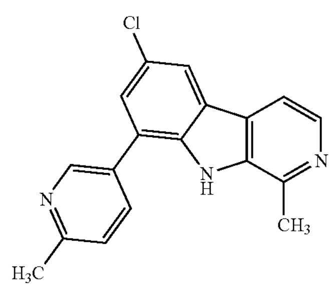 [SMILES: Cc1ccc(-c2cc(Cl)cc3c2[nH]c2c(C)nccc23)cn1] | 6-Chloro-1-methyl-8-(6-methyl-pyridin-3-yl)-9H-pyrido[3,4-b]indole | LC6 | 1.07 | 308.2 [M + H]+ |
| 96 | 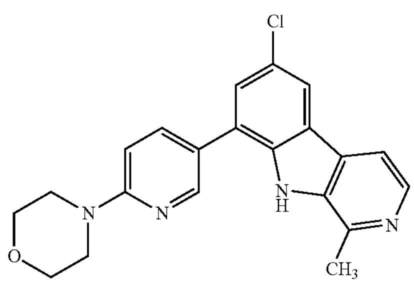 [SMILES: Cc1nccc2c1[nH]c1c(-c3ccc(N4CCOCC4)nc3)cc(Cl)cc12] | 6-Chloro-1-methyl-8-(6-morpholin-4-yl-pyridin-3-yl)-9H-pyrido[3,4-b]indole | LC6 | 1.02 | 377.3 [M − H]− |
| 97 | 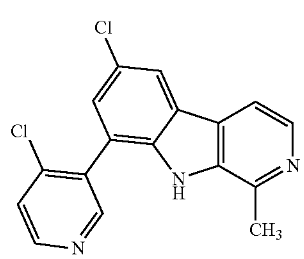 [SMILES: Cc1nccc2c1[nH]c1c(-c3cnccc3Cl)cc(Cl)cc12] | 6-Chloro-8-(4-chloro-pyridin-3-yl)-1-methyl-9H-pyrido[3,4-b]indole | LC4 | 1.52 | 328.0 [M + H]+ |
| 98 | 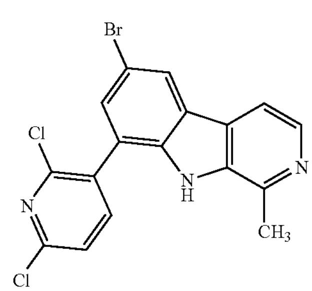 [SMILES: Cc1nccc2c1[nH]c1c(-c3ccc(Cl)nc3Cl)cc(Br)cc12] | 6-Bromo-8-(2,6-dichloro-pyridin-3-yl)-1-methyl-9H-pyrido[3,4-b]indole | LC8 | 3.21 | 406.1 [M + H]+ |

TABLE 1-continued

| Ex. No. | Structure | Name | LC/MS | RT [min] | MS |
|---|---|---|---|---|---|
| 99 | 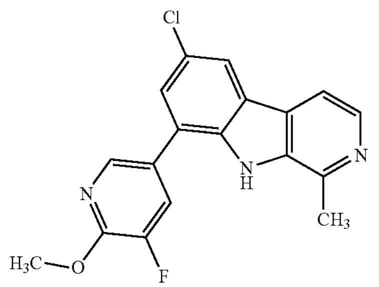 [SMILES: COc1ncc(-c2cc(Cl)cc3c2[nH]c2c(C)nccc23)cc1F] | 6-Chloro-8-(5-fluoro-6-methoxy-pyridin-3-yl)-1-methyl-9H-pyrido[3,4-b]indole | LC6 | 1.09 | 342.1 [M + H]+ |
| 100 | 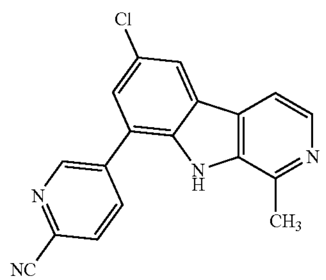 [SMILES: Cc1nccc2c1[nH]c1c(-c3ccc(C#N)nc3)cc(Cl)cc12] | 5-(6-Chloro-1-methyl-9H-pyrido[3,4-b]indol-8-yl)-pyridine-2-carbonitrile | LC6 | 1.01 | 319.1 [M + H]+ |
| 101 | 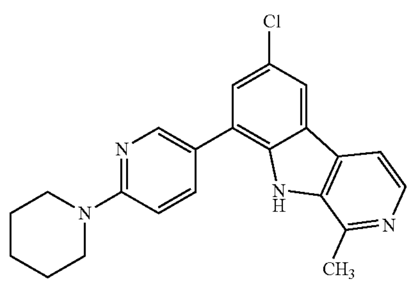 [SMILES: Cc1nccc2c1[nH]c1c(-c3ccc(N4CCCCC4)nc3)cc(Cl)cc12] | 6-Chloro-1-methyl-8-(3,4,5,6-tetrahydro-2H-[1,2']bipyridinyl-5'-yl)-9H-pyrido[3,4-b]indole | LC6 | 1.32 | 377.3 [M + H]+ |
| 102 | 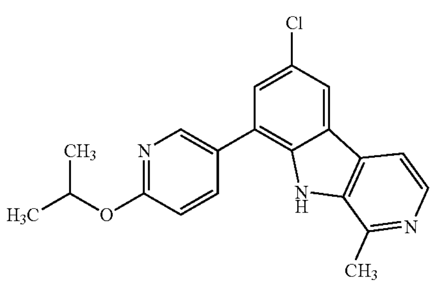 [SMILES: Cc1nccc2c1[nH]c1c(-c3ccc(OC(C)C)nc3)cc(Cl)cc12] | 6-Chloro-8-(6-isopropoxy-pyridin-3-yl)-1-methyl-9H-pyrido[3,4-b]indole | LC3 | 1.02 | 352.1 [M + H]+ |
| 103 | 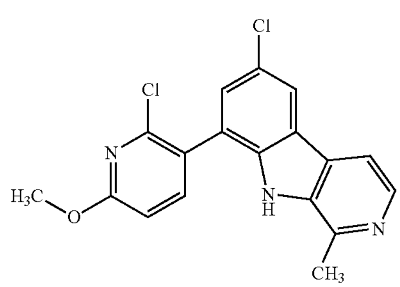 [SMILES: COc1ccc(-c2cc(Cl)cc3c2[nH]c2c(C)nccc23)c(Cl)n1] | 6-Chloro-8-(2-chloro-6-methoxy-pyridin-3-yl)-1-methyl-9H-pyrido[3,4-b]indole | LC3 | 0.99 | 358.1 [M + H]+ |

TABLE 1-continued

| Ex. No. | Structure | Name | LC/MS | RT [min] | MS |
|---|---|---|---|---|---|
| 104 | 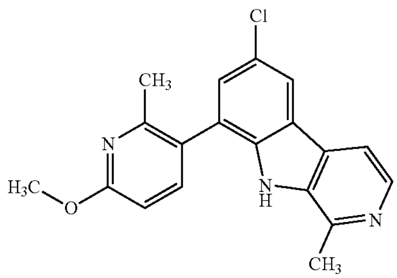 [SMILES: COc1ccc(-c2cc(Cl)cc3c2[nH]c2c(C)nccc23)c(C)n1] | 6-Chloro-8-(6-methoxy-2-methyl-pyridin-3-yl)-1-methyl-9H-pyrido[3,4-b]indole | LC3 | 0.98 | 338.1 [M + H]⁺ |
| 105 | 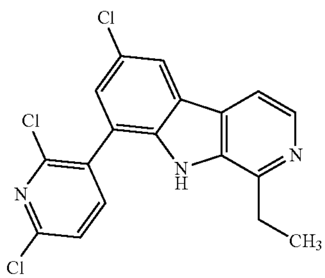 [SMILES: CCc1nccc2c1[nH]c1c(-c3ccc(Cl)nc3Cl)cc(Cl)cc12] | 6-Chloro-8-(2,6-dichloro-pyridin-3-yl)-1-ethyl-9H-pyrido[3,4-b]indole | LC8 | 3.54 | 376.1 [M + H]⁺ |
| 106 | 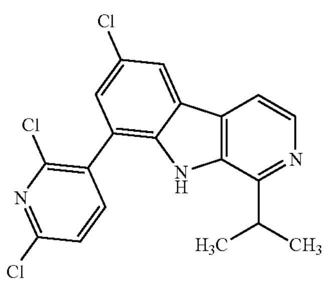 [SMILES: CC(C)c1nccc2c1[nH]c1c(-c3ccc(Cl)nc3Cl)cc(Cl)cc12] | 6-Chloro-8-(2,6-dichloro-pyridin-3-yl)-1-isopropyl-9H-pyrido[3,4-b]indole | LC3 | 1.04 | 390.1 [M + H]⁺ |
| 107 | 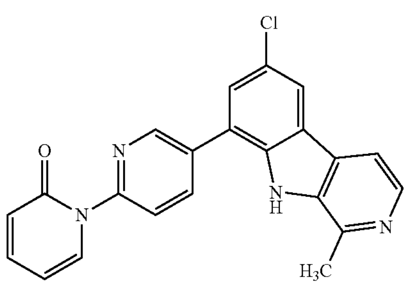 [SMILES: Cc1nccc2c1[nH]c1c(-c3ccc(-n4ccccc4=O)nc3)cc(Cl)cc12] | 5'-(6-Chloro-1-methyl-9H-pyrido[3,4-b]indol-8-yl)-[1,2']bipyridinyl-2-one | LC3 | 1.00 | 387.0 [M + H]⁺ |
| 108 | 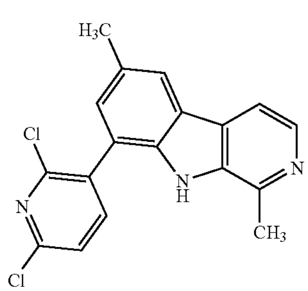 [SMILES: Cc1cc(-c2ccc(Cl)nc2Cl)c2[nH]c3c(C)nccc3c2c1] | 8-(2,6-Dichloro-pyridin-3-yl)-1,6-dimethyl-9H-pyrido[3,4-b]indole | LC8 | 3.27 | 342.1 [M + H]⁺ |

TABLE 1-continued

| Ex. No. | Structure | Name | LC/MS | RT [min] | MS |
|---|---|---|---|---|---|
| 109 | 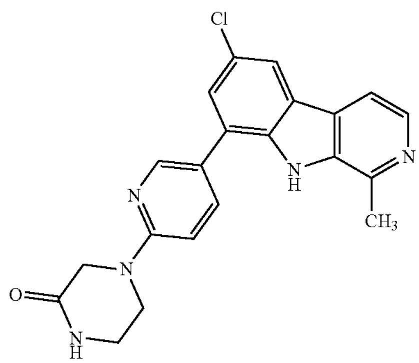 [SMILES: Cc1nccc2c1[nH]c1c(-c3ccc(N4CCNC(=O)C4)nc3)cc(Cl)cc12] | 4-[5-(6-Chloro-1-methyl-9H-pyrido[3,4-b]indol-8-yl)-pyridin-2-yl]-piperazin-2-one | LC3 | 0.94 | 392.0 [M + H]+ |
| 110 | 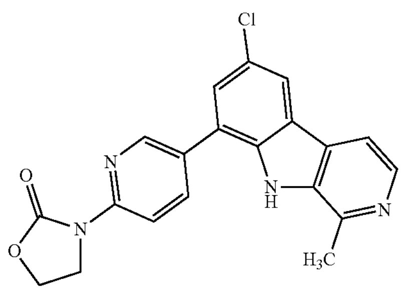 [SMILES: Cc1nccc2c1[nH]c1c(-c3ccc(N4CCOC4=O)nc3)cc(Cl)cc12] | 3-[5-(6-Chloro-1-methyl-9H-pyrido[3,4-b]indol-8-yl)-pyridin-2-yl]-oxazolidin-2-one | LC3 | 1.02 | 379.0 [M + H]+ |
| 111 | 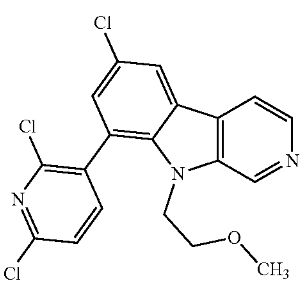 [SMILES: COCCn1c2cnccc2c2cc(Cl)cc(-c3ccc(Cl)nc3Cl)c21] | 6-Chloro-8-(2,6-dichloro-pyridin-3-yl)-9-(2-methoxy-ethyl)-9H-pyrido[3,4-b]indole | LC3 | 1.14 | 406.0 [M + H]+ |
| 112 | 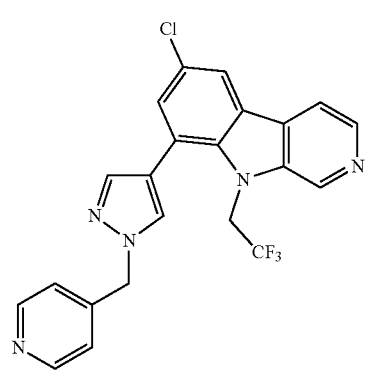 [SMILES: FC(F)(F)Cn1c2cnccc2c2cc(Cl)cc(-c3cnn(Cc4ccncc4)c3)c21] | 6-Chloro-8-(1-pyridin-4-ylmethyl-1H-pyrazol-4-yl)-9-(2,2,2-trifluoro-ethyl)-9H-pyrido[3,4-b]indole | LC3 | 1.01 | 442.0 [M + H]+ |

TABLE 1-continued

| Ex. No. | Structure | Name | LC/MS | RT [min] | MS |
|---|---|---|---|---|---|
| 113 | 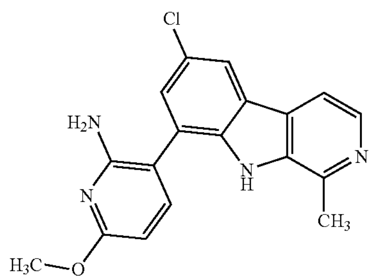 [SMILES: COc1ccc(-c2cc(Cl)cc3c2[nH]c2c(C)nccc23)c(N)n1] | 3-(6-Chloro-1-methyl-9H-pyrido[3,4-b]indol-8-yl)-6-methoxy-pyridin-2-ylamine | LC8 | 3.03 | 339.1 [M + H]+ |
| 114 | 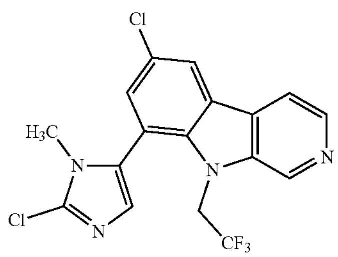 [SMILES: Cn1c(-c2cc(Cl)cc3c4ccncc4n(CC(F)(F)F)c23)cnc1Cl] | 6-Chloro-8-(2-chloro-3-methyl-3H-imidazol-4-yl)-9-(2,2,2-trifluoro-ethyl)-9H-pyrido[3,4-b]indole | LC3 | 1.12 | 399.1 [M + H]+ |
| 115 | 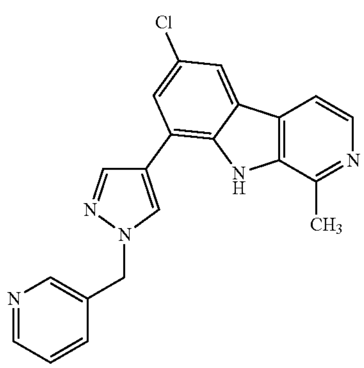 [SMILES: Cc1nccc2c1[nH]c1c(-c3cnn(Cc4cccnc4)c3)cc(Cl)cc12] | 6-Chloro-1-methyl-8-(1-pyridin-3-ylmethyl-1H-pyrazol-4-yl)-9H-pyrido[3,4-b]indole | LC4 | 1.17 | 374.3 [M + H]+ |
| 116 | 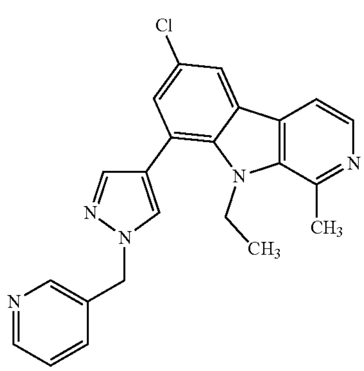 [SMILES: CCn1c2c(-c3cnn(Cc4cccnc4)c3)cc(Cl)cc2c2ccnc(C)c21] | 6-Chloro-9-ethyl-1-methyl-8-(1-pyridin-3-ylmethyl-1H-pyrazol-4-yl)-9H-pyrido[3,4-b]indole | LC4 | 1.22 | 402.3 [M + H]+ |
| 117 | 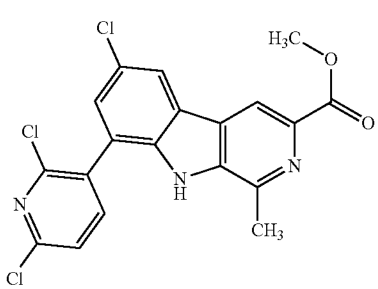 [SMILES: COC(=O)c1cc2c([nH]c3c(-c4ccc(Cl)nc4Cl)cc(Cl)cc32)c(C)n1] | 6-Chloro-8-(2,6-dichloro-pyridin-3-yl)-1-methyl-9H-pyrido[3,4-b]indole-3-carboxylic acid methyl ester | LC4 | 2.06 | 420.1 [M + H]+ |

TABLE 1-continued

| Ex. No. | Structure | Name | LC/MS | RT [min] | MS |
|---|---|---|---|---|---|
| 118 | 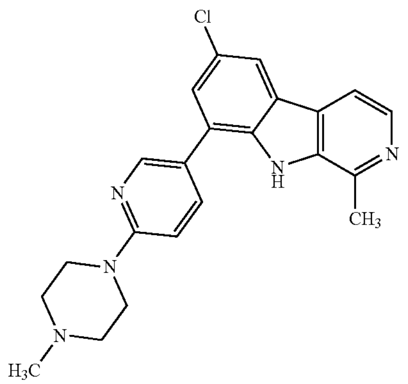 [SMILES: Cc1nccc2c1[nH]c1c(-c3ccc(N4CCN(C)CC4)nc3)cc(Cl)cc12] | 6-Chloro-1-methyl-8-[6-(4-methyl-piperazin-1-yl)-pyridin-3-yl]-9H-pyrido[3,4-b]indole | LC4 | 1.24 | 390.4 [M − H]⁻ |
| 119 | 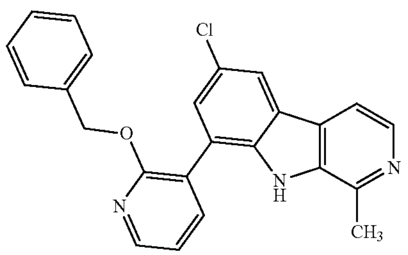 [SMILES: Cc1nccc2c1[nH]c1c(-c3cccnc3OCc3ccccc3)cc(Cl)cc12] | 8-(2-Benzyloxy-pyridin-3-yl)-6-chloro-1-methyl-9H-pyrido[3,4-b]indole | LC4 | 1.73 | 400.1 [M + H]⁺ |
| 120 | 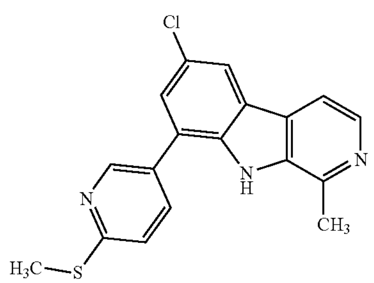 | 6-Chloro-1-methyl-8-(6-methylsulfanyl-pyridin-3-yl)-9H-pyrido[3,4-b]indole | LC4 | 1.45 | 340.1 [M + H]⁺ |
| 121 | 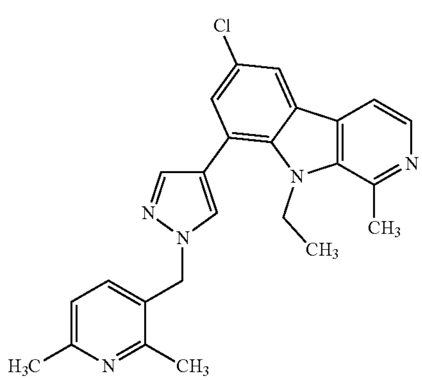 [SMILES: CCn1c2c(-c3cnn(Cc4ccc(C)nc4C)c3)cc(Cl)cc2c2ccnc(C)c21] | 6-Chloro-8-[1-(2,6-dimethyl-pyridin-3-ylmethyl)-1H-pyrazol-4-yl]-9-ethyl-1-methyl-9H-pyrido[3,4-b]indole | LC2 | 1.08 | 430.3 [M + H]⁺ |

TABLE 1-continued

| Ex. No. | Structure | Name | LC/MS | RT [min] | MS |
|---|---|---|---|---|---|
| 122 | 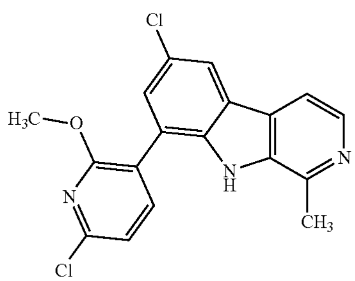 [SMILES: COc1nc(Cl)ccc1-c1cc(Cl)cc2c1[nH]c1c(C)nccc12] | 6-Chloro-8-(6-chloro-2-methoxy-pyridin-3-yl)-1-methyl-9H-pyrido[3,4-b]indole | LC4 | 1.52 | 358.2 [M + H]+ |
| 123 | 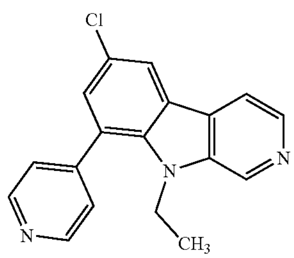 | 6-Chloro-9-ethyl-8-pyridin-4-yl-9H-pyrido[3,4-b]indole | LC9 | 1.49 | 308.2 [M + H]+ |
| 124 | 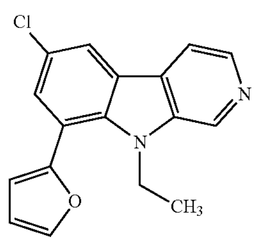 [SMILES: CCn1c2cnccc2c2cc(Cl)cc(-c3ccco3)c21] | 6-Chloro-9-ethyl-8-furan-2-yl-9H-pyrido[3,4-b]indole | LC2 | 1.35 | 297.1 [M + H]+ |
| 125 | 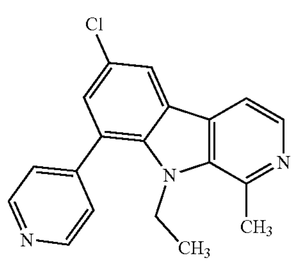 [SMILES: CCn1c2c(-c3ccncc3)cc(Cl)cc2c2ccnc(C)c21] | 6-Chloro-9-ethyl-1-methyl-8-pyridin-4-yl-9H-pyrido[3,4-b]indole | LC3 | 0.95 | 322.1 [M + H]+ |
| 126 | 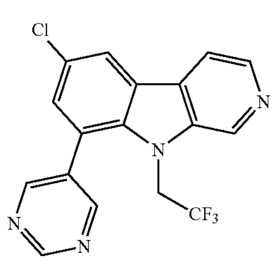 [SMILES: FC(F)(F)Cn1c2cnccc2c2cc(Cl)cc(-c3cncnc3)c21] | 6-Chloro-8-pyrimidin-5-yl-9-(2,2,2-trifluoro-ethyl)-9H-pyrido[3,4-b]indole | LC1 | 1.30 | 363.1 [M + H]+ |

TABLE 1-continued

| Ex. No. | Structure | Name | LC/MS | RT [min] | MS |
|---|---|---|---|---|---|
| 127 | 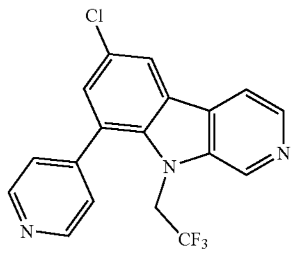 [SMILES: FC(F)(F)Cn1c2cnccc2c2cc(Cl)cc(-c3ccncc3)c21] | 6-Chloro-8-pyridin-4-yl-9-(2,2,2-trifluoro-ethyl)-9H-pyrido[3,4-b]indole | LC1 | 1.20 | 362.1 [M + H]+ |
| 128 | 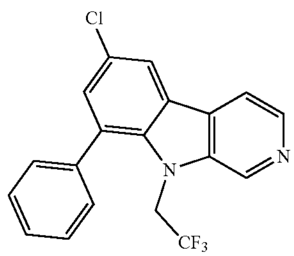 [SMILES: FC(F)(F)Cn1c2cnccc2c2cc(Cl)cc(-c3ccccc3)c21] | 6-Chloro-8-phenyl-9-(2,2,2-trifluoro-ethyl)-9H-pyrido[3,4-b]indole | LC8 | 4.54 | 361.0 [M + H]+ |
| 129 | 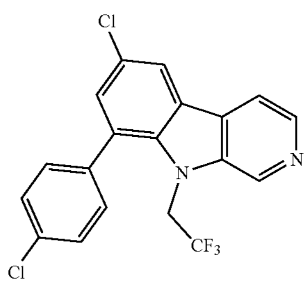 [SMILES: FC(F)(F)Cn1c2cnccc2c2cc(Cl)cc(-c3ccc(Cl)cc3)c21] | 6-Chloro-8-(4-chloro-phenyl)-9-(2,2,2-trifluoro-ethyl)-9H-pyrido[3,4-b]indole | LC3 | 1.35 | 394.9 [M + H]+ |
| 130 | 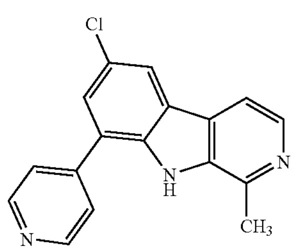 [SMILES: Cc1nccc2c1[nH]c1c(-c3ccncc3)cc(Cl)cc12] | 6-Chloro-1-methyl-8-pyridin-4-yl-9H-pyrido[3,4-b]indole | LC3 | 0.86 | 294.0 [M + H]+ |
| 131 | 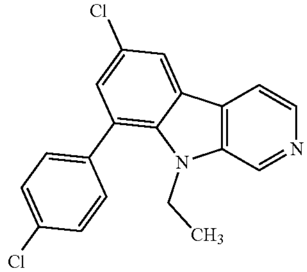 [SMILES: CCn1c2cnccc2c2cc(Cl)cc(-c3ccc(Cl)cc3)c21] | 6-Chloro-8-(4-chloro-phenyl)-9-ethyl-9H-pyrido[3,4-b]indole | LC11 | 3.10 | 341.2 [M + H]+ |

TABLE 1-continued

| Ex. No. | Structure | Name | LC/MS | RT [min] | MS |
|---|---|---|---|---|---|
| 132 | 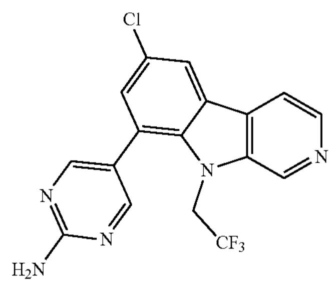 [SMILES: Nc1ncc(-c2cc(Cl)cc3c4ccncc4n(CC(F)(F)F)c23)cn1] | 5-[6-Chloro-9-(2,2,2-trifluoro-ethyl)-9H-pyrido[3,4-b]indol-8-yl]-pyrimidin-2-ylamine | LC11 | 2.39 | 378.2 [M + H]+ |
| 133 | 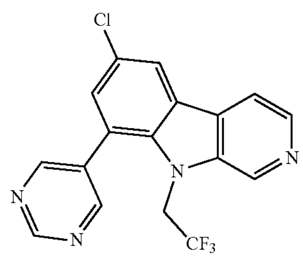 [SMILES: FC(F)(F)Cn1c2cnccc2c2cc(Cl)cc(-c3cncnc3)c21] | 6-Chloro-9-ethyl-8-pyrimidin-5-yl-9H-pyrido[3,4-b]indole | LC1 | 1.20 | 309.1 [M + H]+ |
| 134 | 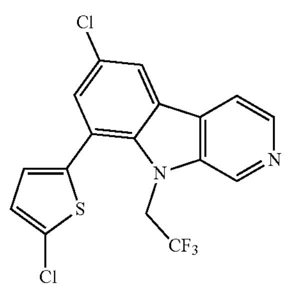 [SMILES: FC(F)(F)Cn1c2cnccc2c2cc(Cl)cc(-c3ccc(Cl)s3)c21] | 6-Chloro-8-(5-chloro-thiophen-2-yl)-9-(2,2,2-trifluoro-ethyl)-9H-pyrido[3,4-b]indole | LC12 | 4.22 | 401.0 [M + H]+ |
| 135 | 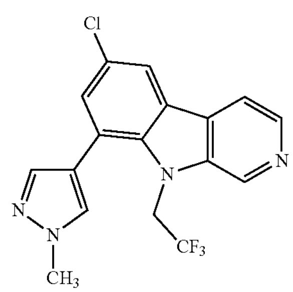 [SMILES: Cn1cc(-c2cc(Cl)cc3c4ccncc4n(CC(F)(F)F)c23)cn1] | 6-Chloro-8-(1-methyl-1H-pyrazol-4-yl)-9-(2,2,2-trifluoro-ethyl)-9H-pyrido[3,4-b]indole | LC12 | 3.17 | 365.1 [M + H]+ |
| 136 | 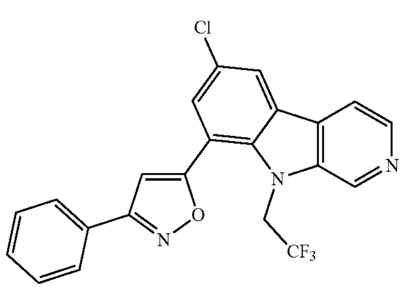 [SMILES: FC(F)(F)Cn1c2cnccc2c2cc(Cl)cc(-c3cc(-c4ccccc4)no3)c21] | 6-Chloro-8-(3-phenyl-isoxazol-5-yl)-9-(2,2,2-trifluoro-ethyl)-9H-pyrido[3,4-b]indole | LC8 | 4.60 | 428.2 [M + H]+ |

TABLE 1-continued

| Ex. No. | Structure | Name | LC/MS | RT [min] | MS |
|---|---|---|---|---|---|
| 137 | 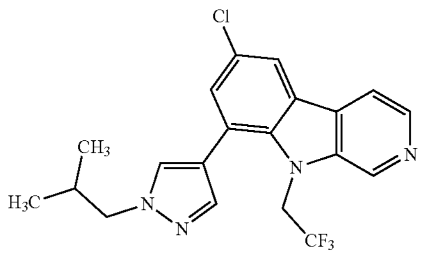 [SMILES: CC(C)Cn1cc(-c2cc(Cl)cc3c4ccncc4n(CC(F)(F)F)c23)cn1] | 6-Chloro-8-(1-isobutyl-1H-pyrazol-4-yl)-9-(2,2,2-trifluoro-ethyl)-9H-pyrido[3,4-b]indole | LC12 | 3.79 | 407.1 [M + H]+ |
| 138 | 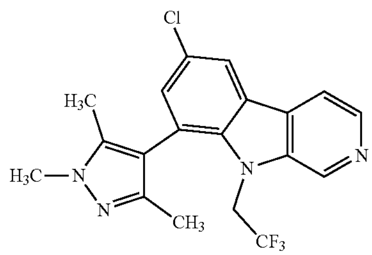 [SMILES: Cc1nn(C)c(C)c1-c1cc(Cl)cc2c3ccncc3n(CC(F)(F)F)c12] | 6-Chloro-9-(2,2,2-trifluoro-ethyl)-8-(1,3,5-trimethyl-1H-pyrazol-4-yl)-9H-pyrido[3,4-b]indole | LC12 | 3.40 | 393.1 [M + H]+ |
| 139 | 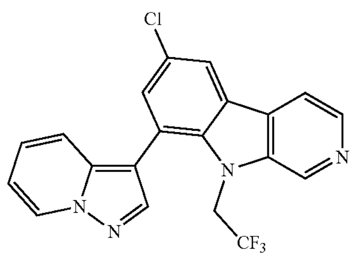 [SMILES: FC(F)(F)Cn1c2cnccc2c2cc(Cl)cc(-c3cnn4ccccc34)c21] | 6-Chloro-8-pyrazolo[1,5-a]pyridin-3-yl-9-(2,2,2-trifluoro-ethyl)-9H-pyrido[3,4-b]indole | LC12 | 3.47 | 401.1 [M + H]+ |
| 140 | 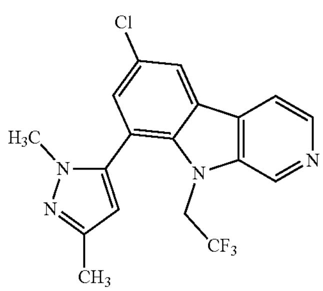 [SMILES: Cc1cc(-c2cc(Cl)cc3c4ccncc4n(CC(F)(F)F)c23)n(C)n1] | 6-Chloro-8-(2,5-dimethyl-2H-pyrazol-3-yl)-9-(2,2,2-trifluoro-ethyl)-9H-pyrido[3,4-b]indole | LC3 | 1.16 | 379.0 [M + H]+ |
| 141 | 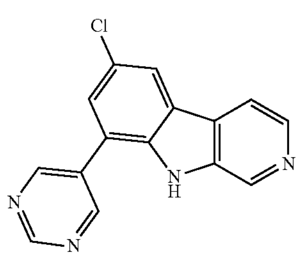 [SMILES: Clc1cc(-c2cncnc2)c2[nH]c3cnccc3c2c1] | 6-Chloro-8-pyrimidin-5-yl-9H-pyrido[3,4-b]indole | LC6 | 0.88 | 281.1 [M + H]+ |

TABLE 1-continued

| Ex. No. | Structure | Name | LC/MS | RT [min] | MS |
|---|---|---|---|---|---|
| 142 | 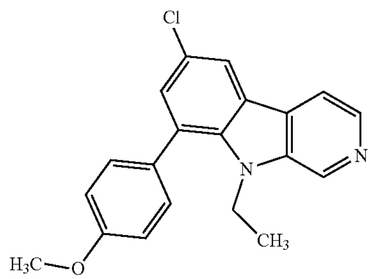 [SMILES: CCn1c2cnccc2c2cc(Cl)cc(-c3ccc(OC)cc3)c21] | 6-Chloro-9-ethyl-8-(4-methoxy-phenyl)-9H-pyrido[3,4-b]indole | LC6 | 1.14 | 337.20 [M + H]+ |
| 143 | 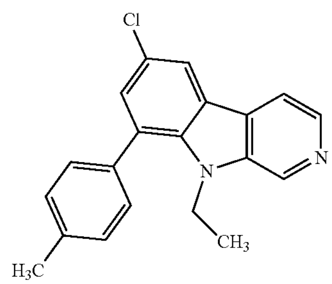 [SMILES: CCn1c2cnccc2c2cc(Cl)cc(-c3ccc(C)cc3)c21] | 6-Chloro-9-ethyl-8-p-tolyl-9H-pyrido[3,4-b]indole | LC6 | 1.22 | 321.1 [M + H]+ |
| 144 | 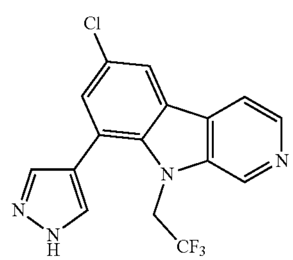 [SMILES: FC(F)(F)Cn1c2cnccc2c2cc(Cl)cc(-c3cn[nH]c3)c21] | 6-Chloro-8-(1H-pyrazol-4-yl)-9-(2,2,2-trifluoro-ethyl)-9H-pyrido[3,4-b]indole | LC12 | 3.09 | 351.1 [M + H]+ |
| 145 | 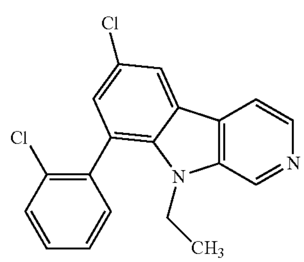 [SMILES: CCn1c2cnccc2c2cc(Cl)cc(-c3ccccc3Cl)c21] | 6-Chloro-8-(2-chloro-phenyl)-9-ethyl-9H-pyrido[3,4-b]indole | LC8 | 3.96 | 341.1 [M + H]+ |
| 146 | 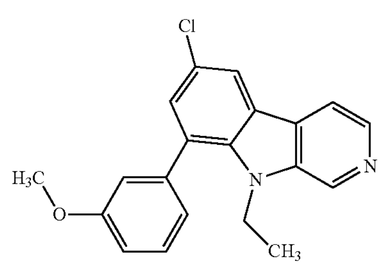 [SMILES: CCn1c2cnccc2c2cc(Cl)cc(-c3cccc(OC)c3)c21] | 6-Chloro-9-ethyl-8-(3-methoxy-phenyl)-9H-pyrido[3,4-b]indole | LC8 | 3.91 | 337.1 [M + H]+ |

TABLE 1-continued

| Ex. No. | Structure | Name | LC/MS | RT [min] | MS |
|---|---|---|---|---|---|
| 147 | 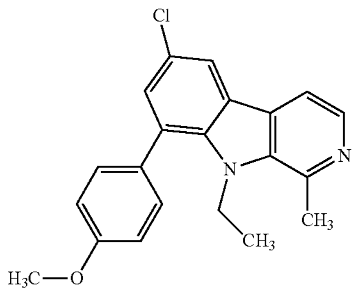 [SMILES: CCn1c2c(-c3ccc(OC)cc3)cc(Cl)cc2c2ccnc(C)c21] | 6-Chloro-9-ethyl-8-(4-methoxy-phenyl)-1-methyl-9H-pyrido[3,4-b]indole | LC8 | 3.70 | 351.2 [M + H]+ |
| 148 | 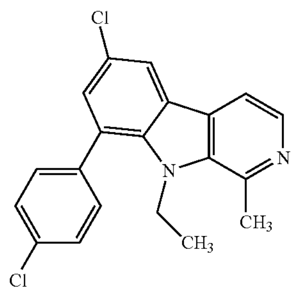 [SMILES: CCn1c2c(-c3ccc(Cl)cc3)cc(Cl)cc2c2ccnc(C)c21] | 6-Chloro-8-(4-chloro-phenyl)-9-ethyl-1-methyl-9H-pyrido[3,4-b]indole | LC4 | 1.64 | 355.1 [M + H]+ |
| 149 | 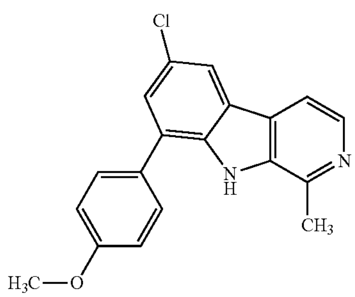 | 6-Chloro-8-(4-methoxy-phenyl)-1-methyl-9H-pyrido[3,4-b]indole | LC3 | 1.10 | 323.1 [M + H]+ |
| 150 | 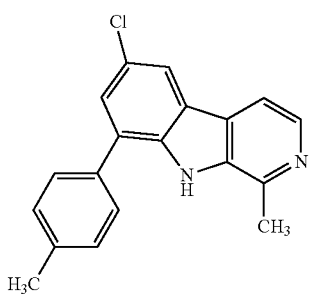 | 6-Chloro-1-methyl-8-p-tolyl-9H-pyrido[3,4-b]indole | LC6 | 1.15 | 305.3 [M − H]− |
| 151 | 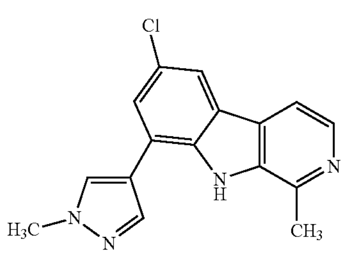 [SMILES: Cc1nccc2c1[nH]c1c(-c3cnn(C)c3)cc(Cl)cc12] | 6-Chloro-1-methyl-8-(1-methyl-1H-pyrazol-4-yl)-9H-pyrido[3,4-b]indole | LC8 | 2.80 | 297.2 [M + H]+ |

TABLE 1-continued

| Ex. No. | Structure | Name | LC/MS | RT [min] | MS |
|---|---|---|---|---|---|
| 152 | 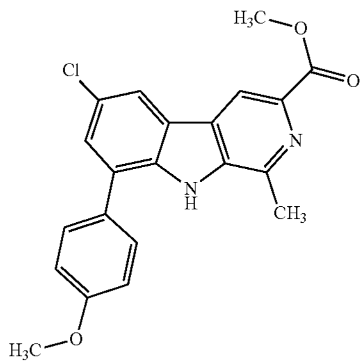 [SMILES: COC(=O)c1cc2c([nH]c3c(-c4ccc(OC)cc4)cc(Cl)cc32)c(C)n1] | 6-Chloro-8-(4-methoxy-phenyl)-1-methyl-9H-pyrido[3,4-b]indole-3-carboxylic acid methyl ester | LC6 | 1.36 | 381.1 [M + H]+ |
| 153 | 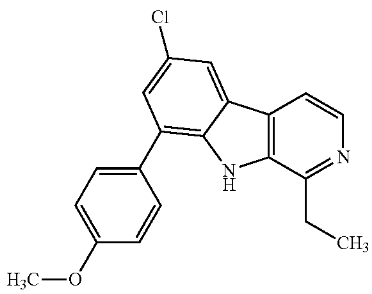 [SMILES: CCc1nccc2c1[nH]c1c(-c3ccc(OC)cc3)cc(Cl)cc12] | 6-Chloro-1-ethyl-8-(4-methoxy-phenyl)-9H-pyrido[3,4-b]indole | LC3 | 1.01 | 337.1 [M + H]+ |
| 154 | 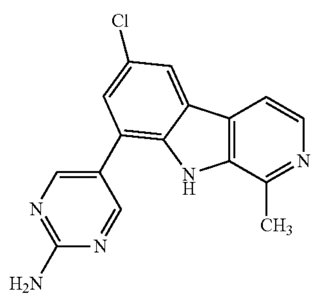 [SMILES: Cc1nccc2c1[nH]c1c(-c3cnc(N)nc3)cc(Cl)cc12] | 5-(6-Chloro-1-methyl-9H-pyrido[3,4-b]indol-8-yl)-pyrimidin-2-ylamine | LC3 | 0.80 | 310.1 [M + H]+ |
| 155 | 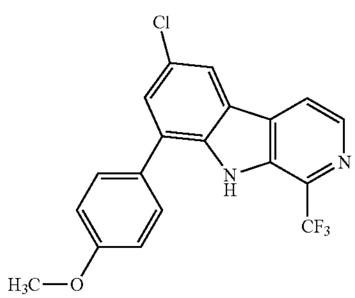 [SMILES: COc1ccc(-c2cc(Cl)cc3c2[nH]c2c(C(F)(F)F)nccc23)cc1] | 6-Chloro-8-(4-methoxy-phenyl)-1-trifluoromethyl-9H-pyrido[3,4-b]indole | LC3 | 1.32 | 377.1 [M + H]+ |
| 156 | 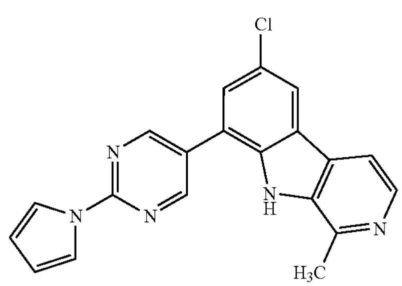 [SMILES: Cc1nccc2c1[nH]c1c(-c3cnc(-n4cccc4)nc3)cc(Cl)cc12] | 6-Chloro-1-methyl-8-(2-pyrrol-1-yl-pyrimidin-5-yl)-9H-pyrido[3,4-b]indole | LC3 | 1.01 | 360.1 [M + H]+ |

TABLE 1-continued

| Ex. No. | Structure | Name | LC/MS | RT [min] | MS |
|---|---|---|---|---|---|
| 157 | 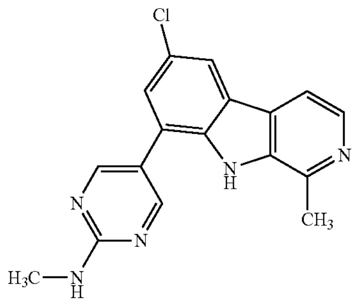 [SMILES: CNc1ncc(-c2cc(Cl)cc3c2[nH]c2c(C)nccc23)cn1] | [5-(6-Chloro-1-methyl-9H-pyrido[3,4-b]indol-8-yl)-pyrimidin-2-yl]-methyl-amine | LC6 | 0.99 | 324.1 [M + H]+ |
| 158 | 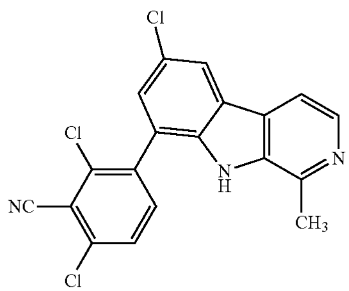 [SMILES: Cc1nccc2c1[nH]c1c(-c3ccc(Cl)c(C#N)c3Cl)cc(Cl)cc12] | 2,6-Dichloro-3-(6-chloro-1-methyl-9H-pyrido[3,4-b]indol-6-yl)-benzonitrile | LC8 | 3.64 | 386.1 [M + H]+ |
| 159 | 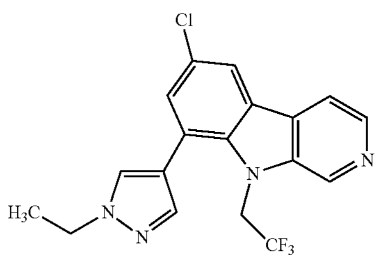 [SMILES: CCn1cc(-c2cc(Cl)cc3c4ccncc4n(CC(F)(F)F)c23)cn1] | 6-Chloro-8-(1-ethyl-1H-pyrazol-4-yl)-9-(2,2,2-trifluoro-ethyl)-9H-pyrido[3,4-b]indole | LC3 | 1.12 | 379.0 [M + H]+ |
| 160 | 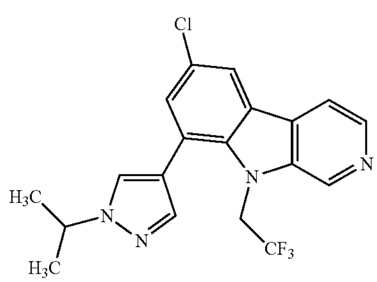 [SMILES: CC(C)n1cc(-c2cc(Cl)cc3c4ccncc4n(CC(F)(F)F)c23)cn1] | 6-Chloro-8-(1-isopropyl-1H-pyrazol-4-yl)-9-(2,2,2-trifluoro-ethyl)-9H-pyrido[3,4-b]indole | LC3 | 1.18 | 393.0 [M + H]+ |
| 161 | 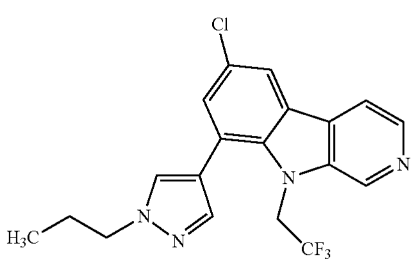 [SMILES: CCCn1cc(-c2cc(Cl)cc3c4ccncc4n(CC(F)(F)F)c23)cn1] | 6-Chloro-8-(1-propyl-1H-pyrazol-4-yl)-9-(2,2,2-trifluoro-ethyl)-9H-pyrido[3,4-b]indole | LC3 | 1.16 | 393.0 [M + H]+ |

TABLE 1-continued

| Ex. No. | Structure | Name | LC/MS | RT [min] | MS |
|---|---|---|---|---|---|
| 162 | 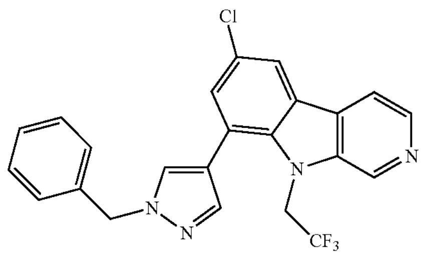 [SMILES: FC(F)(F)Cn1c2cnccc2c2cc(Cl)cc(-c3cnn(Cc4ccccc4)c3)c21] | 8-(1-Benzyl-1H-pyrazol-4-yl)-6-chloro-9-(2,2,2-trifluoro-ethyl)-9H-pyrido[3,4-b]indole | LC8 | 3.91 | 441.2 [M + H]+ |
| 163 | 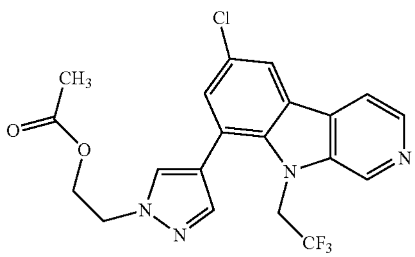 [SMILES: CC(=O)OCCn1cc(-c2cc(Cl)cc3c4ccncc4n(CC(F)(F)F)c23)cn1] | Acetic acid 2-(4-[6-chloro-9-(2,2,2-trifluoro-ethyl)-9H-pyrido[3,4-b]indol-8-yl]-pyrazol-1-yl)-ethyl ester | LC3 | 1.12 | 437.0 [M + H]+ |
| 164 | 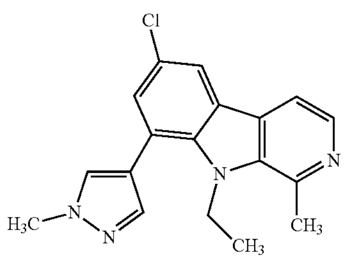 [SMILES: CCn1c2c(-c3cnn(C)c3)cc(Cl)cc2c2ccnc(C)c21] | 6-Chloro-9-ethyl-1-methyl-8-(1-methyl-1H-pyrazol-4-yl)-9H-pyrido[3,4-b]indole | LC8 | 2.87 | 325.1 [M + H]+ |
| 165 | 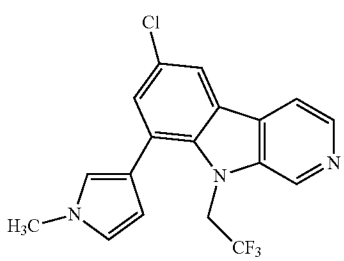 [SMILES: Cn1ccc(-c2cc(Cl)cc3c4ccncc4n(CC(F)(F)F)c23)c1] | 6-Chloro-8-(1-methyl-1H-pyrrol-3-yl)-9-(2,2,2-trifluoro-ethyl)-9H-pyrido[3,4-b]indole | LC3 | 1.25 | 364.0 [M + H]+ |
| 166 | 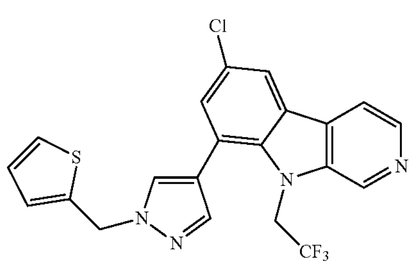 [SMILES: FC(F)(F)Cn1c2cnccc2c2cc(Cl)cc(-c3cnn(Cc4cccs4)c3)c21] | 6-Chloro-8-(1-thiophen-2-ylmethyl-1H-pyrazol-4-yl)-9-(2,2,2-trifluoro-ethyl)-9H-pyrido[3,4-b]indole | LC3 | 1.21 | 491.1 [M − H + FA]− |

TABLE 1-continued

| Ex. No. | Structure | Name | LC/MS | RT [min] | MS |
|---|---|---|---|---|---|
| 167 | 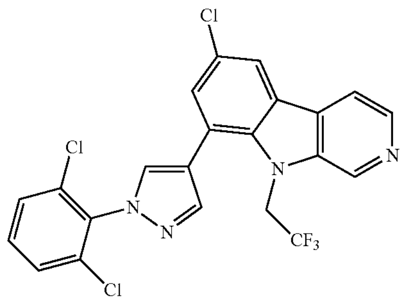 [SMILES: FC(F)(F)Cn1c2cnccc2c2cc(Cl)cc(-c3cnn(-c4c(Cl)cccc4Cl)c3)c21] | 6-Chloro-8-[1-(2,6-dichloro-phenyl)-1H-pyrazol-4-yl]-9-(2,2,2-trifluoro-ethyl)-9H-pyrido[3,4-b]indole | LC3 | 1.28 | 495.1 [M + H]$^+$ |
| 168 | 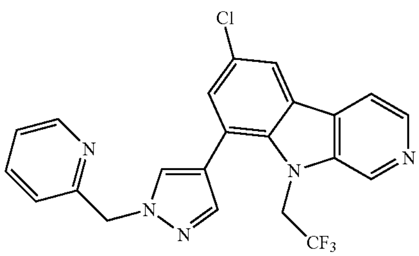 [SMILES: FC(F)(F)Cn1c2cnccc2c2cc(Cl)cc(-c3cnn(Cc4ccccn4)c3)c21] | 6-Chloro-8-(1-pyridin-2-ylmethyl-1H-pyrazol-4-yl)-9-(2,2,2-trifluoro-ethyl)-9H-pyrido[3,4-b]indole | LC3 | 1.10 | 442.1 [M + H]$^+$ |
| 169 | 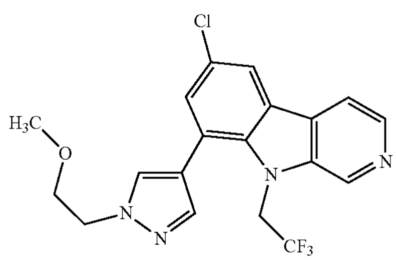 [SMILES: COCCn1cc(-c2cc(Cl)cc3c4ccncc4n(CC(F)(F)F)c23)cn1] | 6-Chloro-8-[1-(2-methoxy-ethyl)-1H-pyrazol-4-yl]-9-(2,2,2-trifluoro-ethyl)-9H-pyrido[3,4-b]indole | LC3 | 1.09 | 409.2 [M + H]$^+$ |
| 170 | 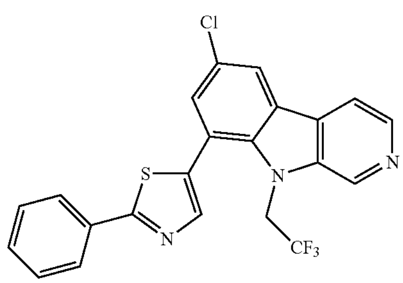 [SMILES: FC(F)(F)Cn1c2cnccc2c2cc(Cl)cc(-c3cnc(-c4ccccc4)s3)c21] | 6-Chloro-8-(2-phenyl-thiazol-5-yl)-9-(2,2,2-trifluoro-ethyl)-9H-pyrido[3,4-b]indole | LC3 | 1.37 | 444.1 [M + H]$^+$ |
| 171 | 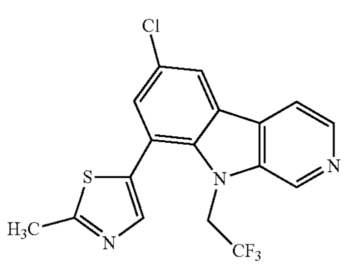 [SMILES: Cc1ncc(-c2cc(Cl)cc3c4ccncc4n(CC(F)(F)F)c23)s1] | 6-Chloro-8-(2-methyl-thiazol-5-yl)-9-(2,2,2-trifluoro-ethyl)-9H-pyrido[3,4-b]indole | LC3 | 1.17 | 382.1 [M + H]$^+$ |

TABLE 1-continued

| Ex. No. | Structure | Name | LC/MS | RT [min] | MS |
|---|---|---|---|---|---|
| 172 | 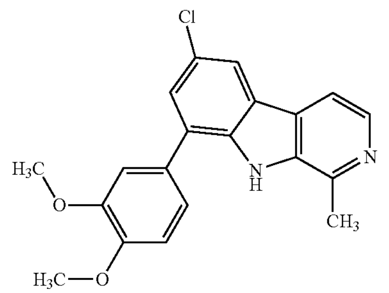 [SMILES: COc1ccc(-c2cc(Cl)cc3c2[nH]c2c(C)nccc23)cc1OC] | 6-Chloro-8-(3,4-dimethoxy-phenyl)-1-methyl-9H-pyrido[3,4-b]indole | LC3 | 0.95 | 353.3 [M + H]+ |
| 173 | 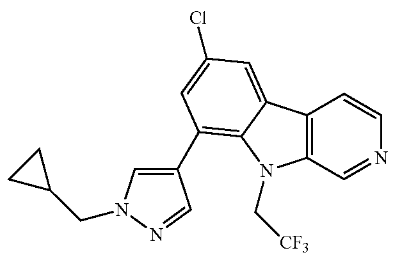 [SMILES: FC(F)(F)Cn1c2cnccc2c2cc(Cl)cc(-c3cnn(CC4CC4)c3)c21] | 6-Chloro-8-(1-cyclopropylmethyl-1H-pyrazol-4-yl)-9-(2,2,2-trifluoro-ethyl)-9H-pyrido[3,4-b]indole | LC3 | 1.18 | 405.2 [M + H]+ |
| 174 | 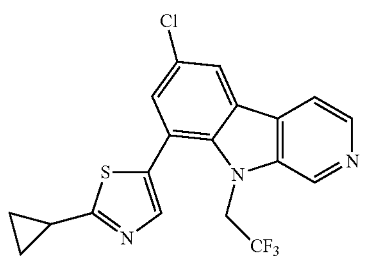 [SMILES: FC(F)(F)Cn1c2cnccc2c2cc(Cl)cc(-c3cnc(C4CC4)s3)c21] | 6-Chloro-8-(2-cyclopropyl-thiazol-5-yl)-9-(2,2,2-trifluoro-ethyl)-9H-pyrido[3,4-b]indole | LC3 | 1.26 | 408.2 [M + H]+ |
| 175 | 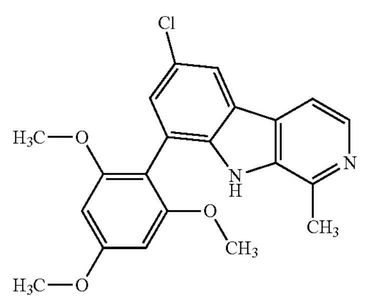 [SMILES: COc1cc(OC)c(-c2cc(Cl)cc3c2[nH]c2c(C)nccc23)c(OC)c1] | 6-Chloro-1-methyl-8-(2,4,6-trimethoxy-phenyl)-9H-pyrido[3,4-b]indole | LC3 | 1.10 | 383.2 [M + H]+ |
| 176 | 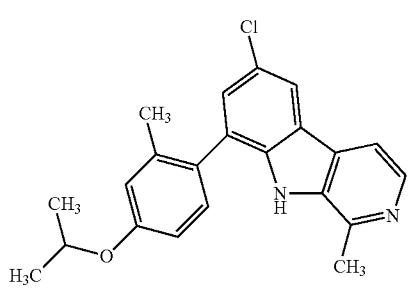 [SMILES: Cc1cc(OC(C)C)ccc1-c1cc(Cl)cc2c1[nH]c1c(C)nccc12] | 6-Chloro-8-(4-isopropoxy-2-methyl-phenyl)-1-methyl-9H-pyrido[3,4-b]indole | LC8 | 4.05 | 365.2 [M + H]+ |

TABLE 1-continued

| Ex. No. | Structure | Name | LC/MS | RT [min] | MS |
|---|---|---|---|---|---|
| 177 | 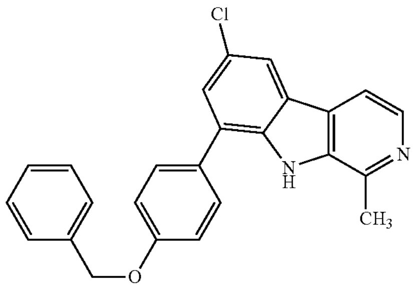 [SMILES: Cc1nccc2c1[nH]c1c(-c3ccc(OCc4ccccc4)cc3)cc(Cl)cc12] | 8-(4-Benzyloxy-phenyl)-6-chloro-1-methyl-9H-pyrido[3,4-b]indole | LC8 | 4.13 | 399.1 [M + H]$^+$ |
| 178 | 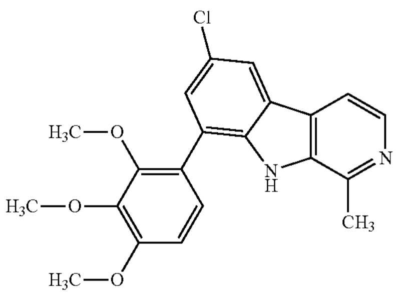 [SMILES: COc1ccc(-c2cc(Cl)cc3c2[nH]c2c(C)nccc23)c(OC)c1OC] | 6-Chloro-1-methyl-8-(2,3,4-trimethoxy-phenyl)-9H-pyrido[3,4-b]indole | LC4 | 1.64 | 381.2 [M − H]$^-$ |
| 179 | 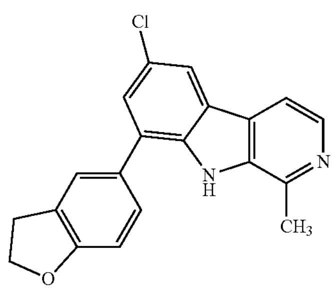 [SMILES: Cc1nccc2c1[nH]c1c(-c3ccc4c(c3)CCO4)cc(Cl)cc12] | 6-Chloro-8-(2,3-dihydro-benzofuran-5-yl)-1-methyl-9H-pyrido[3,4-b]indole | LC4 | 1.64 | 335.2 [M + H]$^+$ |
| 180 | 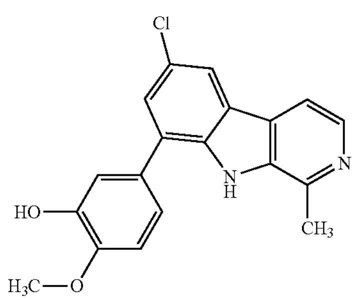 [SMILES: COc1ccc(-c2cc(Cl)cc3c2[nH]c2c(C)nccc23)cc1O] | 5-(6-Chloro-1-methyl-9H-pyrido[3,4-b]indol-8-yl)-2-methoxy-phenol | LC4 | 1.54 | 339.2 [M + H]$^+$ |
| 181 | 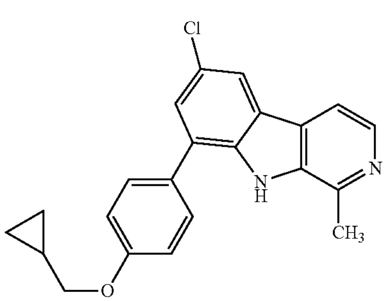 [SMILES: Cc1nccc2c1[nH]c1c(-c3ccc(OCC4CC4)cc3)cc(Cl)cc12] | 6-Chloro-8-(4-cyclopropylmethoxy-phenyl)-1-methyl-9H-pyrido[3,4-b]indole | LC4 | 1.77 | 363.2 [M + H]$^+$ |

TABLE 1-continued

| Ex. No. | Structure | Name | LC/ MS | RT [min] | MS |
|---|---|---|---|---|---|
| 182 | 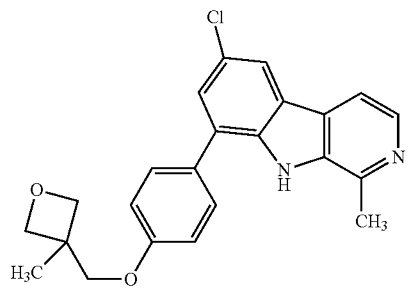 [SMILES: Cc1nccc2c1[nH]c1c(-c3ccc(OCC4(C)COC4)cc3)cc(Cl)cc12] | 6-Chloro-1-methyl-8-[4-(3-methyl-oxetan-3-ylmethoxy)-phenyl]-9H-pyrido[3,4-b]indole | LC4 | 1.67 | 393.2 [M + H]+ |
| 183 | 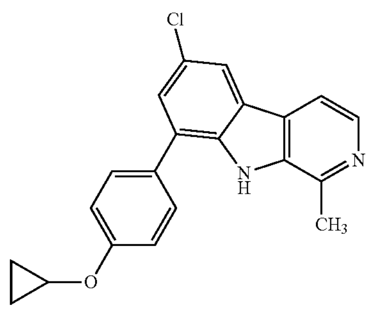 [SMILES: Cc1nccc2c1[nH]c1c(-c3ccc(OC4CC4)cc3)cc(Cl)cc12] | 6-Chloro-8-(4-cyclopropoxy-phenyl)-1-methyl-9H-pyrido[3,4-b]indole | LC4 | 1.73 | 349.2 [M + H]+ |
| 184 | 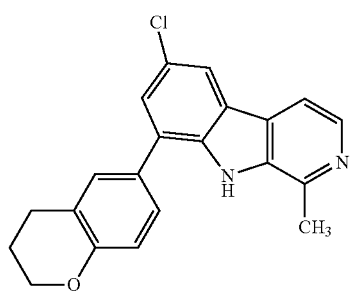 [SMILES: Cc1nccc2c1[nH]c1c(-c3ccc4c(c3)CCCO4)cc(Cl)cc12] | 6-Chloro-8-chroman-6-yl-1-methyl-9H-pyrido[3,4-b]indole | LC4 | 1.69 | 349.2 [M + H]+ |
| 185 | 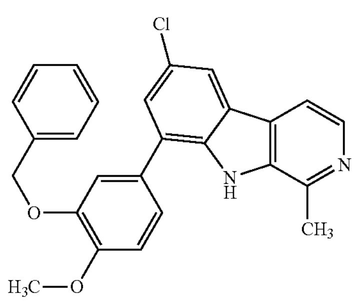 [SMILES: COc1ccc(-c2cc(Cl)cc3c2[nH]c2c(C)nccc23)cc1OCc1ccccc1] | 8-(3-Benzyloxy-4-methoxy-phenyl)-6-chloro-1-methyl-9H-pyrido[3,4-b]indole | LC4 | 1.65 | 429.3 [M + H]+ |
| 186 | 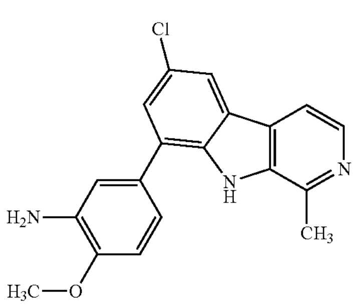 [SMILES: COc1ccc(-c2cc(Cl)cc3c2[nH]c2c(C)nccc23)cc1N] | 5-(6-Chloro-1-methyl-9H-pyrido[3,4-b]indol-8-yl)-2-methoxy-phenylamine | LC4 | 1.52 | 338.2 [M + H]+ |

TABLE 1-continued

| Ex. No. | Structure | Name | LC/MS | RT [min] | MS |
|---|---|---|---|---|---|
| 187 | 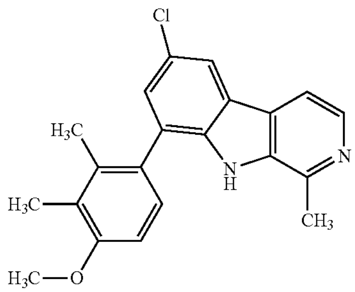 [SMILES: COc1ccc(-c2cc(Cl)cc3c2[nH]c2c(C)nccc23)c(C)c1C] | 6-Chloro-8-(4-methoxy-2,3-dimethyl-phenyl)-1-methyl-9H-pyrido[3,4-b]indole | LC4 | 1.75 | 351.2 [M + H]+ |
| 188 | 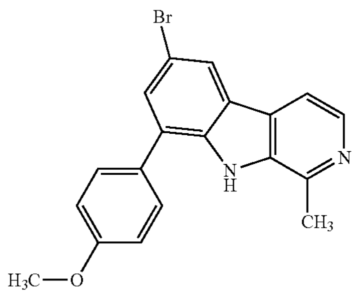 [SMILES: COc1ccc(-c2cc(Br)cc3c2[nH]c2c(C)nccc23)cc1] | 6-Bromo-8-(4-methoxy-phenyl)-1-methyl-9H-pyrido[3,4-b]indole | LC3 | 1.10 | 367.1 [M + H]+ |
| 189 | 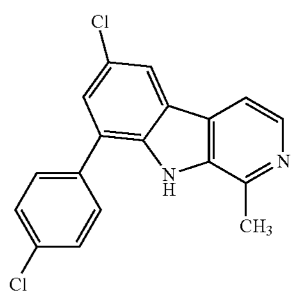 [SMILES: Cc1nccc2c1[nH]c1c(-c3ccc(Cl)cc3)cc(Cl)cc12] | 6-Chloro-8-(4-chloro-phenyl)-1-methyl-9H-pyrido[3,4-b]indole | LC4 | 1.70 | 327.2 [M + H]+ |
| 190 | 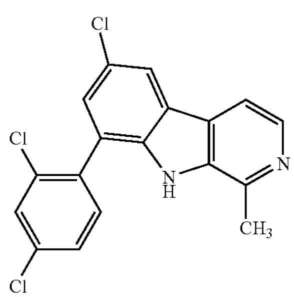 [SMILES: Cc1nccc2c1[nH]c1c(-c3ccc(Cl)cc3Cl)cc(Cl)cc12] | 6-Chloro-8-(2,4-dichloro-phenyl)-1-methyl-9H-pyrido[3,4-b]indole | LC4 | 1.61 | 361.2 [M + H]+ |
| 191 | 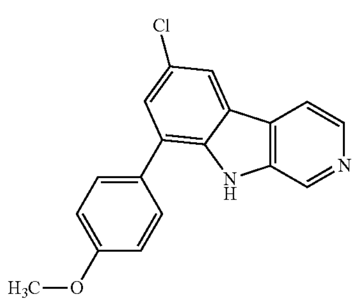 [SMILES: COc1ccc(-c2cc(Cl)cc3c2[nH]c2cnccc23)cc1] | 6-Chloro-8-(4-methoxy-phenyl)-9H-pyrido[3,4-b]indole | LC4 | 1.48 | 309.3 [M + H]+ |

TABLE 1-continued

| Ex. No. | Structure | Name | LC/MS | RT [min] | MS |
|---|---|---|---|---|---|
| 192 | 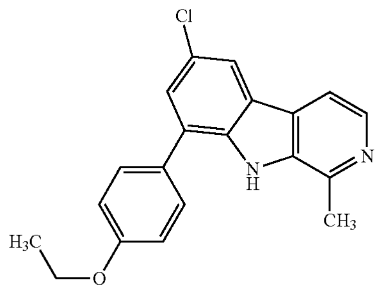 [SMILES: CCOc1ccc(-c2cc(Cl)cc3c2[nH]c2c(C)nccc23)cc1] | 6-Chloro-8-(4-ethoxy-phenyl)-1-methyl-9H-pyrido[3,4-b]indole | LC4 | 1.57 | 337.31 [M + H]+ |
| 193 | 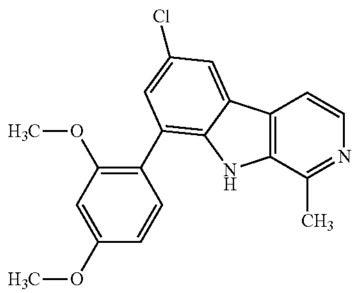 [SMILES: COc1ccc(-c2cc(Cl)cc3c2[nH]c2c(C)nccc23)c(OC)c1] | 6-Chloro-8-(2,4-dimethoxy-phenyl)-1-methyl-9H-pyrido[3,4-b]indole | LC4 | 1.67 | 353.3 [M + H]+ |
| 194 | 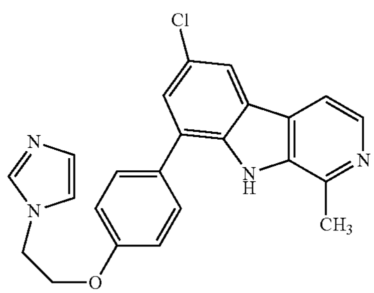 [SMILES: Cc1nccc2c1[nH]c1c(-c3ccc(OCCn4ccnc4)cc3)cc(Cl)cc12] | 6-Chloro-8-[4-(2-imidazol-1-yl-ethoxy)-phenyl]-1-methyl-9H-pyrido[3,4-b]indole | LC4 | 1.13 | 403.3 [M + H]+ |
| 195 | 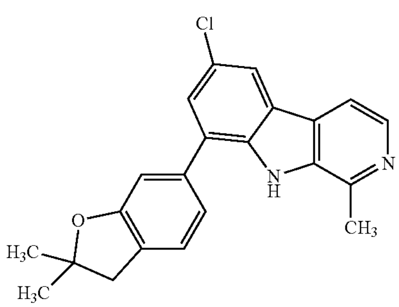 [SMILES: Cc1nccc2c1[nH]c1c(-c3ccc4c(c3)OC(C)(C)C4)cc(Cl)cc12] | 6-Chloro-8-(2,2-dimethyl-2,3-dihydro-benzofuran-6-yl)-1-methyl-9H-pyrido[3,4-b]indole | LC4 | 1.76 | 363.2 [M + H]+ |
| 196 | 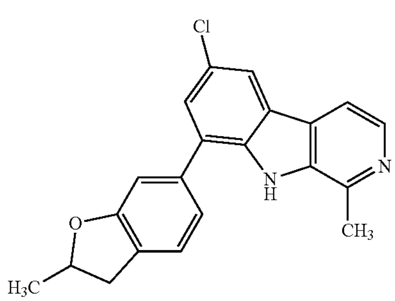 [SMILES: Cc1nccc2c1[nH]c1c(-c3ccc4c(c3)OC(C)C4)cc(Cl)cc12] | 6-Chloro-1-methyl-8-(2-methyl-2,3-dihydro-benzofuran-6-yl)-9H-pyrido[3,4-b]indole | LC4 | 1.56 | 349.2 [M + H]+ |

TABLE 1-continued

| Ex. No. | Structure | Name | LC/MS | RT [min] | MS |
|---|---|---|---|---|---|
| 197 | 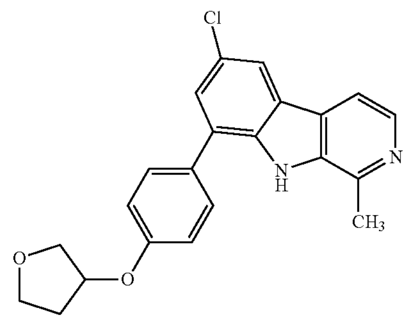 [SMILES: Cc1nccc2c1[nH]c1c(-c3ccc(OC4CCOC4)cc3)cc(Cl)cc12] | 6-Chloro-1-methyl-8-[4-(tetrahydro-furan-3-yloxy)-phenyl]-9H-pyrido[3,4-b]indole | LC4 | 1.64 | 379.3 [M + H]+ |
| 198 | 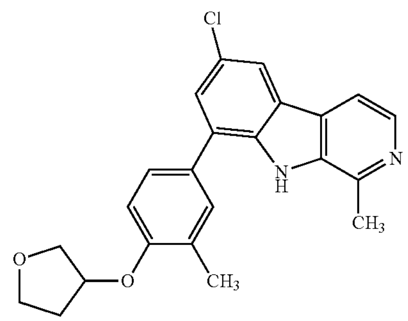 [SMILES: Cc1cc(-c2cc(Cl)cc3c2[nH]c2c(C)nccc23)ccc1OC1CCOC1] | 6-Chloro-1-methyl-8-[3-methyl-4-(tetrahydrofuran-3-yloxy)-phenyl]-9H-pyrido[3,4-b]indole | LC4 | 1.72 | 393.3 [M + H]+ |
| 199 | 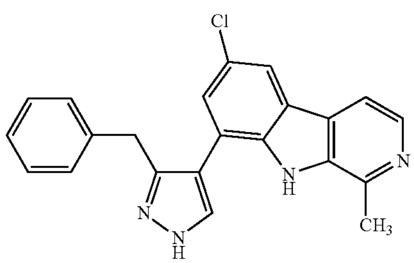 [SMILES: Cc1nccc2c1[nH]c1c(-c3c[nH]nc3Cc3ccccc3)cc(Cl)cc12] | 8-(3-Benzyl-1H-pyrazol-4-yl)-6-chloro-1-methyl-9H-pyrido[3,4-b]indole | LC4 | 1.57 | 373.2 [M + H]+ |
| 200 | 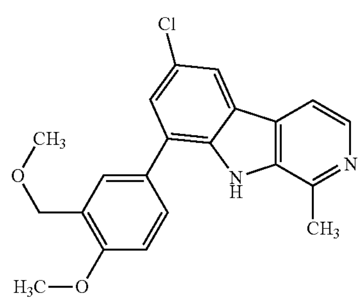 [SMILES: COCc1cc(-c2cc(Cl)cc3c2[nH]c2c(C)nccc23)ccc1OC] | 6-Chloro-8-(4-methoxy-3-methoxymethyl-phenyl)-1-methyl-9H-pyrido[3,4-b]indole | LC8 | 3.53 | 367.2 [M + H]+ |
| 201 | 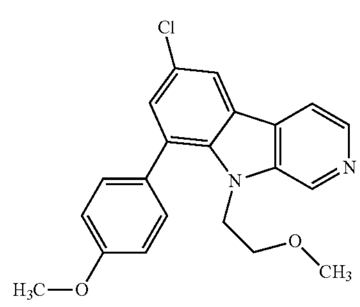 [SMILES: COCCn1c2cnccc2c2cc(Cl)cc(-c3ccc(OC)cc3)c21] | 6-Chloro-9-(2-methoxy-ethyl)-8-(4-methoxy-phenyl)-9H-pyrido[3,4-b]indole | LC4 | 1.71 | 367.2 [M + H]+ |

TABLE 1-continued

| Ex. No. | Structure | Name | LC/MS | RT [min] | MS |
|---|---|---|---|---|---|
| 202 | 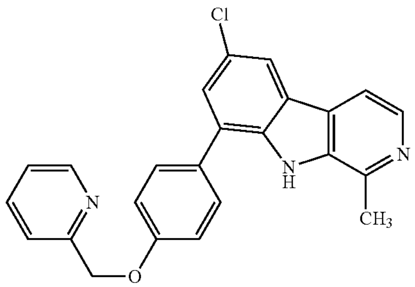 | 6-Chloro-1-methyl-8-[4-(pyridin-2-ylmethoxy)-phenyl]-9H-pyrido[3,4-b]indole | LC8 | 3.30 | 400.2 [M + H]+ |
| 203 | 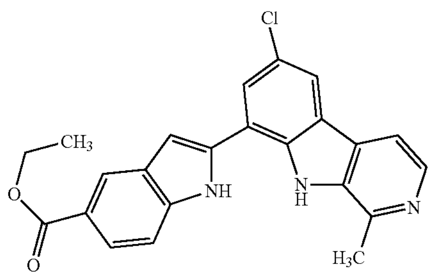 [SMILES: CCOC(=O)c1ccc2[nH]c(-c3cc(Cl)cc4c3[nH]c3c(C)nccc34)cc2c1] | 2-(6-Chloro-1-methyl-9H-pyrido[3,4-b]indol-8-yl)-1H-indole-5-carboxylic acid ethyl ester | LC4 | 1.71 | 402.3 [M − H]− |
| 204 | 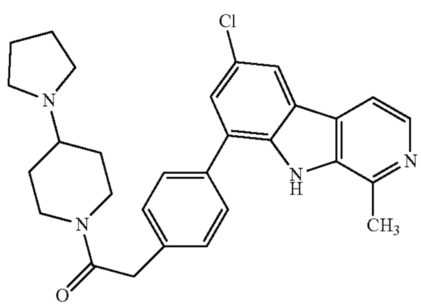 [SMILES: Cc1nccc2c1[nH]c1c(-c3ccc(CC(=O)N4CCC(N5CCCC5)CC4)cc3)cc(Cl)cc12] | 2-[4-(6-Chloro-1-methyl-9H-pyrido[3,4-b]indol-8-yl)-phenyl]-1-(4-pyrrolidin-1-yl-piperidin-1-yl)-ethanone | LC8 | 2.51 | 487.3 [M + H]+ |
| 205 | 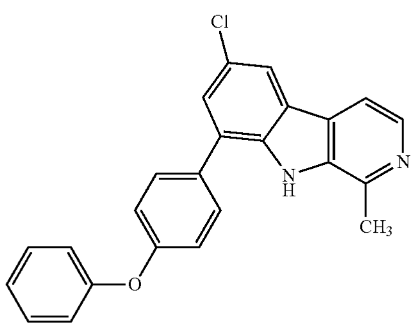 [SMILES: Cc1nccc2c1[nH]c1c(-c3ccc(Oc4ccccc4)cc3)cc(Cl)cc12] | 6-Chloro-1-methyl-8-(4-phenoxy-phenyl)-9H-pyrido[3,4-b]indole (a) | LC4 | 1.68 | 385.2 [M + H]+ |
| 206 | 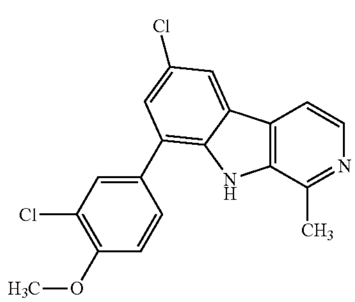 [SMILES: COc1ccc(-c2cc(Cl)cc3c2[nH]c2c(C)nccc23)cc1Cl] | 6-Chloro-8-(3-chloro-4-methoxy-phenyl)-1-methyl-9H-pyrido[3,4-b]indole | LC4 | 1.70 | 357.2 [M + H]+ |

TABLE 1-continued

| Ex. No. | Structure | Name | LC/MS | RT [min] | MS |
|---|---|---|---|---|---|
| 207 | 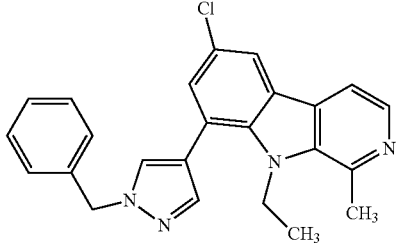 [SMILES: CCn1c2c(-c3cnn(Cc4ccccc4)c3)cc(Cl)cc2c2ccnc(C)c21] | 8-(1-Benzyl-1H-pyrazol-4-yl)-6-chloro-9-ethyl-1-methyl-9H-pyrido[3,4-b]indole | LC4 | 1.57 | 401.2 [M + H]⁺ |
| 208 | 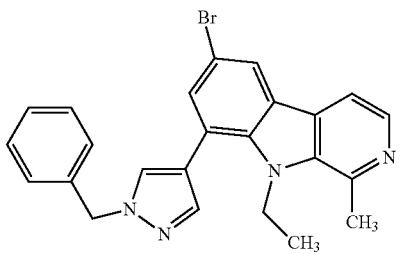 | 8-(1-Benzyl-1H-pyrazol-4-yl)-6-bromo-9-ethyl-1-methyl-9H-pyrido[3,4-b]indole | LC4 | 1.58 | 445.2 [M + H]⁺ |
| 209 | 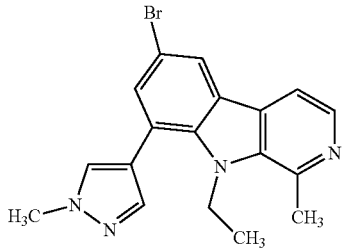 | 6-Bromo-9-ethyl-1-methyl-8-(1-methyl-1H-pyrazol-4-yl)-9H-pyrido[3,4-b]indole | LC4 | 1.34 | 369.1 [M + H]⁺ |
| 210 | 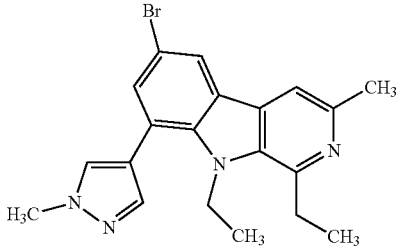 | 6-Bromo-1,9-diethyl-3-methyl-8-(1-methyl-1H-pyrazol-4-yl)-9H-pyrido[3,4-b]indole | LC4 | 1.55 | 397.1 [M + H]⁺ |
| 211 | 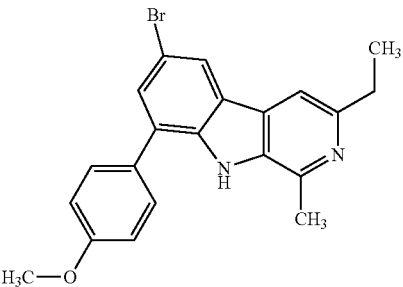 [SMILES: CCc1cc2c([nH]c3c(-c4ccc(OC)cc4)cc(Br)cc32)c(C)n1] | 6-Bromo-3-ethyl-8-(4-methoxy-phenyl)-1-methyl-9H-pyrido[3,4-b]indole | LC4 | 1.80 | 395.1 [M + H]⁺ |

Note: MS values shown as $[M + H]^+$

TABLE 1-continued

| Ex. No. | Structure | Name | LC/MS | RT [min] | MS |
|---|---|---|---|---|---|
| 212 | 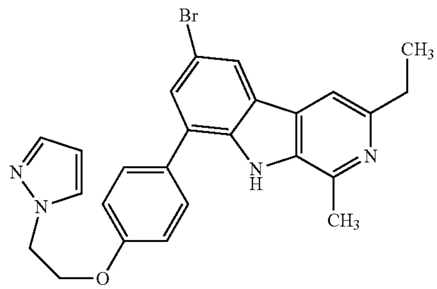 [SMILES: CCc1cc2c([nH]c3c(-c4ccc(OCCn5cccn5)cc4)cc(Br)cc32)c(C)n1] | 6-Bromo-3-ethyl-1-methyl-8-[4-(2-pyrazol-1-yl-ethoxy)-phenyl]-9H-pyrido[3,4-b]indole | LC4 | 1.60 | 475.2 [M + H]+ |
| 213 | 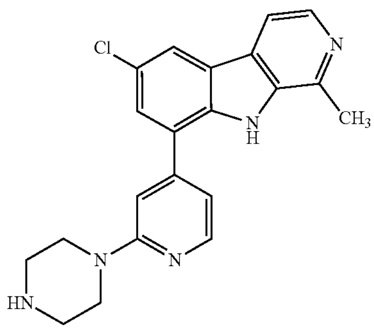 [SMILES: Cc1nccc2c1[nH]c1c(-c3ccnc(N4CCNCC4)c3)cc(Cl)cc12] | 6-Chloro-1-methyl-8-(2-piperazin-1-yl-pyridin-4-yl)-9H-pyrido[3,4-b]indole | LC4 | 1.03 | 376.1 [M − H]− |
| 214 | 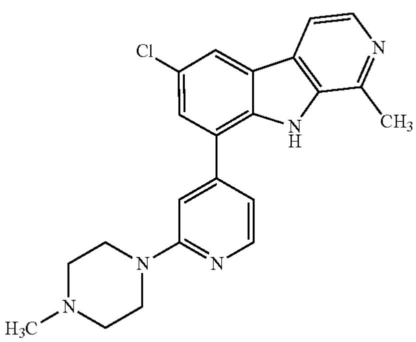 | 6-Chloro-1-methyl-8-[2-(4-methyl-piperazin-1-yl)-pyridin-4-yl]-9H-pyrido[3,4-b]indole | LC4 | 1.04 | 390.1 [M − H]− |
| 215 | 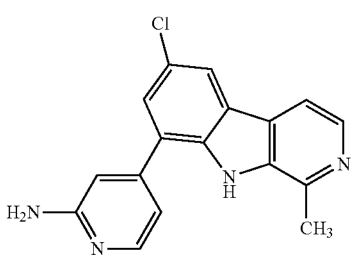 [SMILES: Cc1nccc2c1[nH]c1c(-c3ccnc(N)c3)cc(Cl)cc12] | 4-(6-Chloro-1-methyl-9H-pyrido[3,4-b]indol-8-yl)-pyridin-2-ylamine | LC4 | 1.06 | 309.2 [M + H]+ |
| 216 | 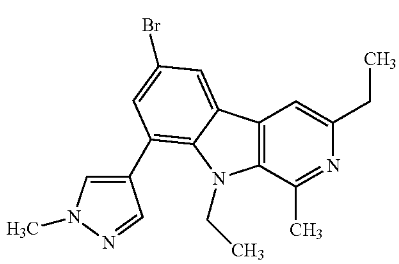 [SMILES: CCc1cc2c3cc(Br)cc(-c4cnn(C)c4)c3n(CC)c2c(C)n1] | 6-Bromo-3,9-diethyl-1-methyl-8-(1-methyl-1H-pyrazol-4-yl)-9H-pyrido[3,4-b]indole | LC4 | 1.43 | 397.2 [M + H]+ |

TABLE 1-continued

| Ex. No. | Structure | Name | LC/ MS | RT [min] | MS |
|---|---|---|---|---|---|
| 217 | 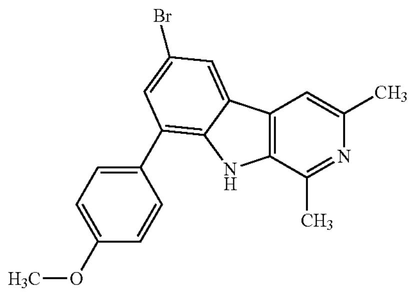 | 6-Bromo-8-(4-methoxy-phenyl)-1,3-dimethyl-9H-pyrido[3,4-b]indole | LC4 | 1.56 | 381.1 [M + H]+ |
| 218 | 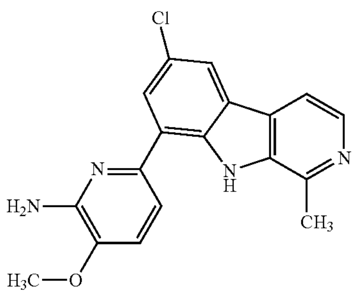 [SMILES: COc1ccc(-c2cc(Cl)cc3c2[nH]c2c(C)nccc23)nc1N] | 6-(6-Chloro-1-methyl-9H-pyrido[3,4-b]indol-8-yl)-3-methoxy-pyridin-2-ylamine | LC4 | 1.51 | 339.2 [M + H]+ |
| 219 | 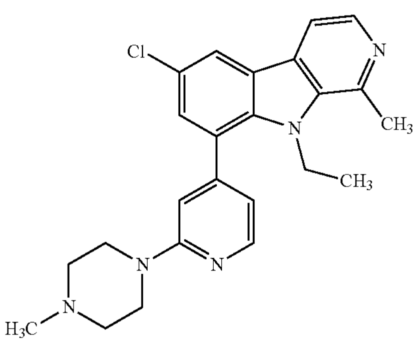 | 6-Chloro-9-ethyl-1-methyl-8-[2-(4-methyl-piperazin-1-yl)-pyridin-4-yl]-9H-pyrido[3,4-b]indole | LC4 | 1.24 | 420.2 [M + H]+ |
| 220 | 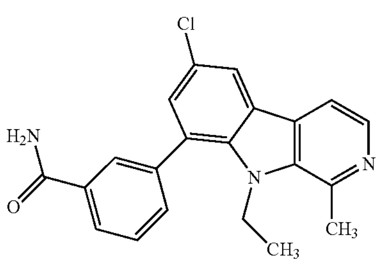 [SMILES: CCn1c2c(-c3cccc(C(N)=O)c3)cc(Cl)cc2c2ccnc(C)c21] | 3-(6-Chloro-9-ethyl-1-methyl-9H-pyrido[3,4-b]indol-8-yl)-benzamide | LC8 | 2.88 | 364.1 [M + H]+ |
| 221 | 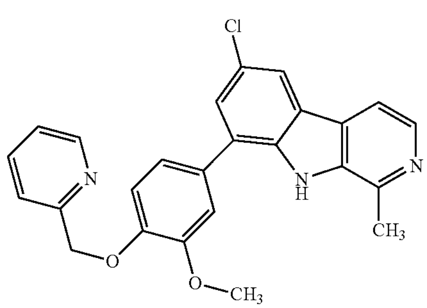 [SMILES: COc1cc(-c2cc(Cl)cc3c2[nH]c2c(C)nccc23)ccc1OCc1ccccn1] | 6-Chloro-8-[3-methoxy-4-(pyridin-2-ylmethoxy)-phenyl]-1-methyl-9H-pyrido[3,4-b]indole | LC4 | 1.62 | 428.2 [M − H]− |

TABLE 1-continued

| Ex. No. | Structure | Name | LC/MS | RT [min] | MS |
|---|---|---|---|---|---|
| 222 | 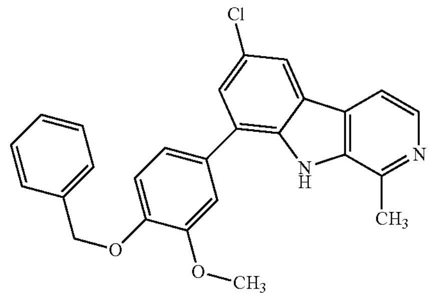 [SMILES: COc1cc(-c2cc(Cl)cc3c2[nH]c2c(C)nccc23)ccc1OCc1ccccc1] | 8-(4-Benzyloxy-3-methoxy-phenyl)-6-chloro-1-methyl-9H-pyrido[3,4-b]indole | LC8 | 3.98 | 429.2 [M + H]+ |
| 223 | 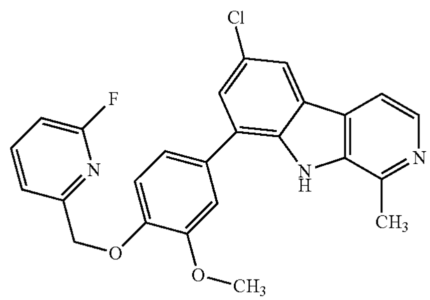 [SMILES: COc1cc(-c2cc(Cl)cc3c2[nH]c2c(C)nccc23)ccc1OCc1cccc(F)n1] | 6-Chloro-8-[4-(6-fluoro-pyridin-2-ylmethoxy)-3-methoxy-phenyl]-1-methyl-9H-pyrido[3,4-b]indole | LC4 | 1.71 | 446.2 [M − H]− |
| 224 | 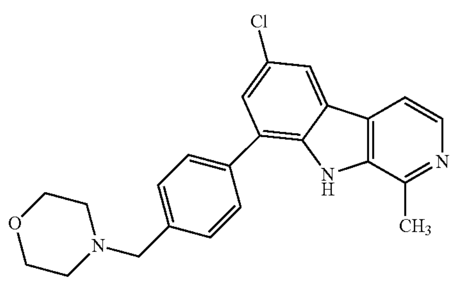 [SMILES: Cc1nccc2c1[nH]c1c(-c3ccc(CN4CCOCC4)cc3)cc(Cl)cc12] | 6-Chloro-1-methyl-8-(4-morpholin-4-ylmethyl-phenyl)-9H-pyrido[3,4-b]indole | LC8 | 2.29 | 392.1 [M + H]+ |
| 225 | 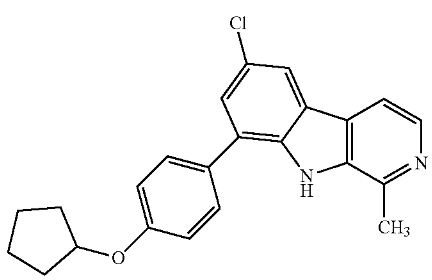 [SMILES: Cc1nccc2c1[nH]c1c(-c3ccc(OC4CCCC4)cc3)cc(Cl)cc12] | 6-Chloro-8-(4-cyclopentyloxy-phenyl)-1-methyl-9H-pyrido[3,4-b]indole | LC8 | 4.18 | 377.2 [M + H]+ |
| 226 | 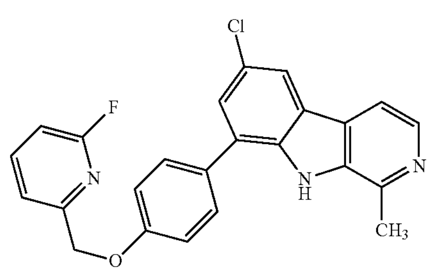 [SMILES: Cc1nccc2c1[nH]c1c(-c3ccc(OCc4cccc(F)n4)cc3)cc(Cl)cc12] | 6-Chloro-8-[4-(6-fluoro-pyridin-2-ylmethoxy)-phenyl]-1-methyl-9H-pyrido[3,4-b]indole | LC4 | 1.75 | 418.1 [M + H]+ |

TABLE 1-continued

| Ex. No. | Structure | Name | LC/MS | RT [min] | MS |
|---|---|---|---|---|---|
| 227 | 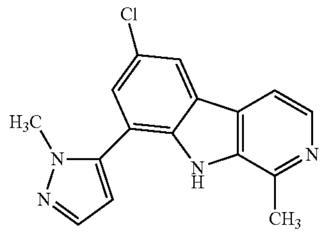 [SMILES: Cc1nccc2c1[nH]c1c(-c3ccnn3C)cc(Cl)cc12] | 6-Chloro-1-methyl-8-(2-methyl-2H-pyrazol-3-yl)-9H-pyrido[3,4-b]indole | LC4 | 1.44 | 295.2 [M − H]− |
| 228 | 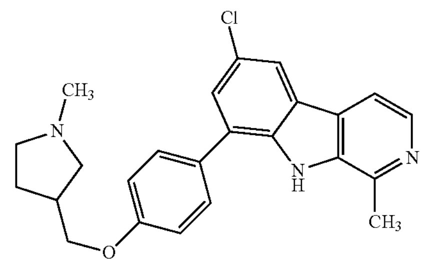 [SMILES: Cc1nccc2c1[nH]c1c(-c3ccc(OCC4CCN(C)C4)cc3)cc(Cl)cc12] | 6-Chloro-1-methyl-8-[4-(1-methyl-pyrrolidin-3-ylmethoxy)-phenyl]-9H-pyrido[3,4-b]indole | LC4 | 1.36 | 406.2 [M + H]+ |
| 229 | 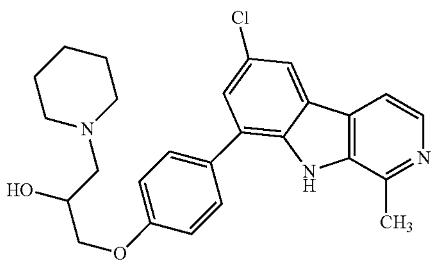 [SMILES: Cc1nccc2c1[nH]c1c(-c3ccc(OCC(O)CN4CCCCC4)cc3)cc(Cl)cc12] | 1-[4-(6-Chloro-1-methyl-9H-pyrido[3,4-b]indol-8-yl)-phenoxy]-3-piperidin-1-yl-propan-2-ol | LC4 | 1.36 | 450.1 [M + H]+ |
| 230 | 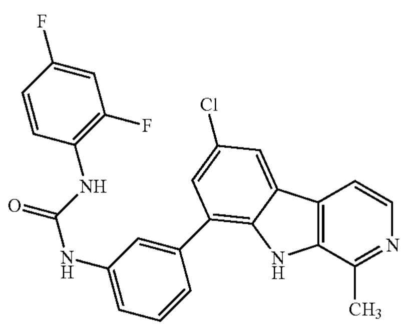 [SMILES: Cc1nccc2c1[nH]c1c(-c3cccc(NC(=O)Nc4ccc(F)cc4F)c3)cc(Cl)cc12] | 1-[3-(6-Chloro-1-methyl-9H-pyrido[3,4-b]indol-8-yl)-phenyl]-3-(2,4-difluoro-phenyl)-urea | LC4 | 1.72 | 463.1 [M + H]+ |
| 231 | 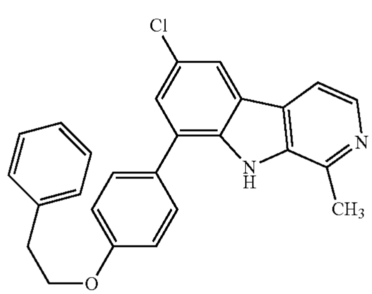 [SMILES: Cc1nccc2c1[nH]c1c(-c3ccc(OCCc4ccccc4)cc3)cc(Cl)cc12] | 6-Chloro-1-methyl-8-(4-phenethyloxy-phenyl)-9H-pyrido[3,4-b]indole | LC4 | 1.87 | 413.1 [M + H]+ |

TABLE 1-continued

| Ex. No. | Structure | Name | LC/MS | RT [min] | MS |
|---|---|---|---|---|---|
| 232 | 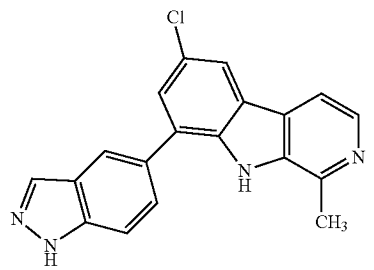 [SMILES: Cc1nccc2c1[nH]c1c(-c3ccc4[nH]ncc4c3)cc(Cl)cc12] | 6-Chloro-8-(1H-indazol-5-yl)-1-methyl-9H-pyrido[3,4-b]indole | LC4 | 1.53 | 333.1 [M + H]+ |
| 233 | 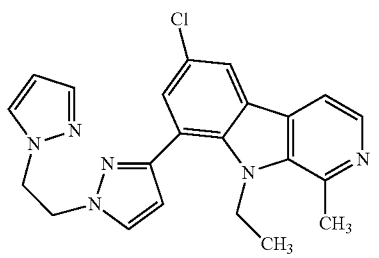 [SMILES: CCn1c2c(-c3ccn(CCn4cccn4)n3)cc(Cl)cc2c2ccnc(C)c21] | 6-Chloro-9-ethyl-1-methyl-8-[1-(2-pyrazol-1-yl-ethyl)-1H-pyrazol-3-yl]-9H-pyrido[3,4-b]indole | LC4 | 1.35 | 405.2 [M + H]+ |
| 234 | 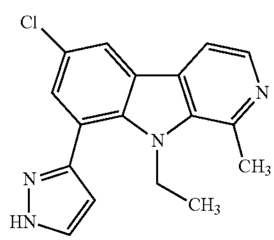 [SMILES: CCn1c2c(-c3cc[nH]n3)cc(Cl)cc2c2ccnc(C)c21] | 6-Chloro-9-ethyl-1-methyl-8-(1H-pyrazol-3-yl)-9H-pyrido[3,4-b]indole | LC8 | 2.83 | 311.0 [M + H]+ |
| 235 | 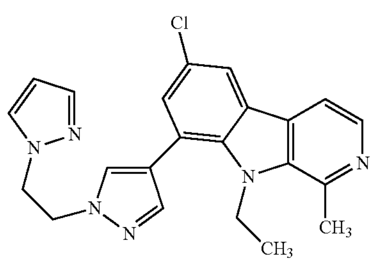 [SMILES: CCn1c2c(-c3cnn(CCn4cccn4)c3)cc(Cl)cc2c2ccnc(C)c21] | 6-Chloro-9-ethyl-1-methyl-8-[1-(2-pyrazol-1-yl-ethyl)-1H-pyrazol-3-yl]-9H-pyrido[3,4-b]indole | LC4 | 1.49 | 405.1 [M + H]+ |
| 236 | 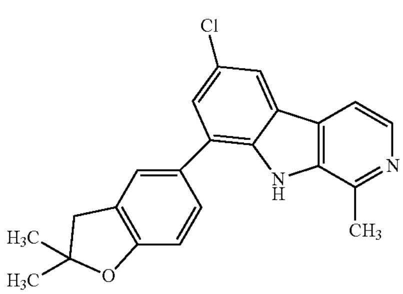 [SMILES: Cc1nccc2c1[nH]c1c(-c3ccc4c(c3)CC(C)(C)O4)cc(Cl)cc12] | 6-Chloro-8-(2,2-dimethyl-2,3-dihydro-benzofuran-5-yl)-1-methyl-9H-pyrido[3,4-b]indole | LC4 | 1.61 | 363.2 [M + H]+ |

TABLE 1-continued

| Ex. No. | Structure | Name | LC/MS | RT [min] | MS |
|---|---|---|---|---|---|
| 237 | 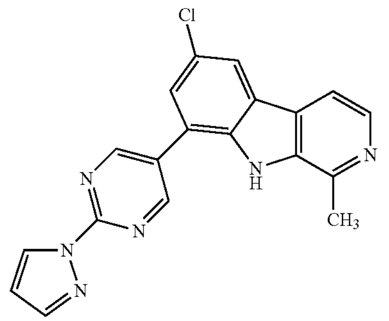 [SMILES: Cc1nccc2c1[nH]c1c(-c3cnc(-n4cccn4)nc3)cc(Cl)cc12] | 6-Chloro-1-methyl-8-(2-pyrazol-1-yl-pyrimidin-5-yl)-9H-pyrido[3,4-b]indole | LC4 | 1.31 | 361.14 [M + H]+ |
| 238 | 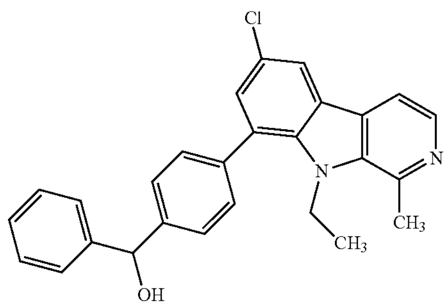 [SMILES: CCn1c2c(-c3ccc(C(O)c4ccccc4)cc3)cc(Cl)cc2c2ccnc(C)c21] | [4-(6-Chloro-9-ethyl-1-methyl-9H-pyrido[3,4-b]indol-8-yl)-phenyl]-phenyl-methanol | LC4 | 1.58 | 427.2 [M + H]+ |
| 239 | 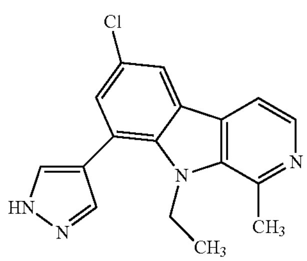 [SMILES: CCn1c2c(-c3cn[nH]c3)cc(Cl)cc2c2ccnc(C)c21] | 6-Chloro-9-ethyl-1-methyl-8-(1H-pyrazol-4-yl)-9H-pyrido[3,4-b]indole | LC4 | 1.20 | 311.1 [M + H]+ |
| 240 | 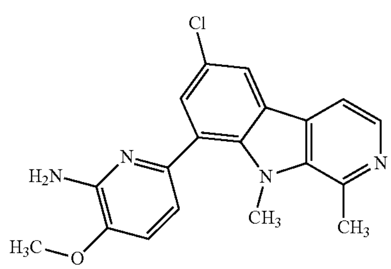 [SMILES: COc1ccc(-c2cc(Cl)cc3c4ccnc(C)c4n(C)c23)nc1N] | 6-(6-Chloro-1,9-dimethyl-9H-pyrido[3,4-b]indol-8-yl)-3-methoxy-pyridin-2-ylamine | LC4 | 1.17 | 353.1 [M + H]+ |
| 241 | 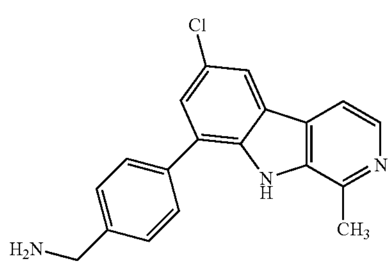 [SMILES: Cc1nccc2c1[nH]c1c(-c3ccc(CN)cc3)cc(Cl)cc12] | 4-(6-Chloro-1-methyl-9H-pyrido[3,4-b]indol-8-yl)-benzylamine | LC7 | 4.51 | 161.6 [M + 2H]++ |

TABLE 1-continued

| Ex. No. | Structure | Name | LC/MS | RT [min] | MS |
|---|---|---|---|---|---|
| 242 | 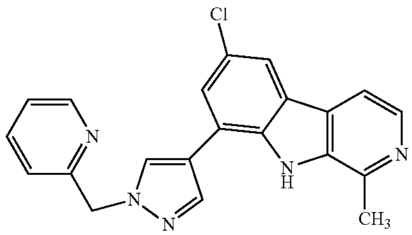 [SMILES: Cc1nccc2c1[nH]c1c(-c3cnn(Cc4ccccn4)c3)cc(Cl)cc12] | 6-Chloro-1-methyl-8-(1-pyridin-2-ylmethyl-1H-pyrazol-4-yl)-9H-pyrido[3,4-b]indole | LC4 | 1.32 | 374.2 [M + H]+ |
| 243 | 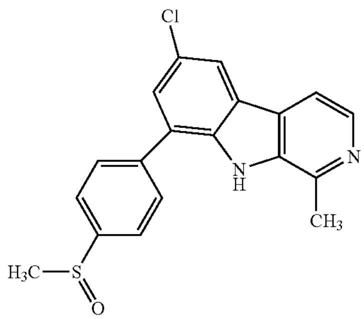 [SMILES: Cc1nccc2c1[nH]c1c(-c3ccc(S(C)=O)cc3)cc(Cl)cc12] | 6-Chloro-8-(4-methanesulfinyl-phenyl)-1-methyl-9H-pyrido[3,4-b]indole | LC4 | 1.27 | 355.1 [M + H]+ |
| 244 | 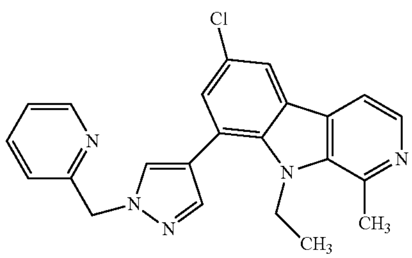 [SMILES: CCn1c2c(-c3cnn(Cc4ccccn4)c3)cc(Cl)cc2c2ccnc(C)c21] | 6-Chloro-9-ethyl-1-methyl-8-(1-pyridin-2-ylmethyl-1H-pyrazol-4-yl)-9H-pyrido[3,4-b]indole | LC4 | 1.34 | 402.2 [M + H]+ |
| 245 | 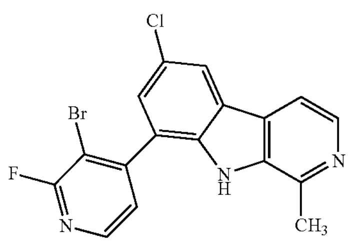 [SMILES: Cc1nccc2c1[nH]c1c(-c3ccnc(F)c3Br)cc(Cl)cc12] | 8-(3-Bromo-2-fluoro-pyridin-4-yl)-6-chloro-1-methyl-9H-pyrido[3,4-b]indole | LC4 | 1.44 | 390.0 [M + H]+ |
| 246 | 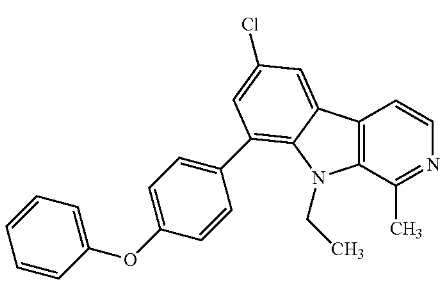 [SMILES: CCn1c2c(-c3ccc(Oc4ccccc4)cc3)cc(Cl)cc2c2ccnc(C)c21] | 6-Chloro-9-ethyl-1-methyl-8-(4-phenoxy-phenyl)-9H-pyrido[3,4-b]indole | LC4 | 1.74 | 413.2 [M + H]+ |
| 247 | 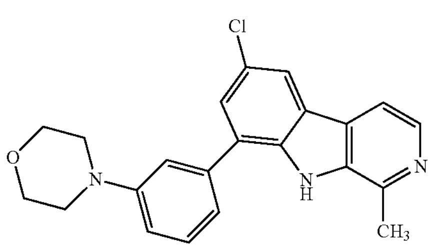 [SMILES: Cc1nccc2c1[nH]c1c(-c3cccc(N4CCOCC4)c3)cc(Cl)cc12] | 6-Chloro-1-mehtyl-8-(3-morpholin-4-yl-phenyl)-9H-pyrido[3,4-b]indole | LC4 | 1.48 | 378.2 [M + H]+ |

TABLE 1-continued

| Ex. No. | Structure | Name | LC/MS | RT [min] | MS |
|---|---|---|---|---|---|
| 248 | 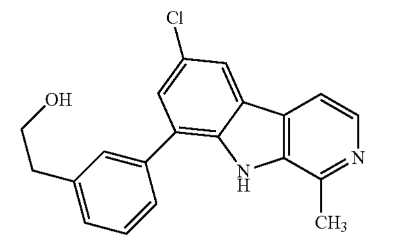 [SMILES: Cc1nccc2c1[nH]c1c(-c3cccc(CCO)c3)cc(Cl)cc12] | 2-[3-(6-Chloro-1-methyl-9H-pyrido[3,4-b]indol-8-yl)-phenyl]-ethanol | LC4 | 1.39 | 337.2 [M + H]+ |
| 249 | 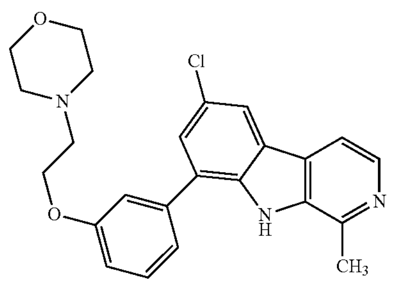 [SMILES: Cc1nccc2c1[nH]c1c(-c3cccc(OCCN4CCOCC4)c3)cc(Cl)cc12] | 6-Chloro-1-methyl-8-[3-(2-morpholin-4-yl-ethoxy)-phenyl]-9H-pyrido[3,4-b]indole | LC4 | 1.11 | 422.1 [M + H]+ |
| 250 | 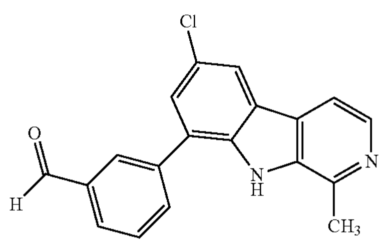 [SMILES: Cc1nccc2c1[nH]c1c(-c3cccc(C=O)c3)cc(Cl)cc12] | 3-(6-Chloro-1-methyl-9H-pyrido[3,4-b]indol-8-yl)-benzaldehyde | LC4 | 1.40 | 321. [M + H]+ |
| 251 | 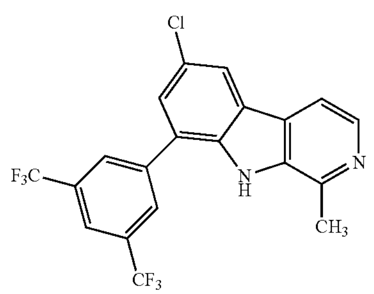 [SMILES: Cc1nccc2c1[nH]c1c(-c3cc(C(F)(F)F)cc(C(F)(F)F)c3)cc(Cl)cc12] | 8-(3,5-Bis-trifluoromethyl-phenyl)-6-chloro-1-methyl-9H-pyrido[3,4-b]indole | LC4 | 1.69 | 429.1 [M + H]+ |
| 252 | 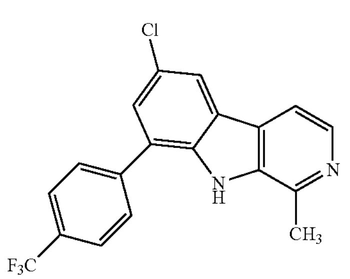 [SMILES: Cc1nccc2c1[nH]c1c(-c3ccc(C(F)(F)F)cc3)cc(Cl)cc12] | 6-Chloro-1-methyl-8-(4-trifluoromethyl-phenyl)-9H-pyrido[3,4-b]indole | LC4 | 1.60 | 361.1 [M + H]+ |

TABLE 1-continued

| Ex. No. | Structure | Name | LC/MS | RT [min] | MS |
|---|---|---|---|---|---|
| 253 | 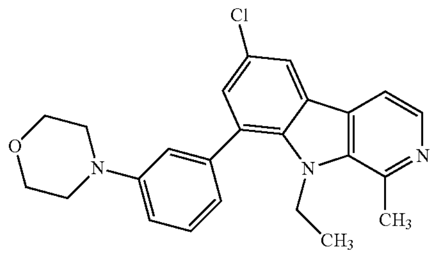 [SMILES: CCn1c2c(-c3cccc(N4CCOCC4)c3)cc(Cl)cc2c2ccnc(C)c21] | 6-Chloro-9-ethyl-1-methyl-8-(3-morpholin-4-yl-phenyl)-9H-pyrido[3,4-b]indole | LC4 | 1.54 | 406.3 [M + H]$^+$ |
| 254 | 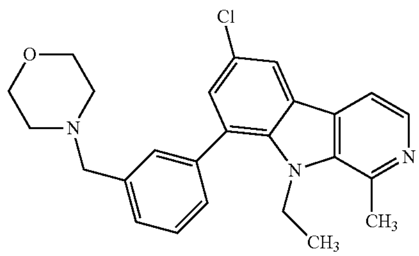 [SMILES: CCn1c2c(-c3cccc(CN4CCOCC4)c3)cc(Cl)cc2c2ccnc(C)c21] | 6-Chloro-9-ethyl-1-methyl-8-(3-morpholin-4-ylmethyl-phenyl)-9H-pyrido[3,4-b]indole | LC4 | 1.06 | 420.3 [M + H]$^+$ |
| 255 | 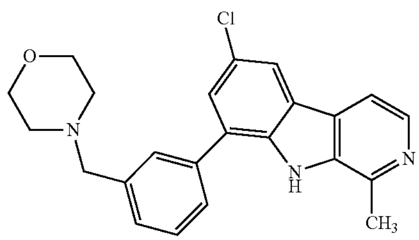 [SMILES: Cc1nccc2c1[nH]c1c(-c3cccc(CN4CCOCC4)c3)cc(Cl)cc12] | 6-Chloro-1-methyl-8-(3-morpholin-4-ylmethyl-phenyl)-9H-pyrido[3,4-b]indole | LC4 | 1.01 | 392.2 [M + H]$^+$ |
| 256 | 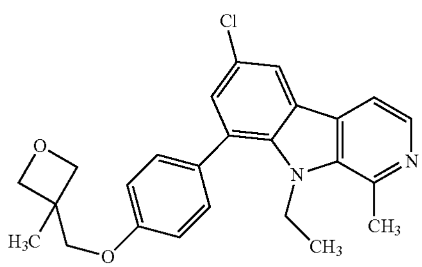 [SMILES: CCn1c2c(-c3ccc(OCC4(C)COC4)cc3)cc(Cl)cc2c2ccnc(C)c21] | 6-Chloro-9-ethyl-1-methyl-8-[4-(3-methyl-oxetan-3-ylmethoxy)-phenyl]-9H-pyrido[3,4-b]indole | LC4 | 1.57 | 421.3 [M + H]$^+$ |
| 257 | 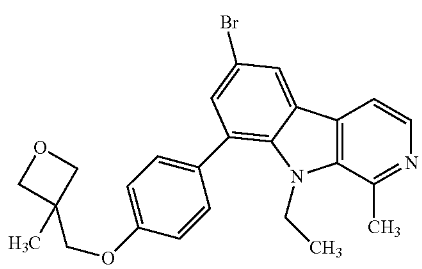 [SMILES: CCn1c2c(-c3ccc(OCC4(C)COC4)cc3)cc(Br)cc2c2ccnc(C)c21] | 6-Bromo-9-ethyl-1-methyl-8-[4-(3-methyl-oxetan-3-ylmethoxy)-phenyl]-9H-pyrido[3,4-b]indole | LC4 | 1.63 | 465.1 [M + H]$^+$ |
| 258 | 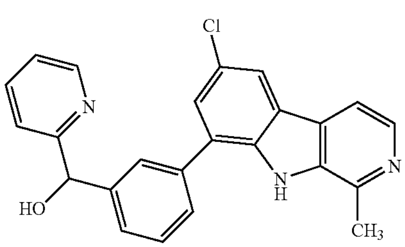 [SMILES: Cc1nccc2c1[nH]c1c(-c3cccc(C(O)c4ccccn4)c3)cc(Cl)cc12] | [3-(6-Chloro-1-methyl-9H-pyrido[3,4-b]indol-8-yl)-phenyl]-pyridin-2-yl-methanol | LC4 | 1.29 | 398.1 [M − H]$^-$ |

TABLE 1-continued

| Ex. No. | Structure | Name | LC/MS | RT [min] | MS |
|---|---|---|---|---|---|
| 259 | 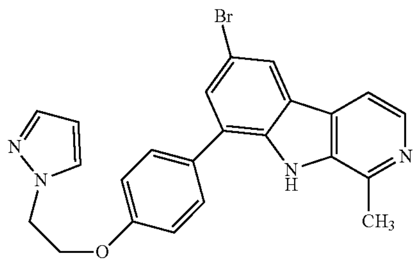 [SMILES: Cc1nccc2c1[nH]c1c(-c3ccc(OCCn4cccn4)cc3)cc(Br)cc12] | 6-Bromo-1-methyl-8-[4-(2-pyrazol-1-yl-ethoxy)-phenyl]-9H-pyrido[3,4-b]indole | LC4 | 1.49 | 447.3 [M + H]+ |
| 260 | 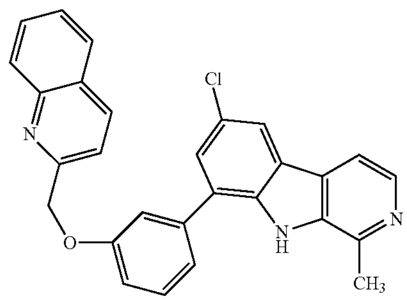 [SMILES: Cc1nccc2c1[nH]c1c(-c3cccc(OCc4ccc5ccccc5n4)c3)cc(Cl)cc12] | 6-Chloro-1-methyl-8-[3-(quinolin-2-ylmethoxy)-phenyl]-9H-pyrido[3,4-b]indole | LC4 | 1.61 | 450.3 [M + H]+ |
| 261 | 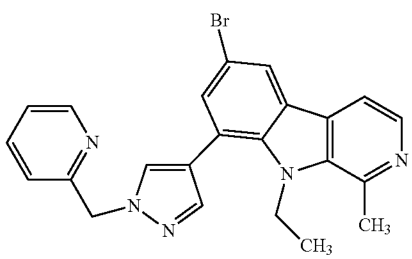 | 6-Bromo-9-ethyl-1-methyl-8-(1-pyridin-2-ylmethyl-1H-pyrazol-4-yl)-9H-pyrido[3,4-b]indole | LC4 | 1.34 | 446.3 [M + H]+ |
| 262 | 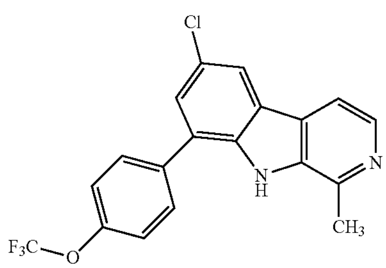 [SMILES: Cc1nccc2c1[nH]c1c(-c3ccc(OC(F)(F)F)cc3)cc(Cl)cc12] | 6-Chloro-1-methyl-8-(4-trifluoromethoxy)-phenyl)-9H-pyrido[3,4-b]indole | LC4 | 1.61 | 377.2 [M + H]+ |
| 263 | 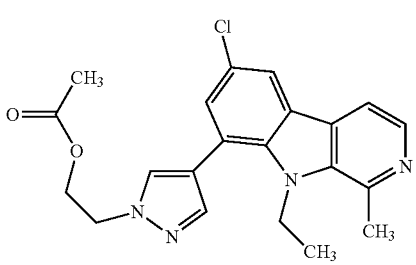 [SMILES: CCn1c2c(-c3cnn(CCOC(C)=O)c3)cc(Cl)cc2c2ccnc(C)c21] | Acetic acid 2-[4-(6-chloro-9-ethyl-1-methyl-9H-pyrido[3,4-b]indol-8-yl)-pyrazol-1-yl]-ethyl ester | LC14 | 0.83 | 397.2 [M + H]+ |

TABLE 1-continued

| Ex. No. | Structure | Name | LC/MS | RT [min] | MS |
|---|---|---|---|---|---|
| 264 | 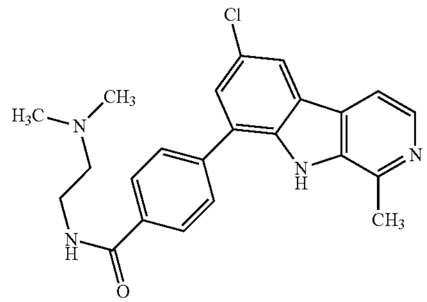 [SMILES: Cc1nccc2c1[nH]c1c(-c3ccc(C(=O)NCCN(C)C)cc3)cc(Cl)cc12] | 4-(6-Chloro-1-methyl-9H-pyrido[3,4-b]indol-8-yl)-N-(2-dimethylamino-ethyl)-benzamide | LC4 | 1.03 | 407.2 [M + H]⁺ |
| 265 | 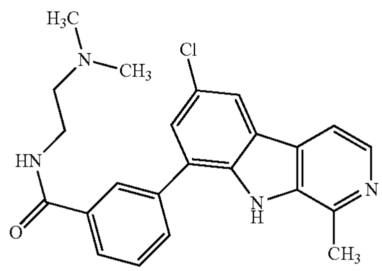 [SMILES: Cc1nccc2c1[nH]c1c(-c3cccc(C(=O)NCCN(C)C)c3)cc(Cl)cc12] | 3-(6-Chloro-1-methyl-9H-pyrido[3,4-b]indol-8-yl)-N-(2-dimethylamino-ethyl)-benzamide | LC4 | 1.01 | 407.2 [M + H]⁺ |
| 266 | 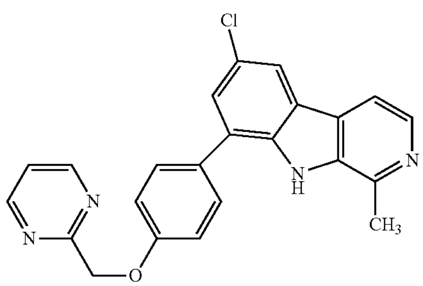 [SMILES: Cc1nccc2c1[nH]c1c(-c3ccc(OCc4ncccn4)cc3)cc(Cl)cc12] | 6-Chloro-1-methyl-8-[4-(pyrimidin-2-ylmethoxy)-phenyl]-9H-pyrido[3,4-b]indole | LC4 | 1.38 | 401.2 [M + H]⁺ |
| 267 | 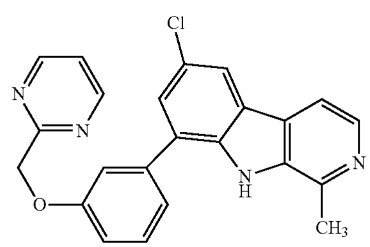 [SMILES: Cc1nccc2c1[nH]c1c(-c3cccc(OCc4ncccn4)c3)cc(Cl)cc12] | 6-Chloro-1-methyl-8-[3-(pyrimidin-2-ylmethoxy)-phenyl]-9H-pyrido[3,4-b]indole | LC4 | 1.42 | 401.2 [M + H]⁺ |
| 268 | 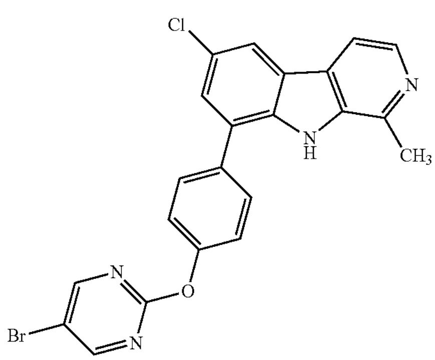 [SMILES: Cc1nccc2c1[nH]c1c(-c3ccc(Oc4ncc(Br)cn4)cc3)cc(Cl)cc12] | 8-[4-(5-Bromo-pyrimidin-2-yloxy)-phenyl]-6-chloro-1-methyl-9H-pyrido[3,4-b]indole | LC4 | 1.53 | 465.2 [M + H]⁺ |

Note: MS values use $[M + H]^+$ notation.

TABLE 1-continued

| Ex. No. | Structure | Name | LC/MS | RT [min] | MS |
|---|---|---|---|---|---|
| 269 | 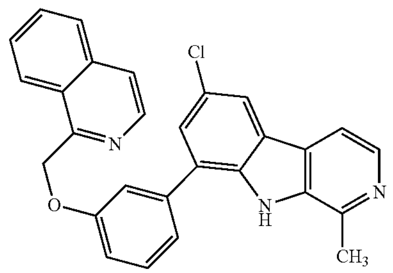 [SMILES: Cc1nccc2c1[nH]c1c(-c3cccc(OCc4nccc5ccccc45)c3)cc(Cl)cc12] | 6-Chloro-8-[3-(isoquinolin-1-ylmethoxy)-phenyl]-1-methyl-9H-pyrido[3,4-b]indole | LC4 | 1.57 | 450.2 [M + H]$^+$ |
| 270 | 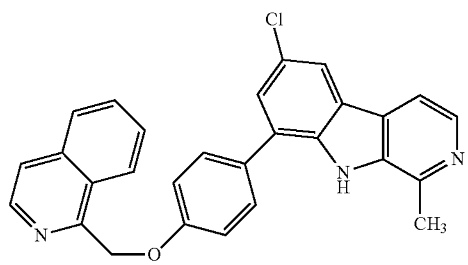 [SMILES: Cc1nccc2c1[nH]c1c(-c3ccc(OCc4nccc5ccccc45)cc3)cc(Cl)cc12] | 6-Chloro-8-[4-(isoquinolin-1-ylmethoxy)-phenyl]-1-methyl-9H-pyrido[3,4-b]indole | LC4 | 1.57 | 450.2 [M + H]$^+$ |
| 271 | 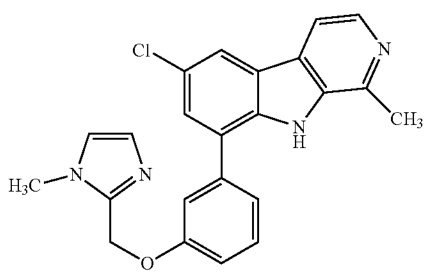 | 6-Chloro-1-methyl-8-[3-(1-methyl-1H-imidazol-2-ylmethoxy)-phenyl]-9H-pyrido[3,4-b]indole | LC4 | 1.14 | 401.2 [M − H]$^-$ |
| 272 | 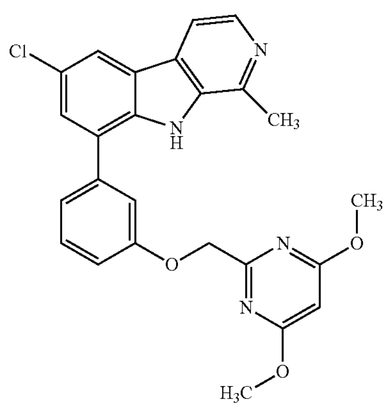 [SMILES: COc1cc(OC)nc(COc2cccc(-c3cc(Cl)cc4c3[nH]c3c(C)nccc34)c2)n1] | 6-Chloro-8-[3-(4,6-dimethoxy-pyrimidin-2-ylmethoxy)-phenyl]-1-methyl-9H-pyrido[3,4-b]indole | LC4 | 1.58 | 461.2 [M + H]$^+$ |
| 273 | 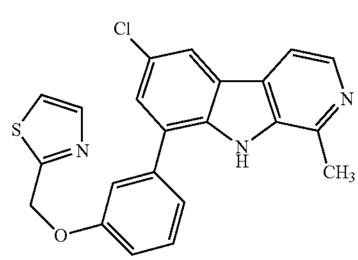 [SMILES: Cc1nccc2c1[nH]c1c(-c3cccc(OCc4nccs4)c3)cc(Cl)cc12] | 6-Chloro-1-methyl-8-[3-(thiazol-2-ylmethoxy)-phenyl]-9H-pyrido[3,4-b]indole | LC4 | 1.51 | 406.2 [M + H]$^+$ |

TABLE 1-continued

| Ex. No. | Structure | Name | LC/MS | RT [min] | MS |
|---|---|---|---|---|---|
| 274 | 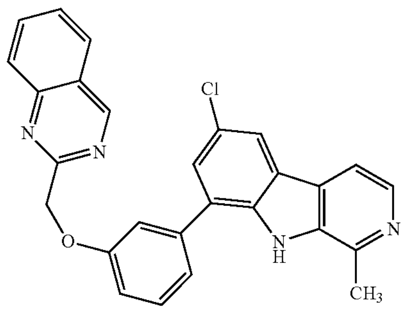 [SMILES: Cc1nccc2c1[nH]c1c(-c3cccc(OCc4ncc5ccccc5n4)c3)cc(Cl)cc12] | 6-Chloro-1-methyl-8-[3-(quinazolin-2-ylmethoxy)-phenyl]-9H-pyrido[3,4-b]indole | LC4 | 1.51 | 451.4 [M + H]+ |
| 275 | 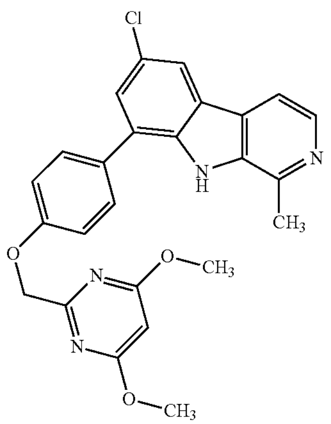 [SMILES: COc1cc(OC)nc(COc2ccc(-c3cc(Cl)cc4c3[nH]c3c(C)nccc34)cc2)n1] | 6-Chloro-8-[4-(4,6-dimethoxy-pyrimidin-2-ylmethoxy)-phenyl]-1-methyl-9H-pyrido[3,4-b]indole | LC4 | 1.58 | 461.3 [M + H]+ |
| 276 | 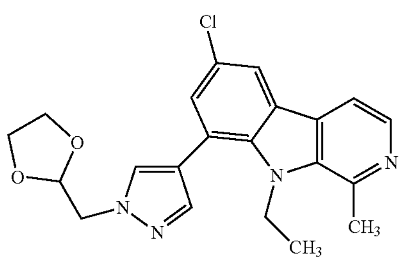 [SMILES: CCn1c2c(-c3cnn(CC4OCCO4)c3)cc(Cl)cc2c2ccnc(C)c21] | 6-Chloro-8-(1-[1,3]dioxolan-2-ylmethyl-1H-pyrazol-4-yl)-9-ethyl-1-methyl-9H-pyrido[3,4-b]indole | LC4 | 1.30 | 397.2 [M + H]+ |
| 277 | 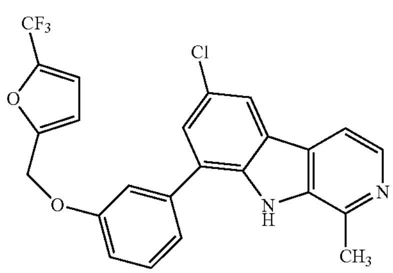 [SMILES: Cc1nccc2c1[nH]c1c(-c3cccc(OCc4ccc(C(F)(F)F)o4)c3)cc(Cl)cc12] | 6-Chloro-1-methyl-8-[3-(5-trifluoromethyl-furan-2-ylmethoxy)-phenyl]-9H-pyrido[3,4-b]indole | LC8 | 4.01 | 457.3 [M + H]+ |
| 278 | 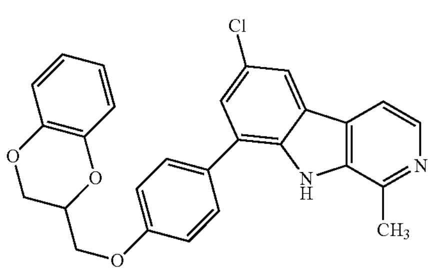 [SMILES: Cc1nccc2c1[nH]c1c(-c3ccc(OCC4COc5ccccc5O4)cc3)cc(Cl)cc12] | 6-Chloro-8-[4-(2,3-dihydro-benzo[1,4]dioxin-2-ylmethoxy)-phenyl]-1-methyl-9H-pyrido[3,4-b]indole | LC4 | 1.66 | 457.3 [M + H]+ |

TABLE 1-continued

| Ex. No. | Structure | Name | LC/MS | RT [min] | MS |
|---|---|---|---|---|---|
| 279 | 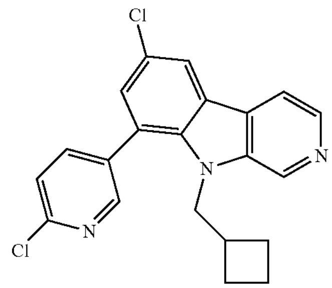 [SMILES: Clc1cc(-c2ccc(Cl)nc2)c2c(c1)c1ccncc1n2CC1CCC1] | 6-Chloro-8-(6-chloro-pyridin-3-yl)-9-cyclobutylmethyl-9H-pyrido[3,4-b]indole | LC6 | 1.08 | 382.1 [M + H]+ |
| 280 | 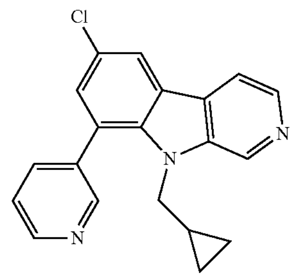 [SMILES: Clc1cc(-c2cccnc2)c2c(c1)c1ccncc1n2CC1CC1] | 6-Chloro-9-cyclopropylmethyl-8-pyridin-3-yl-9H-pyrido[3,4-b]indole | LC6 | 0.92 | 334.1 [M + H]+ |
| 281 | 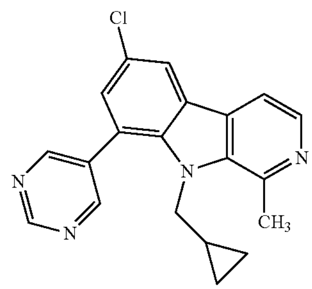 [SMILES: Cc1nccc2c3cc(Cl)cc(-c4cncnc4)c3n(CC3CC3)c12] | 6-Chloro-9-cyclopropylmethyl-1-methyl-8-pyrimidin-5-yl-9H-pyrido[3,4-b]indole | LC8 | 2.82 | 349.2 [M + H]+ |
| 282 | 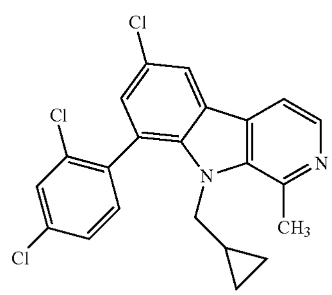 [SMILES: Cc1nccc2c3cc(Cl)cc(-c4ccc(Cl)cc4Cl)c3n(CC3CC3)c12] | 6-Chloro-9-cyclopropylmethyl-8-(2,4-dichlorophenyl)-1-methyl-9H-pyrido[3,4-b]indole | LC6 | 1.24 | 415.1 [M + H]+ |
| 283 | 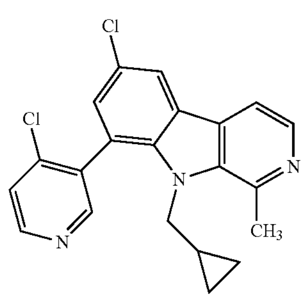 [SMILES: Cc1nccc2c3cc(Cl)cc(-c4cnccc4Cl)c3n(CC3CC3)c12] | 6-Chloro-8-(4-chloro-pyridin-3-yl)-9-cyclopropylmethyl-1-methyl-9H-pyrido[3,4-b]indole | LC6 | 1.08 | 382.1 [M + H]+ |

TABLE 1-continued

| Ex. No. | Structure | Name | LC/MS | RT [min] | MS |
|---|---|---|---|---|---|
| 284 | 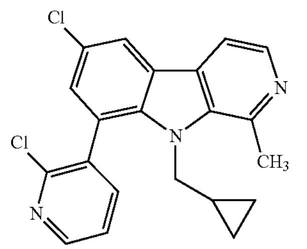 [SMILES: Cc1nccc2c3cc(Cl)cc(-c4cccnc4Cl)c3n(CC3CC3)c12] | 6-Chloro-8-(2-chloro-pyridin-3-yl)-9-cyclopropylmethyl-1-methyl-9H-pyrido[3,4-b]indole | LC6 | 1.11 | 382.1 [M + H]⁺ |
| 285 | 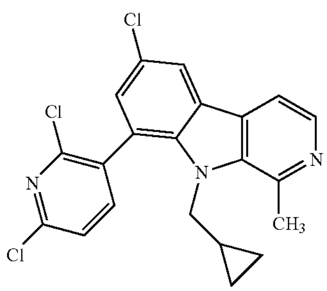 | 6-Chloro-9-cyclopropylmethyl-8-(2,6-dichloro-pyridin-3-yl)-1-methyl-9H-pyrido[3,4-b]indole | LC6 | 1.17 | 416.1 [M + H]⁺ |
| 286 | 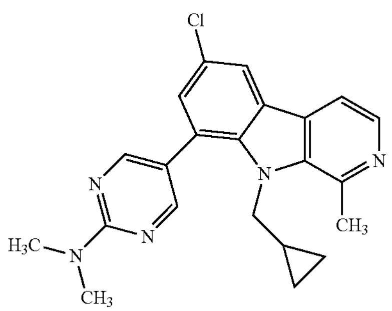 [SMILES: Cc1nccc2c3cc(Cl)cc(-c4cnc(N(C)C)nc4)c3n(CC3CC3)c12] | [5-(6-Chloro-9-cyclopropylmethyl-1-methyl-9H-pyrido[3,4-b]indol-8-yl)-pyrimidin-2-yl]-dimethyl-amine | LC8 | 3.45 | 392.2 [M + H]⁺ |
| 287 | 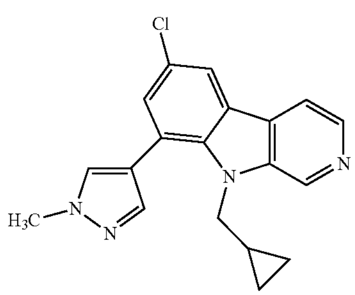 [SMILES: Cn1cc(-c2cc(Cl)cc3c4ccncc4n(CC4CC4)c23)cn1] | 6-Chloro-9-cyclopropylmethyl-8-(1-methyl-1H-pyrazol-4-yl)-9H-pyrido[3,4-b]indole | LC3 | 1.03 | 337.1 [M + H]⁺ |
| 288 | 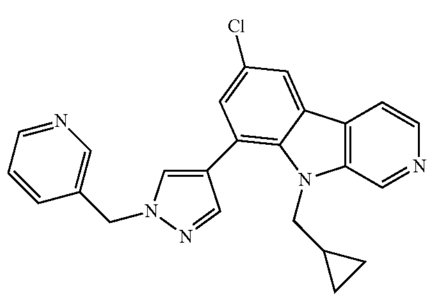 [SMILES: Clc1cc(-c2cnn(Cc3cccnc3)c2)c2c(c1)c1ccncc1n2CC1CC1] | 6-Chloro-9-cyclopropylmethyl-8-(1-pyridin-3-ylmethyl-1H-pyrazol-4-yl)-9H-pyrido[3,4-b]indole | LC4 | 1.46 | 414.2 [M + H]⁺ |

TABLE 1-continued

| Ex. No. | Structure | Name | LC/MS | RT [min] | MS |
|---|---|---|---|---|---|
| 289 | 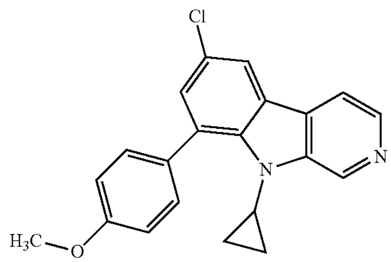 [SMILES: COc1ccc(-c2cc(Cl)cc3c4ccncc4n(C4CC4)c23)cc1] | 6-Chloro-9-cyclopropyl-8-(4-methoxy-phenyl)-9H-pyrido[3,4-b]indole | LC4 | 1.59 | 349.2 [M + H]$^+$ |
| 290 | 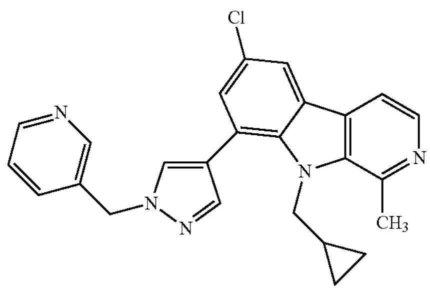 [SMILES: Cc1nccc2c3cc(Cl)cc(-c4cnn(Cc5cccnc5)c4)c3n(CC3CC3)c12] | 6-Chloro-9-cyclopropylmethyl-1-methyl-8-(1-pyridin-3-ylmethyl-1H-pyrazol-4-yl)-9H-pyrido[3,4-b]indole | LC4 | 1.46 | 428.3 [M + H]$^+$ |
| 291 | 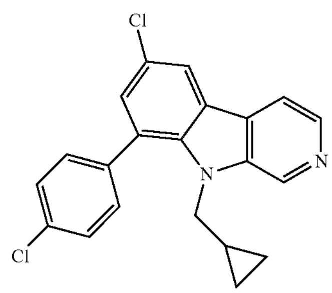 [SMILES: Clc1ccc(-c2cc(Cl)cc3c4ccncc4n(CC4CC4)c23)cc1] | 6-Chloro-8-(4-chloro-phenyl)-9-cyclopropylmethyl-9H-pyrido[3,4-b]indole | LC4 | 1.75 | 367.3 [M + H]$^+$ |
| 292 | 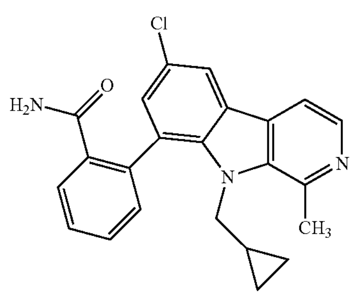 [SMILES: Cc1nccc2c3cc(Cl)cc(-c4ccccc4C(N)=O)c3n(CC3CC3)c12] | 2-(6-Chloro-9-cyclopropylmethyl-1-methyl-9H-pyrido[3,4-b]indol-8-yl)-benzamide | LC4 | 1.52 | 390.2 [M + H]$^+$ |
| 293 | 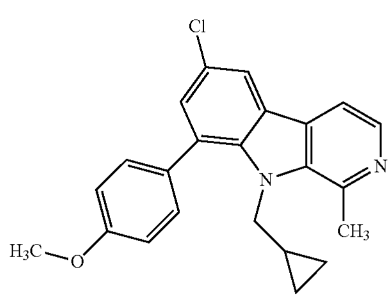 [SMILES: COc1ccc(-c2cc(Cl)cc3c4ccnc(C)c4n(CC4CC4)c23)cc1] | 6-Chloro-9-cyclopropylmethyl-8-(4-methoxy-phenyl)-1-methyl-9H-pyrido[3,4-b]indole | LC8 | 3.88 | 377.2 [M + H]$^+$ |

| Ex. No. | Structure | Name | LC/MS | RT [min] | MS |
|---|---|---|---|---|---|
| 294 | 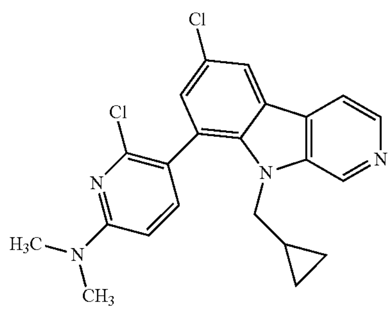 [SMILES: CN(C)c1ccc(-c2cc(Cl)cc3c4ccncc4n(CC4CC4)c23)c(Cl)n1] | [6-Chloro-5-(6-chloro-9-cyclopropylmethyl-9H-pyrido[3,4-b]indol-8-yl)-pyridin-2-yl]-dimethyl-amine | LC4 | 1.85 | 411.1 [M + H]+ |

(a) Isolated in the form of 6-chloro-1-methyl-8-(4-phenoxy-phenyl)-9H-pyrido[3,4-b]indole hydrochloride Exemplary $^1$H NMR data of example compounds Example 6

$^1$H NMR (400 MHz, DMSO-d$_6$): δ (ppm)=8.45 (d, 1H), 8.41 (dd, 1H), 8.27 (d, 1H), 8.10 (d, 1H), 8.06 (d, 1H), 7.42-7.46 (m, 2H), 7.25 (dd, 1H), 6.68 (d, 1H), 5.52 (s, 2H), 4.29 (q, 2H), 2.89 (s, 3H), 2.55 (s, 3H), 0.68 (t, 3H)

Example 7

$^1$H NMR (400 MHz, DMSO-d$_6$): δ (ppm)=8.54 (d, 1H), 8.31 (d, 1H), 8.17 (t, 1H), 8.13 (d, 1H), 7.74 (d, 1H), 7.27 (d, 1H), 6.88 (d, 2H), 6.69 (d, 1H), 5.16-5.28 (m, 1H), 5.04-5.15 (m, 1H), 4.13 (br s, 1H), 3.37 (br s, 1), 2.85 (s, 3H), 2.06 (s, 3H), 0.80 (t, 3H)

Example 8

$^1$H NMR (400 MHz, DMSO-d$_6$): δ (ppm)=11.14 (s, 1H), 8.26 (d, 1H), 8.01 (d, 1H), 7.54-7.75 (m, 2H), 7.46 (s, 1H), 7.16-7.21 (m, 2H), 4.53 (d, 2H), 4.36 (d, 2H), 4.16 (s, 2H), 2.90 (s. 3H), 2.79 (s, 3H), 1.41 (s, 3H)

Example 10

$^1$H NMR (400 MHz, DMSO-d$_6$): δ (ppm)=9.22 (s, 1H), 8.48-8.53 (m, 2H), 8.28 (d, 1H), 8.04 (s, 1H), 7.71 (s, 1H), 7.42 (d, 1H), 5.21 (q, 2H), 4.95 (t, 1H), 4.26 (t, 2H), 3.80 (q, 2H)

Example 13

$^1$H NMR (400 MHz, DMSO-d$_6$): δ (ppm)=11.17 (s, 1H), 8.31 (d, 1H), 8.23 (d, 1H), 8.01 (d, 1H), 7.84 (d, 1H), 7.62-7.68 (m, 2H), 7.49 (d, 1H), 7.43 (d, 1H), 7.10-7.15 (m, 2H), 6.28 (t, 1H), 4.56 (t, 2H), 4.44 (t, 2H), 2.77 (s. 3H)

Example 21

$^1$H NMR (400 MHz, DMSO-d$_6$): δ (ppm)=15.26 (br s, 1H), 8.74 (d, 1H), 8.59 (s, 1H), 8.11 (s, 1H), 7.76 (s, 1H), 7.67 (d, 1H), 4.41 (q, 2H), 3.96 (s, 3H), 3.18 (s, 3H), 2.80 (s, 3H), 0.89 (t, 3H)

Example 22

$^1$H NMR (400 MHz, DMSO-d$_6$): δ (ppm)=8.61-8.73 (m, 2H), 8.51 (br d, 1H), 7.58 (d, 1H), 7.49-7.54 (m, 2H), 7.10-7.15 (m, 2H), 3.86 (s, 3H), 3.68 (s, 3H), 3.14 (s, 3H)

Example 27

$^1$H NMR (400 MHz, DMSO-d$_6$): δ (ppm)=12.31 (br s, 1H), 8.57 (d, 1H), 8.48 (d, 1H), 7.60-7.74 (m, 3H), 7.13-7.21 (m, 2H), 3.87 (s, 3H), 3.05 (s, 3H), 2.98 (s, 3H)

Example 33

$^1$H NMR (600 MHz, DMSO-d$_6$): δ (ppm)=12.66 (br s, 1H), 9.11 (s, 1H), 8.70 (br d, 1H), 8.59 (d, 1H), 8.01 (d, 1H), 7.68-7.73 (m, 2H), 7.18-7.21 (m, 2H), 3.88 (s, 3H), 3.06 (s, 3H)

Example 39

$^1$H NMR (400 MHz, DMSO-d$_6$): δ (ppm)=11.18 (s, 1H), 8.31 (d, 1H), 8.24 (d, 1H), 8.01 (d, 1H), 7.68 (m, 2H), 7.44 (d, 1H), 7.27-7.33 (m, 2H), 7.22 (s, 1H), 6.91 (s, 1H), 5.25 (s, 2H), 3.73 (s, 3H), 2.78 (s, 3H)

Example 45

$^1$H NMR (400 MHz, DMSO-d$_6$): δ (ppm)=11.11 (br s. 1H), 8.25 (d, 1H), 8.00 (d, 1H), 7.83 (d, 1H), 7.58-7.64 (m, 2H), 7.48 (d, 1H), 7.44 (s, 1H), 7.08-7.14 (m, 2H), 6.27 (t, 1H), 4.56 (t, 2H), 4.44 (t, 2H), 2.89 (s, 3H), 2.78 (s, 3H)

Example 46

$^1$H NMR (400 MHz, DMSO-d$_6$): δ (ppm)=9.11 (s, 1H), 8.61 (d, 1H), 8.46 (d, 1H), 8.32 (d, 1H), 8.27 (d, 1H), 7.82 (d, 1H), 7.54 (d, 1H), 4.07 (dd, 1H), 3.76 (dd, 1H), 0.69-0.80 (m, 1H), −0.17-0.28 (m, 2H), 0.03-0.16 (m, 2H)

Example 55

$^1$H NMR (500 MHz, DMSO-d$_6$): δ (ppm)=9.47 (s, 1H), 8.85 (d, 1H), 8.77 (d, 1H), 8.69 (br d, 1H), 8.33 (d, 1H), 7.84 (d, 1H), 7.76 (d, 1H), 4.18-4.36 (m, 1H), 3.74-3.95 (m, 1H), 0.99 (t, 3H)

Example 116

$^1$H NMR (400 MHz, DMSO-d$_6$): δ (ppm)=8.58 (d, 1H), 8.54 (dd, 1H), 8.40 (d, 1H), 8.29 (s, 1H), 8.28 (d, 1H), 8.10

(d, 1H), 7.82 (s, 1H), 7.69-7.74 (m, 1H), 7.40-7.46 (m, 1H), 7.38 (d, 1H), 5.51 (s, 2H), 4.34 (q, 2H), 2.91 (s. 3H), 0.74 (t, 3H)

Example 148

$^1$H NMR (400 MHz, DMSO-d$_6$): δ (ppm)=8.81 (d, 1H), 8.77 (d, 1H), 8.60 (br d, 1H), 7.62-7.68 (m, 4H), 7.61 (d, 1H), 4.18 (q, 2H), 3.12 (s, 3H), 0.86 (t, 3H)

Example 149

$^1$H NMR (500 MHz, DMSO-d$_6$): δ (ppm)=12.45 (s, 1H), 8.71 (d, 1H), 8.65 (d, 1H), 8.54 (brd, 1H), 7.66-7.72 (m, 3H), 7.15-7.22 (m, 2H), 3.88 (s, 3H), 3.06 (s, 3H)

Example 184

$^1$H NMR (500 MHz, DMSO-d$_6$): δ (ppm)=11.18 (s. 1H), 8.29 (d, 1H), 8.23 (d, 1H), 8.00 (d, 1H), 7.40-7.45 (m, 3H), 6.93 (d, 1H). 4.22 (t, 2H), 2.87 (t, 2H), 2.78 (s, 3H), 1.96-2.03 (m, 2H)

Example 209

$^1$H NMR (400 MHz, DMSO-d$_6$): δ (ppm)=8.87 (d. 1H), 8.76 (d, 1H), 8.57 (d, 1H), 8.11 (s, 1H), 7.76 (d, 1H), 7.68 (d, 1H), 4.45 (q, 2H), 3.97 (s, 3H), 3.15 (s, 3H), 0.92 (t, 3H)

Example 215

$^1$H NMR (400 MHz, DMSO-d$_6$): δ (ppm)=11.30 (s, 1H), 8.40 (d, 1H), 8.25 (d, 1H), 8.08 (d, 1H), 8.03 (d, 1H), 7.48 (d, 1H), 6.75-6.84 (m, 2H), 6.10 (s, 2H), 2.79 (s, 3H)

Example 228

$^1$H NMR (400 MHz, DMSO-d$_6$): δ (ppm)=11.18 (s, 1H), 8.31 (d, 1H), 8.24 (d, 1H), 8.01 (d, 1H), 7.63-7.68 (m, 2H), 7.44 (d, 1H), 7.12-7.16 (m, 2H), 3.92-4.00 (m, 2H), 2.78 (s, 3H), 2.53-2.67 (m, 3H), 2.32-2.44 (m, 3H), 2.26 (s, 3H), 1.93-2.03 (m, 1H), 1.49-1.58 (m, 1H)

Example 256

$^1$H NMR (400 MHz, DMSO-d$_6$): δ (ppm)=8.66-8.78 (m, 2H), 8.54 (d, 1H), 7.46-7.59 (m, 3H), 7.14-7.21 (m, 2H), 4.54 (d, 2H), 4.35 (d, 2H), 4.33 (q, 2H), 4.16 (s, 2H), 3.10 (s, 3H), 1.42 (s, 3H), 0.84 (t, 3H)

BIOLOGIC EXAMPLES

A) Chondrogenesis Activity Assay in ATDC5 Cells

The chondrogenic potential of the compounds of the invention was determined using clonal mouse chondrogenic ATDC5 cells (T. Atsumi et al., Cell Differ. Dev. 1990, 30, 109-116). ATDC5 cells are derived from mouse embryonic AT805 teratocarcinoma cells and are used frequently to study the multistep chondrogenic differentiation process from precursor cells into chondrocytes (C. Shukunami et al., Exp. Cell Res. 1998, 241, 1-11; H. Aklyami et al., J. Bone Miner. Res. 1996, 11, 22-28; H. Akiyami et al., Biochem. Biophys. Res. Commun. 1997, 235, 142-147; C. Shukunami et al., J. Cell Biol. 1996, 133, 457-468; C. Shukunami et al., J. Bone Miner. Res. 1997, 12, 1174-1188). Undifferentiated ATDC5 cells grow in vitro until confluence, showing a fibroblast-like morphology. In the presence of insulin, cells undergo transient condensation and form numerous nodular structures (cartilage nodules). The cartilagenous nature of these nodules was shown by Alcian Blue staining as evidence of the production of proteoglycan (aggrecan) and collagen type II expression (by expression analysis), both molecular markers of chondrocytes (C. Shukunami et al., J. Cell Biol. 1996, 133, 457-468).

Chondrogenic differentiation of ATDC5 cells into chondrocytes by the compounds of the invention was determined by measuring the induction of type II collagen protein as a marker of chondrocytes, a structural component of the extracellular matrix which constitutes more than 80% of cartilage mass (D. R. Eyre, Clin. Orthop. Relat. Res. 2004, 427 Suppl, S118-S122). ATDC5 cells were obtained from RIKEN and cultured as monolayer in basal culture medium (Dulbecco's Modified Eagle Medium/Nutrient Mixture F-12 (DMEM/F12, Invitrogen, #31331-093) supplemented with 10 µg/ml Transferrin (Roche, #10652 202001), 3×10E−8 M sodium seienite (Sigma, #S-5261) and 5% Fetal Calf Serum (FCS Gold, PAA, #A15-251)), at 37° C., and 5% $CO_2$ in plastic flasks of 75 $cm^2$ or 300 $cm^2$ subconfluently for propagation. ATDC5 cells were harvested and resuspended in differentiation culture medium that consisted of basal culture medium complemented with 10 µg/ml insulin (Sigma, #19278), to initiate chondrogenic differentiation. For studying the effect of test compounds, the ATDC5 cells were plated in 96-well plates (3.0×10E4 cells per well in 200 µl of differentiation culture medium). Test compounds dissolved in DMSO were added to yield increasing compound concentrations, typically from 40 nM to 10 µM, and a final DMSO concentration of 0.1%. On each 96-well plate, control wells containing no test compound but the same concentration of DMSO, i.e. untreated cells, were included and used as reference for the determination of the effect of the test compounds on the cells, and wells containing an internal reference compound at a concentration of 10 µM were included and used as positive control and for standardizing the results. Cells in the wells were incubated for 4 days at 37° C., and 5% $CO_2$, followed by quantification of intracellular collagen type II.

Quantification of collagen type II in the ATDC5-cells was done by immunofluorescence staining of collagen type II, and fluorescence intensity was measured using a cellular high content imaging system (ImageXpress, Molecular Device). For immunofluorescence staining of intracellular collagen, medium was removed after compound incubation and cells were fixed with 200 µl/well methanol/water (95%/5%). Cells were permeabilized in 200 µl/well phosphate-buffered saline (PBS) containing 0.2% Triton X100 for 15 min and, after removal of the solution, blocked for 30 min with 200 µl/well PBS/0.2% Triton X100 containing 1% bovine serum albumin (BSA) to avoid unspecific binding. After the blocking step, the solution was removed and collagen type II staining solution was added. A primary antibody mouse anti-collagen type II solution (Quartett Immundiagnostika, #031502302) was diluted 1:100 in PBS/1% BSA, and 50 µl of the solution was added to each well and incubated for 1 hour at room temperature. After washing three times with PBS, 50 µl per well of a second antibody solution was added and incubated for 1 hour. The second antibody solution contained PBS/1% BSA with a 1:250 dilution of goat anti-mouse IgG (H+L) antibody coupled with fluorescent dye Alexa Fluor 488 (Invitrogen, #A11029), and fluorescent dye Hoe 33342 for staining nuclei with a final concentration of 2 µg/ml. Fluorescence signal intensity was measured for fluorescent dye Alexa Fluor 488 and for dye Hoe 33342, and the signals integrated over 9 fields within each well of a 96-well plate.

The change of the collagen type II-derived fluorescence signal intensity was calculated for each compound concentration relative to the control (untreated cells, i.e. no test compound added), and an $EC_{50}$ value (effective concentration 50 (in µM (micromol/liter)), i.e. the compound concentration at which the effect of the compound on collagen type II induction reaches 50% of the maximum induction) was calculated using a sigmoidal signal fit procedure. To allow the comparison of compound activities determined in different experiments, given the natural biological variation of the chondrogenic response between different experiments, an internal reference compound at a concentration of 10 µM was included in all experiments, and for each concentration collagen type II induction was calculated in percent in relation to the internal reference compound at 10 µM. The maximum percent induction (relative to the internal reference compound at a concentration of 10 µM) of a compound is termed $E_{max}$. $EC_{50}$ values (in µM) and $E_{max}$ values (in percent) obtained for compounds of the invention in this test are given in Table 2. In Table 2 the $E_{max}$ value "a" denotes a maximum percent induction of less than 20%, the $E_{max}$ value "b" denotes a maximum percent induction from 20% to less than 50%, the $E_{max}$ value "c" denotes a maximum percent induction from 50% to less than 80%, and the $E_{max}$ value "d" denotes a maximum percent induction of more than 80%, in each case relative to the internal reference compound at a concentration of 10 µM.

TABLE 2

| Example no. | $EC_{50}$ [µM] | $E_{max}$ |
|---|---|---|
| 1 | 1.7 | a |
| 2 | 0.71 | d |
| 3 | >10 | b |
| 4 | 0.83 | d |
| 5 | 0.49 | d |
| 6 | 2.2 | c |
| 7 | >3.3 | a |
| 8 | 0.12 | d |
| 9 | 1.4 | d |
| 10 | 0.69 | d |
| 11 | 3.9 | c |
| 12 | >10 | b |
| 13 | 0.12 | d |
| 14 | 0.86 | d |
| 15 | 1.0 | c |
| 16 | 2.8 | c |
| 17 | 3.6 | d |
| 18 | 1.0 | d |
| 19 | >10 | c |
| 20 | 3.9 | c |
| 21 | >3.3 | b |
| 22 | 0.63 | d |
| 23 | 1.6 | c |
| 24 | 2.0 | c |
| 25 | 0.17 | d |
| 26 | 0.53 | c |
| 27 | 0.097 | d |
| 28 | 0.19 | d |
| 29 | >1.1 | a |
| 30 | 0.27 | d |
| 31 | 0.25 | d |
| 32 | 0.37 | c |
| 33 | 0.12 | d |
| 34 | >1.1 | b |
| 35 | 3.1 | d |
| 36 | 0.10 | d |
| 37 | >3.3 | b |
| 38 | 2.6 | c |
| 39 | 0.17 | d |
| 40 | 0.16 | d |

TABLE 2-continued

| Example no. | $EC_{50}$ [µM] | $E_{max}$ |
|---|---|---|
| 41 | 0.24 | c |
| 42 | 0.51 | c |
| 43 | >6.6 | a |
| 44 | 0.67 | d |
| 45 | 0.13 | d |
| 46 | 1.4 | d |
| 47 | >10 | b |
| 48 | 0.041 | a |
| 49 | 0.041 | a |
| 50 | 0.13 | a |
| 51 | >10 | a |
| 52 | 1.2 | c |
| 53 | 2.1 | c |
| 54 | 1.1 | b |
| 55 | 0.65 | d |
| 56 | 0.46 | b |
| 57 | 1.6 | a |
| 58 | 1.5 | b |
| 59 | 1.3 | d |
| 60 | 2.5 | b |
| 61 | 5.6 | d |
| 62 | 1.2 | d |
| 63 | 0.59 | b |
| 64 | 3.9 | d |
| 65 | 2.3 | b |
| 66 | 2.1 | c |
| 67 | 0.74 | b |
| 68 | 7.6 | c |
| 69 | 2.0 | c |
| 70 | 0.57 | d |
| 71 | 1.5 | a |
| 72 | 5.8 | b |
| 73 | 0.44 | b |
| 74 | 0.92 | b |
| 76 | 1.5 | b |
| 76 | >10 | b |
| 77 | 0.58 | d |
| 78 | >10 | a |
| 79 | 3.9 | d |
| 80 | 1.2 | b |
| 81 | 4.1 | d |
| 82 | 2 | b |
| 83 | 2.1 | b |
| 84 | >10 | b |
| 85 | >10 | b |
| 86 | 0.75 | d |
| 87 | 1.5 | c |
| 88 | 1.7 | a |
| 89 | >10 | d |
| 90 | >10 | a |
| 91 | 1.5 | d |
| 92 | 2.5 | d |
| 93 | 2.2 | d |
| 94 | 0.75 | d |
| 95 | 0.68 | c |
| 96 | 0.85 | c |
| 97 | >1.1 | a |
| 98 | 2.4 | d |
| 99 | >10 | a |
| 100 | 1.0 | a |
| 101 | 8.2 | b |
| 102 | 2.1 | b |
| 103 | 1.9 | d |
| 104 | 3.5 | d |
| 105 | 1.0 | c |
| 106 | >10 | b |
| 107 | 0.56 | b |
| 108 | 1.4 | d |
| 109 | 0.72 | c |
| 110 | >10 | b |
| 111 | 1.8 | c |
| 112 | 0.49 | d |
| 113 | 0.78 | d |
| 114 | 5.7 | b |
| 115 | 0.49 | d |
| 116 | 0.39 | d |
| 117 | >10 | a |
| 118 | >1.1 | b |

TABLE 2-continued

| Example no. | EC$_{50}$ [μM] | E$_{max}$ |
|---|---|---|
| 119 | >3.3 | a |
| 120 | 1.4 | c |
| 121 | 0.59 | d |
| 122 | >3.3 | b |
| 123 | 0.26 | b |
| 124 | 2.6 | a |
| 125 | 1.0 | d |
| 126 | >10 | b |
| 127 | 0.38 | c |
| 128 | 3.9 | a |
| 129 | 0.86 | d |
| 130 | 0.38 | d |
| 131 | 0.78 | d |
| 132 | 4.5 | b |
| 133 | >10 | b |
| 134 | >10 | a |
| 135 | 0.33 | c |
| 136 | 4.1 | c |
| 137 | 1.4 | b |
| 138 | >10 | a |
| 139 | >10 | a |
| 140 | 0.91 | b |
| 141 | >10 | a |
| 142 | 0.52 | d |
| 143 | 0.97 | b |
| 144 | 0.58 | a |
| 145 | 0.48 | a |
| 146 | 0.041 | a |
| 147 | 0.84 | d |
| 148 | 0.046 | d |
| 149 | 0.33 | d |
| 150 | 0.51 | d |
| 151 | 0.54 | c |
| 152 | 0.36 | a |
| 153 | 4.5 | c |
| 154 | 8.8 | b |
| 155 | >3.3 | a |
| 156 | 1.5 | a |
| 157 | >10 | b |
| 158 | 1.9 | d |
| 169 | 1.3 | c |
| 160 | >10 | a |
| 161 | 2.0 | d |
| 162 | 0.59 | d |
| 163 | 0.69 | d |
| 164 | 0.23 | d |
| 165 | >10 | a |
| 166 | 0.84 | d |
| 167 | >10 | b |
| 168 | 0.99 | d |
| 169 | 1.1 | d |
| 170 | >10 | b |
| 171 | 1.9 | d |
| 172 | >10 | b |
| 173 | 1.9 | d |
| 174 | 7.3 | c |
| 175 | >10 | a |
| 176 | >10 | b |
| 177 | >10 | b |
| 178 | >10 | b |
| 179 | >10 | d |
| 180 | 0.33 | d |
| 181 | 2.1 | d |
| 182 | 0.22 | d |
| 183 | 2.3 | c |
| 184 | 3.0 | c |
| 185 | >10 | b |
| 186 | 0.10 | d |
| 187 | 2.2 | d |
| 188 | 0.64 | d |
| 189 | 0.50 | d |
| 190 | 0.72 | d |
| 191 | 0.55 | d |
| 192 | 0.64 | d |
| 193 | >10 | b |
| 194 | 0.14 | d |
| 195 | >10 | a |
| 196 | 0.80 | c |
| 197 | 0.63 | d |
| 198 | 1.8 | b |
| 199 | >10 | a |
| 200 | >10 | b |
| 201 | 0.60 | d |
| 202 | 0.64 | d |
| 203 | >10 | a |
| 204 | 0.19 | c |
| 205 | 3.3 | d |
| 206 | >10 | b |
| 207 | 1.6 | d |
| 208 | 1.9 | d |
| 209 | 0.28 | d |
| 210 | >3.3 | a |
| 211 | >3.3 | a |
| 212 | >3.3 | a |
| 213 | >1.1 | a |
| 214 | >3.3 | a |
| 215 | 0.23 | d |
| 216 | >10 | a |
| 217 | >3.3 | b |
| 218 | >1.1 | a |
| 219 | >3.3 | a |
| 220 | >10 | b |
| 221 | >3.3 | b |
| 222 | >10 | a |
| 223 | >3.3 | b |
| 224 | 0.31 | d |
| 225 | 1.7 | d |
| 226 | 0.19 | c |
| 227 | 0.33 | d |
| 228 | 0.15 | c |
| 229 | 0.28 | c |
| 230 | >3.3 | a |
| 231 | >10 | b |
| 232 | 0.33 | d |
| 233 | >10 | b |
| 234 | 5.8 | c |
| 235 | >3.3 | b |
| 236 | >3.3 | a |
| 237 | 0.50 | d |
| 238 | 1.4 | d |
| 239 | 0.25 | c |
| 240 | 0.49 | c |
| 241 | >1.1 | b |
| 242 | 0.57 | d |
| 243 | 0.66 | d |
| 244 | 1.1 | d |
| 245 | >1.1 | a |
| 246 | 2.9 | c |
| 247 | >3.3 | a |
| 248 | >3.3 | b |
| 249 | >3.3 | b |
| 250 | >3.3 | c |
| 251 | >10 | a |
| 252 | 1.6 | d |
| 253 | >10 | b |
| 254 | >3.3 | a |
| 255 | >3.3 | a |
| 256 | 0.16 | d |
| 257 | 0.31 | d |
| 258 | >3.3 | a |
| 259 | 0.43 | d |
| 260 | >1.1 | a |
| 261 | 1.5 | d |
| 262 | 2.3 | d |
| 263 | 0.55 | d |
| 264 | >1.1 | b |
| 265 | >1.1 | a |
| 266 | 0.11 | d |
| 267 | >3.3 | c |
| 268 | 0.34 | d |
| 269 | >3.3 | b |
| 270 | >1.1 | b |
| 271 | >3.3 | b |
| 272 | 1.9 | d |
| 273 | 0.17 | a |
| 274 | >3.3 | a |

TABLE 2-continued

| Example no. | EC$_{50}$ [µM] | E$_{max}$ |
|---|---|---|
| 275 | 0.30 | d |
| 276 | 0.42 | d |
| 277 | >3.3 | a |
| 278 | >3.3 | b |
| 279 | 1.8 | b |
| 280 | >10 | a |
| 281 | 0.11 | a |
| 282 | 3.6 | a |
| 283 | 0.41 | a |
| 284 | 4.2 | a |
| 285 | 6.1 | b |
| 286 | 0.041 | a |
| 287 | 0.23 | c |
| 288 | 0.52 | d |
| 289 | 0.75 | d |
| 290 | >10 | b |
| 291 | 1.7 | c |
| 292 | >6.6 | a |
| 293 | 4.5 | c |
| 294 | 1.2 | d |

B) Chondrogenesis Activity Assay in Primary Human Chondrocyte Pellet Cultures

In this assay human articular chondrocytes are harvested by enzymatic digestion from articular cartilage and passaged several times to dedifferentiate the chondrocytes and to propagate the cells. Cells are cultured as cell pellets in the presence of the compounds of the invention over 2 weeks, and the chondrogenic differentiation is quantified by the production of the chondrogenic marker aggrecan (proteoglycan).

In detail, primary chondrocytes were harvested by enzymatic digestion from cartilage of osteoarthritis patients undergoing knee joint replacement surgery, and cultured in vitro. Cells were passaged one or two times and aliquots were cryopreserved. To initiate chondrogenesis experiments, cell aliquots were thawn, cultured in Chondrocyte Growth Medium (CGM, Lonza, #CC-3216) and passaged twice to further propagate and dedifferentiate cells. Pellet cultures were initiated by seeding 2.5×10E5 cells per well into a 96-well deep well plate in 600 µl chondrocyte differentiation medium consisting of Dulbecco's Modified Eagle Medium (DMEM, Invitrogen, #41966), 1×ITS-solution (Insulin/Transferrin/sodium selenite; 100× solution: Invitrogen, #51500056), 5 µg/mL linoleic acid (Sigma, #L1012-1G), 1× nonessential amino acids (100× solution: Invitrogen, #11140); 10 nM Dexamethasone, 2 ng/ml TGF-β1 (transforming growth factor β1) and 10 µg/ml ascorbic acid. Cells were spun to pellets by centrifugation (10 min, 400×g). Test compounds dissolved in DMSO were added to yield increasing compound concentrations, typically from 40 nM to 10 µM, and a final DMSO concentration of 0.1%, and the cell pellets cultured at 37° C., and 5% CO$_2$ for 2 weeks. On each 96-well plate, control wells containing no test compound but the same concentration of DMSO, i.e. untreated cells, were included and used as reference for the determination of the effect of the test compounds on the cells, and wells containing an internal reference compound at a concentration of 10 µM were included and used as positive control and for standardizing the results. Chondrocyte differentiation medium and the compounds were exchanged twice weekly until harvest of the pellets.

For harvest of the pellets, medium was removed and the pellet was homogenized by enzymatic digestion. 100 µl of protease solution containing 0.4 mg/ml papain, 50 mM sodium phosphate, 4 mM EDTA and 0.48 mg/ml L-cysteine was added to the pellet in each well of a 96-well plate, the plate was sealed with a plate sealer foil (SILVERseal, Greiner Bio-One) and incubated for 4 to 6 hours at 65° C. with agitation.

The concentration of proteoglycan (aggrecan) was determined by quantification of the sulfated glycosaminoglycan side chains of aggrecan using the Blyscan assay (Kit from Biocolor). Aliquots of the papain-digest were transferred to 400 µl of Blyscan dye solution and incubated at room temperature for 45 min with agitation (1200 rpm). The mixture was centrifuged at 3760×g for 45 min, the supernatant was discarded, and the stained pellet was redissolved in 400 µl of Blyscan dissociation reagent by rotation until the precipitate completely resolved. Optical density was measured at 656 nm using a Tecan Saphire2 instrument, and the amount of proteoglycan determined against a standard curve with chondroitin-4-sulfate.

Induction of proteoglycan (aggrecan) was calculated for each compound concentration relative to the control (untreated cells, i.e. no test compound added), and an EC$_{50}$ value (effective concentration 50 (in µM (micromollliter)), i.e. the compound concentration at which the effect of the compound on proteoglycan (aggrecan) induction reaches 50% of the maximum induction) was calculated using a sigmoidal signal fit procedure. To allow the comparison of compound activities determined in different experiments, given the natural biological variation of the chondrogenic response between different experiments, an internal reference compound at a concentration of 10 µM was included in all experiments, and for each concentration proteoglycan (aggrecan) induction was calculated in percent in relation to the internal reference compound at 10 µM. The maximum percent induction (relative to the internal reference compound at a concentration of 10 µM) of a compound is termed E$_{max}$. EC$_{50}$ values (in µM) and E$_{max}$ values (in percent) obtained for compounds of the invention in this test are given in Table 3. In Table 3 the E$_{max}$ value "a" denotes a maximum percent induction of less than 40%, the E$_{max}$ value "b" denotes a maximum percent induction from 40% to less than 100%, the E$_{max}$ value "c" denotes a maximum percent induction from 100% to less than 200%, and the E$_{max}$ value "d" denotes a maximum percent induction of more than 200%, in each case relative to the internal reference compound at a concentration of 10 µM.

TABLE 3

| Example no. | EC$_{50}$ [µM] | E$_{max}$ |
|---|---|---|
| 2 | 4.4 | d |
| 5 | 1.3 | d |
| 8 | 0.26 | c |
| 10 | 2.4 | b |
| 11 | 7.9 | b |
| 13 | 1.1 | d |
| 19 | 6.9 | b |
| 21 | 4.3 | d |
| 22 | 4.0 | d |
| 27 | 3.5 | d |
| 29 | 1.5 | c |
| 33 | 0.83 | c |
| 34 | 3.8 | d |
| 37 | 4.3 | c |
| 39 | 3.7 | d |
| 45 | 0.22 | b |
| 46 | 1.0 | c |
| 55 | 0.95 | c |
| 97 | 5.1 | d |
| 116 | 1.3 | c |
| 117 | 27 | a |
| 118 | 1.3 | c |
| 119 | 21 | b |

TABLE 3-continued

| Example no. | EC$_{50}$ [µM] | E$_{max}$ |
| --- | --- | --- |
| 122 | 3.6 | c |
| 149 | 1.1 | c |
| 167 | 13 | a |
| 171 | 4.0 | d |
| 184 | 1.9 | b |
| 194 | 0.83 | c |
| 195 | 14 | a |
| 199 | 22 | a |
| 200 | 4.4 | c |
| 206 | 19 | a |
| 209 | 2.6 | d |
| 212 | 8.9 | a |
| 213 | 1.2 | c |
| 214 | 1.3 | c |
| 216 | 0.99 | d |
| 217 | 4.9 | d |
| 218 | 40 | a |
| 223 | 27 | a |
| 228 | 0.14 | c |
| 230 | 21 | a |
| 235 | 6.1 | d |
| 236 | 4.6 | d |
| 241 | 1.5 | c |
| 244 | 4.9 | d |
| 245 | 10 | b |
| 247 | 3.8 | d |
| 250 | 4.9 | c |
| 251 | 9.1 | b |
| 256 | 1.3 | d |
| 258 | 8.2 | b |
| 264 | 1.5 | b |
| 265 | 3.8 | a |
| 270 | 4.3 | b |
| 271 | 4.9 | d |
| 288 | 1.2 | d |

The compounds of the invention can also be tested in the animal models described in biological examples C) and D), which are in vivo models of osteoarthritis (OA) in rodents.

C) Joint Instability Induced OA in Rats after Anterior Cruciate Ligament Transection and Partial Meniscectomy (ACLT-pMx)

In this model osteoarthritis is induced via ACLT-pMx surgery in rats and assessment of histopathological joint damage is conducted as primary readout. Under general anesthesia by isoflurane (4%-5% in 3 L/min O$_2$) the right leg of the rats is shaved and disinfected with Cutasept® (Beiersdorf, Germany). Then, with the leg in extension, a para-patellar skin incision is made on the medial side of the joint. After dislocating the patella laterally, an incision of the joint capsule on the medial side of the patellar tendon is made to access the joint space. The anterior cruciate ligament is transected using a modified sharpened hook ("Ohrhebel nach Wagener"; Aesculap, #OF 285 R). Then the medial meniscus is gently retracted and the cranial part of the meniscus (30%) carefully excised by using an Aesculap microscalpel to ensure that the cartilage of the femur and the tibia is not damaged. During the surgery the joint space is lavaged with 0.9% sterile saline to remove all blood from the joint and to prevent damage by drying of the tissue. After repositioning of the patella the joint capsule is closed with Safil® absorbable sutures (B. Braun Melsungen, Germany). The skin is closed with Dafilonr 3/0 sutures (B. Braun Melsungen, Germany). Buprenorphine hydrochloride is given subcutaneously (0.06 mg/kg) as a post-surgical analgesic treatment.

Treatment onset with a test compound is seven days after surgery. The animals receive intra-articular injections of 0.1 to 1 mg/joint of the test compound suspended in 50 µl of vehicle into the operated knee joint in up to weekly intervals, whereas the control animals receive injections of 50 µl of the vehicle. At day 28 post surgery all animals are sacrificed for histology and histopathological analysis, which is performed as described in biological example D).

D) Spontaneous Model of OA in Dunkin Hartley Guinea Pigs

In this model Dunkin Hartley guinea pigs of strain Hsd-Dhl:DH (Harlan Laboratories, The Netherlands), which is a widely used strain for spontaneous animal models of OA since their histological and biochemical changes resemble that of human OA (A. M. Bendele et al., Arthritis Rheum. 1988, 31, 561-565), are used at the age of 6 months. It is known that histological changes start at the age of about 3 months and disease severity increases with age (P. A. Jimenez et al., Lab. Anim. Sci, 1997, 47, 598-601). Therefore treatment onset in this model is at the age of 6 months and continued until animals reach an age of a minimum of 12 months.

The animals receive intra-articular injections of 0.1 to 3 mg/joint of the test compound suspended in 100 µl of vehicle into the right knee joint in up to weekly intervals, whereas the control animals receive injections of 100 µl of the vehicle. After a minimum of 6 months treatment all animals are sacrificed for histology and histopathological analysis.

Evaluation of the tests described in examples C) and D) is done in the following way.

For histological processing of the tissue the right knee joints of the animals are excised at the mid-shaft of femur and tibia and placed in 10% formalin for 3 days, to fix the tissue. After fixing the knees are decalcified in formic acid (Immunocal®, Decal Chemical Corp., NY, USA) for 11 days, dehydrated in the Tissue Processor TP 1020® (Leica, Germany) and embedded in paraffin. The paraffin-embedded complete knee is serially sectioned (coronal sections) on a rotary microtome at a thickness of 7 µm and the sections are stained with Hematoxylin/Eosin (H&E) or Safranin O/Fast Green (SO). For each knee 4 subregions of the knee joint (medial or lateral tibia or femur) are defined. From each subregion 5 sections with the most severe damage are selected and evaluated by two observers blinded to the treatment by using a modified Mankin score.

Digital images from histological H&E-stained as well as SO-stained coronal sections of the whole knee joint are taken using a Zeiss AxioScanner®. After conversion into if files and transfer into the digital image analysis software Visiopharm Integrator System (VIS; Version Nr. 3.0.15.0; Visiopharm, Denmark), the cartilage tissue, the chondrocytes, the SO-stained cartilage area and the subchondral bone are segmented. As region of interest (ROI) a rectangle of 1.2×0.5 mm covering the most affected area of cartilage and the underlying subchondral bone in the medialtibial plateau are chosen. The degree of cartilage destruction and subchondral bone sclerosis is then quantified by measuring the following parameters: fibrillation index (Fl; the width of the region of interest (box) divided by the cartilage surface curvature length, i.e. measures of cartilage surface irregularity); cartilage area; chondrocyte number (cell number per residual cartilage area); absolute number of residual chondrocytes; proteoglycan containing (SO-stained) cartilage area; subchondral solid bone area.

For statistical analysis of the data, results are given as median, inter-quartile and complete data range (histopathological scoring) or mean t SEM (histomorphometry). The statistical significance of the effect of a compound on the histomorphometrically assessed joint pathology is determined by a one way analysis of variance followed by Dunnett's test for multiple comparisons versus the vehicle-treated group. Kruskal-Wallis test and multiple comparisons by Dunn's Test versus the vehicle-treated group are applied for the semi-quantitative histopathological scores. SAS® v8.2 via Everstat software v5.0 interface is used for the statistical analyses.

The invention claimed is:

1. An intermediate compound of formula II

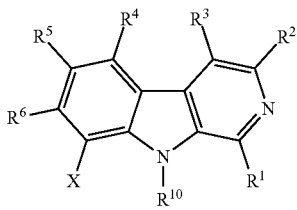

wherein:
R$^1$, R$^3$, R$^4$ and R$^6$ are independently selected from the group consisting of hydrogen, halogen and (C$_1$-C$_4$)-alkyl;
R$^2$ is selected from the group consisting of hydrogen, halogen, (C$_1$-C$_4$)-alkyl and (C$_1$-C$_4$)-alkyl-O—C(O)—;
R$^7$, R$^8$ and R$^9$ are independently selected from the group consisting of hydrogen and (C$_1$-C$_4$)-alkyl;
R$^{10}$ is selected from the group consisting of hydrogen, (C$_1$-C$_6$)-alkyl, (C$_2$-C$_6$)-alkenyl, (C$_2$-C$_6$)-alkynyl and (C$_3$-C$_7$)-cycloalkyl,
wherein the (C$_1$-C$_6$)-alkyl group is unsubstituted or substituted by 1 or 2 identical or different substituents selected from the group consisting of (C$_3$-C$_7$)-cycloalkyl, Het, cyano and (C$_1$-C$_4$)-alkyl-O—, and
wherein each (C$_3$-C$_7$)-cycloalkyl group is unsubstituted or substituted by one or more identical or different substituents selected from the group consisting of fluorine and (C$_1$-C$_4$)-alkyl; and
X is a halogen leaving group selected from iodo and bromo, wherein when X is iodo, R$^5$ is bromo or chloro, and wherein when X is bromo, R$^5$ is chloro;
wherein Het is a monocyclic, 4-membered to 7-membered, saturated heterocyclic group comprising 1 or 2 identical or different hetero ring members selected from the group consisting of N, N(R$^{40}$), O and S(O)$_m$, and which is unsubstituted or substituted on ring carbon atoms by one or more identical or different substituents selected from the group consisting of fluorine and (C$_1$-C$_4$)-alkyl;
R$^{40}$ is selected from the group consisting of hydrogen and (C$_1$-C$_4$)-alkyl;
m is selected from the series consisting of 0, 1 and 2, wherein all numbers m are independent of each other and can be identical or different; and
wherein each alkyl group, independently of any other substituents which can be present on an alkyl group, is optionally substituted by one or more fluorine substituents.

2. The intermediate compound of formula II according to claim 1, which is selected from the group consisting of:
8-Bromo-6-chloro-9H-pyrido[3,4-b]indole,
8-Bromo-6-chloro-9-cyclopropylmethyl-9H-pyrido[3,4-b]indole,
8-Bromo-6-chloro-1-methyl-9H-pyrido[3,4-b]indole,
8-Bromo-6-chloro-9-cyclopropylmethyl-1-methyl-9H-pyrido[3,4-b]indole,
6-Chloro-8-iodo-1-methyl-9H-pyrido[3,4-b]indole,
6-Chloro-9-ethyl-8-iodo-1-methyl-9H-pyrido[3,4-b]indole,
6-Bromo-8-iodo-1-methyl-9H-pyrido[3,4-b]indole,
6-Bromo-9-ethyl-8-iodo-1-methyl-9H-pyrido[3,4-b]indole,
6-Chloro-8-iodo-1,9-dimethyl-9H-pyrido[3,4-b]indole,
8-Bromo-6-chloro-9-ethyl-1-methyl-9H-pyrido[3,4-b]indole,
8-Bromo-6-chloro-9-ethyl-9H-pyrido[3,4-b]indole,
8-Bromo-6-chloro-1-isopropyl-9H-pyrido[3,4-b]indole,
8-Bromo-6-chloro-1-ethyl-9H-pyrido[3,4-b]indole,
8-Bromo-9-but-2-ynyl-6-chloro-9H-pyrido[3,4-b]indole,
8-Bromo-6-chloro-9-(2,2,2-trifluoroethyl)-9H-pyrido[3,4-b]indole,
8-Bromo-6-chloro-9-(2-methoxyethyl)-9H-pyrido[3,4-b]indole,
6-Chloro-8-iodo-1,5-dimethyl-9H-pyrido[3,4-b]indole,
6-Bromo-8-iodo-1,3-dimethyl-9H-pyrido[3,4-b]indole,
6-Bromo-9-ethyl-8-iodo-1,3-dimethyl-9H-pyrido[3,4-b]indole, and
8-Bromo-6-chloro-9-(3-methyloxetan-3-ylmethyl)-9H-pyrido[3,4-b]indole.

3. The compound of formula II according to claim 1, which is selected from the group consisting of:
8-Bromo-6-chloro-9H-pyrido[3,4-b]indole,
8-Bromo-6-chloro-9-cyclopropylmethyl-9H-pyrido[3,4-b]indole,
8-Bromo-6-chloro-1-methyl-9H-pyrido[3,4-b]indole,
8-Bromo-6-chloro-9-cyclopropylmethyl-1-methyl-9H-pyrido[3,4-b]indole,
6-Chloro-8-iodo-1-methyl-9H-pyrido[3,4-b]indole,
6-Chloro-9-ethyl-8-iodo-1-methyl-9H-pyrido[3,4-b]indole,
6-Bromo-9-ethyl-8-iodo-1-methyl-9H-pyrido[3,4-b]indole,
6-Chloro-8-iodo-1,9-dimethyl-9H-pyrido[3,4-b]indole,
8-Bromo-6-chloro-9-ethyl-1-methyl-9H-pyrido[3,4-b]indole,
8-Bromo-9-but-2-ynyl-6-chloro-9H-pyrido[3,4-b]indole,
8-Bromo-6-chloro-9-(2,2,2-trifluoroethyl)-9H-pyrido[3,4-b]indole,
6-Chloro-8-iodo-1,5-dimethyl-9H-pyrido[3,4-b]indole,
6-Bromo-8-iodo-1,3-dimethyl-9H-pyrido[3,4-b]indole, and
6-Bromo-9-ethyl-8-iodo-1,3-dimethyl-9H-pyrido[3,4-b]indole.

4. The compound of formula II according to claim 1, which is selected from the group consisting of:
8-Bromo-6-chloro-9-cyclopropylmethyl-9H-pyrido[3,4-b]indole,
6-Chloro-8-iodo-1-methyl-9H-pyrido[3,4-b]indole,
6-Bromo-9-ethyl-8-iodo-1-methyl-9H-pyrido[3,4-b]indole,
6-Chloro-8-iodo-1,9-dimethyl-9H-pyrido[3,4-b]indole,
8-Bromo-6-chloro-9-ethyl-1-methyl-9H-pyrido[3,4-b]indole,
8-Bromo-9-but-2-ynyl-6-chloro-9H-pyrido[3,4-b]indole,
8-Bromo-6-chloro-9-(2,2,2-trifluoroethyl)-9H-pyrido[3,4-b]indole,
6-Chloro-8-iodo-1,5-dimethyl-9H-pyrido[3,4-b]indole,
6-Bromo-8-iodo-1,3-dimethyl-9H-pyrido[3,4-b]indole.

5. The compound of formula II according to claim 1, which is 8-Bromo-6-chloro-9-cyclopropylmethyl-9H-pyrido [3,4-b]indole.

6. The compound of formula II according to claim 1, which is 6-Chloro-8-iodo-1-methyl-9H-pyrido [3,4-b]indole.

7. The compound of formula II according to claim 1, which is 6-Chloro-8-iodo-1,9-dimethyl-9H-pyrido [3,4-b]indole.

8. The compound of formula II according to claim 1, which is 8-Bromo-6-chloro-9-ethyl-1-methyl-9H-pyrido [3,4-b]indole.

9. The compound of formula II according to claim 1, which is 6-Chloro-8-iodo-1,5-dimethyl-9H-pyrido [3,4-b]indole.

* * * * *